US008039641B2

(12) United States Patent
Quibell et al.

(10) Patent No.: US 8,039,641 B2
(45) Date of Patent: Oct. 18, 2011

(54) TETRAHYDROFURO[3,2-B] PYRROL-3-ONE INTERMEDIATES

(75) Inventors: Martin Quibell, Cambridge (GB); James Nally, Cambridge (GB); Lee Patient, Cambridge (GB); Yikang Wang, Cambridge (GB); Claudio Dagostin, Cambridge (GB); John Paul Watts, Cambridge (GB)

(73) Assignee: Amura Therapeutics Limited, Cambridge (GB)

( * ) Notice: Subject to any disclaimer, the term of this patent is extended or adjusted under 35 U.S.C. 154(b) by 277 days.

(21) Appl. No.: 12/319,562

(22) Filed: Jan. 8, 2009

(65) Prior Publication Data
US 2009/0192322 A1 Jul. 30, 2009

Related U.S. Application Data

(63) Continuation of application No. PCT/GB2007/002669, filed on Jul. 13, 2007.

(30) Foreign Application Priority Data

Jul. 14, 2006 (GB) .................................. 0614040.4

(51) Int. Cl.
*C07D 491/02* (2006.01)
(52) U.S. Cl. ........................................ 548/453; 548/452
(58) Field of Classification Search .................. 548/452, 548/453; 544/336, 358, 359
See application file for complete search history.

(56) References Cited

U.S. PATENT DOCUMENTS

| 7,799,791 | B2 * | 9/2010 | Quibell et al. | ........... | 514/254.02 |
| 7,803,803 | B2 * | 9/2010 | Quibell et al. | ........... | 514/254.08 |
| 7,846,935 | B2 * | 12/2010 | Quibell et al. | ........... | 514/254.08 |

OTHER PUBLICATIONS

Paolucci, et al: "Stereoisomeric Sugar-Derived Indolizines as Versatile Building Blocks: Synthesis of Enantiopure Di- and Tetrahydroxyindolizidines," J. Org. Chem. 2001, 66, 4787-4794.
Quibell, et al: "Bicyclic peptidomimetic tetrahydrofuro[3,2-b]pyrrol-3-one and hexahydrofuro[3,2-b]pyridine-3-one based scaffolds: synthesis and cysteinyl proteinase inhibition," Bioorganic & Medicinal Chemistry 12 (2004) 5689-5710.
Quibell, et al: "Synthesis and evaluation of cis-hexahydropyrrolo[3,2-b]pyrrol-3-one peptidomimetic inhibitors of CAC1 cysteinyl proteinases," Bioorganic & Medicinal Chemistry 13 (2005) 609-625.
Lin, et al: "Enantiomerically Pure Cage-Shaped (1S,4S,5R)-4-Hydroxy-2,6- diazabicyclo[3.3.0]octane and (1S,4R,5R)-4-Hydroxy-2-oxa-6-azabicyclo[3.3.0]octane: Synthesis and Test for Enantioielective Catalysis," Tetrahedron, vol. 53, No. 4, pp. 1369-1382, 1997.
Delle Monache, et al: "A stereocontrolled synthesis of (-) - detoxinine from L-ascorbic acid," Tetrahedron: Asymmetry 10 (1999) 2961-2973.
Paolucci, et al: "Dihydro- and Tetrahydrofuran Building Blocks from 1,4:3,6-Dianhydrohexitols. 2. Synthesis of Acetal, Alcohol, Diol, Epoxide, Hydrocarbon, and Lactone Pheromones," J. Org. Chem. 1995, 60, 169-175.
Preliminary Report on Patentability for Corresponding PCT Application No. PCT/GB2007/002669.
International Search Report for Corresponding PCT Application No. PCT/GB2007/002669.

* cited by examiner

*Primary Examiner* — Golam M M Shameem
(74) *Attorney, Agent, or Firm* — Edwards Angell Palmer & Dodge LLP; Kathleen Williams; Weiying Yang

(57) ABSTRACT

The present invention relates to a process for preparing a compound of formula (Ia), (Ib), (Ic) or (Id), or a pharmaceutically acceptable salt, hydrate, solvate, complex or prodrug thereof, said process comprising the steps of: (A) (i) treating a compound of formula (IVa), where $R^{48}$ is alkyl or tosyl, with an oxidizing agent to form a compound of formula (Va); and (ii) converting said compound of formula (Va) to a compound of formula (Ia) or (Ic); or (B) (i) treating a compound of formula (IVb), where $R^{48}$ is alkyl or tosyl, with an oxidizing agent to form a compound of formula (Vb); and (ii) converting said compound of formula (Vb) to a compound of formula (Ib) or (Id).

Ia

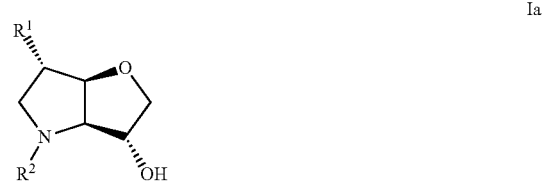

Ib

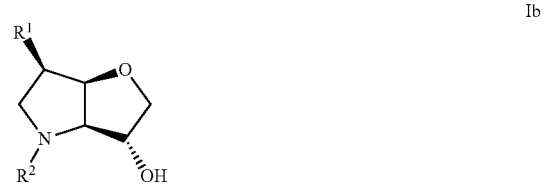

Ic

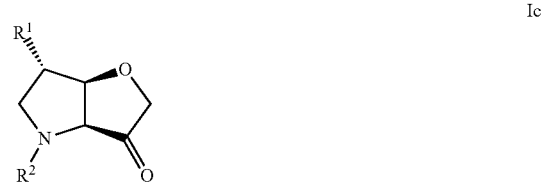

Id

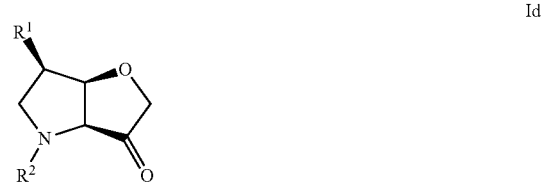

-continued
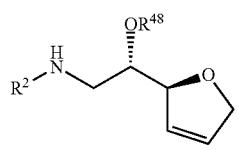
IVa
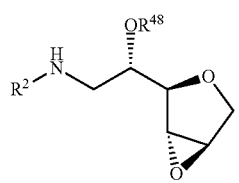
Va
Anti (major)
-continued
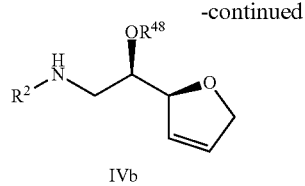
IVb
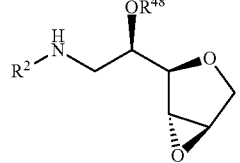
Vb
Anti (major)
6 Claims, No Drawings

TETRAHYDROFURO[3,2-B] PYRROL-3-ONE INTERMEDIATES

CROSS-REFERENCE TO RELATED APPLICATIONS

This application is a continuation of PCT application no. PCT/GB2007/002669, filed Jul. 13, 2007, which claims priority to GB Patent Application No. 0614040.4, filed Jul. 14, 2006. The contents of these applications are incorporated herein by reference in their entirety.

The present invention relates to a process for preparing 5,5-bicyclic building blocks that are useful in the preparation of cysteinyl proteinase inhibitors, especially CAC1 inhibitors. In particular, the invention seeks to provide new methodology for preparing tetrahydrofuro[3,2-b]pyrrol-3-ones and substituted derivatives thereof.

BACKGROUND TO THE INVENTION

Proteinases participate in an enormous range of biological processes and constitute approximately 2% of all the gene products identified following analysis of several completed genome sequencing programmes. Proteinases mediate their effect by cleavage of peptide amide bonds within the myriad of proteins found in nature.

This hydrolytic action involves recognising, and then binding to, specific three-dimensional electronic surfaces of a protein, which aligns the bond for cleavage precisely within the proteinase catalytic site. Catalytic hydrolysis then commences through nucleophilic attack of the amide bond to be cleaved either via an amino acid side-chain of the proteinase itself, or through the action of a water molecule that is bound to and activated by the proteinase.

Proteinases in which the attacking nucleophile is the thiol side-chain of a Cys residue are known as cysteine proteinases. The general classification of "cysteine proteinase" contains many members found across a wide range of organisms from viruses, bacteria, protozoa, plants and fungi to mammals.

Cysteine proteinases are classified into "clans" based upon similarity of their three-dimensional structure or a conserved arrangement of catalytic residues within the proteinase primary sequence. Additionally, "clans" may be further classified into "families" in which each proteinase shares a statistically significant relationship with other members when comparing the portions of amino acid sequence which constitute the parts responsible for the proteinase activity (see Barrett, A. J et al, in 'Handbook of Proteolytic Enzymes', Eds. Barrett, A. J., Rawlings, N. D., and Woessner, J. F. Publ. Academic Press, 1998, for a thorough discussion).

To date, cysteine proteinases have been classified into five clans, CA, CB, CC, CD and CE (Barrett, A. J. et al, 1998). A proteinase from the tropical papaya fruit 'papain' forms the foundation of clan CA, which currently contains over eighty distinct entries in various sequence databases, with many more expected from the current genome sequencing efforts.

Over recent years, cysteinyl proteinases have been shown to exhibit a wide range of disease-related biological functions. In particular, proteinases of the clan CA/family C1 (CAC1) have been implicated in a multitude of disease processes [a) Lecaille, F. et al, Chem. Rev. 2002, 102, 4459; (b) Chapman, H. A. et al, Annu. Rev. Physiol. 1997, 59, 63; Barrett, A. J. et al, Handbook of Proteolytic Enzymes; Academic: New York, 1998]. Examples include human proteinases such as cathepsin K (osteoporosis), cathepsins S and F (autoimmune disorders), cathepsin B (tumour invasion/metastases) and cathepsin L (metastases/autoimmune disorders), as well as parasitic proteinases such as falcipain (malaria parasite *Plasmodium falciparum*), cruzipain (*Trypanosoma cruzi* infection) and the CPB proteinases associated with Leishmaniasis [Lecaille, F. et al, ibid, Kaleta, J., ibid].

The inhibition of cysteinyl proteinase activity has evolved into an area of intense current interest [(a) Otto, H.-H. et al, Chem. Rev. 1997, 97, 133; (b) Heranandez, A. A. et al, Curr. Opin. Chem. Biol. 2002, 6, 459; (c) Veber, D. F. et al, Cur. Opin. Drug Disc. Dev. 2000, 3, 362-369; (d) Leung-Toung, R. et al, Curr. Med. Chem. 2002, 9, 979]. Selective inhibition of any of these CAC1 proteinases offers enormous therapeutic potential and consequently there has been a concerted drive within the pharmaceutical industry towards the development of compounds suitable for human administration [for example, see (a) Bromme, D. et al, Curr. Pharm. Des. 2002, 8, 1639-1658; (b) Kim, W. et al, Expert Opin. Ther. Patents 2002, 12(3), 419]. To date, these efforts have primarily focused on low molecular weight substrate based peptidomimetic inhibitors, the most advanced of which are in early clinical assessment.

Cysteinyl proteinase inhibitors investigated to date include peptide and peptidomimetic nitriles (e.g. see WO 03/041649), linear and cyclic peptide and peptidomimetic ketones, ketoheterocycles (e.g. see Veber, D. F. et al, Curr. Opin. Drug Discovery Dev., 3(4), 362-369, 2000), monobactams (e.g. see WO 00/59881, WO 99/48911, WO 01/09169), α-ketoamides (e.g. see WO 03/013518), cyanoamides (WO 01/077073, WO 01/068645), dihydropyrimidines (e.g. see WO 02/032879) and cyano-aminopyrimidines (e.g. see WO 03/020278, WO 03/020721).

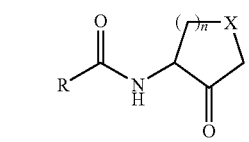

[1'a] X = O, n = 1
[1'b] X = NR', n = 1
[1'c] X = O, n = 2
[1'd] X = NR', n = 2
[1'e] X = NR' n = 3

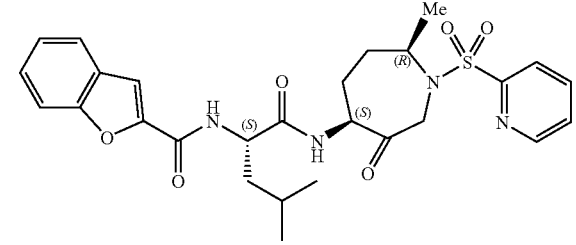

[1'f] SB-462795, relacatib

Prior Art Cyclic Inhibitors of Cathepsin K

The initial cyclic inhibitors of GSK were based upon potent, selective and reversible 3-amido-tetrahydrofuran-4-ones [1'a], 3-amidopyrrolidin-4-ones [1'b], 4-amido-tetrahydropyran-3-ones [1'c], 4-amidopiperidin-3-ones [1'd] and 4-amidoazepan-3-ones [1'e, 1'f] (shown above) [see (a) Marquis, R. W. et al, J. Med. Chem. 2001, 44, 725, and references cited therein; (b) Marquis, R. W. et al, J. Med. Chem. 2001, 44, 1380, and references cited therein; (c) Yamashita, D. S. et al, J. Med. Chem. 2006, 49(5), 1597-1612].

Further studies revealed that cyclic ketones [1'], in particular the five-membered ring analogues [1'a] and [1'b], suffered from configurational instability due to facile epimerisation at the centre situated α to the ketone [Marquis, R. W. et al, J. Med. Chem. 2001, 44, 1380; Fenwick, A. E. et al, J. Bioorg. Med. Chem. Lett. 2001, 11, 199; WO 00/69855]. This precluded the pre-clinical optimisation of inhibitors of formulae [1'a-d] and led to the development of the configurationally more stable azepanone series [1'e], providing the cathepsin K inhibitor clinical candidate relacatib [1'f]. However, literature clearly states that azepanones are still prone to epimerisation and indeed relacatib [1'f] is reported to exist as a 9:1 thermodynamic mixture of 4-S and 4-R isomers [Yamashita, D. S. et al, ibid]. As an alternative to the ring expansion approach, alkylation of the α-carbon removes the ability of cyclic ketones [1'] to undergo α-enolisation and hence leads to configurational stability. However, studies have shown that α-methylation in the 3-amidopyrrolidin-4-one [1'b] system results in a substantial loss in potency versus cathepsin K from $K_{i,app} \approx 0.18$ to 50 nM.

More recent studies have investigated 5,5-bicyclic systems as inhibitors of CAC1 proteinases, for example, N-(3-oxo-hexahydrocyclopenta[b]furan-3α-yl)acylamide bicyclic ketones [2'] [(a) Quibell, M.; Ramjee, M. K., WO 02/57246; (b) Watts, J. et al, Bioorg. Med. Chem. 12 (2004), 2903-2925], tetrahydrofuro[3,2-b]pyrrol-3-one based scaffolds [3'] [(a) Quibell, M. WO02/57270; (b) Quibell, M. et al, Bioorg. Med. Chem. 12 (2004), 5689-5710], cis-6-oxohexahydro-2-oxa-1,4-diazapentalene and cis-6-oxo-hexahydropyrrolo[3,2-c]pyrazole based scaffolds [4'] [Wang, Y. et al, Bioorg. Med. Chem. Lett. 15 (2005), 1327-1331], and cis-hexahydropyrrolo[3,2-b]pyrrol-3-one based scaffolds [5'] [a) Quibell, M. WO04/07501; (b) Quibell, M. et al, Bioorg. Med. Chem. 13 (2005), 609-625].

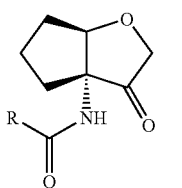

[2']

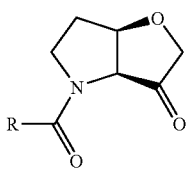

[3']

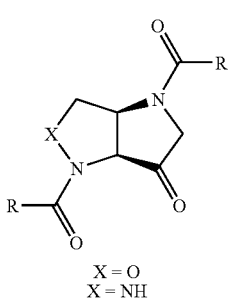

[4']
X = O
X = NH

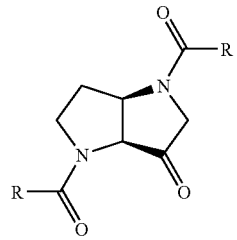

[5']

5,5-bicyclic Inhibitors of CAC1 Cysteinyl Proteinases

Studies have shown that the above-escribed 5,5-bicyclic systems exhibit promising potency as inhibitors of a range of therapeutically attractive mammalian and parasitic CAC1 cysteinyl proteinase targets. Moreover, the 5,5-bicyclic series are chirally stable due to a marked energetic preference for a cis-fused rather than a trans-fused geometry. This chiral stability provides a major advance when compared to monocyclic systems that often show limited potential for preclinical development due to chiral instability.

Literature syntheses of 5,5-bicyclic intermediates have been reported by a variety of routes. One example, a diazomethylketone cyclisation route, has been described in WO 02/057270 (Scheme 1).

Scheme 1: 3-Hydroxyproline based cyclisation route to 5,5-bicyclic intermediates.

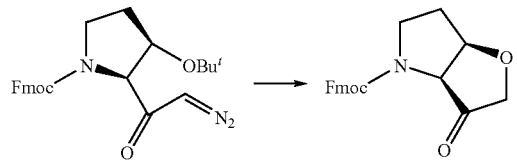

A further example through the preparation of allo-furanose intermediates followed by cyclisation and subsequent reduction of the anomeric oxygen has been detailed by Nilsson, M. et al (WO 05/066180) to introduce a 6-fluoro substituent (Scheme 2). A conceptually similar route commencing from D-glucose has been detailed by Gurjar, M. K., et al, Ind. J. Chem. 26B, 1115-1120, 1987.

Scheme 2: An allo-furanose based route to 6-fluoro-5,5-bicyclic intermediates.

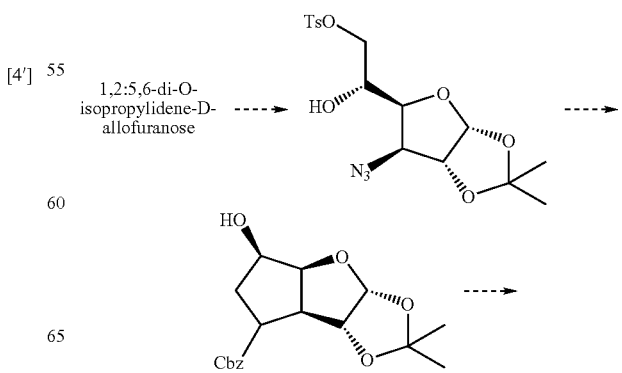

-continued

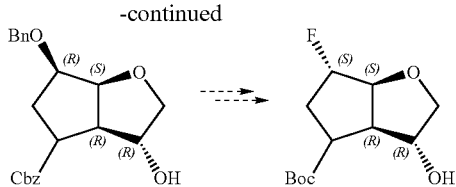

Other literature routes to 5,5-bicyclic intermediates include, but are not limited to, the stereocontrolled vinylation of a chiral α,β-epoxy imine (see Ayad, T.; et al, *Synlett*, 6, 866-868, 2001); preparation of a 4,5-disubstituted oxazolidin-2-one followed by steps which incorporate base cyclisation (see Delle Monache, G., et al, *Tet. Asymm.*, 10(15), 2961-2973, 1999); dihydroxylation of 1-tosyl-2-vinylpyrrolidin-3-yl methanesulfonate followed by based-catalysed ring closure (see Lin, G-Q. and Shi, Z-C., *Tet.*, 53(4), 1369-1382, 1997).

Additional alternative routes include syntheses based upon dihydrofuran derived intermediates detailed in Scheme 3 that are open to the stereoselective epoxidation chemistry pioneered in our syntheses of alternative 5,5-heterobicycles (see (a) Quibell, M et al, Bioorg. Med. Chem., 13, 609-625, 2005; (b) Wang, Y. et al, Bioorg. Med. Chem. Lett., 15, 1327-1331, 2005). Syntheses may commence with the homologation of methyl 2,5-dihydrofuran-2-carboxylate by cyanide displacement of the corresponding mesylate derivative or via homologation to an epoxide intermediate (Scheme 3). In particular, the epoxide intermediate is applicable to the types of amine ring opening reactions typified in the syntheses of HIV-1 protease hydroxyethylamine inhibitors (e.g. see Beaulieu, P. L. et al, J. Org. Chem., 62, 3440-3448, 1997).

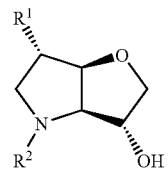

Ia

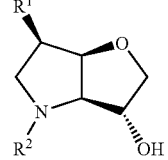

Ib

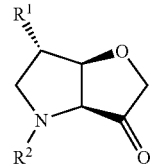

Ic

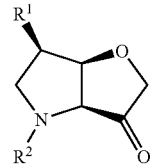

Id wherein:

$R^1$ is selected from H, $N_3$, $NH_2$, $NHR^3$, $NR^4R^5$, OH, $OR^6$, OTs, OMs, Me, Et, $CF_3$, F, Cl, Br, SH, $SR^7$, $SOR^7$, $SO_2R^7$, Scheme 3: Routes involving homologation of methyl 2,5-dihydrofuran-2-carboxylate.

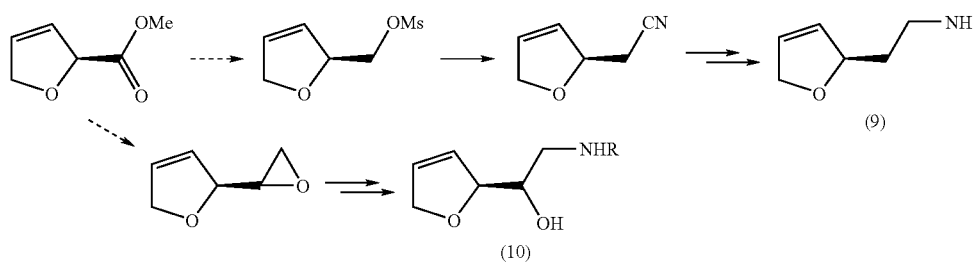

The present invention seeks to provide an improved process for synthesising 5,5-bicyclic building blocks useful in the preparation of cysteinyl proteinase inhibitors. More particularly, the invention seeks to provide new methodology for synthesising tetrahydrofuro[3,2-b]pyrrol-3-ones and substituted derivatives thereof. The invention also seeks to provide new intermediates useful in the synthesis of cysteinyl proteinase inhibitors.

STATEMENT OF INVENTION

A first aspect of the invention relates to a process for preparing a compound of formula Ia, Ib, Ic or Id, or a pharmaceutically acceptable salt, hydrate, solvate, complex or prodrug thereof, NH-$PG_2$, O-$PG_3$ and S-$PG_4$, wherein each of $PG_2$, $PG_3$ and $PG_4$ is independently a protecting group and Ts and Ms are tosyl and mesyl group respectively;

$R^2$ is H or a protecting group $PG_1$ or a group of formula U—$(V)_m$—$(W)_n$—$(X)_o$—Y— or a group of formula $(U)_p$—$(X_2)_s$—$(Y_1)_k$—$Y_2$—;

$R^{3-7}$ are each independently alkyl or cycloalkyl or aryl; or $R^4$ and $R^5$ are linked to form a cyclic group together with the nitrogen to which they are attached;

Y is $CR^8R^9$—CO—, where $R^8$, $R^9$ are each independently selected from H, alkyl, cycloalkyl, Ar, Ar-alkyl, cycloalkyl (alkyl), heteroaryl or heteroaryl(alkyl), each of which may be optionally substituted by $R^{49}$, or $R^8$ and $R^9$ are linked to the adjacent backbone carbon atom to form a spiro-$C_5$-$C_6$ cycloalkyl group;

in the group $(X_o)$, X is $CR^{10}R^{11}$, where $R^{10}$ and $R^{11}$ are independently selected from H, alkyl, cycloalkyl, Ar and Ar-alkyl, and o is 0, 1, 2 or 3;

in the group $(W)_n$, W is O, S, C(O), S(O) or $S(O)_2$ or $NR^{12}$, where $R^{12}$ is selected from H, alkyl, cycloalkyl, Ar and Ar-alkyl, and n is 0 or 1;

in the group $(V)_m$, V is C(O), C(S), S(O), $S(O)_2$, S(O)NH, OC(O), NHC(O), NHS(O), $NHS(O)_2$, OC(O)NH, C(O)NH or $CR^{13}R^{14}$, where $R^{13}$ and $R^{14}$ are independently selected from H, alkyl, cycloalkyl, Ar and Ar-alkyl, and m is 0, 1, 2 or 3; provided that when m is greater than one, $(V)_m$ contains a maximum of one carbonyl or sulphonyl group;

$Y_2$ is OC(O), SC(O)— or

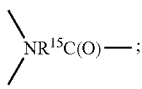

or where $(U)_p$, $(X_2)_s$ and $(Y_1)_k$ are absent, $Y_2$ is $R^{47}OC(O)$—, $R^{47}SC(O)$— or $R^{15}R^{45}NC(O)$—, where $R^{47}$ is alkyl or aryl, and $R^{15}$ and $R^{45}$ are each independently selected from H and alkyl, or $R^{15}$ and $R^{45}$ are linked to form a cyclic group together with the nitrogen to which they are attached;

in the group $(Y_1)_k$, each $Y_1$ is independently

and 'k' is 0, 1, 2 or 3;
or when 'k' is 1, $Y_1$ may additionally be selected from

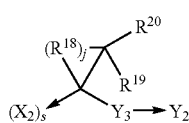

where $Y_3$ is methylene or absent;
$R^{18}$ is selected from

'j' is 1, 2, 3 or 4, where when 'j' is 2, 3 or 4, one $R^{18}$ may additionally be selected from O, S, $SO_2$, $NR^{23}$ and $—N(R^{23})C(O)—$;

or when 'k' is 1, 2, or 3 and $(U)_p$ and $(X_2)_s$ are absent, the terminal $Y_1$ group is selected from $CR^{16}R^{17}R^{43}$ and

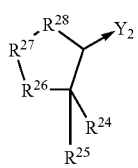

$R^{26}$ is selected from

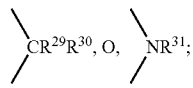

$R^{27}$ is selected from

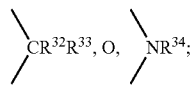

except when $R^{26}$ is O, then $R^{27}$ is selected from

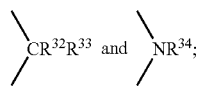

$R^{28}$ is selected from

in the group $(X_2)_s$, each $X_2$ is independently

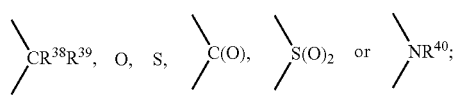

's' is 0, 1 or 2, provided that when $(Y_1)_k$ is absent, $(X_2)_s$ is $CR^{38}R^{39}$ or is absent, and also provided that when 's' is 2, $(X_2)_s$ contains a minimum of one

and when $(U)_p$ is absent and 's' is 1 or 2, the terminal $X_2$ group is $CR^{38}R^{39}R^{44}$;

each U is independently a 5- to 7-membered monocyclic or a 8- to 11-membered bicyclic ring which is either saturated or unsaturated and which includes up to four heteroatoms as shown below:

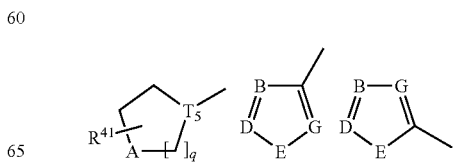

-continued

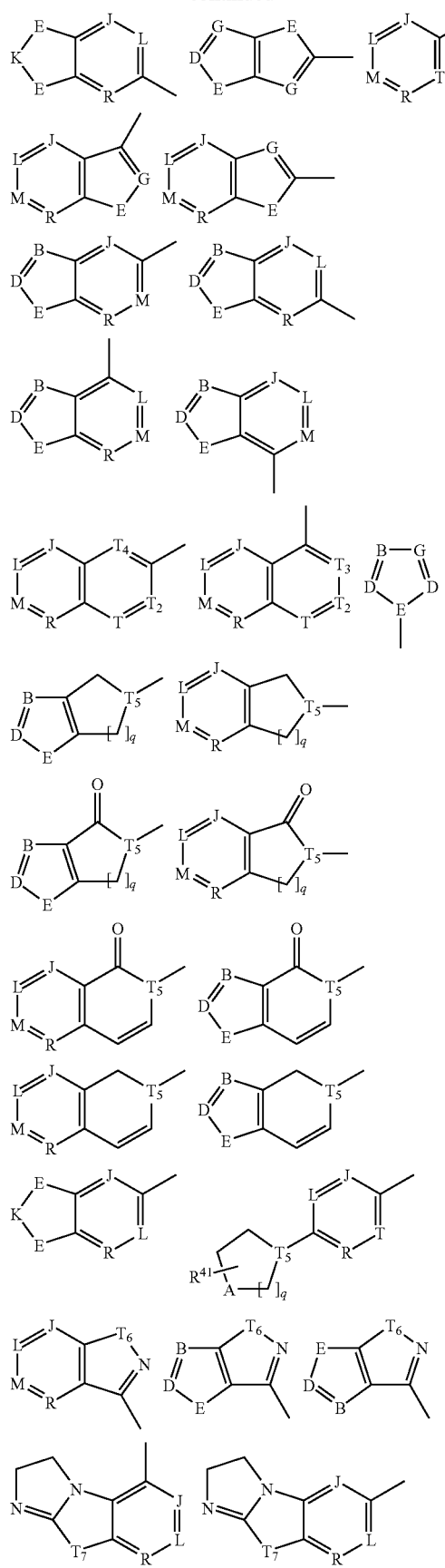
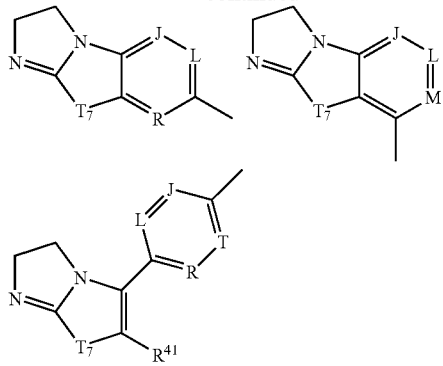

wherein $R^{41}$ is:
H, alkyl, cycloalkyl, Ar-alkyl, Ar, OH, O-alkyl, O-cycloalkyl, O—Ar-alkyl, OAr, SH, S-alkyl, S-cycloalkyl, S—Ar-alkyl, SAr, SO-alkyl, SO-cycloalkyl, SO—Ar-alkyl, SO—Ar, $SO_2H$, $SO_2$-alkyl, $SO_2$-cycloalkyl, $SO_2$—Ar-alkyl, $SO_2Ar$, NH-alkyl, $NH_2$, NH-cycloalkyl, NH—Ar-alkyl, NHAr, NHCO-alkyl, NHCO-cycloalkyl, NHCO—Ar-alkyl, NHCOAr, $N(alkyl)_2$, $N(cycloalkyl)$, or $N(Ar\text{-}alkyl)_2$ or $NAr_2$ or, when part of a $CHR^{41}$ or $CR^{41}$ group, $R^{41}$ may be halogen;

A is selected from:

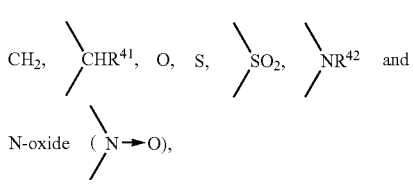

where $R^{41}$ is as defined above; and $R^{42}$ is selected from H, alkyl, cycloalkyl, Ar and Ar-alkyl;

B, D and G are each independently selected from:

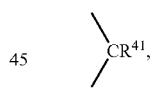

where $R^{41}$ is as defined above, N and N-oxide

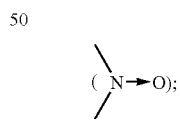

E is selected from:

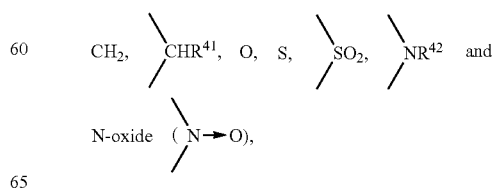

where $R^{41}$ and $R^{42}$ are defined as above;

K is selected from:

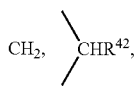

where $R^{42}$ is defined as above;
J, L, M, R, T, $T_2$, $T_3$ and $T_4$ are independently selected from: $CR^{41}$ where $R^{41}$ is as defined above, N and N-oxide

$T_5$ is selected from:
CH and N;
$T_6$ is selected from:

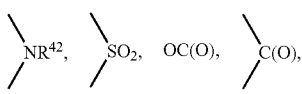

and $N(R^{42})C(O)$;
$T_7$ is selected from:

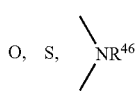

'q' is 1, 2 or 3;
'p' is 0 or 1;
$R^{16-17}$, $R^{19-22}$, $R^{24-25}$, $R^{29-30}$, $R^{32-33}$, $R^{35-36}$, $R^{38-39}$ and $R^{43-44}$ are each independently selected from H, alkyl, cycloalkyl, Ar-alkyl, Ar and halogen; and
$R^{23}$, $R^{31}$, $R^{34}$, $R^{37}$, $R^{10}$ and $R^{46}$ are each independently selected from H, alkyl, cycloalkyl, Ar-alkyl and Ar;
$R^{49}$ is H, alkyl, cycloalkyl, Ar-alkyl, Ar, OH, O-alkyl, O-cycloalkyl, O—Ar-alkyl, OAr, SH, S-alkyl, S-cycloalkyl, S—Ar-alkyl, SAr, SO-alkyl, SO-cycloalkyl, SO—Ar-alkyl, SO—Ar, $SO_2H$, $SO_2$-alkyl, $SO_2$-cycloalkyl, $SO_2$—Ar-alkyl, $SO_2Ar$, NH-alkyl, $NH_2$, NH-cycloalkyl, NH—Ar-alkyl, NHAr, NHCO-alkyl, NHCO-cycloalkyl, NHCO—Ar-alkyl, NHCOAr, $N(alkyl)_2$, N(cycloalkyl), or $N(Ar-alkyl)_2$ or $NAr_2$ or halogen;
said process comprising the steps of:

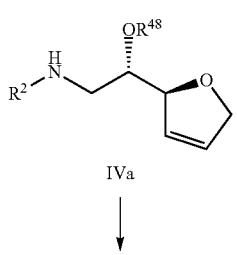

IVa

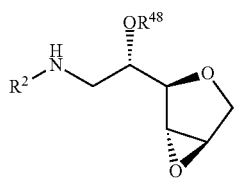

Va
Anti (major)

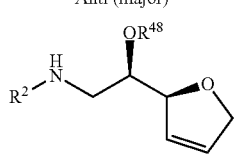

IVb

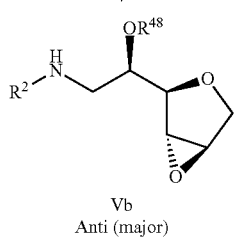

Vb
Anti (major)

(A)
(i) treating a compound of formula IVa, where $R^{48}$ is alkyl or tosyl or mesyl, with an oxidising agent to form a compound of formula Va; and
(ii) converting said compound of formula Va wherein $R^{48}$ is alkyl to a compound of formula Ia or Ic or wherein $R^{48}$ is tosyl or mesyl to a compound of formula Ia, Ib, Ic or Id; or (B)
(i) treating a compound of formula IVb, where $R^{48}$ is alkyl or tosyl or mesyl, with an oxidising agent to form a compound of formula Vb; and
(ii) converting said compound of formula Vb wherein $R^{48}$ is alkyl to a compound of formula Ib or Id or wherein $R^{48}$ is tosyl or mesyl to a compound of formula Ia, Ib, Ic or Id.

Advantageously, the presence of a relatively bulky substituent (—$OR^{48}$), alpha to the dihydrofuran ring, imparts a strong stereofacial preference for forming the desired anti-epoxide during the oxidation step. This is referred to hereinafter as a "directing effect" and is in contrast to prior art reactions on the corresponding unsubstituted analogues, where little stereofacial preference is observed.

A second aspect of the invention relates to a process for preparing a compound of formula IIIa or IIIb,

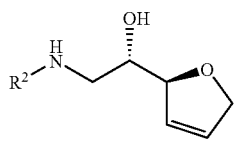

IIIa

-continued

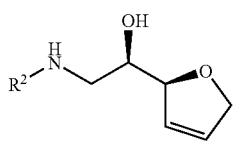
IIIb wherein:
R² is a protecting group PG₁ or a group of formula U—(V)$_m$—(W)$_n$—(X)$_o$—Y— or a group of formula (U)$_p$—(X$_2$)$_s$—(Y$_1$)$_k$—Y$_2$— where Y, X, W, V, U, Y$_2$, Y$_1$, X$_2$, o, n, m, k, s and p are as defined above;
said process comprising:

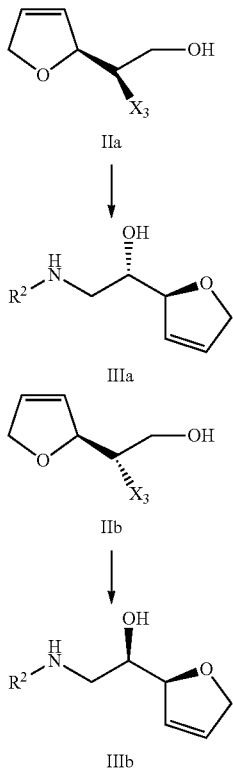

(A')
(i) reacting a compound of formula IIa, wherein X₃ is halogen, OTs or OMs, with aqueous ammonia and alcohol; or alternatively aqueous ammonium hydroxide;
(ii) converting the product formed in step (i) to a compound of formula IIIa; or (B')
(i) reacting a compound of formula IIb, wherein X₃ is halogen, OTs or OMs, with aqueous ammonia and alcohol; or alternatively aqueous ammonium hydroxide;
(ii) converting the product formed in step (i) to a compound of formula IIIb.

The above process provides an alternative route for preparing enantiomerically pure diastereomers IIIa and IIIb, which are key intermediates useful in the synthesis of 5,5-bicylic building blocks for the preparation of cysteinyl proteinase inhibitors. Advantageously, the reaction can be carried out in a high yielding, one-pot reaction, which represents a significant improvement over prior art multi-step processes used to produce these derivatives to date.

A third aspect of the invention relates to a compound of formula IVa, IVb, Va or Vb, or pharmaceutically acceptable salts, hydrates, solvates, complexes or prodrugs thereof,

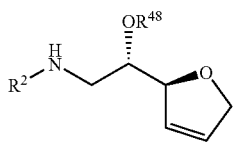
IVa

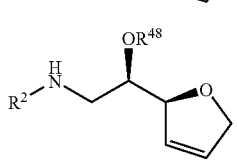
IVb

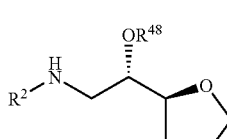
Va

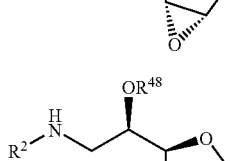
Vb wherein:
R⁴⁸ is alkyl, tosyl or mesyl;
R² is a protecting group PG₁ or a group of formula U—(V)$_m$—(W)$_n$—(X)$_o$Y— or a group of formula (U)$_p$—(X$_2$)$_n$—(Y$_1$)$_k$—Y$_2$— where Y, X, W, V, U, Y$_2$, Y$_1$, X$_2$, o, n, m, k, s and p are as defined above;

Advantageously, the above compounds are easily accessible, enantiomerically pure intermediates which are useful in the preparation of a wide range of cysteinyl proteinase inhibitors.

A fourth aspect of the invention relates to the use of a compound of formula IVa, IVb, Va or Vb, as an intermediate in the preparation of a cysteinyl proteinase inhibitor.

A fifth aspect relates to a method of preparing a cysteinyl proteinase inhibitor which comprises using the process of the invention.

DETAILED DESCRIPTION

Definitions

As mentioned above, a first aspect of the invention relates to a process for preparing a compound of formula Ia, Ib, Ic or Id, or a pharmaceutically acceptable salt, hydrate, solvate, complex or prodrug thereof.

Unless the context requires otherwise, throughout the specification different enantiomers of the same generic structure are labelled as "a" and "b" respectively. For individual compounds labelled numerically, the number alone (i.e. without a label "a" or "b") refers to one enantiomer, with the other enantiomer being labelled as "b".

As used herein, the term "alkyl" includes both saturated straight chain and branched alkyl groups which may be substituted (mono- or poly-) or unsubstituted. Examples of suitable substituents include halo, CF₃, OH, CN, NO₂, SH, SO$_3$H, SO$_2$H, SO$_2$NH$_2$, SO$_2$Me, NH$_2$, COOH, and CONH$_2$. The alkyl group may also contain one or more heteroatoms, for example, to give ethers, thioethers, sulphones, sulphonamides, substituted amines, amidines, guanidines, carboxylic acids, esters, carboxamides. If the heteroatom is located at a chain terminus then it is appropriately substituted with one or two hydrogen atoms. Preferably, the alkyl group is a C$_{1-20}$alkyl group, more preferably a Cl$_{15}$, more preferably still a C$_{1-12}$ alkyl group, more preferably still, a C$_{1-7}$ alkyl group, even more preferably a C$_{1-6}$ alkyl group, more preferably a C$_{1-3}$ alkyl group.

Particularly preferred alkyl groups include, for example, methyl, ethyl, propyl, isopropyl, butyl, isobutyl, tert-butyl, pentyl and hexyl.

As used herein, the term "aryl" or "Ar" refers to a C$_{6-12}$ aromatic group which may be substituted (mono- or poly-) or unsubstituted. Typical examples include phenyl and naphthyl etc. Examples of suitable substituents include alkyl, halo, CF$_3$, OH, CN, NO$_2$, SO$_3$H, SO$_2$NH$_2$, SO$_2$Me, NH$_2$, COOH, and CONH$_2$.

As used herein, the term "heteroaryl" refers to a C$_{4-12}$ aromatic, substituted (mono- or poly-) or unsubstituted group, which comprises one or more heteroatoms as part of the aromatic ring. Preferred heteroaryl groups include pyrrole, indole, benzofuran, pyrazole, benzimidazole, benzothiazole, pyrimidine, imidazole, pyrazine, pyridine, quinoline, triazole, tetrazole, thiophene and furan. Again, suitable substituents include, for example, halo, alkyl, CF$_3$, OH, CN, NO$_2$, SO$_3$H, SO$_2$NH$_2$, SO$_2$Me, NH$_2$, COOH, and CONH$_2$.

The term "heteroaryl(alkyl)" is used as a conjunction of the terms alkyl and heteroaryl as given above.

As used herein, the term "cycloalkyl" refers to a cyclic alkyl group which may be substituted (mono- or poly-) or unsubstituted. Preferably, the cycloalkyl group is a C$_{3-6}$ cycloalkyl group. Suitable substituents include, for example, halo, alkyl, CF$_3$, OH, CN, NO$_2$, SO$_3$H, SO$_2$NH$_2$, SO$_2$Me, NH$_2$, COOH, CONH$_2$ and alkoxy.

The term "cycloalkyl(alkyl)" is used as a conjunction of the terms alkyl and cycloalkyl(alkyl) as given above.

The term "aralkyl" is used as a conjunction of the terms alkyl and aryl as given above. Preferred aralkyl groups include CH$_2$Ph and CH$_2$CH$_2$Ph and the like.

As used herein, the term "alkenyl" refers to a group containing one or more carbon-carbon double bonds, which may be branched or unbranched, substituted (mono- or poly-) or unsubstituted. Preferably the alkenyl group is a C$_{2-20}$ alkenyl group, more preferably a C$_{2-15}$ alkenyl group, more preferably still a C$_{2-12}$ alkenyl group, or preferably a C$_{2-6}$ alkenyl group, more preferably a C$_{2-3}$ alkenyl group. Suitable substituents include, for example, alkyl, halo, CF$_3$, OH, CN, NO$_2$, SO$_3$H, SO$_2$NH$_2$, SO$_2$Me, NH$_2$, COOH, CONH$_2$ and alkoxy.

As used herein, the term "alicyclic" refers to a cyclic aliphatic group which optionally contains one or more heteroatoms and which is optionally substituted. Preferred alicyclic groups include piperidinyl, pyrrolidinyl, piperazinyl and morpholinyl. More preferably, the alicyclic group is selected from N-piperidinyl, N-pyrrolidinyl, N-piperazinyl and N-morpholinyl. Suitable substituents include, for example, alkyl, halo, CF$_3$, OH, CN, NO$_2$, SO$_3$H, SO$_2$NH$_2$, SO$_2$Me, NH$_2$, COOH, CONH$_2$ and alkoxy.

The term "aliphatic" takes its normal meaning in the art and includes non-aromatic groups such as alkanes, alkenes and alkynes and substituted derivatives thereof.

PG$_1$ and PG$_2$ are each independently nitrogen protecting groups. Suitable nitrogen protecting groups will be familiar to the skilled artisan (see for example, "Protective Groups in Organic Synthesis" by Peter G. M. Wuts and Theodora W. Greene, 2$^{nd}$ Edition). Preferred nitrogen protecting groups are described hereinafter.

PG$_3$ is an oxygen protecting group. Suitable oxygen protecting groups will be familiar to the skilled artisan (see for example, "Protective Groups in Organic Synthesis" by Peter G. M. Wuts and Theodora W. Greene, 2$^{nd}$ Edition). Preferred oxygen protecting groups include tert-butyl ether and benzyl (PhCH$_2$) ether or substituted benzyl ether (e.g. 4-MeOPhCH$_2$).

PG$_4$ is a sulphur protecting group. Suitable sulphur protecting groups will be familiar to the skilled artisan (see for example, "Protective Groups in Organic Synthesis" by Peter G. M. Wuts and Theodora W. Greene, 2$^{nd}$ Edition). Preferred sulphur protecting groups include tert-butyl thioether (Bu$^t$-S), tert-butyl thiodisulphide (Bu$^t$S-S), benzyl thioether (PhCH$_2$—S) or substituted benzyl thioether (e.g. 4-MeOPhCH$_2$—S), trityl thioether ([Ph]$_3$C—S) or substituted trityl thioether or S-acetamidomethyl (Acm).

Salts, Hydrates, Solvates, Complexes and Prodrugs

The present invention relates to the preparation and use of all salts, hydrates, solvates, complexes and prodrugs of the compounds described herein. The term "compound" is intended to include all such salts, hydrates, solvates, complexes and prodrugs, unless the context requires otherwise.

Appropriate pharmaceutically and veterinarily acceptable salts include salts of organic acids, especially carboxylic acids, including but not limited to acetate, trifluoroacetate, lactate, gluconate, citrate, tartrate, maleate, malate, pantothenate, adipate, alginate, aspartate, benzoate, butyrate, digluconate, cyclopentanate, glucoheptanate, glycerophosphate, oxalate, heptanoate, hexanoate, fumarate, nicotinate, palmoate, pectinate, 3-phenylpropionate, picrate, pivalate, proprionate, tartrate, lactobionate, pivolate, camphorate, undecanoate and succinate, organic sulphonic acids such as methanesulphonate, ethanesulphonate, 2-hydroxyethane sulphonate, camphorsulphonate, 2-naphthalenesulphonate, benzenesulphonate, p-chlorobenzenesulphonate and p-toluenesulphonate; and inorganic acids such as hydrochloride, hydrobromide, hydroiodide, sulphate, bisulphate, hemisulphate, thiocyanate, persulphate, phosphoric and sulphonic acids. Salts which are not pharmaceutically or veterinarily acceptable may still be valuable as intermediates.

The invention furthermore relates to the preparation of compounds in their various crystalline forms, polymorphic forms and (an)hydrous forms. It is well established within the pharmaceutical industry that chemical compounds may be isolated in any of such forms by slightly varying the method of purification and or isolation form the solvents used in the synthetic preparation of such compounds.

It will be appreciated that the ketone group of the bicycle may exist in alternative forms such as the hydrate and the invention extends to all such alternative forms.

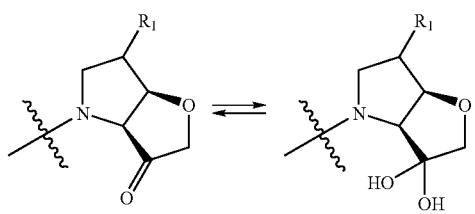

Oxidation Step A(i), (B)(i)

Steps (A)(i) and (B)(i) of the process involve oxidation to form an epoxide intermediate (Va, Vb).

In one preferred embodiment, the oxidising agent is mCPBA.

In another preferred embodiment, the oxidising agent is a hydrogen peroxide and alkylnitrile mixture.

The use of hydrogen peroxide with alkylnitriles as oxidising agents is well documented in the literature [see (a) Chaudhuri, N. K. and Ball, T. J. J. Org. Chem., 47(26), 5196-5198, (1982); (b) von Holleben, M. L. A. et al, J. Braz. Chem. Soc. 12(1), 4246, (2001)]

In another preferred embodiment, the oxidising agent is a dioxirane.

The use of dioxiranes as oxidising agents is well documented in the literature [see (a) Hodgson, D. M. et al, Synlett, 310 (2002); (b) Adam, W. et al, Ace. Chem. Res. 22, 205, (1989); (c) Yang, D. et al, J. Org. Chem., 60, 3887, (1995); (d) Mello, R. et al, J. Org. Chem., 53, 3890, (1988); (e) Curci, R. et al, Pure & Appl. Chem., 67(5), 811 (1995); (f) Emmons, W. D. et al, J. Amer. Chem. Soc. 89, (1955)].

Preferably, the dioxirane is generated in situ by the reaction of $KHSO_5$ with a ketone. However, step (i) can also be carried out using an isolated dioxirane, for example a stock solution of the dioxirane formed from acetone.

More preferably, the dioxirane is generated in situ using Oxone®, which is a commercially available oxidising agent containing $KHSO_5$ as the active ingredient.

Thus, in one preferred embodiment, step (i) of the claimed process involves the in situ epoxidation using Oxone® (2 $KHSO_5 \cdot KHSO_4 \cdot K_2SO_4$) and a ketone co-reactant.

As mentioned above, the active ingredient of Oxone® is potassium peroxymonosulfate, $KHSO_5$[CAS-RN 10058-23-8], commonly known as potassium monopersulfate, which is present as a component of a triple salt with the formula 2 $KHSO_5 \cdot KHSO_4 \cdot K_2SO_4$ [potassium hydrogen peroxymonosulfate sulfate (5:3:2:2), CAS-RN 70693-62-8; commercially available from DuPont]. The oxidation potential of Oxone® is derived from its peracid chemistry; it is the first neutralization salt of peroxymonosulfuric acid $H_2SO_5$ (also known as Caro's acid).

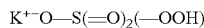

Potassium Monopersulfate

Under slightly basic conditions (pH 7.5-8.0), persulfate reacts with the ketone co-reactant to form a three membered cyclic peroxide (a dioxirane) in which both oxygens are bonded to the carbonyl carbon of the ketone. The cyclic peroxide so formed then epoxidises the compound of formula III by syn specific oxygen transfer to the alkene bond.

Preferably, the ketone is of formula XVII

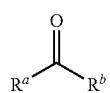

XVII wherein $R^a$ and $R^b$ are each independently alkyl, aryl, haloalkyl or haloaryl.

Where $R^a$ and/or $R^b$ are alkyl, the alkyl group may be a straight chain or branched alkyl group. Preferably, the alkyl group is a $C_{1-20}$ alkyl group, more preferably a $C_{1-15}$, more preferably still a $C_{1-12}$ alkyl group, more preferably still, a $C_{1-7}$ or $C_{1-6}$ alkyl group, more preferably a $C_{1-3}$ alkyl group. Particularly preferred alkyl groups include, for example, methyl, ethyl, propyl, isopropyl, butyl, isobutyl, tert-butyl, pentyl and hexyl.

As used herein, the term "haloalkyl" refers to an alkyl group as described above in which one or more hydrogens are replaced by halo.

Where $R^a$ and/or $R^b$ are aryl, the aryl group is typically a $C_{6-12}$ aromatic group. Preferred examples include phenyl and naphthyl etc.

As used herein, the term "haloaryl" refers to an aryl group as described above in which one or more hydrogens are replaced by halo.

By way of example, the reaction of $KHSO_5$ (Oxone®) with a ketone of formula XVII would form a dioxirane of formula:

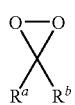

wherein $R^a$ and $R^b$ are as defined above.

More preferably, $R^a$ and $R^b$ are each independently alkyl or haloalkyl.

In a highly preferred embodiment, at least one of $R^a$ and $R^b$ is a haloalkyl, more preferably, $CF_3$ or $CF_2CF_3$.

In one preferred embodiment, $R^a$ and $R^b$ are each independently methyl or trifluoromethyl.

In one preferred embodiment of the invention, the ketone is selected from acetone and a 1,1,1-trifluoroalkyl ketone.

In a more preferred embodiment of the invention, the trifluoroalkyl ketone is 1,1,1-trifluoroacetone or 1,1,1-trifluoro-2-butanone, more preferably 1,1,1-trifluoro-2-butanone.

Preferred Structures of Formula Ia, Ib, Ic and Id

In one preferred embodiment, Y is $CR^8R^9$—CO—, where $R^8$, $R^9$ are each independently selected from H, alkyl, cycloalkyl, Ar and Ar-alkyl, or $R^8$ and $R^9$ are linked to the adjacent backbone carbon atom to form a spiro-$C_5$-$C_6$ cycloalkyl group.

In one preferred embodiment, $R^2$ is a protecting group $PG_1$ or a group of formula U—$(V)_m$—$(W)_n$—$(X)_o$—Y— or a group of formula $(U)_p$—$(X_2)_s$—$(Y_1)_k$—$Y_2$— as defined above.

In one particularly preferred embodiment of the invention, $R^2$ is a protecting group $PG_1$, i.e. the process is used to prepare a compound of formula Ie, If, Ig or Ih,

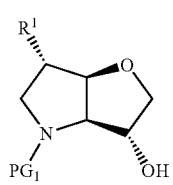

Ie

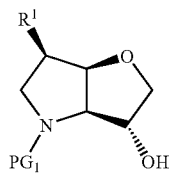

If

-continued

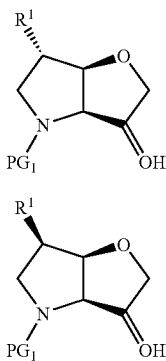
Ig

Ih

Preferably, PG₁ is a urethane protecting group.

More preferably, the urethane protecting group is selected from benzyloxycarbonyl, tert-butoxycarbonyl, fluoren-9-yl-methoxycarbonyl, 1-(biphenyl-4-yl) 1-methylethoxycarbonyl, α,α-dimethyl-3,5-dimethoxybenzyloxycarbonyl, p-methoxybenzyloxycarbonyl, p-nitrobenzyloxycarbonyl, allyloxycarbonyl and trichloroethoxycarbonyl.

Even more preferably, the urethane protecting group is benzyloxycarbonyl (Cbz), tert-butoxycarbonyl (Boc) or fluoren-9-ylmethoxycarbonyl (Fmoc).

In one preferred embodiment of the invention, $R^{48}$ is methyl, tert-butyl or tosyl.

In one preferred embodiment of the invention, $R^1$ is H, $N_3$, $NH_2$, NH-Boc, tert-BuO, MeO, MeS or OTs.

In one highly preferred embodiment of the invention, $R^1$ is H.

In another highly preferred embodiment of the invention, $R^1$ is F or Cl.

The process of the present invention is also suitable for preparing a wide range of 5,5-bicyclic structures wherein $R^2$ is a group of formula U—(V)$_m$—(W)$_n$—(X)$_o$—Y—, i.e. compounds of formula Ii, Ij, Ik and Il or (U)$_p$—(X$_2$)$_s$—(Y$_1$)$_k$—Y$_2$— i.e. compounds of formula Im, In, Io and Ip,

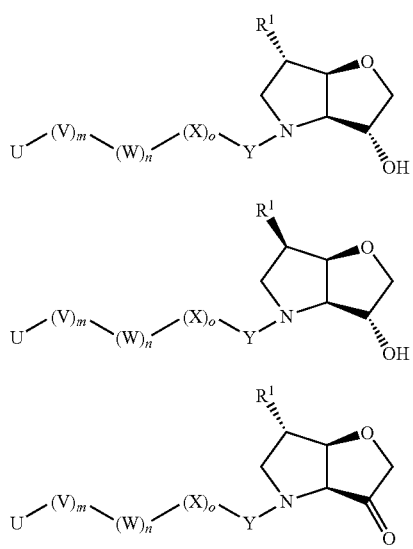

Ii

Ij

Ik

-continued

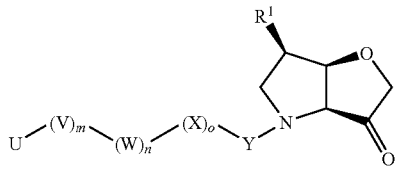
Il

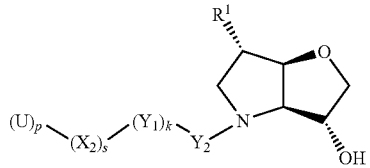
Im

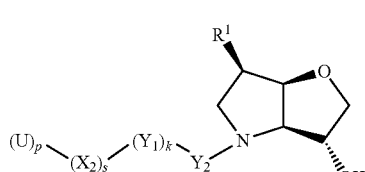
In

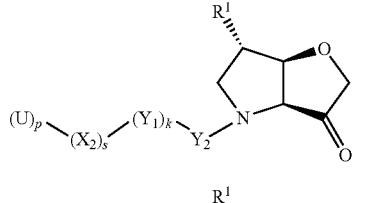
Io

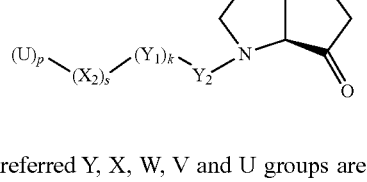
Ip

Preferred Y, X, W, V and U groups are described in WO 02/057270 (Incenta Limited).

For potent inhibition of cathepsin K, preferred Y, X, W, V and U groups are described in co-pending PCT applications [Agent's reference P024640WO], claiming priority from GB0614046.1; [Agent's reference P024641WO], claiming priority from GB0614037.0; [Agent's reference P025198WO], claiming priority from GB0614073.5; [Agent's reference P025199WO], claiming priority from GB0614044.6; [Agent's reference P0025200WO], claiming priority from GB0614052.9; [Agent's reference P025201WO], claiming priority from GB0614042.0; and [Agent's reference P025202WO], claiming priority from GB0614053.7 (Amura Therapeutics Ltd).

Particularly preferred U, X, $Y_1$ and $Y_2$ groups are described in WO 07/023,281 (Amura Therapeutics Limited).

Preferably, Y is CHR⁹CO where $R^9$ is selected from H, $C_{1-7}$-alkyl or Ar—$C_{1-7}$-alkyl, for example hydrogen, a straight or branched alkyl chain, a straight or branched heteroalkyl chain, an optionally substituted arylalkyl chain or an optionally substituted arylheteroalkyl chain. Additionally, $R^9$ may be $C_{3-6}$-cycloalkyl or $C_{3-6}$-cycloalkyl(alkyl), for example cyclopentyl, cyclohexyl or cyclohexylmethyl or cyclohexylmethyl.

In another preferred embodiment, Y is CR⁸R⁹CO where $R^8$ and $R^9$ are linked to the adjacent backbone carbon atom to form a spiro-5 or 6-membered cycloalkyl group;

Examples of preferred $(X)_o$—Y— groups include the following:

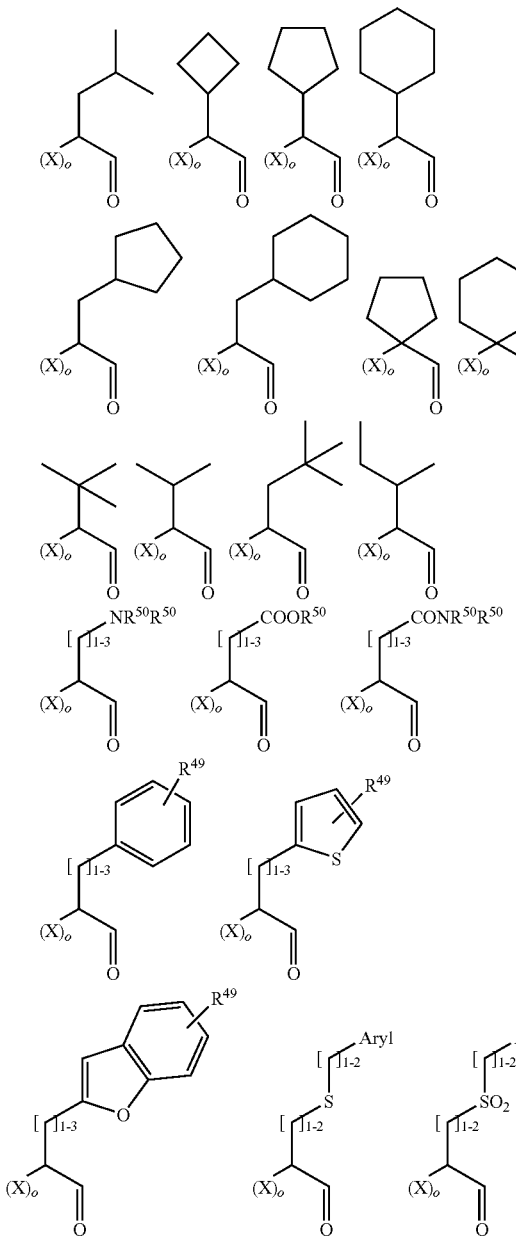

wherein $R^{49}$ is H, alkyl, cycloalkyl, Ar-alkyl, Ar, OH, O-alkyl, O-cycloalkyl, O—Ar-alkyl, OAr, SH, S-alkyl, S-cycloalkyl, S—Ar-alkyl, SAr, SO-alkyl, SO-cycloalkyl, SO—Ar-alkyl, SO—Ar, $SO_2H$, $SO_2$-alkyl, $SO_2$-cycloalkyl, $SO_2$—Ar-alkyl, $SO_2Ar$, NH-alkyl, $NH_2$, NH-cycloalkyl, NH—Ar-alkyl, NHAr, NHCO-alkyl, NHCO-cycloalkyl, NHCO—Ar-alkyl, NHCOAr, N(alkyl)$_2$, N(cycloalkyl), or N(Ar-alkyl)$_2$ or NAr$_2$ or halogen;

$R^{50}$ is selected from H, alkyl, cycloalkyl, Ar and Ar-alkyl and Ar/aryl is as defined above.

More preferred $R^9$ groups include $C_{1-5}$-alkyl, or $C_{4-6}$-cycloalkyl or $C_{3-6}$-cycloalkylmethyl or Ar—$C_{1-4}$-alkyl, where the aryl group may be substituted with $R^{49}$; wherein each $R^{49}$ and $R^{50}$ is independently as defined above.

Even more preferred $R^9$ groups comprise $C_{4-5}$-alkyl, or $C_{5-6}$-cycloalkyl or $C_{5-6}$-cycloalkylmethyl. Additionally even more preferred $R^9$ groups comprise Ar—$CH_2$—, where the aromatic ring is an optionally substituted phenyl, or heteroaryl-$CH_2$—, where the heteroaryl group is monocyclic. Additionally even more preferred $R^9$ groups also comprise heteroalkyl chains such as benzylsulfanylmethyl or benzylsulphonylmethyl. Examples of even more preferred $(X)_o$—Y— substituents include the following,

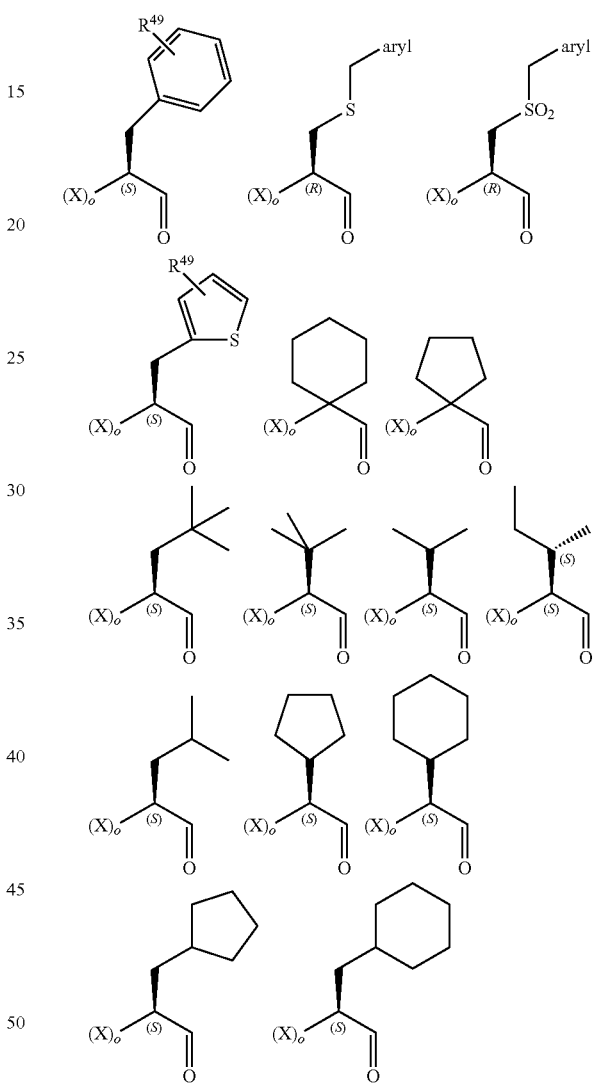

wherein $R^{49}$ and aryl are as defined previously

It is preferred that in the group X, each of $R^{10}$ and $R^{11}$ is selected from H, $C_{1-7}$-alkyl or Ar, Ar—$C_{1-7}$-alkyl, for example hydrogen, a straight or branched alkyl chain, a straight or branched heteroalkyl chain, an optionally substituted arylalkyl chain or an optionally substituted arylheteroalkyl chain.

More preferably, $R^{10}$ is hydrogen and $R^{11}$ is $C_{1-4}$-alkyl, which may be substituted with OH, $NR^{50}R^{50}$, $COOR^{50}$, or $CONR^{50}$; or Ar—$C_{1-4}$-alkyl, where the aryl group may be substituted with $R^{49}$, wherein each $R^{49}$ and $R^{50}$ is independently as defined above.

Examples of preferred $(W)_n$—$(X)_o$—Y— groups include the following:

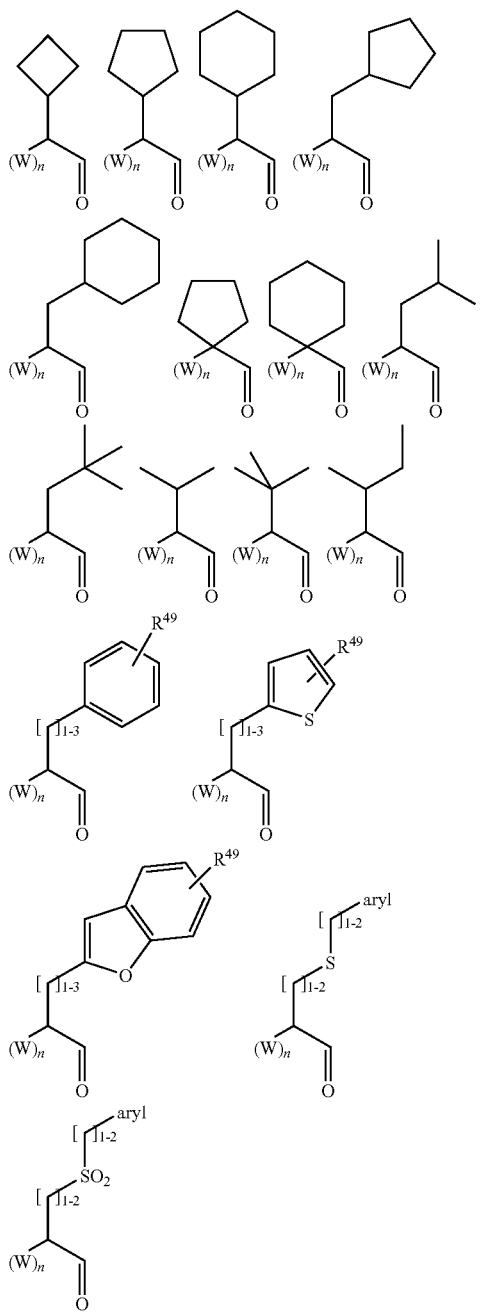

wherein $R^{49}$ and aryl are as defined previously.

Even more preferably, X is a simple alkyl group such as methylene and o is 0 or 1.

In the group $(W)_n$, W is preferably O, S, SO$_2$, S(O), C(O) or NR$^{51}$, where R$^{51}$ is H, C$_{1-4}$-alkyl; and n is 0 or 1.

More preferred $(W)_n$ groups include O, S, SO$_2$, C(O) and NH where n is 0 or 1.

Even more preferred $(W)_n$ groups include NH where n=1.

In the group $(V)_m$, V is preferably C(O), OC(O), NHC(O) or CHR$^{52}$, where R$^{52}$ is H, C$_{1-4}$-alkyl; and m is 0 or 1.

Even more preferred $(V)_m$ groups include C(O) where m=1.

Preferred U—$(V)_m$—$(W)_n$—$(X)_o$— combinations include, but are not limited to:

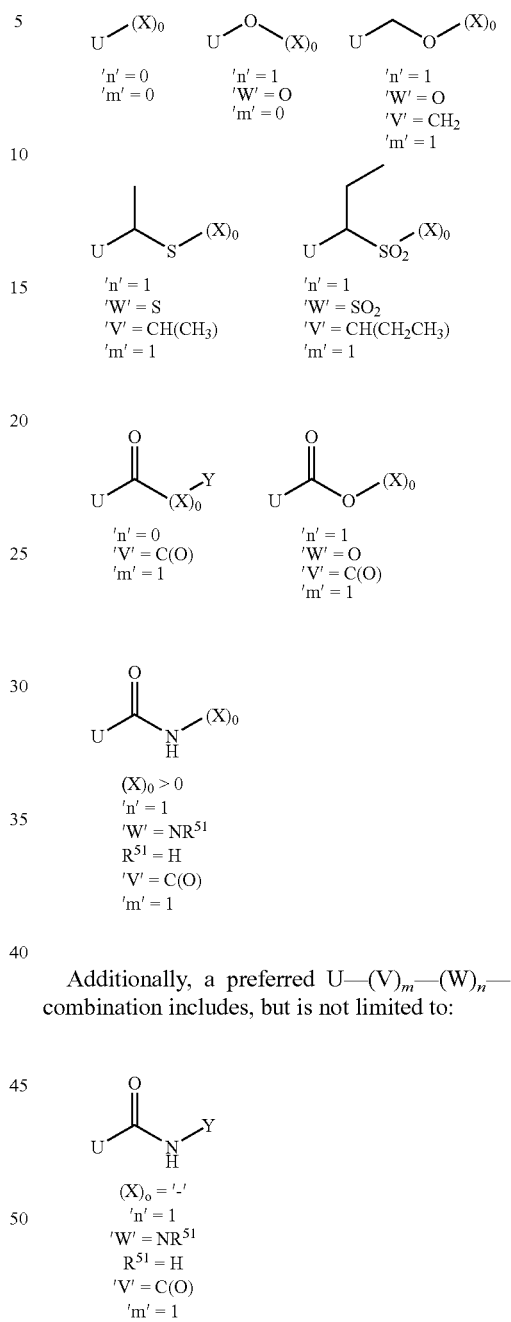

Additionally, a preferred U—$(V)_m$—$(W)_n$—$(X)_o$—Y— combination includes, but is not limited to:

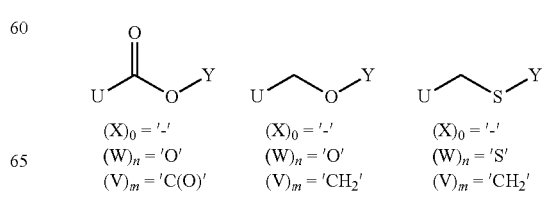

More preferred U—$(V)_m$—$(W)_n$—(X) O—Y combinations include, but are not limited to -continued

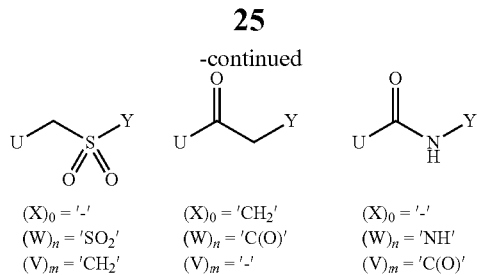

Preferably, U comprises an optionally substituted 5- or 6-membered saturated or unsaturated heterocycle or Ar group or an optionally substituted saturated or unsaturated 9- or 10-membered heterocycle or Ar group. Examples of such preferred U rings include the following:

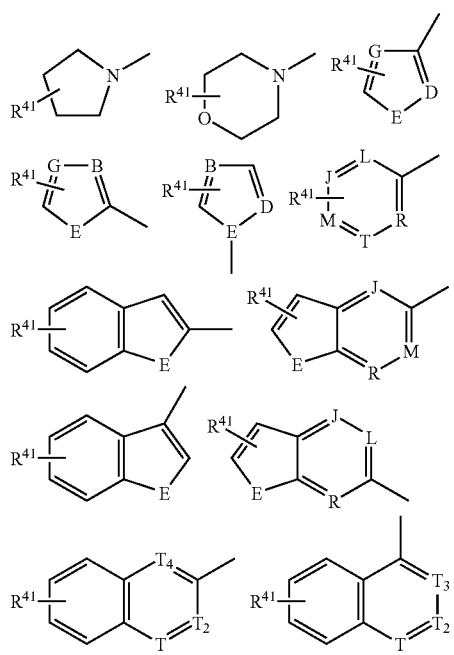

wherein B, D, E, G, J, L, M, R, T, $T_2$, $T_3$, $T_4$ and $R^{41}$ are as defined previously.

More preferably, the U group comprises a branched alkyl or cycloalkyl or alicyclic or aryl group in the para position of an aryl Ar. Also, more preferred compounds contain a meta or para-biaryl Ar—Ar, where Ar is as previously defined. Examples of more preferred U groups are:

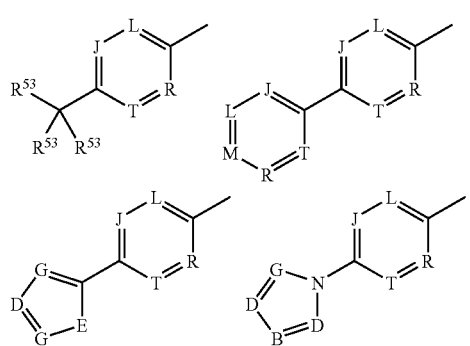

-continued

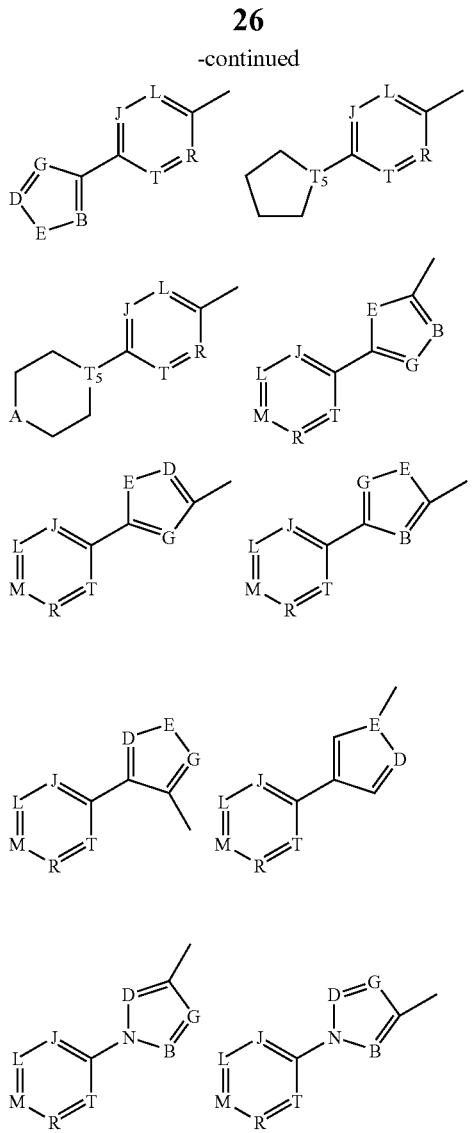

wherein A, B, D, E, G, J, L, M, R, T and $T_5$ are as defined previously and $R^{53}$ is H or $C_{1-4}$-alkyl Even more preferably, the U group comprises a 6-membered Ar ring containing a alicyclic or aryl or heteroaryl group in the para position of the aryl ring. Even more preferably still, the U group is selected from the following:

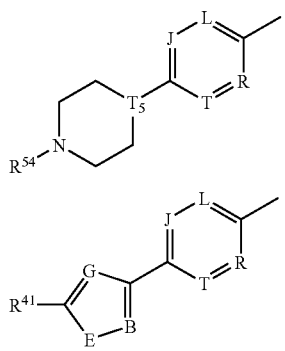

-continued

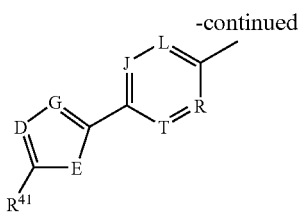

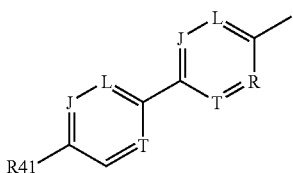

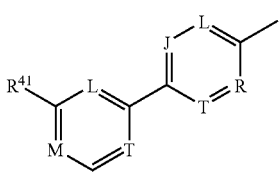

wherein B, D, E, G, J, L, M, R, T and $T_5$ are as defined previously and $R^{54}$ is $C_{1-6}$-alkyl or $C_{3-4}$-cycloalkyl.

Compounds of formulae Ii-Il in which $R^2$ is a group of formula U—$(V)_m$—$(W)_n$—$(X)_o$—Y—, may be prepared from the precursors of formulae Ie-h (wherein $R^2$ is a protecting group $PG_1$). Typically, the protecting group $PG_1$ is removed by conventional means to yield the corresponding free base compound wherein $R^2$ is hydrogen.

Compounds of formula Ii-Il may be prepared (1) by the stepwise addition of P2 and P3 synthons (see later descriptions) representing Y, $(X)_o$, $(W)_n$, $(V)_m$ and U to the bicyclic tetrahydrofuro[3,2-b]pyrrol-3-one core; or (2) by reaction of the bicyclic tetrahydrofuro[3,2-b]pyrrol-3-one core with a U—$(V)_m$—$(W)_n$—$(X)_n$—Y— precursor molecule, (i.e. where the U—$(V)_m$—$(W)_n$—$(X)_o$—Y— group is already constructed); or (3) by introducing the U—$(V)_m$—$(W)_n$—$(X)_o$—Y— group as the $R^2$ substituent prior to formation of the bicyclic tetrahydrofuro[3,2-b]pyrrol-3-one core, i.e. prior to the oxidation step or prior to the intramolecular cyclisation step.

Similarly, compounds of formula Im-Ip may be prepared (1) by the stepwise addition of P2 and P3 synthons (see later descriptions) representing $Y_2$, $(Y_1)_k$, $(X_2)_s$ and $(U)_p$ to the bicyclic tetrahydrofuro[3,2-b]pyrrol-3-one core; or (2) by reaction of the bicyclic tetrahydrofuro[3,2-b]pyrrol-3-one core with a $(U)_p$—$(X_2)_n$—$(Y_1)_k$—$Y_2$— prescursor molecule, (i.e. where the $(U)_p$—$(X_2)_s$—$(Y_1)_k$—$Y_2$—$_p$ group is already constructed); or (3) by introducing the $(U)_p$—$(X_2)_s$—$(Y_1)_k$—$Y_2$— group as the $R^2$ substituent prior to formation of the bicyclic tetrahydrofuro[3,2-b]pyrrol-3-one core, i.e. prior to the oxidation step or prior to the intramolecular cyclisation step.

In one preferred embodiment of the invention, compounds of formula Ik, Il, Io, Ip may be prepared using conventional solid phase chemistry, for example, as described in Quibell M, et al (Bioorg. Med. Chem., 12, 5689-5710, 2004, see in particular, Scheme 3 and Section 3.2, and references cited therein; and Bioorg. Med. Chem., 13, 609-625, 2005, see Scheme 5 and Section 2.2, and references cited therein). The synthetic strategy is based on reversible anchorage of the ketone functionality via a hydrazide linker bond using general multipin techniques previously described in the art (Watts J. et al, Bioorg. Med. Chem. 12(11), 2903, 2004; Quibell M., et al, Bioorg. Med. Chem. 5689-5710, 2004; Grabowksa U. et al, J. Comb. Chem. 2000, 2(5), 475).

In an alternative preferred embodiment of the invention, compounds of formulae Ii-Ip may be prepared using conventional solution phase chemistry, for example, as described in Quibell, M et al, Bioorg. Med. Chem., 13, 609-625, 2005 (see in particular, Schemes 3 and 4).

Compounds of formulae Ig-Ih, $PG_1$, may be utilised in a solid phase synthesis of inhibitor molecules Ic-Id. The solid phase linkage of an aldehyde or ketone, has previously been described by a variety of methods (e.g. see (a) James, I. W., 1999, (b) Lee, A., Huang, L., Ellman, J. A., J. Am. Chem. Soc, 121(43), 9907-9914, 1999, (c) Murphy, A. M., et al, J. Am. Chem. Soc, 114, 3156-3157, 1992). A suitable method amenable to the reversible linkage of an alkyl ketone functionality such as Ih is through a combination of the previously described chemistries. The semicarbazide, 4-[[(hydrazinocarbonyl)amino]methyl]cyclohexane carboxylic acid. trifluoroacetate (Murphy, A. M., et al, J. Am. Chem. Soc, 114, 3156-3157, 1992), may be utilised as illustrated in Scheme 4, exemplified by linkage of the tetrahydrofuro[3,2-b]pyrrol-3-one (Ih; $R^2$=Fmoc).

Scheme 4:

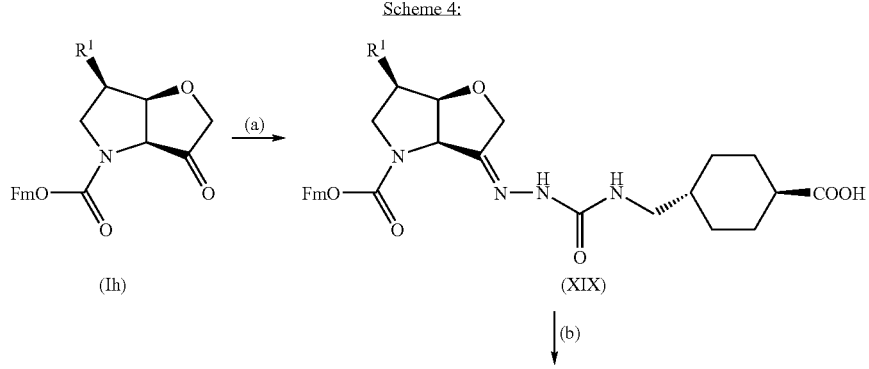

(Ih)          (XIX)

(b)

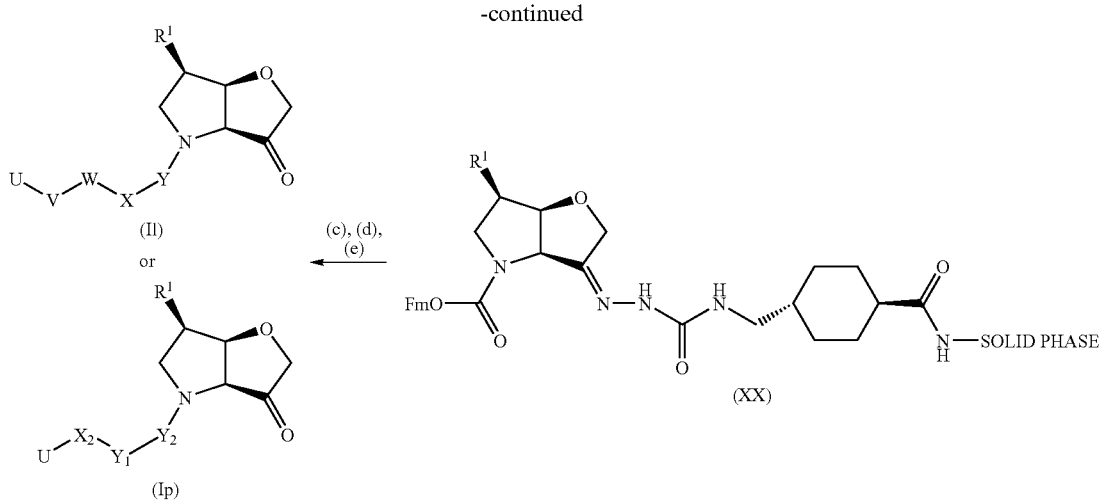

(a) (Ih) in 90% EtOH/H₂O/1.5 eq NaOAc/4-[[(hydrazinocarbonyl)amino]methyl]-cyclohexane carboxylic acid.trifluoroacetate, 2 hr reflux; (b) 3 eq construct XIX/3 eq HBTU/3 eq HOBt/6 eq NMM, NH₂-SOLID PHASE, DMF, RT, o/n; (c) 20% piperdine/DMF, 30 mins; (d) Range of chemistries to introduce U—V—W—X—Y— or U—X₂—Y₁—Y₂—; (e) TFA/H₂O (95:5, v/v), RT, 2 hr. For ease of reference, Scheme 4 refers to U—V—W—X—Y— rather than U—(V)$_m$—(W)$_n$—(X)$_o$—Y—, and U—X₂—Y₁—Y₂— rather than (U)$_p$-(X₂)$_s$—(Y₁)$_k$—Y₂—. These are used interchangeably throughout.

Construct XIX is prepared through reaction of the linker molecule and the tetrahydrofuro[3,2-b]pyrrol-3-one Ih (PG₁=Fmoc) by reflux in aqueous ethanol/sodium acetate. Standard solid phase techniques (e.g. see Atherton, E. and Sheppard, R. C., 1989) are used to anchor the construct to an amino-functionalised solid phase through the free carboxylic acid functionality of XIX, providing the loaded construct XX. Loaded construct XX may be reacted with a wide range of carboxylic acids available commercially or in the literature, to introduce the left-hand portion 'U—V—W—X—Y'. Alternatively introduction of the '(U)$_p$—(X₂)$_s$—(Y₁)$_k$—Y₂' group is through the use of chloroformates (Y₂ is OC(O)—, (U)$_p$—(X₂)$_s$—(Y₁)$_k$—OC(O)Cl), chlorothiolformates (Y₂ is SC(O)—, (U)$_p$—(X₂)$_s$—(Y₁)$_k$—SC(O)Cl), isocyanates (Y₂ is NHC(O)—, (U)$_p$—(X₂)$_s$—(Y₁)$_k$—N=C=O) or carbamoyl chlorides (Y₂ is NR$^{15}$C(O)—, (U)$_p$—(X₂)$_n$—(Y₁)$_k$—NR$^{15}$COCl) as a single step reaction.

Compounds of II and Ip are finally released from the solid phase by treatment with trifluoroacetic acid/water, followed by evaporation, lyophylis and standard analytical characterisation. By analogy compounds of Ik and Io can be prepared by identical methods to those described for Ih but commencing from Ig.

A second strategy for the synthesis of compounds of general formulae Ic-Id comprises:—
(a) preparation of an appropriately functionalised and protected 5,5-bicyclic alcohol building block in solution such as Ie and If (preferred protecting groups for solution phase chemistry are the Nα-tert-butoxycarbonyl group and the Nα-benzyloxycarbonyl group);
(b) standard organic chemistry methods for the conversion of the building block formed in (a) towards compounds of general formulae Ia-Ib
(c) oxidation of compounds of general formulae Ia-Ib towards compounds of general formulae Ic-Id In the simplest example, the entire left hand portion of the inhibitor molecule can be prepared in solution by traditional organic chemistry methods and coupled to building block (a) (see Scheme 5 exemplified by preparation and use of the 6-R¹-3-hydroxy-tetrahydrofuro[3,2-b]pyrrole-4-carboxylic acid tert-butyl ester XXI).

Scheme 5:

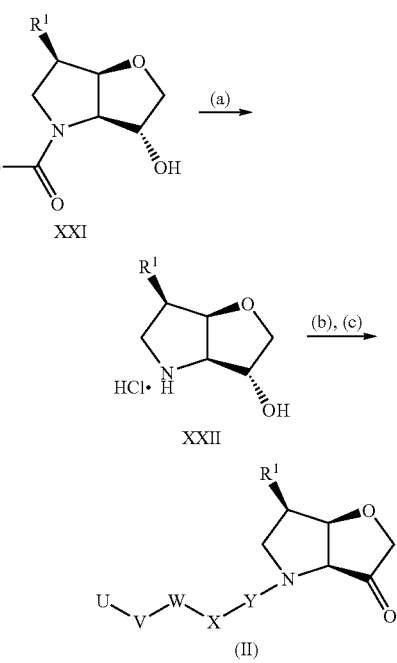

(a) 4M HCl in dioxan, 0° C., 2 hrs. (b) (i) Pre-prepared U—V—W—X—Y—OH /activation e.g. HATU/NMM, DMF, RT, o/n. or (ii) Stepwise construction of U—V—W—X—Y—; (c) Oxidation By analogy, U—X₂—Y₁-Y₂— reagents such as chloroformates, chlorothioformates, isocyanates, carbarnoylchlorides as detailed above could be used in place of the carboxylic acid reagent in Scheme 5. The alcohol oxidation route is particularly useful when the compound of general formulae Ic-Id contains a substituent that is labile to trifluoroacetic acid, this being the final reagent used in the solid phase Scheme 4.

A third strategy for the synthesis of compounds where the addition of U—V—W—X—Y— to the protected building block involves multistep organic reactions comprises:—
(a) Preparation of an appropriately functionalised and protected tetrahydrofuro[3,2-b]pyrrol-3-one building block in solution such as Ig or Ih (preferred protecting groups for this particular solution phase chemistry include the Nα-benzyloxycarbonyl group);
(b) Protection of the ketone functionality of the tetrahydrofuro[3,2-b]pyrrol-3-one, e.g. as the dimethylketal.
(c) Standard organic chemistry methods for the conversion of the building block from step (b) towards compounds of general formulae Ic-Id.

Such a method is detailed and exemplified in Scheme 6 by the preparation and use of 6-$R^1$—3,3-dimethoxyhexahydrofuro[3,2-b]pyrrole-4-carboxylic acid benzyl ester XXIV.

Preferably, said compound of formula IVb is prepared from a compound of formula IIIb

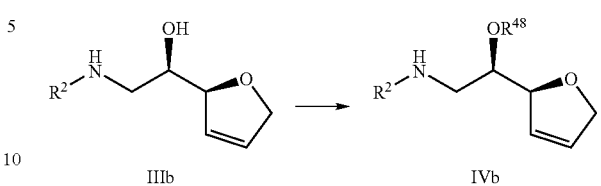

IIIb      IVb

In one preferred embodiment, $R^{48}$ is Me. For this embodiment, preferably the process comprises treating a compound Scheme 6:

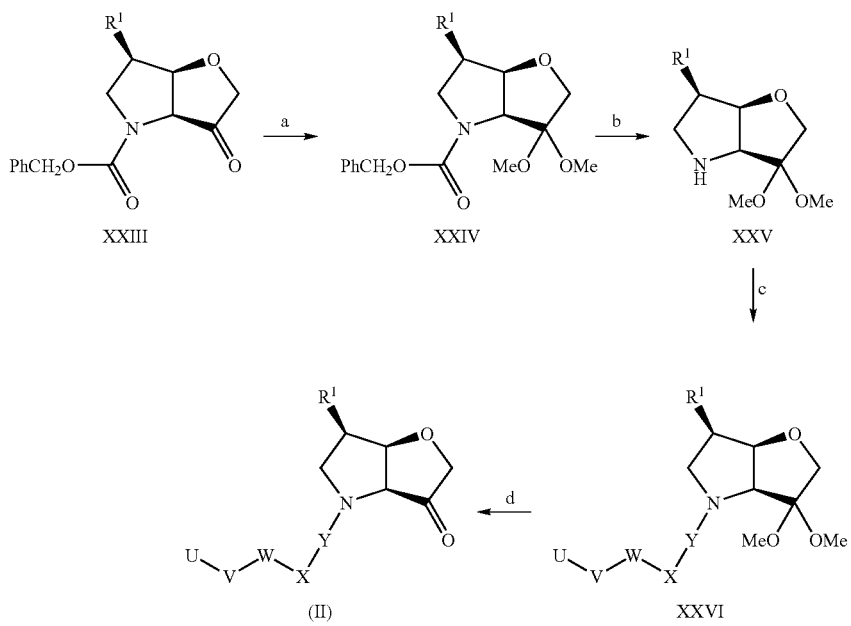

(a) Triethylorthoformate/pTSA/MeOH. (b) $H_2$, Pd-C. (c) (i) Pre-prepared U-V-W-X-Y-OH/activation e.g. HATU/HOAt/NMM, DMF, RT, o/n. or (ii) Stepwise construction of U-V-W-X-Y-;-(d) Trifluoroacetic acid/$CH_2Cl_2/H_2O$.

By analogy, U—$X_2$—$Y_1$-$Y_2$— reagents such as chloroformates, chlorothioformates, isocyanates, carbamoylchlorides as detailed earlier could be used in place of the carboxylic acid reagent in Scheme 6.

Synthesis of Compounds of Formula IIIa and IIIb

In one particularly preferred embodiment, said compound of formula IVa is prepared from a compound of formula IIIa

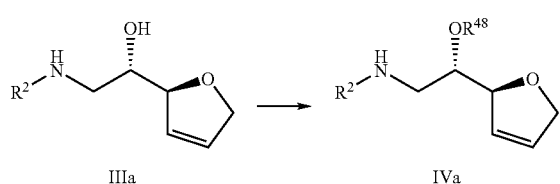

IIIa      IVa of formula IIIa or IIIb with MeI in the presence of a silver (I) oxide catalyst. Preferably, the reaction is carried out using acetonitrile as solvent.

In an even more preferred embodiment, $R^{48}$ is Me and the process comprises treating a compound of formula IIIa or IIIb with trimethyloxonium fluoroborate, proton sponge[1,8-bis(dimethylamino)naphthalene] and molecular sieves in dichloromethane.

In another preferred embodiment, $R^{48}$ is tert-Bu. For this embodiment, preferably the process comprises treating a compound of formula IIIa or IIIb with gaseous 2-methylpropene in dichloromethane in the presence of concentrated $H_2SO_4$.

In another preferred embodiment, $R^{48}$ is tosyl. For this embodiment, preferably the process comprises treating a compound of formula IIIa or IIIb with tosyl chloride in pyridine.

In one preferred embodiment of the invention, said compound of formula IIIa is prepared by the steps of:

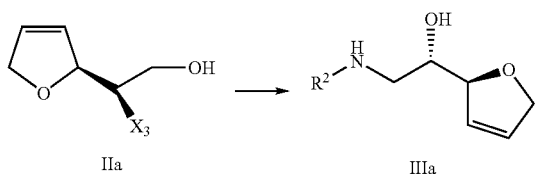

IIa    IIIa (a) reacting a compound of formula IIa, where $X_3$ is halogen or OTs, with aqueous ammonia and alcohol, or with aqueous ammonium hydroxide; and (b) converting the product formed in step (a) to a compound of formula IIIa;

In one preferred embodiment of the invention, said compound of formula IIIb is prepared by the steps of:

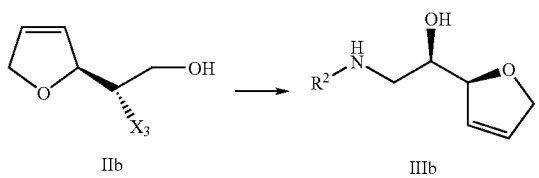

IIb    IIIb (a) reacting a compound of formula IIb, where $X_3$ is halogen or OTs, with aqueous ammonia and alcohol, or with aqueous ammonium hydroxide; and (b) converting the product formed in step (a) to a compound of formula IIIb.

Preferably, the above process is a one-pot process, i.e. the product of step (a) is not isolated or purified from the reaction mixture.

In one particularly preferred embodiment, $R^2$ is benzyloxycarbonyl, and step (b) comprises treating the mixture formed in step (a) with benzyloxycarbonyl chloride.

Preferably, $X_3$ is I, Br or OTs.

Preferably, the alcohol is isopropyl alcohol or ethanol.

In one preferred embodiment of the invention, said compound of formula IIa is prepared from a compound of formula XVIIIa

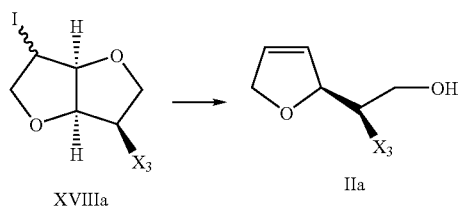

XVIIIa    IIa

Preferably, the above process comprises treating said compound of formula XVIIIa with methyl lithium.

In one highly preferred embodiment of the invention, said compound of formula IIa is compound (13), i.e. $X_3$ is OTs, and compound (13) is prepared from compound (38)

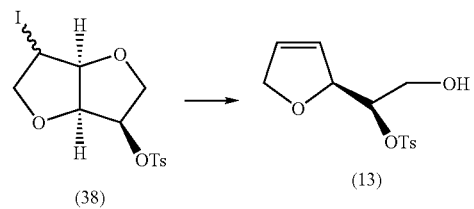

(38)    (13)

Preferably, the above process comprises treating compound (38) with methyl lithium.

More preferably, compound (38) is prepared from compound (39);

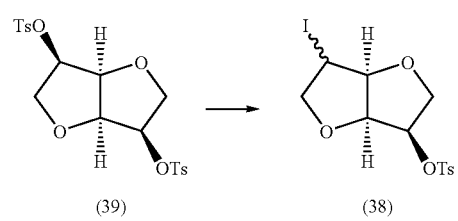

(39)    (38)

Preferably, the above process comprises treating compound (39) with sodium iodide in DMF.

Preferably, compound (39) is prepared from compound (40);

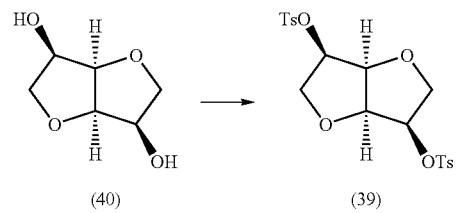

(40)    (39)

Preferably, the above process comprises treating compound (40) with tosyl chloride in pyridine.

In one preferred embodiment of the invention, said compound of formula IIb is prepared from a compound of formula XVIIIb

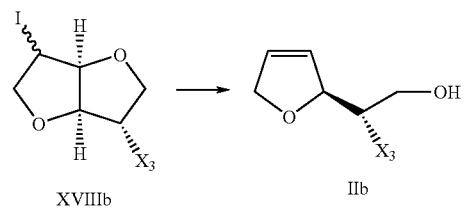

XVIIIb    IIb

In one highly preferred embodiment of the invention, said compound of formula IIb is compound (14), i.e. $X_3$ is OTs, and compound (14) is prepared from compound (41)

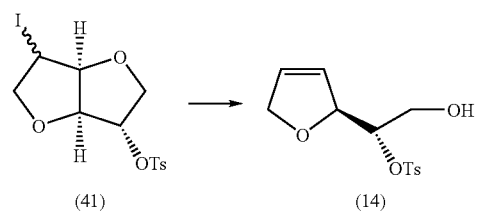

(41)    (14)

Preferably, the above process comprises treating said compound (41) with methyl lithium.

More preferably, compound (41) is prepared from compound (42);

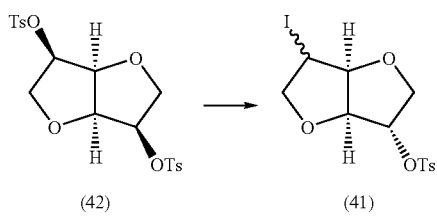

Preferably, the above process comprises treating compound (42) with sodium iodide in DMF.

More preferably, compound (42) is prepared from compound (43)

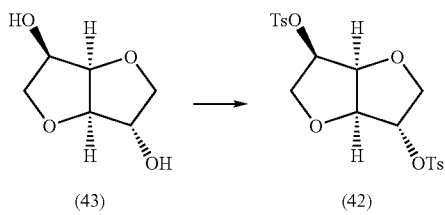

Preferably, the above process comprises treating compound (43) with tosyl chloride in pyridine.

Still commencing from the commercially available sugars isomannide and isosorbide, the present invention also provides alternative preparations of alcohols (13) and (14). One highly preferred preparation is shown below in Scheme 15 yield. Mono-bromination is effected by 2.5 eq lithium bromide in DMSO (or DMF) with temperature control 110° C.→120° C. The product bromide is isolated following extractive work-up and purification either by column chromatography (74%) or attractive for large scale by recrystallisation from methanol giving a first crop of 55% plus mother liquors containing good quality material that may be pooled from batch runs and purified later. This is a particularly attractive, simple and scalable route to monobromotosylate (47) with defined stereochemistry. Reaction (c) Scheme 15 then forms a new method for opening the sugar intermediate towards dihydrofurans. Paolucci describes treatment of halo-analogues (halo-tosylate, di-bromide, di-iodide) with alkyl lithium reagents. When considering the iodo analogues (either iodidotosylate or di-iodide) yields with methyl lithium are high. However, preparation of mono-iodotosylate or di-iodide through iodination of the di-tosylate can lead to mixed products and in practice the desired mono-iodotosylate or di-iodide are purified out by chromatography prior to alkyl lithium treatment otherwise mixtures of alcohols (11-14) are subsequently produced. Thus, preparation of monobromotosylate (47) with defined stereochemistry by methods in Scheme 15 is attractive for large scale applications. However, treatment of monobromotosylate under Paolucci conditions with either methyl lithium/lithium iodide complex or methyl lithium or butyl lithium at −70° C. gave alcohol (14) in 20, 38 and 27% isolated yield respectively. Alternatively, treatment of monobromotosylate with butyl lithium and completion of the one-pot conversion gave alcohol (18) in 22% yield. Although probably scalable, these conditions would need significant improvement for large scale preparations.

We have now discovered that simple treatment of monobromotosylate (47) with zinc dust at room temperature in organic/aqueous mixtures (most preferably an isopropanol, tetrahydrofuran, water, ammonium chloride mixture) provided alcohol (14) in 80% isolated yield. Additionally, Scheme 15:

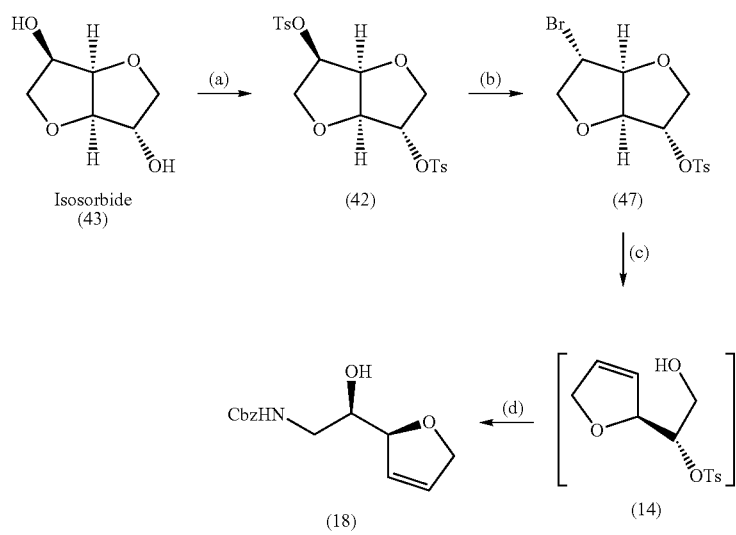

(a) TsCl, triethylamine, DCM, 25° C. → 50° C., 20h under Ar; (b) LiBr, DMSO, 110° C. → 120° C., 10 h under Ar; (c) Zn, $^i$PrOH, THF, H$_2$O, NH$_4$Cl, RT, 16 h; (d) (i) NH$_4$OH, NH$_3$ in $^i$PrOH, 75° C., 16 h (ii) Cbz-Cl, Na$_2$CO$_3$, dioxane, water.

Isosorbide (43) is converted to the di-tosylate (42) which is obtained following recrystallisation from methanol in 97% completion of the one-pot conversion gave alcohol (18) in 58% yield from starting monobromotosylate.

Scheme 16:

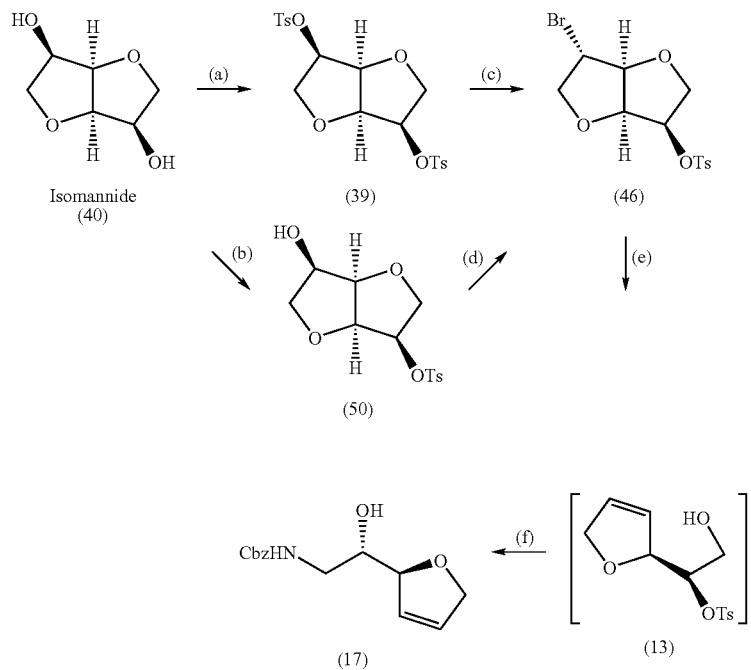

(a) 2.2eq TsCl, KOH(aq), DCM, CCl4, 0° C., 24 h under Ar; (b) (i) 0.5eq TsCl, KOH(aq), DCM, CCl4, 0° C., 7 h under Ar or (ii) 1.0eq TsCl, pyridine, 0° C. → RT, 1 h; (c) LiBr, DMF, 100° C., 27 h (d) CBr4, Ph3P, pyridine, 65° C., 2 h under Ar; (e) Zn, PrOH, THF, H2O NH4Cl, RT, 16 h; (f) (i) NH4OH, NH3 in iPrOH, 75°C., 16 h; (ii) Cbz-Cl, Na2CO3, dioxane, water.

Treatment of isomannide (40) (Scheme 16) with tosylchloride (2.2 eq) in a bi-phasic potassium hydroxide/dichloromethane/carbon tetrachloride mixture at 0° C. gives ditosylate (39) in 48% yield following simple filtration and trituration with methanol. Alternatively, treatment of isomannide (40) with tosylchloride (0.5 eq) in a bi-phasic potassium hydroxide/dichloromethane/carbon tetrachloride mixture at 0° C. gives monotosylate in 38% yield following simple extraction and re-crystallisation from carbon tetrachloride (conditions as described in U.S. Pat. No. 6,858,632). Although the monotosylate can be obtained in higher yield by treatment of isomannide (40) with tosylchloride in pyridine, purification currently requires column chromatography which may becomes undesirable at large scale. Monobromotosylate (46) may then be prepared by treatment of ditosylate (39) with lithium bromide in DMF (29% yield following chromatography) or by treatment of monotosylate under Mitsunobu conditions with carbon tetrabromide (63% yield following chromatography). Finally, application of our new conditions with simple treatment of monobromotosylate (46) with zinc dust at room temperature in organic/aqueous mixtures (most preferably an isopropanol, tetrahydrofuran, water, ammonium chloride mixture) provided alcohol (13) in 75% isolated yield. Similar treatment of the monoiodotosylate with zinc dust also provides alcohol (13) in high yield. Additionally, completion of the one-pot conversion gave alcohol (17) in 53% yield from starting monobromotosylate (46).

One embodiment of the invention relates to a process for preparing a compound of formula (13) from a compound of formula (46)

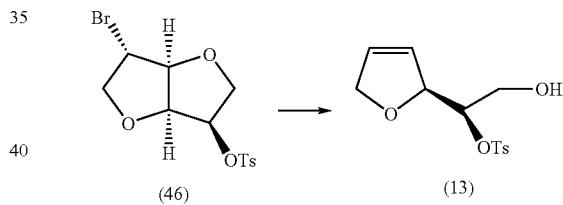

Preferably, compound (46) is treated with zinc dust at room temperature in an organic/aqueous mixture. More preferably, the organic/aqueous mixture is a mixture of isopropanol, tetrahydrofuran, water and ammonium chloride.

More preferably, compound (46) is prepared from compound (39)

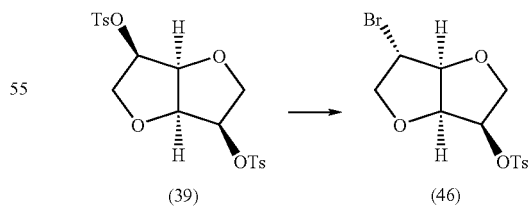

Preferably, the above process comprises monobromination of compound (39) with lithium bromide. Preferably, the solvent is DMSO or DMF.

Preferably, compound (39) is prepared from compound (40), isomannide. Preferably, the above process comprises treating compound (40) with tosyl chloride in pyridine.

Another embodiment of the invention relates to a process of preparing a compound of formula (14) from a compound of formula (47)

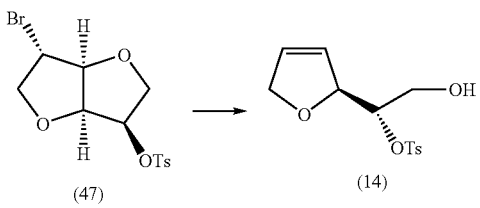

Preferably, said compound (47) is treated with zinc dust at room temperature in an organic/aqueous mixture. More preferably, the organic/aqueous mixture is a mixture of isopropanol, tetrahydrofuran, water and ammonium chloride.

More preferably, compound (47) is prepared from compound (42)

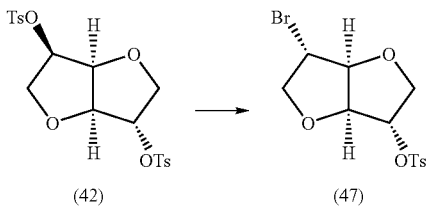

Preferably, the above process comprises treating said compound (42) with lithium bromide. Preferably, the solvent is DMSO or DMF.

More preferably, compound (42) is prepared from compound (43), isosorbide. Preferably, the above process comprises treating compound (43) with tosyl chloride in dichloromethane with triethylamine.

Step A(ii)/B(ii)

In one particularly preferred embodiment,

Step (A) (ii) comprises the step of converting a compound of formula Va into a compound of formula VIa, and converting said compound of formula VIa, wherein $R^{48}$ is alkyl, to a compound of formula Ia or Ic, or wherein $R^{48}$ is tosyl or mesyl, to a compound of formula Ia, Ib, Ic or Id; and Step (B) (ii) comprises the step of converting a compound of formula Vb into a compound of formula VIb, and converting said compound of formula VIb, wherein $R^{48}$ is alkyl, to a compound of formula Ib or Id, or wherein $R^{48}$ is tosyl or mesyl, to a compound of formula Ia, Ib, Ic or Id;.

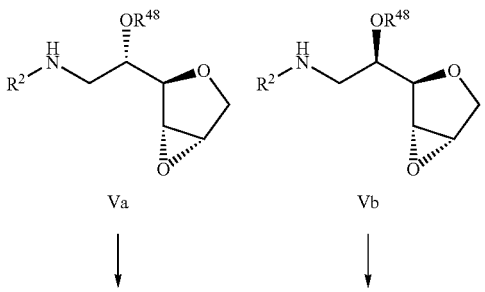

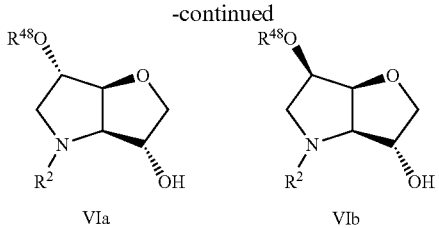

More preferably, the process comprises treating a compound of formula Va or Vb with sodium hydride. Preferably, the reaction is carried out in THF.

In an alternative preferred embodiment of the invention, $R^2$ is a protecting group $PG_1$, and intramolecular cyclisation of compound Va or Vb is induced by removal of the protecting group $PG_1$. Preferably, for this embodiment, $R^2$ is benzyloxycarbonyl (Cbz), and the process comprises hydrogenating a compound of formula Va or Vb in the presence of a palladium catalyst.

In another preferred embodiment,

Step (A) (ii) further comprises the step of converting a compound of formula VIa into a compound of formula VIIIa, and optionally converting said compound of formula VIIa into a compound of formula Ic; and Step (B) (ii) further comprises the step of converting a compound of formula VIb into a compound of formula VIIb, and optionally converting said compound of formula VIIb into a compound of formula Id;

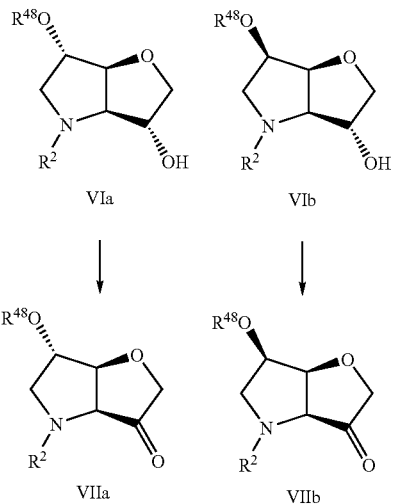

Any suitable oxidising agent may be used to convert the secondary alcohol group of VIa or VIb into the corresponding ketone. Suitable oxidising agents will be familiar to the skilled artisan. By way of example, the oxidation may be carried out via a Dess-Martin periodinane reaction [Dess, D. B. et al, J. Org. Chem. 1983, 48, 4155; Dess, D. B. et al, J. Am. Chem. Soc. 1991, 113, 7277], or via a Swem oxidation [Mancuso, A. J. et al, J. Org. Chem. 1978, 43, 2480]. Alternatively, the oxidation can be carried out using $SO_3$/pyridine/$Et_3N$/DMSO [Parith, J. R. et al., J. Am. Chem. Soc. 1967, 5505; U.S. Pat. No. 3,444,216, Parith, J. R. et al.], $P_2O_5$/DMSO or $P_2O_5$/$Ac_2O$ [Christensen, S. M. et al, Organic Process Research and Development, 2004, 8, 777]. Other alternative oxidation reagents include activated dimethyl sulphoxide [Mancuso, A. J., Swern, D. J., Synthesis, 1981, 165], pyridinium chlorochromate [Pianeatelli, G. et al, Sythesis, 1982, 245] and Jones' reagent [Vogel, A, I., Textbook of Organic Chemistry, 6$^{th}$ Edition]. More preferably, the process comprises treating a compound of formula VIa or VIb with Dess Martin periodinane. Preferably, the reaction is carried out using dichloromethane as solvent.

In one highly preferred embodiment, R$^2$ is benzyloxycarbonyl (Cbz) and:

Step (A) (ii) comprises the steps of:
  converting a compound of formula VIIIa into a compound of formula IXa;
  optionally converting said compound of formula IXa into a compound of formula Xa; and
  optionally converting said compound of formula Xa wherein R$^{48}$ is alkyl into a compound of formula Ic or wherein R$^{48}$ is tosyl or mesyl to a compound of formula Ic or Id;

Step (B) (ii) comprises the steps of:
  converting a compound of formula VIIIb into a compound of formula IXb;
  optionally converting said compound of formula IXb into a compound of formula Xb; and
  optionally converting said compound of formula Xb, wherein R$^{48}$ is alkyl into a compound of formula Id, or wherein R$^{48}$ is tosyl or mesyl, to a compound of formula Ic or Id;

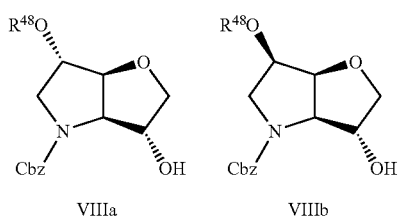

VIIIa     VIIIb

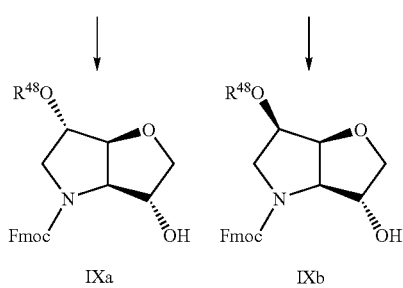

IXa     IXb

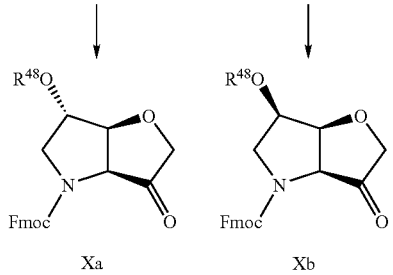

Xa     Xb

More preferably, the process comprises hydrogenating a compound of formula VIIIa or VII b in the presence of a palladium catalyst, and reacting the intermediate so produced with Fmoc-Cl.

In one particularly preferred embodiment of the invention, R$^{48}$ is tosyl, i.e. said compound of formula VIIIa is of the subformula XIa (and said compound of formula VIIIb is of the subformula XIb). For this embodiment, preferably, Step (A) (ii) comprises the step of converting a compound of formula XIa to a compound of XIIa; and
Step (B) (ii) comprises the step of converting a compound of formula XIb to a compound of XIIb

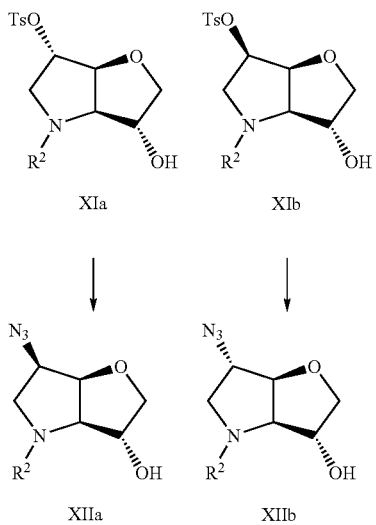

For this embodiment, even more preferably the process comprises treating a compound of formula XIa or XIb with sodium azide in DMF.

In an even more preferred embodiment,
Step (A) (ii) further comprises the step of converting a compound of formula XIIa to a compound of XIIIa; and
Step (B) (ii) further comprises the step of converting a compound of formula XIIb to a compound of XIIIb

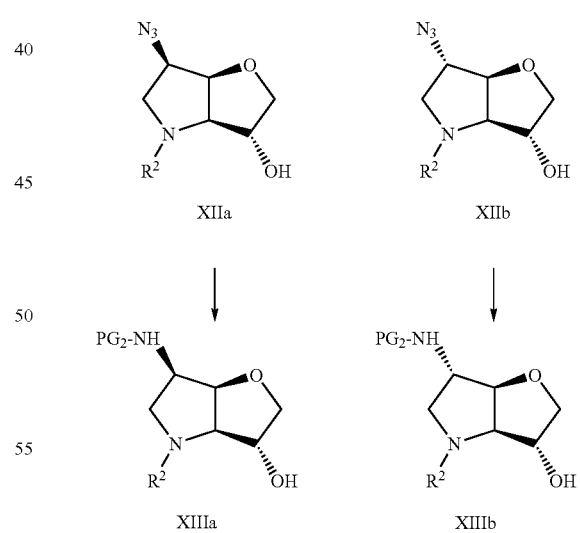

Preferably, for this embodiment, the process comprises treating a compound of formula XIIa or XIIb with (a) triphenylphosphine; and (b) protecting the intermediate formed in step (a) with a protecting group, PG$_2$.

More preferably still, PG$_2$ is tert-butoxycarbonyl (Boc), and the process comprises reacting the product formed in step (a) with tert-butylcarbonate and Na$_2$CO$_3$ in a dioxan/water mixture.

In an even more preferred embodiment of the invention,

Step (A) (ii) comprises the additional step of converting a compound of formula XIIIa to a compound of XIVa; and Step (B) (ii) comprises the additional step of converting a compound of formula XIIIb to a compound of XIVb

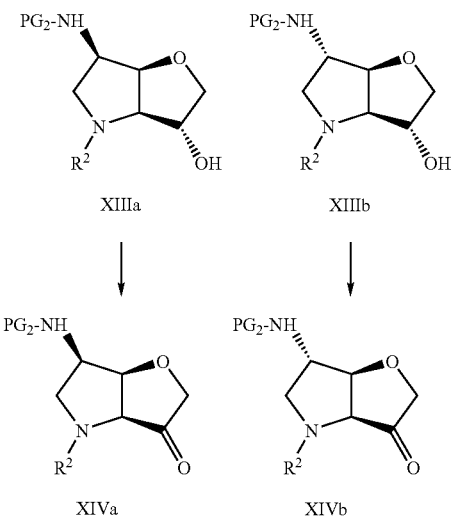

XIIIa    XIIIb

XIVa    XIVb

More preferably still, $R^2$ is benzyloxycarbonyl (Cbz) and $PG_2$ is tert-butoxycarbonyl (Boc), or following standard hydrogenation of subformulae XIII to remove Cbz and treatment with Fmoc-Cl, $R^2$ is converted to fluoren-9-ylmethoxycarbonyl (Fmoc).

As before, any suitable oxidising agent can be used to convert the secondary alcohol group to the corresponding ketone (as described above).

Even more preferably, the process comprises treating a compound of formula XIIIa or XIIIb with Dess Martin periodinane in dichloromethane.

In an alternative preferred embodiment, the process of the invention allows for the preparation of 6-unsubstituted 5,5-bicyclic species (see for example, compounds of formula XV and XVI below).

For this embodiment, preferably,

Step (A) (i) comprises the step of converting a compound of formula XIa to a compound of XV; and Step (B) (i) comprises the step of converting a compound of formula XIb to a compound of XV

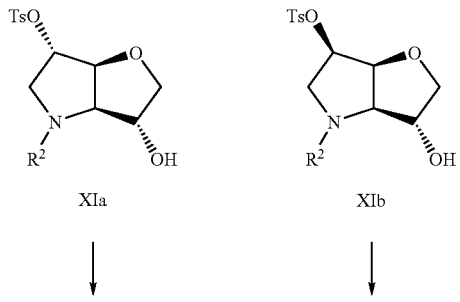

XIa    XIb

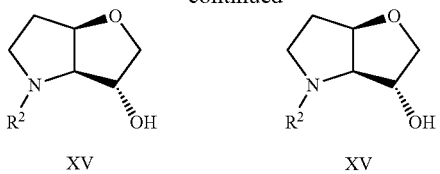

XV    XV

Preferably, this embodiment involves the step of treating a compound of formula XIa or formula XIb with lithium triethylborohydride; wherein $R^2$ is chosen from $PG_1$ or hydrogen.

More preferably, this embodiment involves the step of treating a compound of formula XIb with lithium triethylborohydride wherein $R^2$ is chosen from $PG_1$ or hydrogen.

In one particularly preferred embodiment, the process of the invention involves the step of treating a compound of formula XIb with lithium aluminium hydride wherein $R^2$ is preferably chosen as hydrogen.

In one highly preferred embodiment,

Step (A) (ii) comprises the step of converting a compound of formula XV to a compound of XVI

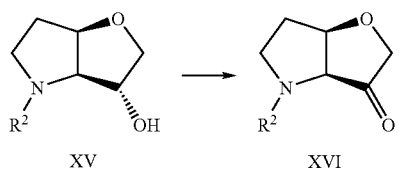

XV    XVI

As before, any suitable oxidising agent can be used to convert the secondary alcohol group to the corresponding ketone (as described above).

In one highly preferred embodiment for the reduction reaction, $R^2$ is tert-butoxycarbonyl (Boc).

In another highly preferred embodiment for the reduction reaction, $R^2$ is hydrogen.

In a further highly preferred embodiment for the oxidation reaction, $R^2$ is fluoren-9-ylmethoxycarbonyl (Fmoc). Preferably, the process comprises treating a compound of formula XV with Dess Martin periodinane in dichloromethane.

Synthesis of Cysteinyl Proteinase Inhibitors

The processes of the invention involve a variety of synthetic methods through solution chemistry, solid phase chemistry or a combination of techniques.

In one preferred embodiment of the invention, for compounds of formula Ic and Id, $R^2$ is a group of formula $U—(V)_m—(W)_n—(X)_o—Y—$. These compounds may be conveniently considered as a combination of three building blocks (P1, P2 and P3) that respectively occupy the S1, S2 and S3 binding sites of the protease (see Berger, A. and Schechter, I., *Philos. Trans. R. Soc. Lond [Biol.]*, 257, 249-264, 1970 for a description of the designation of enzyme S-subsites and substrate P-subsites within enzyme-substrate or enzyme-inhibitor complexes). The notional concepts of P1, P2 and P3 are used herein for convenience only and the above-mentioned compounds are intended to be within the scope of the invention regardless of binding mode.

By way of illustration, a preferred example of a compound in which $R^2$ is $U—(V)_m—(W)_n—(X)_o—Y—$ is shown below. In essence, the P1 building block represents the substituted 5,5-bicyclic portion of general formulae Ic and Id, whilst the P2 building block represents the central amino acid portion and the P3 building block represents the substituted aroyl or heteroaroyl portion as depicted below.

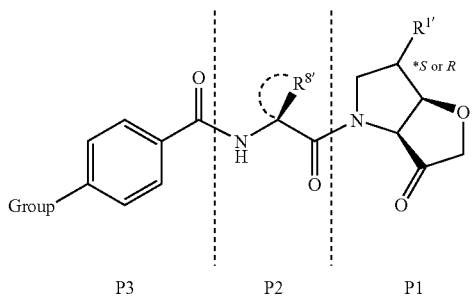

A suitably protected and/or activated building block may then be prepared and subsequently chemically bonded (coupled) together with other building blocks to provide compounds of the above general formulae. Alternative orders of coupling of the building blocks are possible, for example P2+P1→P2-P1 then addition of P3→P3-P2-P1 or P3+P2→P3-P2 then addition to P1→P3-P2-P1. Within each of these combinations each of the P1, P2 or P3 building blocks may contain additional alternative functionalities that are further transformed following coupling to give the final compound. For example the ketone functionality of the P1 building block may be protected as a ketal during coupling of building blocks and transformed to the final ketone by hydrolysis following completion of the coupling reactions. Alternatively, the ketone functionality of the P1 building block may be initially introduced via a lower oxidation state such as the corresponding alcohol and following completion of the coupling reactions be re-introduced by oxidation of the alcohol. Alternatively, the ketone functionality of the P1 building block may be protected through a semi-carbazone suitable for solid phase synthesis (e.g. see WO 02/057270 and references cited therein) and following completion of the coupling reactions released from the solid phase by acidolytic reaction.

The chemical bond formed by coupling of the building blocks is a secondary amide (P3-P2) or a tertiary amide (P2-P1) that is formed through reaction of an activated carboxylic acid with a primary and secondary amine respectively. Many methods are available for activation of a carboxylic acid prior to coupling to an amine and in principle, any of these methods may be used herein. Typical carboxylic acid activation methods are exemplified but not restricted to the azide method, mixed anhydride method (e.g. via isobutylchloroformate), carbodiimide methods (e.g. via dicyclohexylcarbodiimide, diisopropylcarbodiimide, 1-ethyl-3-(3'-dimethylamino propyl)carbodiimide), active ester method (e.g. via p-nitrophenyl ester, N-hydroxysuccinic imido ester, pentafluorophenyl ester), uronium method (e.g. via addition of HBTU, PyBop, BOP), carbonyldiimidazole method or via pre-formation of acyl fluorides or acyl chlorides. In some instances the coupling reaction may be enhanced by the addition of a further activation catalyst such as 1-hydroxybenzotriazole, or 4-dimethylaminopyridine. A general description of carboxylic acid activation techniques and the use of activation additives may be found in Bodanszky, M. 'Principles of Peptide Synthesis', $2^{nd}$ rev. ed., Springer-Verlag, Berlin, 1993 and references cited therein.

The α-amino group of the P2 aminoacid building block is usually protected during coupling reactions to the P1 building block to avoid the formation of undesired self-condensation products. The art of α-amino protection is well known in peptide chemistry (e.g. see Bodanszky, M. 'Principles of Peptide Synthesis', $2^{nd}$ rev. ed., Springer-Verlag, Berlin, 1993 and references cited therein) and example protection groups include, but are not limited to, 9-fluorenylmethoxycarbonyl (Fmoc), tert-butoxycarbonyl (Boc), benzyloxycarbonyl (Cbz), allyloxycarbonyl (Alloc) and trichloroethoxycarbonyl (Treoc). The Fmoc group is particularly well suited for solid phase syntheses (e.g. see Atherton, E.; Sheppard, R. C. in 'Solid Phase Peptide Synthesis A Practical Approach', IRL Press, Oxford, U.K., 1989) typically being removed by treatment with 20% v/v piperidine in dimethylformamide or 1% v/v 1,8-diazabicyclo[5.4.0]undec-7-ene in dimethylformamide. The Boc group is particularly well suited to solution phase syntheses typically being removed by treatment with trifluoroacetic acid based mixtures or HCl in dioxane or ethyl acetate. The Cbz group is also particularly well suited for solution phase syntheses typically being removed by catalytic hydrogenation with hydrogen and palladium catalysis or by treatment with HBr in acetic acid. Once the coupling sequence is complete, any protecting groups are removed in whatever manner is dictated by the choice of protecting groups (for a general description of protecting groups and their respective stabilities and methods of removal see Greene, T. W. and Wuts, P. G. M. 'Protective Groups in Organic Synthesis' John Wiley and Sons, New York, 1991 and references therein).

Typically the first stage in the synthesis is the preparation in solution of a functionalized and appropriately protected P1 building block. Preferred P1 building blocks include but are not limited to general formulae (1a-8a) below;

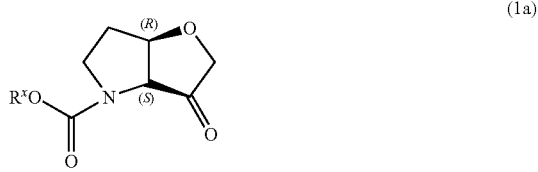

(1a)

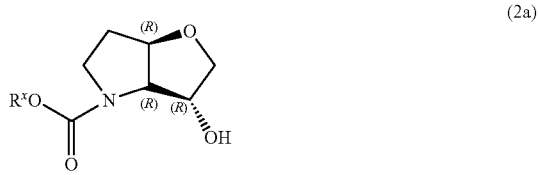

(2a)

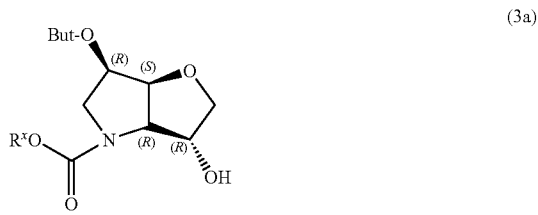

(3a)

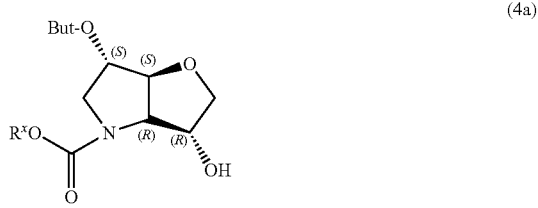

(4a)

(5a) 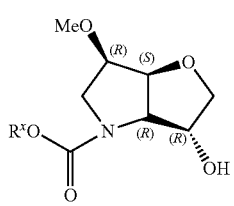

(6a) 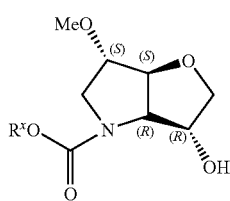

(7a) 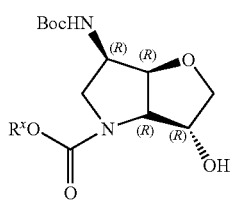

(8a) 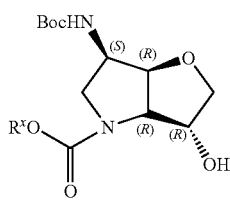

(1a) (3aS,6aR)-alkyl 3-oxotetrahydro-2H-furo[3,2-b]pyrrole-4(5H)-carboxylate
(2a) (3R,3aR,6aR)-alkyl 3-hydroxytetrahydro-2H-furo[3,2-b]pyrrole-4(5H)-carboxylate;
(3a) (3R,3aR,6R,6aS)-alkyl 6-tert-butoxy-3-hydroxytetrahydro-2H-furo[3,2-b]pyrrole-4(5H)-carboxylate;
(4a) (3R,3aR,6S,6aS)-alkyl 6-tert-butoxy-3-hydroxytetrahydro-2H-furo[3,2-b]pyrrole-4(5H)-carboxylate;
(5a) (3R,3aR,6R,6aS)-alkyl 3-hydroxy-6-methoxytetrahydro-2H-furo[3,2-b]pyrrole-4(5H)-carboxylate;
(6a) (3R,3aR,6S,6aS)-alkyl 3-hydroxy-6-methoxytetrahydro-2H-furo[3,2-b]pyrrole-4(5H)-carboxylate;
(7a) (3R,3aR,6S,6aR)-alkyl 6-(tert-butoxycarbonylamino)-3-hydroxytetrahydro-2H-furo[3,2-b]pyrrole-4(5H)-carboxylate;
(8a) (3R,3aR,6S,6aR)-alkyl 6-(tert-butoxycarbonylamino)-3-hydroxytetrahydro-2H-furo[3,2-b]pyrrole-4(5H)-carboxylate.

Within these P1 building blocks, the $R^x$ group forms part of the amine urethane protecting group ($R^xOC(O)$) and confers particular chemical properties to the intermediate compound. For example, when $R^x$ is 9-methyl-9H-fluorene, the protecting group is the well known Fmoc group and oxidation of the alcohol functionality of (2b) to the corresponding ketone functionality (e.g. for general oxidation of bicyclic alcohols see Quibell, M et al, Bioorg. Med. Chem., 13, 609-625, 2005) provides PI building block (2c) that is particularly useful in solid phase syntheses (for utilisation of Fmoc-protected bicyclic ketones in solid phase synthesis see (a) Quibell, M et al, Bioorg. Med. Chem., 12, 5689-5710, 2004, (b) WO-A-02057270). As a further example when $R^x$ is benzyl, the protecting group is the well known Cbz group and oxidation of the alcohol functionality to the corresponding ketone functionality followed by protection of the ketone as a ketal, for example the dimethylketal, provides protected intermediate (2d). Removal of the Cbz protection from (2d), typically by catalytic hydrogenation, provides P1 building block (2e) that is particularly useful in solution phase syntheses (for general utilisation of bicyclic aminoketals in solution phase synthesis see Quibell, M et al, Bioorg. Med. Chem., 13, 609-625, 2005). As a further example when $R^x$ is tert-butyl, the protecting group is the well known Boc group providing protected intermediate (2f). Acidolytic removal of the Boc group and neutralisation of the amine salt provides P1 building block (2g) that is particularly useful in solution phase syntheses (for general utilisation of bicyclic aminoalcohols in solution phase synthesis see Quibell, M et al, Bioorg. Med. Chem., 13, 609-625, 2005). The P1 building block (2g) may also be accessed via numerous alternative intermediates for example, but not limited to, removal of the Fmoc group from (2b) or removal of the Cbz group from the corresponding Cbz-protected bicyclic alcohol.

(2b) 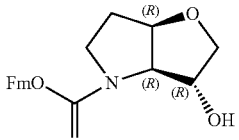

(2c) 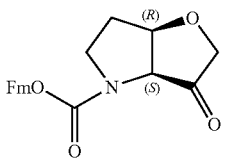

(2d) 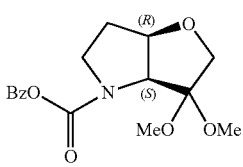

(2e) 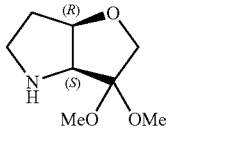

(2f) 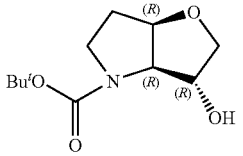

(2g) 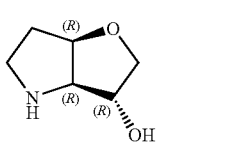

The corresponding equivalent analogues to (2b-2g) such as analogues (3b-3g), (4b-4g), (5b-5g), (6b-6g), (7b-7g) and (8b-8g) described hereinafter, are also useful for syntheses of compounds having an additional functional group at the 6-position of the bicycle. Those skilled in the art of organic synthesis will recognise that the presence of additional reactive functionalities within P1 building blocks such as (3a) and (4a) (alcohol functional group at the 6-position of bicycle) or (7a) and (8a) (primary amine functional group at the 6-position of bicycle) will also require protection during subsequent synthetic reactions. For instance when the 6-substituent is protected through the acid labile tert-butyl ether (as in (3a), (4a)) or the acid labile Boc group (as in (7a) and (8a)) then the amine urethane protecting group ($R^xOC(O)$) should have orthogonal liability (see Greene, T. W. and Wuts, P. G. M. 'Protective Groups in Organic Synthesis' John Wiley and Sons, New York, 1991 and references therein). A particularly useful combination for solution phase syntheses is the Cbz amine urethane protecting group (BzOC(O)) in conjunction with acid labile Boc amine protection or tert-butyl ether alcohol protection or dimethylketal protection of the ketone.

The present invention is based on the finding that dihydrofuran derived intermediates offer convenient access to a broad range of 6-substituted bicyclic intermediates (e.g. building blocks 3-8) as well as the corresponding 6-unsubstituted (herein termed saturated) analogues (e.g. building block 1 and 2) with high optical purity of final products.

Robust access to dihydrofuran intermediates has been described by Paolucci and co-workers (see (a) Paolucci, C. et al, Synthesis, 12, 1415-1419, 1997; (b) Paolucci, C. et al, Tet. Lett., 36(44), 8127-8, 1995; (c) Paolucci, C. et al, J. Org. Chem., 60(1), 169-175, 1995; (d) Cere, V. et al, J. Org. Chem., 58(17), 4567-71, 1993; (e) Cere, V. et al, Tet. Lett., 30(48), 6737-40, 1989). The above-described literature references commence from the commercially available sugars isomannide and isosorbide that are readily transformed into halo-dihydrofurans (11), (12) and the dihydrofuryl para-toluene sulphonates (tosylates, Ts) (13) and (14).

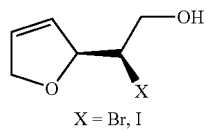
X = Br, I
(11)

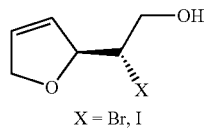
X = Br, I
(12)

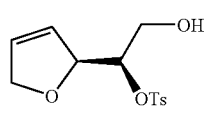
(13)

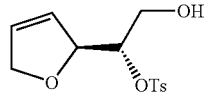
(14)

Furthermore, Paolucci and co-workers have detailed the treatment of alcohols (11-14) with base (e.g. sodium methoxide in methanol) to give the corresponding chiral epoxides (15) and (16) (see Cere, V. et al, *J. Org. Chem.*, 58(17), 4567-71, 1993; Paolucci, C. et al, J. Org. Chem., 60(1), 169-175, 1995).

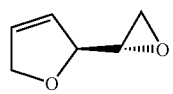
(15)

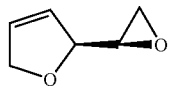
(16)

Synthesis of Intermediates IIa and IIb

As mentioned above, one aspect of the present invention relates to a new process for preparing compounds of formula IIIa or IIIb. Said process comprises:

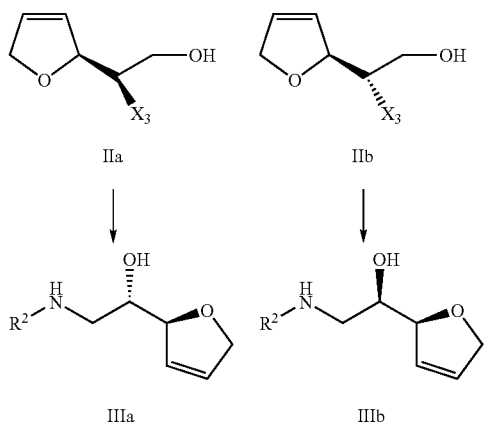

(A')
(i) reacting a compound of formula IIa, wherein $X_3$ is halogen or OTs, with aqueous ammonia and alcohol; or with aqueous ammonium hydroxide;
(ii) converting the product formed in step (i) to a compound of formula IIIa; or (B')
(i) reacting a compound of formula IIb, wherein $X_3$ is halogen or OTs, with aqueous ammonia and alcohol; or with aqueous ammonium hydroxide; (ii) converting the product formed in step (i) to a compound of formula IIIb.

Preferably, step (A')(i) and step (B')(i) are one-pot processes.

In one preferred embodiment, the group $R^2$ is a urethane protecting group $PG_1$. Preferred protecting groups are as defined above for the first aspect of the invention.

In one preferred embodiment, protecting group $PG_1$ is benzyloxycarbonyl, and step (ii) involves treating the mixture formed in step (i) with benzyloxycarbonyl chloride.

In one preferred embodiment, $X_3$ is I or Br.

Preferably, the alcohol is isopropyl alcohol or ethanol.

Advantageously, the above process provides an alternative route for preparing enantiomerically pure diastereomers IIIa and IIIb, which are key intermediates useful in the synthesis of 5,5-bicylic building blocks for the preparation of cysteinyl proteinase inhibitors.

By way of illustration, heating halo-dihydrofurans (11) or the dihydrofuryl tosylate (13) with an aqueous ammonia/alcohol (e.g. isopropanol or ethanol) mixture followed by amine urethane protection provides benzyl (S)-2-((S)-2,5-dihydrofuran-2-yl)-2-hydroxyethyl carbamate (17) in good yield. By analogy, the one pot sequence from halo-dihydrofurans (12) or the dihydrofuryl tosylate (14) provides benzyl (R)-2-((S)-2,5-dihydrofuran-2-yl)-2-hydroxyethyl carbamate (18). In this sequence ammonia acts initially as a base to promote ring closure (and inversion) of intermediates to give chiral epoxides (15) and (16) that are then opened by ammonia acting as a nucleophile.

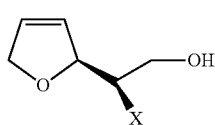

(11) X = Br or I
(13) X = OTs

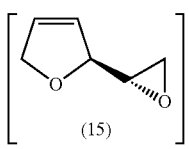

(15)

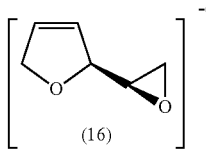

(16)

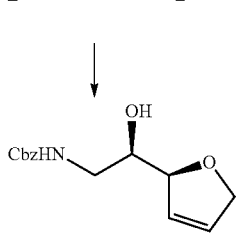

(18)

Furthermore, the iodo-dihydrofurans (11), (12) may be converted to alkene intermediate (23) via de-iodination to alcohol (19), then standard conversions to mesylate (20), azide (21), azide reduction to amine (22) (e.g. see Mandville, G. et al, J. Org. Chem, 61, 1122, 1996) and amine urethane protection (23) (see Paolucci refs), as shown below in Scheme 7.

Scheme 7: Example route towards (R)-benzyl 2-(2,5-dihyrofuran-2-yl)ethyl carbamate;

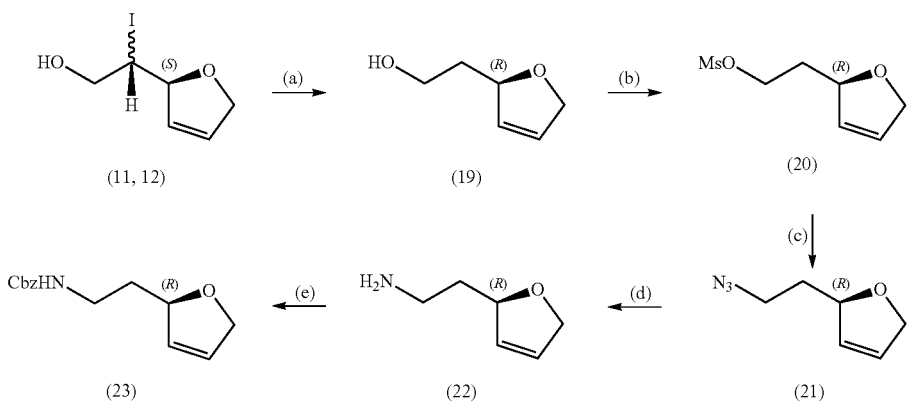

(a) "Bu₃SnH, THF, H₂O, benzoyl peroxide, 0° C.;
(b) Et₃N, MeSO₂Cl;
(c) NaN₃, DMF, 60° C.;
(d) Ph₃P, H₂O, RT → 45° C.;
(e) Cbz—Cl, Na₂CO₃, dioxane, H₂O, 0° C.

-continued

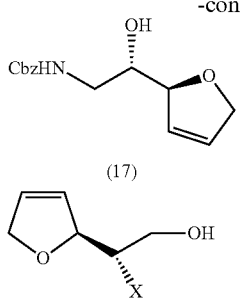

(17)

(12) X = Br or I
(14) X = OTs

Alkene (23) may then be converted to bicyclic ketone (2c) following the conditions detailed in Scheme 8. Epoxidation of alkene (23) can be achieved under many conditions (for example see (a) Bonini, C. and Righi, G. Tet. 58, 4981-5021, 2002; (b) Yang, D. Acc. Chem. Res., 37, 497-505, 2004; (c) Chaudhuri, N. K. and Ball, T. J. J. Org. Chem., 47(26), 5196-5198, 1982). However, only modest stereoselective ratios of the desired anti-(24a) have been achieved. Conversion of (24a) to (2c) then proceeds in an analogous manner to that previously detailed for alternative 5,5-heterobicycles (see (a) Quibell, M et al, Bioorg. Med. Chem., 13, 609-625, 2005; (b) Wang, Y. et al, Bioorg. Med. Chem. Lett., 15, 1327-1331, 2005). Removal of the urethane protection from (24a) by hydrogenation provides the free amine intermediate that spontaneously undergoes intramolecular cyclisation to give the 5,5-bicyclic framework. Protection with Fmoc-Cl e.g. under standard Schotten-Baumarn conditions provides alcohol (2b) which may be oxidised e.g. with Dess-Martin periodinane in DCM to give the ketone building block (2c). Alternatively, treatment of anti-(24a) with sodium hydride in anhydrous THF provides the Cbz urethane analogue of Fmoc-bicyclic alcohol (2b).

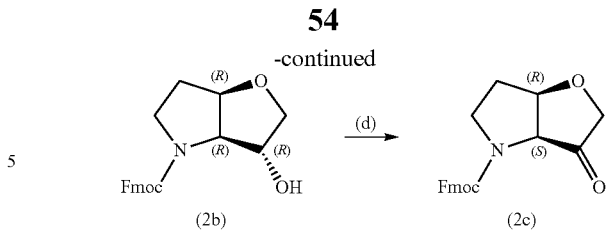

(a) (i) 30% $H_2O_2$, $H_2O$, $NaHCO_3$, MeOH, $CH_3CN$, RT or 55° C.; or (ii) mCPBA, DCM, RT; or (iii) OXONE®, $NaHCO_3$, 1,1,1-trifluoroacetone, $CH_3CN$, $H_2O$, $Na_2$•EDTA, 0° C.;
(b) Pd—C, $H_2$, ethanol;
(c) Fmoc-Cl, $Na_2CO_3$, dioxane, $H_2O$;
(d) Dess-Martin periodinane, DCM, RT.

Scheme 8:

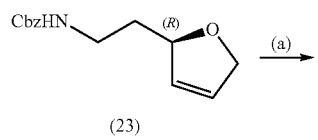

(23)

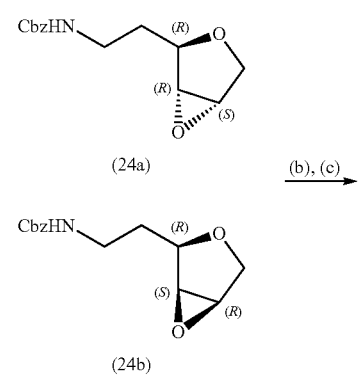

By extension, compounds of formulae Ic or Id, where U—(V)$_m$—(W)$_n$—(X))$_o$—Y—, may be prepared directly by a modification of Scheme 8 as detailed in Scheme 9. Intermediate amine (22) may alternatively be acylated directly with the P3-P2-COOH building block providing alkene (23b). Epoxidation of alkene (23b) provides anti-epoxide (24c) which can undergo intramolecular cyclisation to alcohol (25) through treatment with sodium hydride. Final oxidation of alcohol then provides ketone compounds of general formulae Ic and Id. Additionally by extension, such routes will also be applicable to the corresponding building blocks leading to 6-functionalised derivatives i.e. through appropriately protected intermediates derived from alcohols (17) and (18) and their respective free amines. Such routes are attractive where the chemical moieties within the P3-P2 building block are fully compatible with epoxidation, sodium hydride and final oxidative conditions.

Scheme 9:

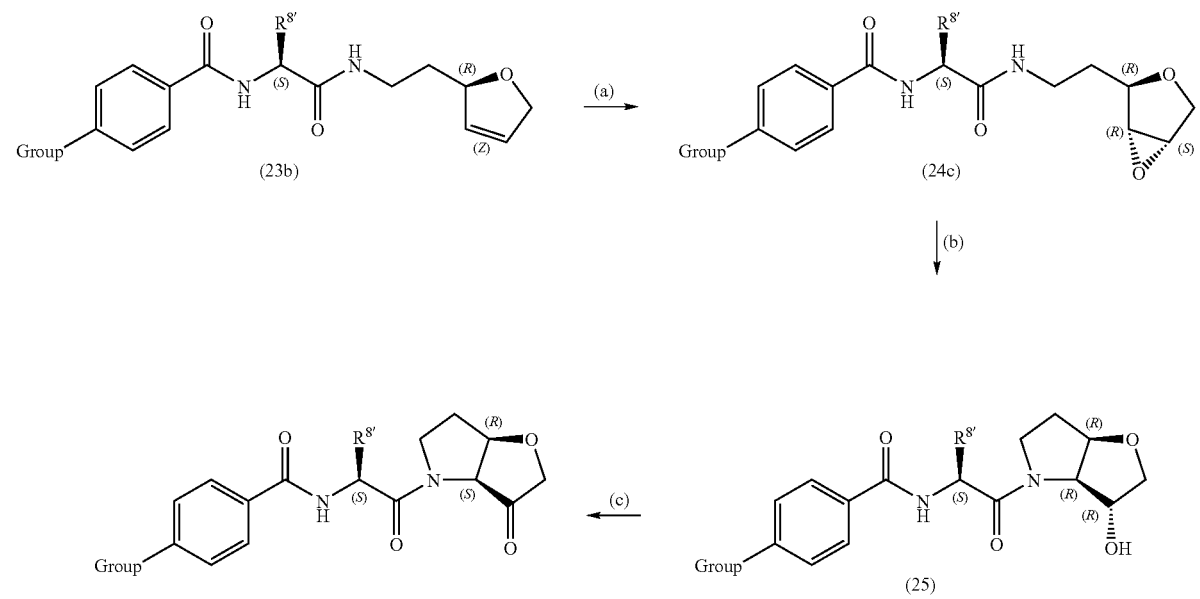

(a) Epoxidation; (b) NaH, anhydrous THF; (c) Oxidation e.g. Dess-Martin periodinane, DCM, RT.

Synthesis of 6-substituted Derivatives of Formula Ia-Id

As mentioned above, one aspect of the invention relates to the synthesis of compounds of formula Ia-Id via intermediates IVa and Va (or IVb and Vb) shown below.

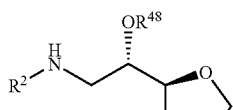

IVa

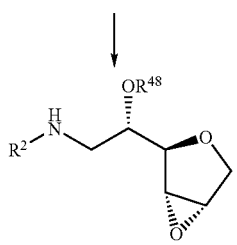

Va
Anti (major)

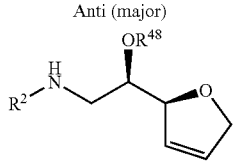

IVb

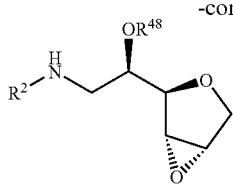

Vb
Anti (major)

By way of illustration, the controlled syntheses of diastereoisomeric alcohols (17) and (18) provide attractive intermediates useful in the preparation of compounds of general formulae Ia-Id that contain a substituent other than hydrogen in the 6-position of the 5,5-bicyclic ring (i.e. $R^1 \neq H$).

For example, the alcohol functionality of (17) may be protected e.g. as the acid labile tert-butyl ether and utilised as detailed in Scheme 10 below, wherein benzyl (S)-2-((S)-2,5-dihydrofuran-2-yl)-2-hydroxyethyl carbamate (17) proceeds through the anti-epoxide benzyl (S)-2-((1S,2R,5S)-3,6-dioxabicyclo[3.1.0]hexan-2-yl)-2-tert-butoxyethyl carbamate (28). An analogous reaction scheme can be applied to benzyl (R)-2-((S)-2,5-dihydrofuran-2-yl)-2-hydroxyethyl carbamate (18) proceeding through the analogous anti-epoxide benzyl (R)-2-((1S,2R,5S)-3,6-dioxabicyclo[3.1.0]hexan-2-yl)-2-tert-butoxyethyl carbamate (28b). Preparation of tert-butyl ethers is typically performed through reaction of alcohol with 2-methylpropene in a solvent such as dichloromethane with acid catalysis (e.g. see Wunsch, E. and Jentsch, J. *Chem. Ber.*, 97, 2490, 1964).

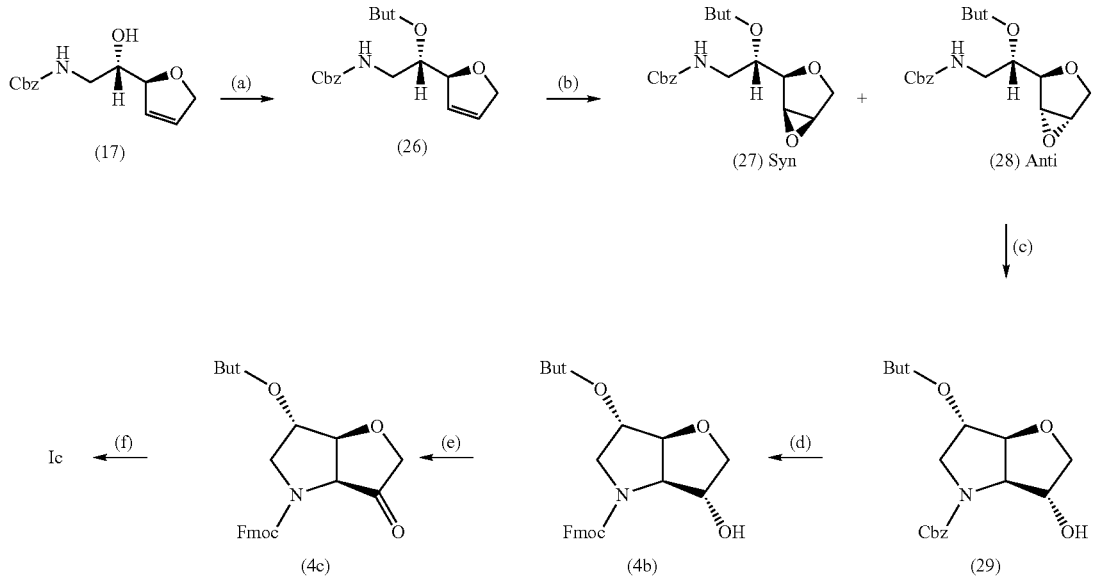

Scheme 10:

(a) 2-methylpropene(g), DCM, cat. conc. H₂SO₄, -78° C.; (b) (i) 10 eq mCPBA, DCM, RT or (ii) OXONE®, NaHCO₃, 1,1,1-trifluoroacetone, CH₃CN, H₂O, Na₂•EDTA; (c) NaH, anhydrous THF; (d) (i) Pd-C, H₂, ethanol or methanol (ii) 1.05 eq Fmoc-Cl, 2.1 eq Na₂CO₃, dioxan, H₂O; (e) Dess-Martin periodinane, anhydrous DCM, RT; (f) Standard linker-construct and 'Solid-Phase' e.g. see WO 02/057270 pg 105-106, 124-127, 135-136.

Advantageously, tert-butyl ether protection leads to a substantial increase in the stereoselectivity of epoxidation when compared to that observed for alkene (23) (Table 1). The presence of either tert-butyl ether isomer (26 [S,S], 26b [SR]) produces a substantial increase in the yield of desired anti-epoxide (28, 28b) when oxone based reagents are used for epoxidation when compared to the saturated analogue (23). A similar increase in ratio may also be observed when using hydrogen peroxide/alkylnitrile e.g. acetonitrile reagents (see Chaudhuri, N. K. and Ball, T. J. *J. Org. Chem.,* 47(26), 5196-5198, 1982 and Table 2 data for tosylates (32, 32b)).

((S)-2,5-dihydrofuran-2-yl)-2-hydroxyethyl carbamate (18) proceeding through the analogous anti-epoxide benzyl (R)-2-((1S,2R,5S)-3,6-dioxabicyclo[3.1.0]hexan-2-yl)-2-methoxyethyl carbamate (31b). Preparation of methyl ethers is typically performed through reaction of alcohol with methyl iodide in a solvent such as acetonitrile with silver(I) oxide catalysis (e.g. see Finch, N. et al, J. Org. Chem, 40, 206, 1975 and refs. cited therein). Alternatively, methyl ethers (30) and (30b) are prepared from alcohols (17) and (18) by reaction with trimethyloxonium fluoroborate, proton sponge [1,8-bis(dimethylamino)naphthalene] and molecular sieves in dichloromethane.

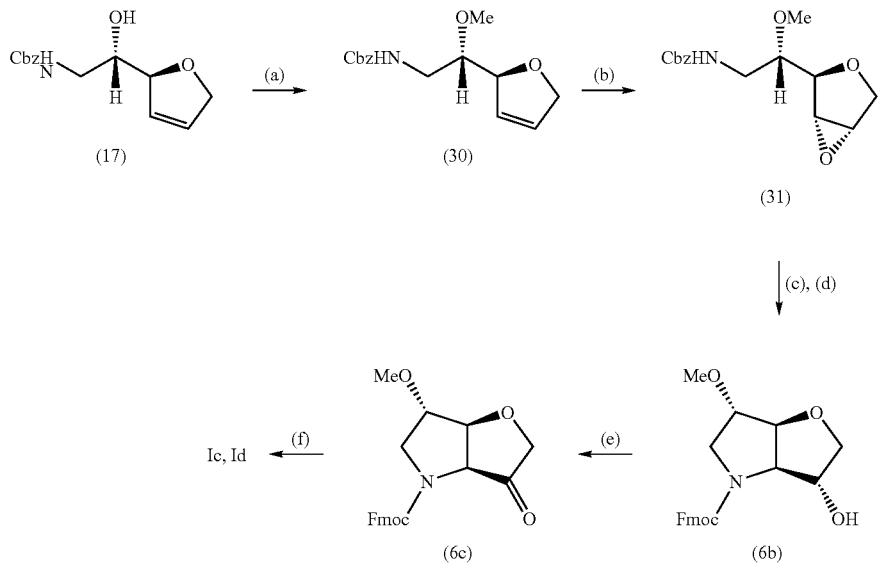

Scheme 11:

(a) MeI, Ag$_2$O, CH$_3$CN, 75-80° C.; or Me$_3$OBF$_4$, 4Å sieves, Proton Sponge, DCM; (b) OXONE®, NaHCO$_3$, 1,1,1-trifluoroacetone, CH$_3$CN, H$_2$O, Na$_2$·EDTA, 0° C.; (c) Pd-C, H$_2$, ethanol; (d) Fmoc-Cl, Na$_2$CO$_3$, dioxane, H$_2$O; (e) Dess-Martin periodinane, DCM. (f) Standard linker-construct and 'Solid-Phase' e.g. see WO02057270 pg 105-106, 124-127, 135-136.

TABLE 1

Ratio of anti:syn epoxides for alkenes (23), (26) and (26b) under various epoxidation conditions.

| | | Ratio of Anti:Syn epoxides | | |
|---|---|---|---|---|
| | | mCPBA | Oxone | H$_2$O$_2$/ CH$_3$CN |
| Alkene (23) | Anti-epoxide (24a) | 17 | 5 | 2 |
| | Syn-epoxide (24b) | 19 | 4 | 1 |
| Alkene (26) | Anti-epoxide (28) | 2 | 10 | — |
| | Syn-epoxide (27) | 1 | 1 | — |
| Alkene (26b) | Anti-epoxide (28b) | 1 | 10 | — |
| | Syn-epoxide (27b) | 3 | 1 | — |

(—) denotes experiment not assessed.

As a further example, the alcohol functionality of (17) may be derivatised as the methyl ether (30) and utilised as detailed in Scheme 11, wherein benzyl (S)-2-((S)-2,5-dihydrofuran-2-yl)-2-hydroxyethyl carbamate (17) proceeds through the anti-epoxide benzyl (S)-2-((1S,2R,5S)-3,6-dioxabicyclo[3.1.0]hexan-2-yl)-2-methoxyethyl carbamate (31). An analogous reaction scheme can be applied to benzyl (R)-2-

Again an increase in the stereoselectivity of epoxidation is observed for methoxy substituted compounds 30, 30b, when compared to that observed for alkene (23). The presence of the (R)-methyl ether moiety in (30b) produces a 3-fold increase in the yield of desired anti-epoxide (31b) when oxone based reagents are used for epoxidation when compared to the saturated analogue (23).

As a further example, the alcohol functionality of (18) may be derivatised as the para-toluene sulphonate (Ts) giving (R)-2-(benzyloxycarbonylamino)-1-((S)-2,5-dihydrofuran-2-yl)ethyl 4-methylbenzenesulfonate (32b) and utilised as detailed in Scheme 12, proceeding through the anti-epoxide (R)-2-(benzyloxycarbonylamino)-1-((1S,2S,5S)-3,6-dioxabicyclo[3.1.0]hexan-2-yl)ethyl 4-methylbenzenesulphonate (33b). An analogous reaction scheme can be applied to benzyl (S)-2-((S)-2,5-dihydrofuran-2-yl)-2-hydroxyethyl carbamate (17) proceeding through the analogous anti-epoxide (S)-2-(benzyloxycarbonylamino)-1-((1S,2S,5S)-3,6-dioxabicyclo[3.1.0]hexan-2-yl)ethyl 4-methylbenzenesulphonate (33) to give (3R,3aR,6S,6aS)-benzyl 3-hydroxy-6-(tosyloxy)tetrahydro-2H-furo[3,2-b]pyrrole-4(5H)-carboxylate (34) and (3R,3a,6S,6aS)-tert-butyl 3-hydroxy-6-(tosyloxy)tetrahydro-2H-furo[3,2-b]pyrrole-4(5H)-carboxylate (35).

Scheme 12:

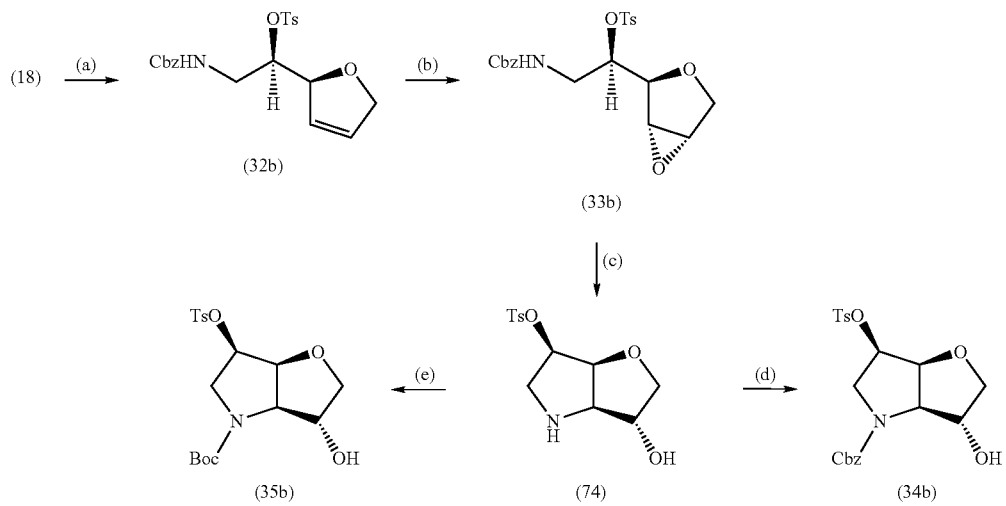

(a) TsCl, pyridine: (b) (i) mCPBA, DCM or (ii) OXONE®, NaHCO₃, 1,1,1-trifluoroacetone, CH₃CN, H₂O, Na₂·EDTA 0° C. or (iii) 30% H₂O₂, CH₃CN, MeOH, NaHCO₃; (c) Pd-C, H₂, ethanol; (d) Cbz-Cl, Na₂CO₃, dioxane, H₂O; (e) Boc₂O, Na₂CO₃, dioxane, H₂O.

Advantageously, tosyl protection of alcohols (17) and (18) leads to a substantial increase in the stereoselectivity of epoxidation when compared to that observed for alkene (23) (Table 2). The presence of either tosyl isomer in (32, 32b) produces a substantial increase in the yield of desired anti-epoxide (33, 33b) when oxone based reagents are used for epoxidation when compared to the saturated analogue (23). A significant increase in ratio is also observed when using hydrogen peroxide/alkylnitrile e.g. acetonitrile reagents (see Chaudhuri, N. K. and Ball, T. J. *J. Org. Chem.*, 47(26), 5196-5198, 1982).

TABLE 2

Ratio of anti:syn epoxides for alkenes (23), (32) and (32b) under various epoxidation conditions.

| | | Ratio of Anti:Syn epoxides | | |
|---|---|---|---|---|
| | | mCPBA | Oxone | H₂O₂/CH₃CN |
| Alkene (23) | Anti-epoxide (24a) | 17 | 5 | 2 |
| | Syn-epoxide (24b) | 19 | 4 | 1 |
| Alkene (32) | Anti-epoxide (33) | 3 | >10 | — |
| | Syn-epoxide | 1 | 1 | — |
| Alkene (32b) | Anti-epoxide (33b) | 2 | >10 | 10 |
| | Syn-epoxide | 1 | 1 | 1 |

(—) denotes experiment not assessed.

Furthermore, the tosyl group of bicyclic intermediates (34), (34b), (35), (35b) can act as a leaving group by employing a suitable nucleophile to provide access to additional 6-substituted analogues.

For example, treatment of tosylate (34b) with sodium azide in dimethylformamide with heating provides 6-azido analogue (3R,3aR,6S,6aS)-benzyl 6-azido-3-hydroxytetrahydro-2H-furo[3,2-b]pyrrole-4(5H)-carboxylate (36b) Scheme 13. Reduction of azide to amine e.g. with triphenylphosphine/water (e.g. see Mandville, G. et al, J. Org. Chem., 61, 1122, 1996) provides the 6-amino intermediate which is Boc-protected under standard Schotten-Baumann conditions providing (37b). Conversion of Cbz to Fmoc-protection and oxidation then provides building blocks (8b) and (8c) that can be utilised in a solid phase method to prepare 6-amino analogues of general formula Ic and Id. An analogous reaction sequence may be applied to tosylate (34) to provide the opposite 6-amino epimers (7b) and (7c). One skilled in the art will appreciate that tosylates (34), (34b), (35), (35b) are exceptionally versatile analogues that open-up synthetic routes to a wide range of 6-substituted compounds.

Scheme 13:

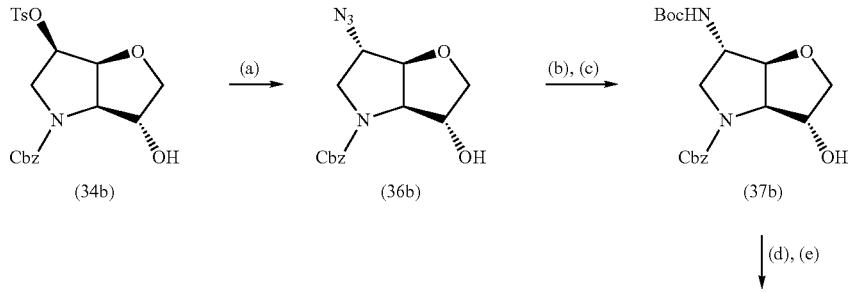

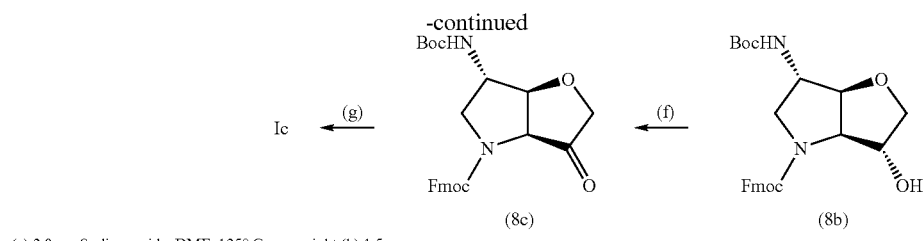

(a) 2.0 eq. Sodium azide, DMF, 135° C., overnight (b) 1.5 eq. Triphenylphosphine, 10 eq. water, THF, 45° C., overnight; (c) 1.5 eq. tert-butylcarbonate, 2.1 eq $Na_2CO_3$, dioxan, $H_2O$; (d) Pd-C, $H_2$, ethanol or methanol; (e) 1.05 eq Fmoc-Cl, 2.1 eq $Na_2CO_3$, dioxan, $H_2O$; (f) Dess-Martin periodinane, anhydrous DCM, RT; (g) Standard linker-construct and 'Solid-Phase' e.g. see WO02057270 pg 105-106, 124-127, 135-136.

Synthesis of 6-unsubstituted Compounds of Formula Ia-Id

The present invention also provides an alternative route for preparing 6-unsubstituted compounds of formula Ia-Id, i.e. where $R^1$ is H.

As for Scheme 12 above, the alcohol functionality of (18) may be derivatised as the para-toluene sulphonate (Ts) giving (R)-2-(benzyloxycarbonylamino)-1-((S)-2,5-dihydrofuran-2-yl)ethyl 4-methylbenzenesulfonate (32b) which proceeds through the anti-epoxide (R)-2-(Benzyloxycarbonylamino)-1-((1S,2S,5S)-3,6-dioxabicyclo[3.1.0]hexan-2-yl)ethyl 4-methylbenzenesulphonate (33b) Scheme 14. An analogous reaction scheme can be applied to benzyl (S)-2-((S)-2,5-dihydrofuran-2-yl)-2-hydroxyethyl carbamate (17) proceeding through the analogous anti-epoxide (S)-2-(Benzyloxycarbonylamino)-1-((1S,2S,5S)-3,6-dioxabicyclo[3.1.0]hexan-2-yl)ethyl 4-methylbenzenesulphonate (33) to give (3R,3aR,6S,6aS)-benzyl 3-hydroxy-6-(tosyloxy)tetrahydro-2H-furo[3,2-b]pyrrole-4(5H)-carboxylate (34) and (3R,3aR,6S,6aS)-tert-butyl 3-hydroxy-6-(tosyloxy)tetrahydro-2H-furo[3,2-b]pyrrole-4(5H)-carboxylate (35).

Subsequent treatment of tosylate (35b) with super-hydride (for general refs. see (a) Brown, H. C., et al, J. Org. Chem., 45(1), 1-12, 1980; (b) Krishnamurthy, S and Brown, H. C., J. Org. Chem., 41(18), 3064-3066, 1976) reduces out the tosyl group giving the saturated bicycle intermediate, which through transformation of Boc to Fmoc-protection provides another route towards building blocks (2b) and (2c). Alternatively, treatment of aminotosylate (74) with super-hydride (for general refs. see (a) Brown, H. C., et al, J. Org. Chem., 45(1), 1-12, 1980; (b) Krishnamurthy, S and Brown, H. C., J. Org. Chem., 41(18), 3064-3066, 1976) reduces out the tosyl group giving the saturated bicycle intermediate (2g) which may be Fmoc-protected to towards building blocks (2b) and (2c). Additionally, treatment of aminotosylate (74) with lithium aluminium hydride reduces out the tosyl group giving the saturated bicycle intermediate (2g) which may be Fmoc-protected to towards building blocks (2b) and (2c). Suprisingly, analogous reduction of tosylate (35b) with lithium aluminium hydride is a significantly less efficient reaction, which constasts the efficient reduction observed with super-hydride. These routes towards (2b) and (2c) has the advantage that epoxidation to give the desired anti-epoxide is directed by the presence of the tosylate group whilst only modest stereoselectivity can be achieved for saturated alkene (23). Thus, although this route to the 6-unsubstituted derivatives involves additional synthetic steps, the stereoselectivity of the epoxidation is controlled to allow much higher yields of the desired anti-epoxide.

Scheme 14:

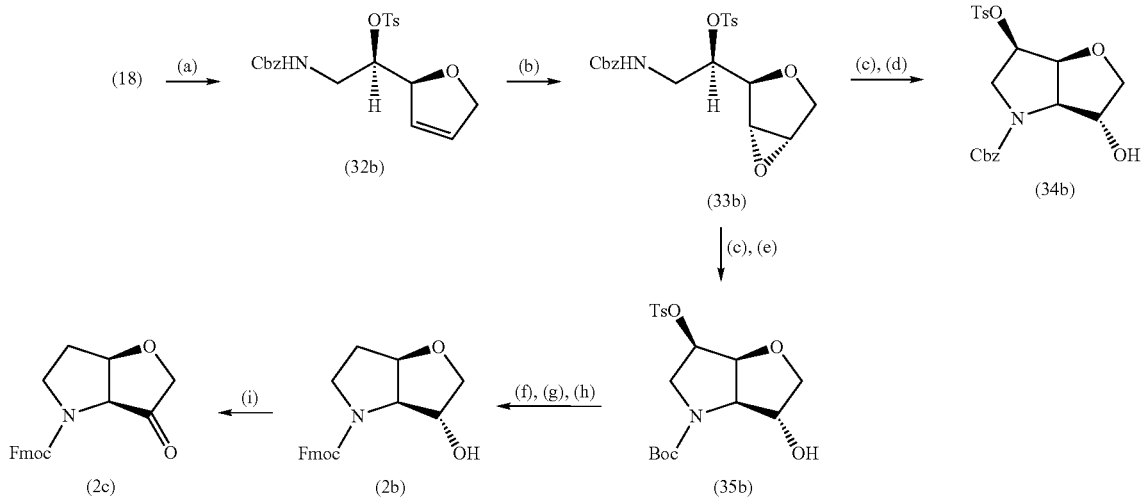

(a) TsCl, pyridine: (b) (i) mCPBA, DCM or (ii) OXONE®, NaHCO$_3$, 1,1,1-trifluoroacetone, CH$_3$CN, H$_2$O, Na$_2$•EDTA 0 °C. or (iii) 30% H$_2$O$_2$, CH$_3$CN, MeOH, NaHCO$_3$; (c) Pd-C, H$_2$, ethanol; (d) Cbz-Cl, Na$_2$CO$_3$, dioxane, H$_2$O; (e) Boc$_2$O, Na$_2$CO$_3$, dioxane, H$_2$O; (f) Super-Hydride®, THF, 35 °C.; (g) 4.0N HCl in dioxan, RT, 1h; (h) Fmoc-Cl, Na$_2$CO$_3$, dioxane, H$_2$O; (i) Dess-Martin periodinane, anhydrous DCM, RT.

Intermediates of Formula IVa, IVb, Va and Vb

Another aspect of the invention relates to compounds of formula IVa, IVb, Va or Vb, and pharmaceutically acceptable salts, hydrates, solvates, complexes or prodrugs thereof,

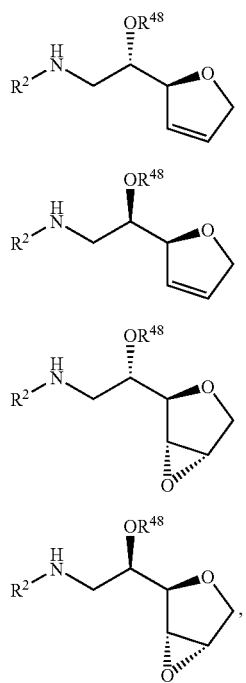

wherein $R^{48}$ is alkyl or tosyl, and $R^2$ is a protecting group $PG_1$ or a group of formula $U—(V)_m—(W)_n—(X)_o—Y—$ or a group of formula $(U)_p—(X_2)_s—(Y_1)_k—Y_2—$ as defined above. Advantageously, the above compounds are easily accessible, enantiomerically pure intermediates which are useful in the preparation of a wide range of cysteinyl proteinase inhibitors.

By way of summary, the present invention provides a new synthetic route to oxygen bicyclic structures such as tetrahydrofuro[3,2-b]pyrrol-3-ones (for example, as disclosed in WO 02/057270). Advantageously, the process involves the use of commercially available starting materials (such as isomannide, isosorbide) coupled with an improved 'one pot ammonia reaction' to give key enantiomerically pure diastereoisomers (for example, compounds 17 and 18), which are generally known in literature, but previously obtained via alternative longer routes. The present invention additionally provides an improved process for preparing alcohol intermediates (13) and (14) by the simple treatment of monobromotosylate derivatives of isomannide and isosorbide respectively with zinc dust at room temperature in organic/aqueous mixtures.

The present invention is also centred on the discovery that alcohol protected compounds of formula IVa and IVb (for example, alcohol protected analogues of 17 and 18), in particular bulky groups such as tert-butyl, tosyl, provide a strong stereofacial preference for desired anti-epoxide during oxidation to the corresponding epoxides. This 'directing effect' is in stark contrast to equivalent reactions on unsubstituted analogues (such as compound 23), where little stereofacial preference is observed.

Furthermore, the processes of the invention open up access to 5,5-bicyclic compounds having a substituent other than hydrogen in the 6-position (i.e. $R^1 \neq H$), either by direct synthesis (e.g. —OH, 6-OMe etc) or by nucleophilic substitution of the 6-tosylates (e.g. compounds 34/35 and 74) or 6-mesylates. By way of example, nucleophilic substitution of the tosyl analogue (compound 34b) with azide provides the 6-azido analogue ($R^1=N_3$); one skilled in the art will appreciate that protection of the alcohol (e.g. with trimethylsilyl) functionality within this analogue followed by reduction of the 6-azido to 6-amino functionality (e.g. as detailed in scheme 13) provides a primary that may be N-alkylated (e.g. displacement of an alkyl halide [$R^3$-halogen] or reductive amination [with aldehydes such as $R^2CHO$ or ketones such as $R^3R^2C=O$]) providing compounds wherein $R^1=NR^4R^5$. Alternatively, nucleophilic substitution of the tosyl analogue (compound 34b) with methylamine provides an additional route towards N-alkylated compounds wherein $R^1=NHMe$. One skilled in the art will appreciate that use of alternative alkylamine reagents provides access to other 6-alkylamino analogues. Also, within $NR^3R^4$ when either $R^3$ or $R^4$ are hydrogen, it is preferred that the secondary amino function is further protected, for example with the tert-butoxycarbonyl group, providing compounds of formula (Ia) or (Ib) wherein $R^2$ is Cbz and $R^1$ is $BocNR^4$. Alternatively, nucleophilic substitution of the tosyl analogue (compounds 34 or 35) with sodium thiomethoxide [CAS 5188-07-8] in dimethylacetamide at 90° C. provides the 6-SMe analogue; one skilled in the art will appreciate that use of alternative thioalkyl reagents provides access to other 6-alkylsulphide analogues (formula Ia,b $R^1$ is $SR^7$ wherein $R^7$ is as previously defined); additionally one skilled in the art will appreciate that oxidation of the 6-alkylsulphide analogues provides access to the 6-sulphoxides (formula Ia,b $R^1$ is $SOR^7$ wherein $R^7$ is as previously defined) and 6-alkylsulphones (formulae Ia,b $R^1$ is $SO_2R^7$ wherein $R^7$ is as previously defined). Compounds of formulae (Ia) and (Ib) wherein $R^1$ is alkoxy ($OR^6$) can be prepared by direct synthesis (e.g. see scheme 11). Alternatively, for example the $R^1$=ethoxy analogue can be prepared by displacement of tosylate (e.g. 35b) typically performed with sodium ethoxide in ethanol with heat. One skilled in the art will appreciate that use of alternative alkoxy reagents provides access to other 6-alkoxy analogues. Within carbocyclic and heterocarbocyclic rings, nucleophilic displacement of a secondary tosylate by halides is well known in the literature. For example, treatment of morphine tosylate analogues with tert-butyl ammonium fluoride and heat gives excellent yields of the inverted fluoro analogues (see Zhang, A. et al, Org. Lett. 2005, 7(15), 3239); pyrrolidine tosylate analogues with potassium fluoride and heat (see Giardina, G. et al, Synlett. 1995, 1, 55; Bouzard, D. et al, J. Med. Chem., 1990, 33(5), 1344)); nucleoside tosylate analogues with tert-butyl ammonium fluoride and heat (e.g. see EP576231; Brimacombe, J. S. et al, Can. J. Chem., 1970, 48(24), 3946); fluoride displacement of tosylates (34b) and (74) with TBAF and heat proceeds efficiently; or with potassium fluoride in acetamide with heat (e.g. see Reichman, U. et al, Carbohydate Res., 1975, 42(2), 233) or with potassium fluoride/kryptofix and heat gives excellent yields of the inverted fluoro analogues (see Cai, L. et al, J. Med. Chem., 2004, 47(9), 2208), under the later conditions nucleophilic substitution of the tosyl analogue (compound 34b) provides the 6-fluoro analogue; macrolide tosylate analogues with HF pyridine give good yields of the inverted fluoro analogues (see Mrozik, H. et al, J. Med. Chem., 1989, 32(2), 375); steroid tosylates analogues with potassium fluoride and heat gives excellent yields of the inverted fluoro analogues (see Badone, D. et al, Synthesis. 1987, 10, 921). Alternatively, displacement under lithium chloride based conditions has successfully given chloro analogues from carbocyclic and heterocarbocyclic tosylates on a wide variety of substrates (e.g. nucleosides, see Mikhailopulo, I. A. et al, J. Org. Chem., 2003, 68(15), 5897; steroids, see Back, T. G. et al, Tet. Lett., 1991, 32(45), 6517; morphine analogues, see Berenyi, S. et al, Acta Chimica Hungarica, 1989, 126(2), 275). Lithium chloride displacement of tosylate (34b) provides (3R,3aR,6S,6aS)-Benzyl 6-chloro-3-hydroxytetrahydro-2H-furo[3,2-b]pyrrole-4 (5H)-carboxylate (68); or tosylate (34) provides (3R,3aR,6R, 6aS)-Benzyl 6-chloro-3-hydroxy tetrahydro-2H-furo[3,2-b] pyrrole-4(5H)-carboxylate (76); or tosylate (74) provides (3R,3aR,6S,6aS)-6-chlorohexahydro-2H-furo[3,2-b]pyrrol-3-ol (69). Use of pyridine.HCl has also been successful on nucleoside tosylate substrates (e.g. see Lee, C. K. et al, Carbohydate Res., 1988, 177, 247; Makinabakan, O. et al, Carbohydate Res., 1996, 280(2), 339).

Other displacement reagents may be suitable for access to other 6-functionalised analogues, e.g. LiBr, DMF, heat towards the 6-Br analogue; alkylmetal reagents such as methyllithium (e.g. see Hanessian, S. et al, J. Am. Chem. Soc., 1990, 112(13), 5276-5290) towards the 6-Me analogue; trifluoromethylating reagents such as trifluoromethyl trimethylsilane (e.g. see Sevenard. D. V. et al, Syn. Lett., 2001, 3, 379-381) or trifluoromethyl magnesium iodide towards the 6-$CF_3$ analogue. Thus, these tosyl analogues not only direct the stereofacial preference of the epoxidation step, but also provide versatile intermediates to access a host of 6-substituted bicyclic species.

Finally, the above-described tosyl analogues (35b), (74) can also be reduced to give the corresponding unsubstituted analogues (i.e. 5,5-bicyclic systems unsubstituted in the 6-position, where $R^1$ is H), with the advantage that although this involves an additional synthetic step, the stereoselectivity of the epoxidation is controlled to ultimately allow much higher yields of the desired anti-epoxide.

The present invention is further described by way of the following non-limiting examples.

EXAMPLES

General Procedures

Solvents were purchased from ROMIL Ltd, U.K. at SpS or Hi-Dry grade unless otherwise stated. $^1$H NMR and $^{13}$C NMR were obtained on a Bruker DPX400 (400 MHz $^1$H frequency and 100 MHz $^{13}$C frequency; QXI probe) or Bruker Avance 500 MHz (TXI probe with ATM) in the solvents indicated. Chemical shifts are expressed in parts per million ($\delta$) and are referenced to residual signals of the solvent. Coupling constants (J) are expressed in Hz. All analytical HPLC were obtained on Phenomenex Jupiter $C_4$, 5μ, 300 Å, 250×4.6 mm, using mixtures of solvent A (0.1% aq trifluoroacetic acid (TFA)) and solvent B (90% acetonitrile/10% solvent A) on automated Agilent systems with 215 and/or 254 nm UV detection. Unless otherwise stated a gradient of 10 to 90% B in A over 25 min at 1.5 mL/min was performed for full analytical HPLC. HPLC-MS analysis was performed on an Agilent 1100 series LC/MSD, using automated Agilent HPLC systems, with a gradient of 10 to 90% B in A over 10 min on Phenomenex Luna $C_8$, 5μ, 300 Å, 50×2.0 mm at 0.6 mL/min. Semi-preparative HPLC purification was performed on Phenomenex Jupiter $C_4$, 5μ, 300 Å, 250×10 mm, using a gradient of 10 to 90% B in A over 25 min at 4 mL/min on automated Agilent systems with 215 and/or 254 nm UV detection. Flash column purification was performed on silica gel 60 (Merck 9385) or using isolute SPE flash silica columns (Biotage, hengoed, UK).

Preparation of Benzyl (S)-2-((S)-2,5-dihydrofuran-2-yl)-2-hydroxyethyl Carbamate (i) Preparation of (3R,3aS,6R,6aS)-Hexahydrofuro[3,2-b]furan-3,6-diyl bis(4-methylbenzenesulfonate) (39). A solution of p-toluenesulfonyl chloride (52 g, 273 mmol) in pyridine (150 mL) was added to a stirred solution of isomannide (40) (19.0 g, 130 mmol) in pyridine (150 mL) over 15 minutes then stirred at ambient temperature for 5 hours. The mixture was heated at 90° C. for 1.25 hours then stirred at ambient temperature for 16 hours, then heated at 90° C. for 1.25 hours before being poured onto iced-water (1 L). The aqueous was extracted with tert-butyl methyl ether (750 mL) then the organic phase washed with water (2×500 mL), diluted with dichloromethane (1 L), dried ($MgSO_4$), filtered and reduced in vacuo to leave an oil (60.3 g). The oil was crystallized from hot methanol (400 mL), and the white solid filtered in vacuo, washed with methanol (150 mL) then dried in vacuo to obtain ditosylate (39) (44.0 g, 74%). TLC ($R_f$=0.30, EtOAc:heptane 2:3), analytical HPLC single main peak, $R_t$=20.513 min., HPLC-MS 455.1 $[M+H]^+$, 931.2 $[2M+Na]^+$, $[\alpha]_D^{20}$+99.2° (c=1.839, $CHCl_3$); $\delta_H$ (500 MHz, $CDCl_3$) 2.44 (6H, s, $CH_3$), 3.71 (2H, dd, J=9.55 and 7.67 Hz, $CH_2$), 3.89 (2H, dd, J=9.57 and 6.67 Hz, $CH_2$), 4.44-4.47 (2H, m, CHCHOTs), 4.80-4.85 (2H, m, CHOTs), 7.33 (4H, d, J=7.97 Hz, $CH_3CCH$), 7.79 (4H, brd, J=8.33 Hz, $OSO_2CCH$); $\delta_C$ (125 MHz, $CDCl_3$) 21.679 ($CH_3$), 70.073 ($CH_2$), 77.790 (OCHCHOTs), 79.910 (OCHCHOTs), 127.961 and 129.898 (aromatic CH), 132.990 ($CHOSO_2C$ quaternary), 145.288 ($CH_3C$ quaternary).

(ii) Preparation of (3S,3aS,6S,6aS)-3,6-Diiodohexahydrofuro[3,2-b]furan (48) and (3R,3aS,6S,6aS)-3,6-diiodohexahydrofuro[3,2-b]furan (49) and (3R,3aS,6aS)-6-iodohexahydrofuro[3,2-b]furan-3-yl 4-methylbenzenesulfonate (38). Sodium iodide (116 g, 770 nmol) was added to a stirred solution of ditosylate (39) (43.8 g, 96.5 mmol) in dimethylformamide (250 mL) under nitrogen. The mixture was heated at 100° C. for 2 hours then at 125-135° C. for 3.5 hours then stood at ambient temperature for 16 hours. The reaction was heated at 135° C. for 1.5 hours then allowed to cool to ambient temperature before adding water (500 mL). The mixture was extracted with tert-butyl methyl ether (4×250 mL) then the organic phase washed with water (3×250 mL), brine (250 mL), dried ($MgSO_4$), filtered and reduced in vacuo to leave a brown oil (35g). Flash chromatography over silica, eluting with ethyl acetate:heptane mixtures 0:100 to 20:80 gave (in order of elution) a mixture (approximately 3:1 respectively) of diiodide (48) and diiodide (49) (20.35 g, 58%) as a white solid, and iodotosylate (38) (6.04 g, 15%) as a white solid. Data for iodotosylate (38); TLC ($R_f$=0.40, EtOAc:heptane 3:2), analytical HPLC single main peak, $R_t$=17.044 min., HPLC-MS 411.0 $[M+H]^+$, 843.0 $[2M+Na]^+$; $\delta_H$ (500 MHz, $CDCl_3$) 2.44 (3H, s, $CH_3$), 3.75 (1H, dd, J=11.21 and 8.72 Hz, $CH_2$), 3.79 (1H, dd, J=9.99 and 6.34 Hz, $CH_2$), 3.91 (1H, dd, J=9.99 and 6.22 Hz, $CH_2$), 3.98-4.03 (1H, m, CHI), 4.14 (11H, dd, J=8.56 and 7.56 Hz, $CH_2$), 4.39 and 4.57 (each 1H, t, J=4.51 and 4.94 Hz respectively, CHCHCHI), 4.95 (1H, dd, J=11.77 and 6.20 Hz, CHOTs), 7.34 (2H, d, J=8.00 Hz, aromatic $CH_3CCH$), 7.82 (2H, brd, J=8.33 Hz, aromatic $OSO_2CCH$); $\delta_C$ (125 MHz, $CDCl_3$) 21.258 (CHI), 21.688 ($CH_3$), 70.569 ($CH_2CHOTs$), 75.998 ($CH_2CHI$), 79.021, 79.383 and 82.387 (CHCHCHOTs), 127.958 and 129.883 (aromatic CH), 133.208 ($CHOSO_2C$ quaternary), 145.206 ($CH_3C$ quaternary).

(iii) Preparation of (R)-1-((S)-2,5-Dihydrofuran-2-yl)-2-hydroxyethyl 4-methylbenzenesulfonate (13). A solution of methyllithium lithium iodide complex (2.68 mL, 1.0M in diethyl ether, 2.68 mmol) was added dropwise to a stirred solution of iodotosylate (38) (0.8 g, 2.19 mmol) in tetrahydrofuran (10 mL) under argon at −70° C. over 2 minutes. The mixture was stirred for 1 hour then saturated aqueous ammonium chloride solution (15 mL) was added dropwise. The mixture was allowed to warm to ambient temperature, diluted with water (10 mL) then the product extracted into dichloromethane (2×50 mL). The organic phase was washed with brine (50 mL), then dried ($MgSO_4$), filtered and reduced in vacuo. Flash chromatography over silica, eluting with ethyl acetate:heptane mixtures 10:90 to 50:50 gave alcohol (13) (648 mg, 93%) as a white solid. TLC ($R_f$=0.33, EtOAc:heptane 1:1), analytical HPLC single main peak, $R_t$=12.67 min., HPLC-MS 285.1 $[M+H]^+$, 591.2 $[2M+Na]^+$; $[\alpha]_D^{16.5}$−72.1° (c=7.072, $CHCl_3$); $\delta_H$ (500 MHz, $CDCl_3$) 2.45 (3H, s, aryl-$CH_3$), 3.77 (1H, dd, J=12.67 and 5.15 Hz, $CH_2OH$), 3.83 (1H, dd, J 12.67 and 3.75 Hz, $CH_2OH$), 4.45-4.47 (3H, m, $CH_2OCH$), 4.92 (1H, m, CHOTs), 5.74 and 5.95 (2H total, m, $CH_2CH=CH$), 7.34 (2H, brd, J=8.21 Hz, aromatic $CH_3CCH$), 7.81 (2H, brd, J=8.32 Hz, aromatic $OSO_2CCH$); $\delta_C$ (125 MHz, $CDCl_3$) 21.673 ($CH_3$), 62.148 ($CH_2OH$), 75.836 ($OCH_2CH=CH$), 83.844 and 85.099 (OCHCHOTs), 125.396, 127.891, 129.027 and 129.815 ($OCH_2CH=CH$ and aromatic CH), 133.583 ($CHOSO_2C$ quaternary), 145.036 ($CH_3C$ quaternary).

(iv) A stirred mixture of alcohol (13) (4.2 g, 14.8 mmol), ammonium hydroxide (20 mL) and ammonia in 2-propanol (15 mL, 2.0M, 30 mmol) was heated in a sealed tube at 70° C. for 16 hours then the solvents were removed in vacuo. The residue was azeotroped with diethyl ether to obtain (S)-2-amino-1-((S)-2,5-dihydrofuran-2-yl)ethanol which was used without further purification. TLC ($R_f$=0.01, EtOAc:heptane 1:1), HPLC-MS 130.2 $[M+RH]^+$. A solution of sodium carbonate (2.35 g, 22.2 mmol) in water (20 mL) was added whilst stirring to a solution of (S)-2-amino-1-((S)-2,5-dihydrofuran-2-yl)ethanol in 1,4-dioxane (20 mL). A solution of benzylchloroformate (2.64 mL, 18.5 mmol) in 1,4-dioxane (5 mL) was added dropwise over 5 minutes. The mixture was stirred for 1.5 hours, then water (40 mL) added and the product extracted into dichloromethane (2×100 mL). The organic layer was dried ($MgSO_4$), filtered and reduced in vacuo. Flash chromatography over silica, eluting with ethyl acetate:heptane mixtures 20:80 to 50:50 gave alcohol (17) as a colourless oil (2.62 g, 67%) as a white solid. TLC ($R_f$=0.10, EtOAc:heptane 1:1), analytical HPLC two main peaks, $R_t$=10.913 and 11.061 min., HPLC-MS 264.1 $[M+H]^+$, 286.1 $[M+Na]^+$, 549.2 $[2M+Na]^+$; $[\alpha]_D^{14.5}$−88.1° (c=3.46, $CHCl_3$); $\delta_H$ (500 MHz, $CDCl_3$) 2.45 (1H, d, J=4.83 Hz, OH), 3.22-3.27 (1H, m, $CH_2NH$), 3.42-3.48 (1H, m, $CH_2NH$), 3.64-3.69 (1H, m, CHOH), 4.60-4.64 (2H, m, $OCH_2CH=CH$), 4.74-4.77 (1H, m, $OCHCH=CH$), 5.10 (2H, brs, $OCH_2Ph$), 5.23 (1H, brs, NH), 5.79-5.84 and 6.00-6.03 (2H total, m, $CH_2CH=CH$), 7.28-7.36 (5H, m, aromatic CH); $\delta_C$ (125 MHz, $CDCl_3$) 43.846 ($CH_2NHCbz$), 66.838 ($CH_2Ph$), 72.719 (CHOH), 75.719 ($OCH_2CH=CH$), 87.284 ($OCHCH=CH$), 126.093, 128.093, 128.125, 128.510 and 128.877 ($OCH_2CH=CH$ and Cbz aromatic CH), 136.423 (Cbz quaternary), 156.887 (Cbz C=O).

Alternative Preparation of Benzyl (S)-2-((S)-2,5-dihydrofuran-2-yl)-2-hydroxyethylcarbamate (17); Zinc and 'One-Pot' Procedure. A solution of ammonium chloride (140 mg, 2.62 mmol) in water (1.5 mL) was added to a solution of iodotosylate (38) (800 g, 1.95 mmol) in propan-2-ol (3 mL) and tetrahydrofuran (6 mL) under argon. Zinc dust (140 mg, 2.15 mmol) was then added in portions over 5 minutes then the suspension stirred for 16 hours before filtering through celite in vacuo. The filter cake was washed with diethyl ether (15 mL). Hydrochloric acid (1M, 15 mL) was added to the filtrate then the organic phase separated. The aqueous layer was extracted with diethyl ether (15 mL) then the combined organic phase was washed with brine (15 mL), then dried ($MgSO_4$), filtered and reduced in vacuo. The residue (0.54 g) was dissolved in ammonium hydroxide (4.5 mL) and a solution of ammonia in 2-propanol (3 mL, 2.0M, 6 mmol) then heated in a sealed tube at 75° C. for 16 hours. The solvents were removed in vacuo (transfer assisted with methanol) then the residue azeotroped with diethyl ether (5 mL) before adding ammonium hydroxide (4.5 mL) and ammonia in 2-propanol (3 mL, 2.0M, 6 mmol). The suspension was heated in a sealed tube at 75° C. for 16 hours. The solvents were removed in vacuo (transfer assisted with methanol) then the residue azeotroped with diethyl ether (3×5 mL) to obtain (S)-2-amino-1-((S)-2,5-dihydrofuran-2-yl)ethanol which was used without further purification.

A solution of sodium carbonate (0.43 g, 4.10 mmol) in water (4 mL) was added whilst stirring to a solution of (S)-2-amino-1-((S)-2,5-dihydrofuran-2-yl)ethanol (assumed to be 1.95 mmol) in 1,4-dioxane (5 mL). The mixture was cooled to 0° C. then benzylchloroformate (0.42 mL, 2.93 mmol) was added dropwise over 10 minutes. The mixture was stirred at 0° C. for 95 minutes, then dichloromethane (25 mL) and water (30 mL) added. The organic phase was separated and the aqueous extracted with dichloromethane (2×10 mL). The organic layer was washed with brine (10 mL), then dried ($Na_2SO_4$), filtered and reduced in vacuo to leave a residue (1.31 g). Flash chromatography over silica, eluting with ethyl acetate:heptane mixtures 20:80 to 70:30 gave alcohol (17) (278 mg, 54%). $[\alpha]_D^{18}$−72.95° (c=6.01, $CHCl_3$).

Preparation of Benzyl (R)-2-((S)-2,5-dihydrofuran-2-yl)-2-hydroxyethyl Carbamate (18)

(i) Preparation of (S)-2-((S)-2,5-Dihydrofuran-2-yl)-2-iodoethanol (12). A solution of methyllithium lithium iodide complex (40.6 mL, 11.0M in diethyl ether, 40.6 mmol) was added dropwise to a stirred solution containing diiodide mixture (48) and (49) (13.5 g, 36.9 mmol) in tetrahydrofuran (140 mL) under nitrogen at −70° C. over 12 minutes. The cloudy white suspension was stirred for 2.5 hours then saturated aqueous ammonium chloride solution (175 mL) was added dropwise over 30 minutes. Water (200 mL) was added then the mixture was allowed to warm to ambient temperature. The product was extracted into dichloromethane (2×250 mL) then the organic phase was washed with a mixture of brine and water (1:1, 200 mL), then dried ($Na_2SO_4$), filtered and reduced in vacuo to leave a colourless oil (8.6 g). Flash chromatography over silica, eluting with ethyl acetate:heptane mixtures 0:100 to 20:80 gave iodoalcohol (12) (5.41 g, 61%) as a yellow-brown oil, TLC ($R_f$=0.20, EtOAc:heptane 3:2), analytical HPLC single main peak, $R_t$=7.11 min., HPLC-MS 223.0 $[M−18+H]^+$, 258.0, 263.0 $[M+Na]^+$; $[\alpha]_D^{19}$−111.1° (c=0.270, $CHCl_3$); $\delta_H$ (500 MHz, $CDCl_3$) 2.40 (1H, brs, OH), 3.83-3.99 (2H, m, $CH_2OH$), 4.30-4.34 (1H, m, CHI), 4.60-4.65 (1H, m, $OCH_2CH=CH$), 4.73-4.78 (1H, m, $OCH_2CH=CH$), 4.83-4.87 (1H, m, OCHCHI), 5.75-5.78 and 6.07-6.10 (2H total, m, $CH_2CH=CH$); $\delta_C$ (125 MHz, $CDCl_3$) 41.717 (CHI), 66.282 ($CH_2OH$), 76.794 ($OCH_2CH=CH$), 87.058 ($OCHCH=CH$), 127.977 and 129.037 ($CH_2CH=CH$).

(ii) A stirred mixture of iodoalcohol (12) (85 mg, 0.35 mmol), ammonium hydroxide (2.0 mL) and ammonia in 2-propanol (2.0 mL, 2.0M, 4 mmol) was heated in a sealed tube at 80° C. for 3.5 hours then the solvents were removed in vacuo. The residue was azeotroped with diethyl ether (3×5 mL) to obtain (R)-2-amino-1-((S)-2,5-dihydrofuran-2-yl)ethanol as a yellow oil which was used without further purification. TLC ($R_f$=0.01, EtOAc:heptane 3:2), HPLC-MS 130.1 [M+H]$^+$. A solution of sodium carbonate (79 mg, 0.74 mmol) in water (1.75 mL) was added whilst stirring to a solution of (R)-2-amino-1-((S)-2,5-dihydrofuran-2-yl)ethanol in 1,4-dioxane (2.5 mL). The mixture was cooled to 0° C. then a solution of benzylchloroformate (75 μL, 0.53 mmol) in 1,4-dioxane (1 mL) was added dropwise over 15 minutes. The mixture was stirred at 0° C. for 25 minutes, then water (10 mL) added and the product extracted into dichloromethane (1×10 mL then 2×5 mL). The organic layer was washed with brine (5 mL), then dried ($Na_2SO_4$), filtered and reduced in vacuo to leave a residue (0.128 g). Flash chromatography over silica, eluting with ethyl acetate:heptane mixtures 20:80 to 60:40 gave alcohol (18) as a colourless oil (72 mg, 77%) that solidified to a white solid after storage at −20° C. TLC ($R_f$=0.55, EtOAc:heptane 4:1), analytical HPLC single main peak, $R_t$=10.91 min., HPLC-MS 220.1, 264.1 [M+H]$^+$, 286.1 [M+Na]$^+$, 549.2 [2M+Na]$^+$; [α]$_D^7$ −59.1° (c=3.636, CHCl$_3$); δ$_H$ (500 MHz, CDCl$_3$) 2.78 (1H, d, J=5.18 Hz, OH), 3.15-3.22 (1H, m, CH$_2$NH), 3.49-3.56 (1H, m, CH$_2$NH), 3.67-3.73 (1H, m, CHOH), 4.58-4.67 (2H, m, OCH$_2$CH═CH), 4.76-4.83 (1H, m, OCHCH═CH), 4.97-5.13 (2H, m, OCH$_2$Ph), 5.22 (1H, brs, NH), 5.84-5.89 and 5.98-6.02 (2H total, m, CH$_2$CH═CH), 7.29-7.36 (5H, aromatic CH); δ$_C$ (125 MHz, CDCl$_3$) 43.526 (CH$_2$NHCbz), 66.991 (CH$_2$Ph), 73.629 (CHOH), 75.723 (OCH$_2$CH═CH), 87.352 (OCHCH═CH), 126.036, 128.121, 128.179 and 128.529 (OCH$_2$CH═CH and Cbz aromatic CH), 136.305 (Cbz quaternary), 157.426 (Cbz C═O).

(iii) Alternative 'One-pot' procedure. A solution of methyllithium lithium iodide complex (42.8 mL, 1.0M in diethyl ether, 42.8 mmol) was added dropwise to a stirred solution containing a 7:3 mixture of diiodide (48) and diiodide (49) (12.53 g, 34.24 mmol) in tetrahydrofuran (150 mL) under argon at −70° C. over 5 minutes. The mixture was stirred for 2.25 hours then ammonium hydroxide solution (140 mL) was added dropwise over 3 minutes. The mixture was allowed to warm to ambient temperature then reduced in vacuo to leave a mixture of iodoalcohols (11,12) as an oil which was used without further purification.

The mixture of iodoalcohols (11,12) was dissolved in ammonium hydroxide (80 mL) and a solution of ammonia in ethanol (50 mL, 2.0M, 100 mmol) then heated in a sealed tube at 75° C. for 3 hours. After standing at ambient temperature for 16 hours the solution was transferred using methanol then the solvents were removed in vacuo. The residue was azeotroped with diethyl ether (3×100 mL) to obtain a mixture of alcohols (13) and (14) which was used without further purification.

A solution of sodium carbonate (7.62 g, 71.9 mmol) in water (100 mL) was added whilst stirring to a solution of alcohols (13) and (14) (assumed to be 34.24 mmol) in 1,4-dioxane (50 mL). The mixture was cooled to 0° C. then a solution of benzylchloroformate (7.33 mL, 51.36 mmol) in 1,4-dioxane (50 mL) was added dropwise over 15 minutes. The mixture was stirred at 0° C. for 1.5 hours then dichloromethane (200 mL) and water (200 mL) added. The organic phase was separated and the aqueous extracted with dichloromethane (2×200 mL). The combined organic phase was washed with brine (200 mL), then dried ($Na_2SO_4$), filtered and reduced in vacuo to leave a residue. Flash chromatography over silica, eluting with ethyl acetate:heptane mixtures 0:100 to 35:65 gave a 7:1 partially separated mixture of alcohol (18) and alcohol (17) as colourless oils (5.84 g, 65%).

(iv) Alternative 'One-pot' procedure. A solution of methyllithium (7.4 mL, 1.6M in diethyl ether, 11.8 mmol) was added dropwise to a stirred solution containing a 1.12:1 mixture of diiodides (48) and (49) (3.46 g, 9.45 mmol) in tetrahydrofuran (40 mL) under nitrogen at −70° C. over 5 minutes. The mixture was stirred for 2.25 hours then saturated aqueous ammonium chloride solution (75 mL) was added dropwise. The mixture was allowed to warm to ambient temperature, diluted with water (75 mL) then the product extracted into dichloromethane (2×75 mL). The organic phase was washed with a mixture of brine and water (1:1, 75 mL), then dried ($Na_2SO_4$), filtered and reduced in vacuo to leave a mixture of iodoethanols (11,12) as an oil which was used without further purification.

The mixture of iodoethanols (11,12) was dissolved in ammonium hydroxide (15 mL) and a solution of ammonia in 2-propanol (10 mL, 2.0M, 20 mmol) then divided into three equal portions and heated in three sealed tubes at 75° C. for 16 hours. Two of the tubes were combined (using methanol to assist with the transfer) then the solvents were removed in vacuo. The residue was azeotroped with diethyl ether (3×10 mL) to obtain a mixture of (R)- and (S)-2-amino-1-((S)-2,5-dihydrofuran-2-yl)ethanol as a yellow-brown oil which was used without further purification.

A solution of sodium carbonate (1.3 g, 12.3 mmol) in water (12 mL) was added whilst stirring to a solution of (R)- and (S)-2-amino-1-((S)-2,5-dihydrofuran-2-yl)ethanol (assumed to be 5.86 nmol) in 1,4-dioxane (12 mL). The mixture was cooled to 0° C. then a solution of benzylchloroformate (1.25 mL, 8.79 mmol) in 1,4-dioxane (4 mL) was added dropwise over 15 minutes. The mixture was stirred at 0° C. for 1.5 hours, then water (100 mL) added and the product extracted into dichloromethane (3×100 mL). The organic layer was washed with brine (100 mL), then dried ($Na_2SO_4$), filtered and reduced in vacuo to leave a residue (1.86 g). Flash chromatography over silica, eluting with ethyl acetate:heptane mixtures 20:80 to 40:60 gave a 2.9:1 partially separated mixture of alcohol (18) and alcohol (17) as colourless oils (0.75 g, 49%).

(v) Alternative 'One-pot' procedure. A solution of methyllithium (1.1 mL, 1.6M in diethyl ether, 1.71 mmol) was added dropwise to a stirred solution containing a 1.12:1 mixture of diiodides (48) and (49) (0.50 g, 1.37 mmol) in tetrahydrofuran (6 mL) under nitrogen at −70° C. over 5 minutes. The mixture was stirred for 2.25 hours then ammonium hydroxide solution (1.1 mL) was added dropwise. The mixture was allowed to warm to ambient temperature then reduced in vacuo to leave a mixture of iodoethanols (11, 12) as an oil which was used without further purification.

The mixture of iodoethanols (11, 12) was dissolved in ammonium hydroxide (3 mL) and a solution of ammonia in 2-propanol (2 mL, 2.0M, 4 mmol) then heated in a sealed tube at 75° C. for 2.75 hours. After standing at ambient temperature for 16 hours the solution was transferred using methanol then the solvents were removed in vacuo. The residue was azeotroped with diethyl ether (3×5 mL) to obtain a mixture of (R)- and (S)-2-amino-1-((S)-2,5-dihydrofuran-2-yl)ethanol which was used without further purification.

A solution of sodium carbonate (305 mg, 2.88 mmol) in water (3 mL) was added whilst stirring to a solution of (R)- and (S)-2-amino-1-((S)-2,5-dihydrofuran-2-yl)ethanol (assumed to be 1.37 mmol) in 1,4-dioxane (3 mL). The mixture was cooled to 0° C. then a solution of benzylchloroformate (0.293 mL, 2.06 mmol) in 1,4-dioxane (1 mL) was added dropwise over 5 minutes. The mixture was stirred at 0° C. for 1.5 hours then dichloromethane (25 mL) and water (25 mL) added. The organic phase was separated and the aqueous extracted with dichloromethane (2×25 mL). The combined organic phase was washed with brine (25 mL), then dried ($Na_2SO_4$), filtered and reduced in vacuo to leave a residue (0.37 g). Flash chromatography over silica, eluting with ethyl acetate:heptane mixtures 20:80 to 40:60 gave a 2.7:1 partially separated mixture of alcohol (18) and alcohol (17) as colourless oils (216 mg, 60%).

Preparation of (S)-1-((S)-2,5-Dihydrofuran-2-yl)-2-hydroxyethyl 4-methyl benzenesulfonate (14). A solution of methyllithium lithium iodide complex (5.4 mL, 1.0M in diethyl ether, 5.4 mmol) was added dropwise to a stirred solution of iodotosylates (41) (ref. Paolucci, D. et al, J. Org. Chem. 60, 169-175, 1995) (2.0 g, 4.88 mmol) in tetrahydrofuran (25 mL) under argon at −20° C. over 10 minutes. The mixture was stirred for 1 hour, then further methyllithium lithium iodide complex (0.54 mL, 11.0M in diethyl ether, 0.54 mmol) was added and stirred a further 30 mins, then saturated aqueous ammonium chloride solution (10 mL) was added dropwise. The mixture was allowed to warm to ambient temperature, diluted with water (10 mL) then the product extracted into ethyl acetate (3×50 mL). The organic phase was washed dried ($Na_2SO_4$), filtered and reduced in vacuo. Flash chromatography over silica, eluting with ethyl acetate: heptane mixtures 1:2 to 1:1 gave alcohol (14) (648 mg, 93%) as a white solid. TLC ($R_f$=0.1, EtOAc:heptane 1:2), analytical HPLC main peak, $R_t$=12.5 min; HPLC-MS 285.1 [M+H]$^+$, 302.1, 591.2 [2M+Na]$^+$; $\delta_H$ (500 MHz, CDCl$_3$) 2.12 (1H, brs, OH), 2.48 (3H, s, aryl-CH$_3$), 3.77 (2H, d, J=4.85 Hz, CH$_2$OH), 4.54-4.58 (3H, m, CH$_2$OCH), 4.94-4.98 (1H, m, CHOTs), 5.64-5.67 and 5.97-6.00 (2H total, m, CH$_2$CH=CH), 7.33 (2H, brd, J=8.23 Hz, aromatic CH$_3$CCH), 7.79 (2H, brd, J=8.31 Hz, aromatic OSO$_2$CCH); $\delta_C$ (125 MHz, CDCl$_3$) 21.660 (CH$_3$), 62.303 (CH$_2$OH), 75.940 (OCH$_2$CH=CH), 82.720 and 85.221 (OCHCHOTs), 124.792, 127.977, 129.479 and 129.749 (OCH$_2$CH=CH and aromatic CH), 133.496 (CHOSO$_2$C quaternary), 144.973 (CH$_3$C quaternary).

Alternative preparation of (3R,3aS,6R,6aS)-Hexahydrofurol-[3,2-b]furan-3,6-diyl bis(4-methylbenzenesulfonate) (39). Isomannide (40) (50 g, 342.5 mmol) and p-toluenesulphonyl chloride (143.6 g, 753.2 mmol) were dissolved in a mixture of carbon tetrachloride (300 mL), dichloromethane (30 mL) and water (250 mL). The flask was cooled to 0° C. and a solution of potassium hydroxide (42.0 g, 750.0 mmol) in water (42 mL) added dropwise over 2 hours with stirring under argon. The resulting biphasic mixture was stirred vigorously at 0° C. for 24 hours. The resulting off-white precipitate, comprising a mixture of mono- and bistosylates (approximately 1:1), was collected by filtration in vacuo. The filter cake was washed with water then triturated with methanol (500 mL). The solid was isolated by filtration in vacuo to obtain ditosylate (39) as an off-white powder (75 g, 48%). $[\alpha]_D^{18}$+96.7° (c=10.5, CHCl$_3$).

Preparation of (3R,3aS,6S,6aS)-6-Bromohexahydrofurol[3,2-b]furan-3-yl 4-methylbenzenesulfonate (46). A stirred mixture of ditosylate (39) (16.9 g, 37.22 mmol) and lithium bromide (4.85 g, 55.84 mmol) in N,N-dimethylformamide (100 mL) was heated at 100° C. for 27 hours. The mixture was allowed to cool then water (150 mL) added before extracting with tert-butyl methyl ether (1×100 mL then 5×50 mL). The organic phase was dried (MgSO$_4$), filtered and reduced in vacuo to give a colourless oil which solidified on standing. Flash chromatography over silica, eluting with ethyl acetate: heptane mixtures 0:100 to 80:20 gave bromotosylate (46) as a white solid (2.86 g, 29%). TLC ($R_f$=0.45 diethyl ether: heptane, 1:1), analytical HPLC: $R_t$=16.768 min; HPLC-MS: 363.1/365.0 [M+H]$^+$, 380.1/382.1, 749.0/751.0 [2M+Na]$^+$; $[\alpha]_D^{18}$+64.7° (c=8.5, CHCl$_3$); $\delta_H$ (500 MHz, CDCl$_3$) 2.45 (3H, s, CH$_3$), 3.74 (1H, dd, J=9.60 and 7.05 Hz, CH$_2$), 3.95 (1H, dd, J=9.60 and 6.47 Hz, CH$_2$), 4.14-4.22 (2H, m, CH$_2$), 4.29 (1H, d, J=3.03 Hz, CHBr), 4.68 (1H, d, J=4.03 Hz, CHCH), 4.76 (1H, t, J=4.48 Hz, CHOTs), 4.87 (1H, m, CHCH), 7.36 (2H, brd, J=7.97 Hz, aromatic CH$_3$CCH), 7.83 (2H, brd, J=8.33 Hz, aromatic OSO$_2$CCH). $\delta_C$ (125 MHz, CDCl$_3$) 21.69 (CH$_3$), 50.06 (CHBr), 70.26 (CH$_2$CHOTs), 76.54 (CH$_2$CHBr), 78.27 (CHOTs), 80.17 and 88.80 (CHCHCHOTs), 127.98 and 129.94 (aromatic CH), 133.01 (CHOSO$_2$C quaternary), 145.28 (CH$_3$C quaternary).

Preparation of (3R,3aS,6R,6aR)-6-Hydroxyhexahydrofuro[3,2-b]furan-3-yl 4-methylbenzenesulfonate (50). Isomannide (40) (10 g, 68.49 mmol) and p-toluenesulphonyl chloride (6.53 g, 34.25 mmol) were dissolved in a mixture of carbon tetrachloride (50 mL), dichloromethane (5 mL) and water (40 mL). The flask was cooled to 0° C. and a solution of potassium hydroxide (1.92 g, 34.25 mmol) in water (5 mL) added dropwise over 30 minutes with stirring. The resulting biphasic mixture was stirred at 0° C. for 7 hours. Then off-white precipitate was collected by filtration in vacuo then partitioned between dichloromethane (30 mL) and water (10 mL). The organic phase was washed with brine (2×10 mL) then dried (Na$_2$SO$_4$), filtered and reduced in vacuo to leave a colourless solid. Recrystallisation from carbon tetrachloride gave monotosylate (50) as colourless granules (3.92 g, 38%). TLC ($R_f$=0.11, EtOAc:heptane 1:1); analytical HPLC main peak, $R_t$=10.692 min; HPLC-MS 318.2, 323.1 [M+Na]$^+$, 623.2 [2M+Na]$^+$; $[\alpha]_D^{18}$+72.2° (c=5.4, CHCl$_3$); $\delta_H$ (500 MHz, CDCl$_3$) 2.44 (3H, s, CH$_3$), 3.54 (1H, dd, J=9.31 and 7.23 Hz, OCH$_2$CHOH), 3.78 (1H, dd, J=9.18 and 7.59 Hz, OCH$_2$CHOTs), 3.95 (1H, dd, J=9.36 and 6.45 Hz, OCH$_2$CHOH), 4.01 (1H, dd, J=9.33 and 6.64 Hz, OCH$_2$CHOTs), 4.26 (1H, m, CHOH), 4.42 and 4.48 (each 1H, brt, J=5.03 and 5.00 Hz respectively, CHCHCHOH and CHCHCHOTs), 4.90 (1H, dd, J=12.15 and 6.84 Hz, CHOTs), 7.37 (2H, d, J=8.13 Hz, aromatic CH$_3$CCH), 7.82 (2H, d, J=8.20 Hz, aromatic OSO$_2$CCH); $\delta_C$ (125 MHz, CDCl$_3$) 21.69 (CH$_3$), 70.03 (CH$_2$CHOTs), 72.29 (CHOTs), 74.02 (CH$_2$CHOH), 80.00 (CH$_2$CHOH), 81.36 (CHCHOTs), 81.76 (CHCHOH), 128.00 and 129.89 (aromatic CH), 133.04 (CHOSO$_2$C quaternary), 145.26 (CH$_3$C quaternary).

Alternative preparation of (3R,3aS,6R,6aR)-6-Hydroxyhexahydrofurol-[3,2-b]furan-3-yl 4-methylbenzenesulfonate (50). A solution of p-toluenesulfonyl chloride (24.8 g, 130 mmol) in pyridine (150 mL) was added to a stirred solution of isomannide (40) (19.0 g, 130 mmol) in pyridine (150 mL) over 1 hour at 0° C. then stirred at ambient temperature for 1 hour. The mixture was poured onto iced-water (1 L) then extracted with dichloromethane (3×300 mL). The organic phase washed with brine (300 mL), dried (MgSO$_4$), filtered and reduced in vacuo to leave a residue. Flash chromatography over silica, eluting with ethyl acetate:heptane mixtures 0:100 to 50:50 gave monotosylate (50) (23.4 g, 60%) as a white solid.

Alternative preparation of (3R,3aS,6S,6aS)-6Bromohexahydrofuro[3,2-b]furan-3-yl 4-methylbenzenesulfonate (46). A solution of carbon tetrabromide (18.12 g, 54.63 mmol) in pyridine (100 mL) was added to a solution of monotosylate (50) (14.9 g, 49.66 mmol) and triphenylphosphine (26.1 g, 99.32 mmol) in pyridine (150 mL) over 30 minutes, then the mixture heated at 65° C. for 1.5 hours under an atmosphere of argon. Water (200 mL) was added then the aqueous phase extracted with dichloromethane (5×100 mL). The organic phase was washed with brine (50 mL), then dried (MgSO$_4$), filtered and reduced in vacuo to leave a residue which was azeotroped with toluene (5×50 mL). Flash chromatography over silica, eluting with diethyl ether:heptane mixtures 0:100 to 100:0 gave bromotosylate (46) (7.70 g, 43%) as a white solid. $[\alpha]_D^{17}$+68.6° (c=0.51, CHCl$_3$).

Alternative preparation of (R)-1-((S)-2,5-Dihydrofuran-2-yl)-2-hydroxyethyl 4-methyl benzenesulfonate (13). A solution of ammonium chloride (100 mg, 1.87 mmol) in water (1.25 mL) then zinc dust (100 mg, 1.54 mmol) were added to a solution of bromotosylate (46) (0.5 g, 1.38 mmol) in tetrahydrofuran (5 mL) and propan-2-ol (2.5 mL) under argon. The mixture was stirred for 16 hours before filtering the suspension through celite in vacuo. The filter cake was washed with diethyl ether (20 mL). Hydrochloric acid (1M, 20 mL) was added to the filtrate then the organic phase separated. The aqueous layer was extracted with diethyl ether (20 mL) then the combined organic phase was washed with brine (20 mL), then dried (MgSO$_4$), filtered and reduced in vacuo to leave a residue. Flash chromatography over silica, eluting with ethyl acetate:heptane mixtures 20:80 to 50:50 gave alcohol (13) (292 mg, 75%) as a white solid. $[\alpha]_D^{15}$−64.8° (c=9.8, CHCl$_3$).

Alternative preparation of Benzyl (S)-2-((S)-2,5-dihydrofuran-2-yl)-2-hydroxyethylcarbamate (17); Zinc and 'One-pot' procedure. A solution of ammonium chloride (560 mg, 10.5 mmol) in water (7 mL) was added to a solution of bromotosylate (46) (2.86 g, 7.88 mmol) in propan-2-ol (14 mL) under argon. Zinc dust (560 mg, 8.67 mmol) was then added in portions over 4 minutes then the suspension stirred for 16 hours before filtering through celite in vacuo. The filter cake was washed with diethyl ether (60 mL). Hydrochloric acid (1M, 60 mL) was added to the filtrate then the organic phase separated. The aqueous layer was extracted with diethyl ether (60 mL) then the combined organic phase was washed with brine (60 mL), then dried (MgSO$_4$), filtered and reduced in vacuo. The residue was dissolved in ammonium hydroxide (18 mL) and a solution of ammonia in propan-2-ol (12 mL, 2.0M, 24 mmol) then divided into three equal portions and heated in sealed tubes at 75° C. for 16 hours. The mixtures were combined using methanol then the solvents were removed in vacuo. The residue was azeotroped with diethyl ether (3×10 mL) to obtain (S)-2-amino-1-((S)-2,5-dihydrofuran-2-yl)ethanol which was used without further purification.

A solution of sodium carbonate (1.75 g, 16.6 mmol) in water (16 mL) was added whilst stirring to a solution of (S)-2-amino-1-((S)-2,5-dihydrofuran-2-yl)ethanol (assumed to be 7.88 mmol) in 1,4-dioxane (20 mL). The mixture was cooled to 0° C. then benzylchloroformate (1.69 mL, 11.82 mmol) was added dropwise over 10 minutes. The mixture was stirred at 0° C. for 85 minutes, then dichloromethane (75 mL) and water (100 mL) added. The organic phase was separated and the aqueous extracted with dichloromethane (2×50 mL). The organic layer was washed with brine (50 mL), then dried (Na$_2$SO$_4$), filtered and reduced in vacuo to leave a residue (3.1 g). Flash chromatography over silica, eluting with ethyl acetate:heptane mixtures 20:80 to 70:30 gave alcohol (17) (1.10 g, 53%). $[\alpha]_D^{18}$−83.1° (c=9.9, CHCl$_3$).

Preparation of (3R,3aS,6S,6aS)-Hexahydrofuro[3,2-b]furan-3,6-diyl bis(4-methylbenzenesulfonate) (42). A stirred solution of p-toluenesulfonyl chloride (57.4 g, 301 mmol) and isosorbide (43) (20 g, 137 mmol) in pyridine (315 mL) was heated at 95° C. for 4.5 hours under an atmosphere of argon then stood at ambient temperature for 16 hours before being poured onto iced-water (1 L). The aqueous was extracted with dichloromethane (2×500 mL), then the combined organic layers were washed with water (2×500 mL), then dried (Na$_2$SO$_4$), filtered then reduced in vacuo to leave a viscous oil (65.22 g). The oil was crystallized from hot methanol (350 mL). The white solid was collected by filtration in vacuo, then washed with methanol (100 mL) and dried in vacuo to obtain ditosylate (42) as a white solid (45.87 g, 74%). TLC (R$_f$=0.30, EtOAc:heptane 2:3), analytical HPLC single main peak, R$_t$=20.219 min., HPLC-MS 455.1 [M+H]$^+$, 931.2 [2M+Na]$^+$, $[\alpha]_D^{20}$+57.2° (c=10.2, CHCl$_3$); $\delta_H$ (500 MHz, CDCl$_3$) 2.44 (6H, s, CH$_3$), 3.68 (1H, dd, J=9.80 and 6.46 Hz, CH$_2$), 3.82-3.87 (2H, m, CH$_2$), 3.94 (1H, d, J=11.28 Hz, CH$_2$), 4.46 (1H, d, J=4.44 Hz, CHCHOTs), 4.58 (1H, t, J=4.74 Hz, CHCHOTs), 4.82-4.86 (2H, m, CHOTs), 7.32-7.36 (4H, m, aromatic CH$_3$CCH), 7.74-7.80 (4H, m, aromatic OSO$_2$CCH).

Alternative preparation of (3R,3aS,6S,6aS)-Hexahydrofurol-[3,2-b]furan-3,6-diyl bis(4-methylbenzenesulfonate) (42). Triethylamine (123.2 mL, 876 mmol) was added dropwise to a stirred solution of p-toluenesulfonyl chloride (156.6 g, 822 mmol) and isosorbide (43) (40 g, 274 mmol) in dichloromethane (600 mL) over 15 minutes. The mixture was stirred at 25° C. for 16 hours then at 50° C. for 4 hours before diluting with dichloromethane (1 L). The organic layer was washed with water (2×1 L), then dried (Na$_2$SO$_4$), filtered then reduced in vacuo to leave a viscous oil. The oil was crystallized from hot methanol (600 mL) to obtain ditosylate (42) as a white solid (120.1 g, 97%). $[\alpha]_D^{15}$+56.3° (c=11.2, CHCl$_3$).

Alternative preparation of (3R. 3aS,6S,6aS)-Hexahydrofuro[3,2-b]furan-3,6-diyl bis(4-methylbenzenesulfonate) (42). Triethylamine (123.2 mL, 876 mmol) was added over 15 minutes to a stirred solution of isosorbide (43) (40 g, 274 mmol) and p-toluenesulfonyl chloride (156.6 g, 822 mmol) in dichloromethane (600 mL). The mixture was heated at 25° C. for 4 hours, then at 50° C. for 4 hours. Dichloromethane (1 L) was added then the mixture was washed with water (2×1 L), then dried (Na$_2$SO$_4$), filtered then reduced in vacuo to leave a viscous oil. The oil was crystallized from methanol (600 mL) to obtain ditosylate (42) (123.7 g, 99%) as an off-white solid.

Preparation of (3S,3aS,6s,6aS)-6-Bromohexahydrofuro[3,2-b]furan-3-yl 4-methylbenzenesulfonate (47). Lithium bromide (9.6 g, 110.1 mmol) was added to a stirred solution of ditosylate (42) (20.0 g, 44.05 mmol) in dimethylformamide (100 mL) under an atmosphere of argon. The mixture was heated at 110° C. for 5 hours then stood at ambient temperature for 3 days, then heated at 90° C. for 3.5 hours. The mixture was diluted with water (250 mL) extracted with tert-butyl methyl ether (4×125 mL) then the organic phase washed with water (3×125 mL), brine (125 mL), dried (MgSO$_4$), filtered and reduced in vacuo to leave a brown oil (16.8 g). Flash chromatography over silica, eluting with ethyl acetate: heptane mixtures 0:100 to 30:70 gave bromotosylate (47) (11.88 g, 74%) as a pale yellow solid. TLC (R$_f$=0.20, EtOAc: heptane 1:3); analytical HPLC main peak, R$_t$=18.050 min; HPLC-MS 381.0/383.0 [M+H$_2$O+H]$^+$, 385.0/387.0 [M+Na]$^+$; $[\alpha]_D^{18}$+51.0° (c=5.0, CHCl$_3$); $\delta_H$ (500 MHz, CDCl$_3$) 2.45 (3H, s, CH$_3$), 3.84 (1H, dd, J=11.19 and 3.51 Hz, CH$_2$), 4.05-4.15 (3H, m, CH$_2$), 4.28 (1H, d, J=3.40 Hz, CHBr), 4.78 (1H, d, J=3.37 Hz, CHCH), 4.84 (1H, d, J=3.42 Hz, CHOTs), 4.90 (1H, d, J=3.37 Hz, CHCH), 7.36 (2H, brd, J=7.98 Hz, aromatic CH$_3$CCH), 7.79 (2H, brd, J=8.32 Hz, aromatic OSO$_2$CCH).

Alternative preparation of (3S,3aS,6S,6 as)-6-Bromohexahydrofuro[3,2-b]furan-3-yl 4-methylbenzenesulfonate (47). Lithium bromide (38.4 g, 440 mmol) was added to a stirred solution of ditosylate (42) (80 g, 176 mmol) in dimethylformamide (400 mL) under an atmosphere of argon. The mixture was heated at 110° C. for 8 hours. The mixture was diluted with water (1 L) extracted with tert-butyl methyl ether (4×500 mL) then the organic phase washed with water (3×500 mL), brine (500 mL), dried (MgSO$_4$), filtered and reduced in vacuo to leave a brown oily residue. The residue was triturated with diethyl ether then the solid collected by filtration in vacuo to obtain bromotosylate (47) (22.02 g) as an off-white solid. The diethyl ether layer was concentrated in vacuo, then the residue was recrystallised from methanol (50 mL) to bromotosylate (47) (17.6 g) as pale brown solid (combined yield 62%).

Alternative preparation of (3S,3aS,6S,6aS)-6-Bromo-hexahydrofuro[3,2-b]furan-3-yl 4-methylbenzenesulfonate (47). Lithium bromide (19.2 g, 220.2 mmol) was added to a stirred solution of ditosylate (42) (40.0 g, 88.1 mmol) in dimethyl sulfoxide (200 mL) under an atmosphere of argon. The mixture was heated at 110° C. for 8 hours then at 120° C. for 1.75 hours. The mixture was diluted with water (500 mL) then extracted with tert-butyl methyl ether (4×250 mL). The organic phase was washed with water (3×250 mL) then brine (250 mL), dried (MgSO$_4$), filtered and reduced in vacuo to leave an orange solid. Recrystallisation from methanol (100 mL) gave bromotosylate (47) (17.47 g, 55%) as a pale yellow solid. $[\alpha]_D^{15}$+49.5° (c=11.7, CHCl$_3$).

Alternative preparation of (S)-1-((S)-2,5-Dihydrofuran-2-yl)-2-hydroxyethyl 4 methyl benzenesulfonate (14). Ammonium chloride (20 mg, 0.37 mmol) then zinc dust (20 mg, 0.31 mmol) were added to a solution of bromotosylate (47) (100 mg, 0.28 mmol) in ethanol (1.5 mL) under argon. The mixture was stirred for 16 hours before filtering the suspension through celite in vacuo. The filter cake was washed with ethanol (20 mL) then the filtrate reduced in vacuo to leave a residue (111 mg). Flash chromatography over silica, eluting with ethyl acetate:heptane mixtures 20:80 to 40:60 gave alcohol (14) (53 mg, 68%) as a white solid. TLC (R$_f$=0.15, EtOAc:heptane 1:2); analytical HPLC main peak, R$_t$=12.543 min; HPLC-MS 285.1 [M+H]$^+$, 302.1, 591.2 [2M+Na]$^+$; $[\alpha]_D^{15}$–86.8° (c=5.3, CHCl$_3$); $\delta_H$ (500 MHz, CDCl$_3$) 2.12 (1H, brs, OH), 2.44 (3H, s, aryl-CH$_3$), 3.77 (2H, d, J=4.85 Hz, CH$_2$OH), 4.54-4.58 (3H, m, CH$_2$OCH), 4.94-4.98 (1H, m, CHOTs), 5.64-5.67 and 5.97-6.00 (2H total, m, CH$_2$CH=CH), 7.33 (2H, brd, J=8.23 Hz, aromatic CH$_3$CCH), 7.79 (2H, brd, J=8.31 Hz, aromatic OSO$_2$CCH); $\delta_C$ (125 MHz, CDCl$_3$) 21.660 (CH$_3$), 62.303 (CH$_2$OH), 75.940 (OCH$_2$CH=CH), 82.720 and 85.221 (OCHCHOTs), 124.792, 127.977, 129.479 and 129.749 (OCH$_2$CH=CH and aromatic CH), 133.496 (CHOSO$_2$C quaternary), 144.973 (CH$_3$C quaternary).

Alternative preparation of (S)-1-((S)-2,5-Dihydrofuran-2-yl)-2-hydroxyethyl 4-methyl benzenesulfonate (14). Ammonium chloride (200 mg, 3.7 mmol) then zinc dust (200 mg, 3.1 mmol) were added to a suspension of bromotosylate (47) (1 g, 2.75 mmol) in propan-2-ol (15 mL) under argon. The mixture was stirred for 16 hours before filtering the suspension through celite in vacuo. The filter cake was washed with propan-2-ol (20 mL) then the filtrate reduced in vacuo to leave a residue (1.43 g). Flash chromatography over silica, eluting with ethyl acetate:heptane mixtures 20:80 to 50:50 gave alcohol (14) (566 mg, 72%) as a white solid. $[\alpha]_D^{16}$–850.8° (c=10.2, CHCl$_3$).

Alternative preparation of (S)-14(S)-2,5-Dihydrofuran-2-yl)-2-hydroxyethyl 4-methyl benzenesulfonate (14). A solution of ammonium chloride (200 mg, 3.7 mmol) in water (2.5 mL) then zinc dust (200 mg, 3.1 mmol) were added to a solution of bromotosylate (47) (1 g, 2.75 mmol) in tetrahydrofuran (10 mL) under argon. The mixture was stirred for 16 hours before filtering the suspension through celite in vacuo. The filter cake was washed with tert-butyl methyl ether (20 mL). Water (20 mL) and brine (20 mL) were added to the filtrate then the organic phase separated. The aqueous layer was extracted with tert-butyl methyl ether (20 mL) then the combined organic phase was washed with brine (20 mL), dried (MgSO$_4$), filtered and reduced in vacuo to leave a residue (0.82 g). Flash chromatography over silica, eluting with ethyl acetate:heptane mixtures 20:80 to 50:50 gave alcohol (14) (544 mg, 70%) as a white solid. $[\alpha]_D^{15}$–86.1° (c=10.8, CHCl$_3$).

Alternative preparation of (S)1-(S)-2,5-Dihydrofuran-2-yl)-2-hydroxyethyl 4 methyl benzenesulfonate (14). A solution of ammonium chloride (200 mg, 3.7 mmol) in water (2.5 mL) then zinc dust (200 mg, 3.1 mmol) were added to a solution of bromotosylate (47) (1 g, 2.75 mmol) in tetrahydrofuran (10 mL) and propan-2-ol (5 mL) under argon. The mixture was stirred for 16 hours before filtering the suspension through celite in vacuo. The filter cake was washed with diethyl ether (20 mL). Hydrochloric acid (1M, 20 mL) was added to the filtrate then the organic phase separated. The aqueous layer was extracted with diethyl ether (20 mL) then the combined organic phase was washed with brine (20 mL), then dried (MgSO$_4$), filtered and reduced in vacuo to leave a residue (1.06 g). Flash chromatography over silica, eluting with ethyl acetate:heptane mixtures 20:80 to 50:50 gave alcohol (14) (528 mg, 68%) as a white solid. $[\alpha]_D^{16}$–82.7° (c=11.3, CHCl$_3$).

Alternative preparation of (S)-1-((S)-2,5-Dihydrofuran-2-yl)-2-hydroxyethyl 4-methyl benzenesulfonate (14). A solution of methyllithium lithium iodide complex (6.6 mL, 11.0M in diethyl ether, 6.6 mmol) was added dropwise to a stirred solution of bromotosylate (47) (2.0 g, 5.5 mmol) in tetrahydrofuran (25 mL) under argon at –70° C. over 10 minutes. The mixture was stirred for 2 hours before dropwise addition of saturated aqueous ammonium chloride solution (12 mL). The mixture was allowed to warm to ambient temperature then extracted with ethyl acetate (3×25 mL). The organic phase was dried (Na$_2$SO$_4$), filtered and reduced in vacuo to leave a residue (1.5 g). Flash chromatography over silica, eluting with ethyl acetate:heptane mixtures 25:75 to 35:65 gave alcohol (14) (315 mg, 20%) as a white solid.

Alternative preparation of (S)-1-((S)-2,5-Dihydrofuran-2-yl)-2-hydroxyethyl 4-methyl benzenesulfonate (14). A solution of n-butyllithium (4.1 mL, 1.6M in hexanes, 6.6 mmol) was added dropwise to a stirred solution of bromotosylate (47) (2.0 g, 5.5 mmol) in tetrahydrofuran (25 mL) under argon at –70° C. over 10 minutes. The mixture was stirred for 1 hour before dropwise addition of saturated aqueous ammonium chloride solution (12 mL). The mixture was allowed to warm to ambient temperature then extracted with ethyl acetate (3×25 mL). The organic phase was dried (Na$_2$SO$_4$), filtered and reduced in vacuo to leave a residue (0.935 g). Flash chromatography over silica, eluting with ethyl acetate:heptane mixtures 25:75 to 35:65 gave alcohol (14) (590 mg, 38%) as a white solid.

Alternative preparation of (S)-1-((S)-2,5-Dihydrofuran-2-yl)-2-hydroxyethyl 4-methyl benzenesulfonate (14). A solution of methyllithium (6.6 mL, 0.98M in diethyl ether, 6.6 mmol) was added dropwise to a stirred solution of bromotosylate (47) (2.0 g, 5.5 mmol) in tetrahydrofuran (25 mL) under argon at –70° C. over 10 minutes. The mixture was stirred for 2 hours before dropwise addition of saturated aqueous ammonium chloride solution (12 mL). The mixture was allowed to warm to ambient temperature then extracted with ethyl acetate (3×25 mL). The organic phase was dried (Na₂SO₄), filtered and reduced in vacuo to leave a residue (1.8 g). Flash chromatography over silica, eluting with ethyl acetate:heptane mixtures 25:75 to 50:50 gave alcohol (14) (419 mg, 27%) as a white solid.

Alternative preparation of (S)-1-((S)-2,5-Dihydrofuran-2-yl)-2-hydroxyethyl 4-methyl benzenesulfonate (14). A solution of ammonium chloride (4 g, 74.8 mmol) in water (50 mL) then zinc dust (4 g, 61.6 mmol) were added to a solution of bromotosylate (47) (20 g, 55 mmol) in tetrahydrofuran (200 mL) and propan-2-ol (100 mL). The mixture was stirred for 16 hours before filtering the suspension through celite in vacuo. The filter cake was washed with diethyl ether (400 mL). Hydrochloric acid (1M, 400 mL) was added to the filtrate then the organic phase separated. The aqueous layer was extracted with diethyl ether (400 mL) then the combined organic phase was washed with brine (400 mL), then dried (MgSO₄), filtered and reduced in vacuo to leave a residue. Flash chromatography over silica, eluting with ethyl acetate:heptane mixtures 0:100 to 50:50 gave alcohol (14) (11.28 g, 72%) as a pale yellow oil. $[\alpha]_D^{14}$–77.1° (c=9.15, CHCl₃).

Alternative preparation of Benzyl (R)-2-(S)-2,5-dihydrofuran-2-yl)-2-hydroxyethylcarbamate (18). Alcohol (14) (4.3 g, 15.1 mmol) was dissolved in ammonium hydroxide (30 mL) and a solution of ammonia in 2-propanol (20 mL, 2.0M, 80 mmol). The solution was divided into two equal portions then heated at 75° C. in sealed tubes for 16 hours. The mixtures were combined using methanol then the solvents were removed in vacuo. The residue was azeotroped with diethyl ether (3×20 mL) to obtain (R)-2-amino-1-((S)-2,5-dihydrofuran-2-yl)ethanol which was used without further purification.

A solution of sodium carbonate (3.37 g, 31.8 mmol) in water (24 mL) was added whilst stirring to a suspension of (R)-2-amino-1-((S)-2,5-dihydrofuran-2-yl)ethanol (assumed to be 15.1 mmol) in 1,4-dioxane (30 mL). The mixture was cooled to 0° C. then benzylchloroformate (2.7 mL, 18.9 mmol) was added dropwise over 10 minutes. The mixture was stirred at 0° C. for 45 minutes then dichloromethane (100 mL) and water (150 mL) added. The organic phase was separated and the aqueous extracted with dichloromethane (2×50 mL). The organic layer was washed with brine (50 mL), then dried (Na₂SO₄), filtered and reduced in vacuo to leave a residue (5.2 g). Flash chromatography over silica, eluting with ethyl acetate:heptane mixtures 20:80 to 70:30 gave alcohol (18) (3.09 g, 78%). $[\alpha]_D^{16.5}$–58.7° (c=5.88, CHCl₃).

Alternative preparation of Benzyl (R)-2-((S)-2,5-dihydrofuran-2-yl)-2-hydroxyethylcarbamate (18); Zinc and 'One-pot' procedure. A solution of ammonium chloride (600 mg, 11.2 mmol) in water (7.5 mL) was added to a solution of bromotosylate (47) (3.0 g, 8.26 mmol) in propan-2-ol (15 mL) under argon. Zinc dust (600 mg, 9.2 mmol) was then added in portions over 4 minutes and the mixture was stirred for 16 hours before filtering the suspension through celite in vacuo. The filter cake was washed with diethyl ether (60 mL). Hydrochloric acid (1M, 60 mL) was added to the filtrate then the organic phase separated. The aqueous layer was extracted with diethyl ether (60 mL) then the combined organic phase was washed with brine (60 mL), then dried (MgSO₄), filtered and reduced in vacuo. The residue was dissolved in ammonium hydroxide (18 mL) and a solution of ammonia in propan-2-ol (12 mL, 2.0M, 24 mmol), then divided into two equal portions and heated in sealed tubes at 75° C. for 16 hours. The mixtures were combined using methanol then the solvents were removed in vacuo. The residue was azeotroped with diethyl ether (3×10 mL) to obtain (R)-2-amino-1-((S)-2,5-dihydrofuran-2-yl)ethanol which was used without further purification.

A solution of sodium carbonate (1.84 g, 17.4 mmol) in water (16 mL) was added whilst stirring to a suspension of (R)-2-amino-1-((S)-2,5-dihydrofuran-2-yl)ethanol (assumed to be 8.26 mmol) in 1,4-dioxane (20 mL). The mixture was cooled to 0° C. then benzylchloroformate (1.77 mL, 12.4 mmol) was added dropwise over 5 minutes. The mixture was stirred at 0° C. for 55 minutes then dichloromethane (75 mL) and water (100 mL) added. The organic phase was separated and the aqueous extracted with dichloromethane (2×50 mL). The organic phase was washed with brine (50 mL), then dried (Na₂SO₄), filtered and reduced in vacuo to leave a residue (3.7 g). Flash chromatography over silica, eluting with ethyl acetate:heptane mixtures 20:80 to 70:30 gave alcohol (18) (1.26 g, 58%). $[\alpha]_D^{16}$–62.0° (c=5.0, CHCl₃).

Alternative preparation of Benzyl (R)-2-((S)-2,5-dihydrofuran-2-yl)-2-hydroxyethylcarbamate (18); Zinc and 'One-Pot' Procedure 2. A solution of ammonium chloride (4 g, 74.8 mmol) in water (50 mL) then zinc dust (4 g, 61.6 mmol) were added to a solution of bromotosylate (47) (20 g, 55 mmol) in tetrahydrofuran (200 mL) and propan-2-ol (100 mL). The mixture was stirred for 6 hours then zinc dust (4 g, 61.6 mmol) was added. The mixture was stirred for an additional 16 hours before filtering the suspension through celite in vacuo. The filter cake was washed with diethyl ether (400 mL). Hydrochloric acid (1M, 400 mL) was added to the filtrate then the organic phase separated. The aqueous layer was extracted with diethyl ether (400 mL) then the combined organic phase was washed with brine (400 mL), then dried (MgSO₄), filtered and reduced in vacuo to leave a residue. The residue was partially dissolved in ammonium hydroxide (92 mL) and a solution of ammonia in 2-propanol (60 mL, 2.0M, 120 mmol) then divided into 6 equal portions and heated in sealed tubes at 75° C. for 16 hours. The mixtures were combined using methanol, then the solvents were removed in vacuo. The residue was azeotroped with diethyl ether (3×50 mL) to obtain (R)-2-amino-1-((S)-2,5-dihydrofuran-2-yl)ethanol which was used without further purification.

A solution of sodium carbonate (12.26 g, 115.7 mmol) in water (80 mL) was added whilst stirring to a solution of (R)-2-amino-1-((S)-2,5-dihydrofuran-2-yl)ethanol (assumed to be 55 mmol) in tetrahydrofuran (100 mL). The mixture was cooled to 0° C. then benzylchloroformate (9.69 mL, 68.87 mmol) was added. The mixture was stirred at 0° C. for 45 minutes, then dichloromethane (400 mL) and water (400 mL) added. The organic phase was separated and the aqueous reextracted with dichloromethane (2×400 mL). The organic layer was washed with brine (400 mL), then dried (Na₂SO₄), filtered and reduced in vacuo to leave a residue. Flash chromatography over silica, eluting with ethyl acetate:heptane mixtures 0:100 to 65:35 gave alcohol (18) (11.58 g, 80%) as a pale yellow oil.

Alternative preparation of Benzyl (R)-2-((S)-2,5-dihydrofuran-2-yl)-2-hydroxyethylcarbamate (18); 'One-pot' procedure 3; Aqueous Conditions. (S)-1-((S)-2,5-Dihydrofuran-2-yl)-2-hydroxyethyl 4-methylbenzenesulfonate (14) (0.95 g, 3.35 mmol) was suspended in ammonium hydroxide (4 mL) then stirred and heated at 75° C. in a sealed tube for 6 hours during which time the two liquid phases became a single phase solution. The mixture was stirred at ambient temperature for 20 hours then the solvents were removed in vacuo. The residue was azeotroped with diethyl ether (3×10 mL) to obtain (R)-2-amino-1-((S)-2,5-dihydrofuran-2-yl)ethanol which was used without further purification.

1,4-Dioxane (7 mL) then a solution of sodium carbonate (745 mg, 7.02 mmol) in water (6 mL) was added whilst stirring to the crude (R)-2-amino-1-((S)-2,5-dihydrofuran-2-yl)ethanol (assumed to be 3.35 mmol) then the mixture was cooled to 0° C. Benzylchloroformate (0.597 mL, 4.18 mmol) was added dropwise over 25 minutes then the mixture was stirred at 0° C. for 4 hours before adding dichloromethane (25 mL) and water (30 mL). The organic phase was separated and the aqueous reextracted with dichloromethane (2×10 mL). The organic layer was washed with brine (10 mL), then dried ($Na_2SO_4$), filtered and reduced in vacuo to leave an orange oil (1.14 g). Flash chromatography over silica, eluting with ethyl acetate:heptane mixtures 20:80 to 55:45 gave alcohol (18) (613 mg, 70%). $[\alpha]_D^{22}$ –38.5° (c=2.99, $CHCl_3$).

Preparation of tert-Butyl (R)-2-((S)-2,5-dihydrofuran-2-yl)-2-hydroxyethyl carbamate (80). (S)-1-((S)-2,5-dihydrofuran-2-yl)-2-hydroxyethyl 4-methylbenzenesulfonate (14) (1.0 g, 3.52 mmol) was suspended in ammonium hydroxide (8 mL) then stirred and heated at 75° C. in a sealed tube for 6.5 hours during which time the two liquid phases became a single phase solution. The mixture was stood at ambient temperature for 2 days then the solvents were removed in vacuo. The residue was azeotroped with diethyl ether (3×10 mL) to obtain (R)-2-amino-1-((S)-2,5-dihydrofuran-2-yl) ethanol which was used without further purification.

Ethyl acetate (20 mL) then di-tert-butyl dicarbonate (806 mg, 3.70 mmol) were added whilst stirring to the crude (R)-2-amino-1-((S)-2,5-dihydrofuran-2-yl)ethanol (assumed to be 3.52 mmol) then the suspension was stirred for 30 minutes before adding dichloromethane (5 mL). The mixture was stirred for 3 hours then di-tert-butyl dicarbonate (806 mg, 3.70 mmol) was added. The mixture was stirred for 45 minutes then dichloromethane (10 mL) and water (10 mL) were added. The mixture was stirred for 20 hours then a solution of sodium carbonate (930 mg, 8.8 mmol) in water (5 mL) was added The mixture was stirred for 2 hours then di-tert-butyl dicarbonate (403 mg, 1.85 mmol) was added. The mixture was stirred for 2.5 hours then water (75 mL) and dichloromethane (50 mL) were added. The organic phase was separated and the aqueous reextracted with dichloromethane (2×50 mL). The combined organic layers were dried ($Na_2SO_4$), filtered and reduced in vacuo to leave a pale yellow oil (2.03 g). Flash chromatography over silica, eluting with ethyl acetate:heptane mixtures 20:80 to 70:30 gave alcohol (80) as a colourless oil (637 mg, 79%). TLC ($R_f$=0.45, EtOAc: heptane 1:1), analytical HPLC single main peak, $R_t$=6.77 min., HPLC-MS 130.1 [M+2H–$^t$BuOCO]$^+$, 174.1 [M+2H–$^t$Bu]$^+$, 252.1 [M+Na]$^+$, 481.2 [2M+Na]$^+$; $[\alpha]_D^{24}$–71.3° (c=3.715, $CHCl_3$); $\delta_H$ (500 MHz, $CDCl_3$) 1.42 (9H, s, $C(CH_3)_3$), 3.08 (1H, brs, OH), 3.09 (1H, dd, J=14.2 and 7.5 Hz, $CH_2NH$), 3.43 (1H, dd, J=14.1 and 2.3 Hz, $CH_2NH$), 3.62-3.67 (1H, m, CHOH), 4.57-4.67 (2H, m, $OCH_2CH$=CH), 4.73-4.80 (1H, m, OCHCH=CH), 5.08 (1H, brs, NH), 5.85-5.89 and 5.96-6.00 (1H each, m, $CH_2CH$=CH); $\delta_C$ (125 MHz, $CDCl_3$) 28.327 ($C(CH_3)_3$), 43.272 ($CH_2NHBoc$), 73.924 (CHOH), 75.674 ($OCH_2CH$=CH), 79.800 ($C(CH_3)_3$), 87.391 (OCHCH=CH), 126.381 and 128.220 ($OCH_2CH$=CH), 157.190 (Boc C=O).

Preparation of (R)-2-(tert-Butoxycarbonylamino)-1-((S)-2,5-dihydrofuran-2-yl)ethyl 4-methylbenzenesulfonate (81). A solution of p-toluenesulfonyl chloride (799 mg, 4.19 mmol) in pyridine (5 mL) was added to alcohol (80) (600 mg, 2.62 mmol). The mixture was stirred for 23 hours then diluted with water (40 mL) then extracted with tert-butyl methyl ether (2×40 mL). The organic layer was dried ($MgSO_4$), filtered and reduced in vacuo to leave an orange oily solid (1.11 g). Flash chromatography over silica, eluting with ethyl acetate:heptane mixtures 10:90 to 30:70 gave tosylate (81) (883 mg, 88%) as a white solid. TLC ($R_f$=0.35, EtOAc:heptane 3:2), analytical HPLC $R_t$=15.86 min., HPLC-MS 284.1 [M+2H–$^t$BuOCO]$^+$, 328.1 [M+2H–$^t$Bu]$^+$, 789.2 [2M+Na]$^+$; $[\alpha]_D^{23}$–28.18° (c=2.307, $CHCl_3$); $\delta_H$ (500 MHz, $CDCl_3$) 1.41 (9H, s, $C(CH_3)_3$), 2.43 (3H, s, aryl-$CH_3$), 3.21-3.27 and 3.48-3.56 (2H total, m, $CH_2NH$), 4.42 (1H, brdd, J=12.83 and 6.11 Hz, 1×$OCH_2CH$=CH), 4.52 (1H, brd, J=12.93 Hz, 1×$OCH_2CH$=CH), 4.61-4.66 (1H, m, OCHCH=CH), 4.79 (1H, brs, NH), 4.85-4.90 (1H, m, CHOTs), 5.68-5.73 and 5.93-5.98 (2H total, m, $CH_2CH$=CH), 7.32 (2H, dd, J=8.55 and 0.60 Hz, aromatic $CH_3CCH$), 7.79 (2H, d, J=8.26 Hz, aromatic $OSO_2CCH$); $\delta_C$ (125 MHz, $CDCl_3$) 21.667 (aryl-$CH_3$), 28.317 ($C(CH_3)_3$), 40.578 ($CH_2NHBoc$), 75.913 ($OCH_2CH$=CH), 79.642 ($C(CH_3)_3$), 82.801 (CHOTs), 85.691 (OCHCH=CH), 124.724, 127.825, 129.491 and 129.784 ($OCH_2CH$=CH and aromatic CH), 133.896 ($CHOSO_2C$ quaternary), 144.792 ($CH_3C$ quaternary), 155.750 (Cbz C=O).

Preparation of (R)-1-((1S,2S,5S)-3,6-Dioxabicyclo[3.1.0] hexan-2-yl)-2-(tert-butoxy carbonylamino)ethyl 4-methylbenzenesulphonate (82). To a solution of tosylate (81) (250 mg, 0.653 mmol) in acetonitrile (6 mL) and aqueous $Na_2$.EDTA (6 mL, 0.4 mmol solution) at 0° C. was added 1,1,1-trifluoroacetone (0.7 mL, 7.83 mmol) via a pre-cooled syringe. To this solution was added in portions a mixture of sodium bicarbonate (461 mg, 5.48 mmol) and OXONE® (1.24 g, 2.02 mmol) over a period of 1 hour. The mixture was stirred for 1 hour 50 minutes then diluted with water (50 mL) and the product extracted into dichloromethane (3×25 mL). The combined organic layers were washed with water (25 mL) then aqueous sodium hydrogen sulphite solution (5%, 25 mL), then water (15 mL), then dried ($Na_2SO_4$), filtered and reduced in vacuo to leave a pale yellow oil (217 mg). Flash chromatography over silica, eluting with ethyl acetate:heptane 10:90 to 50:50 gave anti-epoxide (82) (139 mg, 53%) as a white solid and bicycle (3R,3aR,6R,6aS)-tert-butyl 3-hydroxy-6-(tosyloxy)tetrahydro-2H-furo[3,2-b]pyrrole-4(5H)-carboxylate (35b) (26 mg, 10%). Data for anti-epoxide (82): TLC ($R_f$=0.46, EtOAc:heptane 3:2), analytical HPLC single main peak, $R_t$=14.81 min., HPLC-MS 300.1 [M+2H–$^t$BuOCO]$^+$, 344.1 [M+2H–$^t$Bu]$^+$, 422.1 [M+Na]$^+$, 821.2 [2M+Na]$^+$; $\delta_H$ (500 MHz, $CDCl_3$) 1.42 (9H, s, $C(CH_3)_3$), 2.42 (3H, s, aryl-$CH_3$), 3.23-3.30 and 3.51-3.68 (2H total, m, $CH_2NH$), 3.63 (1H, d, J=10.49 Hz, 1×$OCH_2CH$), 3.74 and 3.79 (each 1H, d, J=2.69 and 2.86 Hz respectively, $OCH_2CHCH$), 3.90 (1H, d, J=10.53 Hz, 1×$OCH_2CH$), 4.06 (1H, d, J=6.29 Hz, OCHCHOTs), 4.59-4.65 (1H, m, CHOTs), 4.80 (1H brs, NH), 7.35 (2H, d, J=8.31 Hz, aromatic $CH_3CCH$), 7.80 (2H, d, J=8.19 Hz, aromatic $OSO_2CCH$); $\delta_C$ (125 MHz, $CDCl_3$) 21.681 (aryl-$CH_3$), 28.283 ($C(CH_3)_3$), 41.465 ($CH_2NHBoc$), 56.293 and 56.987 ($OCH_2CHCH$), 67.678 ($OCH_2CH$), 76.833 (OCHCHOTs), 79.868 ($C(CH_3)_3$), 80.088 (CHOTs), 127.756 and 130.007 (aromatic CH), 133.443 ($CHOSO_2C$ quaternary), 145.329 ($CH_3C$ quaternary), 155.641 (Boc C=O).

Preparation of (S)-2-(Benzyloxycarbonylamino)-1-((S)-2, 5-dihydrofuran-2-yl)ethyl 4-methylbenzenesulfonate (32) A solution of p-toluenesulfonyl chloride (252 mg, 1.32 mmol) in pyridine (7.0 mL), alcohol (17) (290 mg, 1.10 mmol) was stirred at 24° C. for 2 days then diluted with water (15 mL). The product was extracted into tert-butyl methyl ether (3×20 mL) then dried ($MgSO_4$), filtered and reduced in vacuo. Flash chromatography over silica, eluting with ethyl acetate:heptane mixtures 7:93 to 20:80 gave tosylate (32) (282 mg, 61%) as a colourless oil. TLC ($R_f$=0.35, EtOAc:heptane 1:1), analytical HPLC single main peak, $R_t$=19.02 min., HPLC-MS 418.2 [M+H]$^+$, 857.3 [2M+Na]$^+$; $[\alpha]_D^{11}$–86.1° (c=1.103, $CHCl_3$; $\delta_H$ (500 MHz, $CDCl_3$) 2.37 (3H, s, aryl-$CH_3$), 3.29-3.37 and 3.50-3.56 (2H total, m, $CH_2NH$), 4.53-4.56 (2H total, m, OCH$_2$CH=CH), 4.62-4.66 (1H, m, OCHCH=CH), 4.85-4.90 (1H, m, CHOTs), 5.02-5.08 (2H, m, OCH$_2$Ph), 5.02 (1H, brs, NH), 5.65-5.70 and 5.94-5.98 (2H total, m, CH$_2$CH=CH), 7.27 (2H, d, J=8.12 Hz, aromatic CH$_3$CCH), 7.29-7.37 (5H, m, phenyl CH), 7.76 (2H, d, J=8.23 Hz, aromatic OSO$_2$CCH); δ$_C$ (125 MHz, CDCl$_3$) 21.609 (aryl-CH$_3$), 41.749 (CH$_2$NHCbz), 66.833 (CH$_2$Ph), 75.939 (OCH$_2$CH=CH), 81.235 (CHOTs), 85.203 (OCHCH=CH), 124.702, 127.887, 128.026, 128.128, 128.504, 129.687 and 129.757 (OCH$_2$CH=CH and aromatic CH), 133.591 (CHOSO$_2$C quaternary), 136.368 (Cbz quaternary), 144.906 (CH$_3$C quaternary), 156.271 (Cbz C=O).

Alternative preparation of (S)-2-(Benzyloxycarbonylamino)-1-((S)-2,5-dihydro furan-2-yl)ethyl 4-methylbenzenesulfonate (32). A solution of p-toluenesulfonyl chloride (760 mg, 3.99 mmol) in pyridine (10.0 mL), alcohol (17) (600 mg, 2.28 mmol) was stirred at 40° C. for a total of 6 hours and stood at 24° C. for 16 hours then diluted with water (20 mL). The product was extracted into tert-butyl methyl ether (2×50 mL) then dried (MgSO$_4$), filtered and reduced in vacuo. Flash chromatography over silica, eluting with ethyl acetate:heptane mixtures 10:90 to 30:70 gave tosylate (32) (789 mg, 83%) as a white solid.

Preparation of (R)-2-(Benzyloxycarbonylamino)-1-((S)-2,5-dihydrofuran-2-yl)ethyl 4-methyl benzenesulfonate (32b). A solution of p-toluenesulfonyl chloride (368 mg, 2.03 mmol) in pyridine (1.5 mL) was added to alcohol (18) (333 mg, 1.27 mmol). The mixture was stirred at 14° C. for 16 hours and at 24° C. for 3.5 hours then diluted with tert-butyl methyl ether (35 mL). The organic layer was washed with water (15 mL), brine (15 mL), then dried (MgSO$_4$), filtered and reduced in vacuo to leave a pale yellow oil (0.712 g). Flash chromatography over silica, eluting with ethyl acetate heptane mixtures 15:85 to 30:70 gave tosylate (32b) (429 mg, 81%) as a white solid. TLC (R$_f$=0.75, EtOAc:heptane 3:1), analytical HPLC single main peak, R$_t$=18.93 min., HPLC-MS 374.2, 418.2 [M+H]$^+$, 857.3 [2M+Na]$^+$; [α]$_D^{18.5}$ –30.2° (c=1.326, CHCl$_3$); δ$_H$ (500 MHz, CDCl$_3$) 2.39 (3H, s, aryl-CH$_3$), 3.29-3.37 and 3.53-3.62 (2H total, m, CH$_2$NH), 4.44-4.50 and 4.52-4.57 (2H total, m, OCH$_2$CH=CH), 4.59-4.65 (1H, m, OCHCH=CH), 4.87-4.92 (1H, m, CHOTs), 5.05 (2H, m, OCH$_2$Ph), 5.03 (1H, brs, NH), 5.69-5.73 and 5.94-5.98 (2H total, m, CH$_2$CH=CH), 7.28 (2H, d, J=8.10 Hz, aromatic CH$_3$CCH), 7.29-7.37 (5H, phenyl CH), 7.77 (2H, d, J=8.10 Hz, aromatic OSO$_2$CCH); δ$_C$ (125 MHz, CDCl$_3$) 21.627 (aryl-CH$_3$), 41.119 (CH$_2$NHCbz), 66.856 (CH$_2$Ph), 75.987 (OCH$_2$CH=CH), 82.352 (CHOTs), 85.622 (OCHCH=CH), 124.792, 127.825, 128.027, 128.126, 128.504, 129.357 and 129.537 (OCH$_2$CH=CH and aromatic CH), 133.674 (CHOSO$_2$C quaternary), 136.348 (Cbz quaternary), 144.941 (CH$_3$C quaternary), 156.273 (Cbz C=O).

Alternative preparation of (R)-2-(Benzyloxycarbonylamino)-1-((S)-2,5-dihydrofuran-2-yl)ethyl 4-methyl benzenesulfonate (32b). A solution of p-toluenesulfonyl chloride (21.74 g, 114 mmol) in pyridine (200 mL) was added to alcohol (18) (17.15 g, 65.2 mmol). The mixture was stirred at 40° C. for 16 hours then diluted with water (150 mL) then extracted with tert-butyl methyl ether (3×150 mL). The combined organic layers were dried (MgSO$_4$), filtered and reduced in vacuo to leave a residue. The residue was extracted with diethyl ether (300 mL) and the extract collected by decanting. The diethyl ether phase was concentrated in vacuo to leave tosylate (32b) (20.4 g) as a pale yellow solid which was used without further purification.

Preparation of (3aS,6aR)-(9H-Fluoren-9-yl)methyl 3-oxotetrahydro-2H-furo[3,2-b]pyrrole-4(5H)-carboxylate (2c); Route 1.

(i) Preparation of (R)-2-(2,5-Dihydrofuran-2-yl)ethyl methanesulfonate (20). Tributyltin hydride (7.6 mL, 28.18 mmol) then benzoyl peroxide (70%, remainder water, 20 mg) were added consecutively to a stirred solution of iodoethanol (12) (4.41 g, 22.54 mmol) in tetrahydrofuran (65 mL) at 0° C. The mixture was stirred for 2.5 hours with two additional aliquots of benzoyl peroxide (70%, remainder water, 20 mg each) added after 20 and 45 minutes. Triethylamine (4.9 mL, 35.2 mmol) was added dropwise over 2 minutes followed by methanesulfonyl chloride (2.8 mL, 36.2 mmol) over 5 minutes then the cloudy suspension stirred for 1 hour. The mixture was diluted with acetonitrile (750 mL) then washed with heptane (5×200 mL). The acetonitrile layer was dried (MgSO$_4$), filtered and reduced in vacuo to leave a brown oil. Flash chromatography over silica, eluting with ethyl acetate:heptane mixtures 0:100 to 30:70 gave mesylate (20) (3.92 g, 90%) as a yellow-brown oil. TLC (R$_f$=0.40, EtOAc heptane 1:1), HPLC-MS 193.1 [M+H]$^+$, 215.0 [M+Na]$^+$; [α]$_D^{18.5}$ –44.4° (c=5.524, CHCl$_3$); δ$_H$ (500 MHz, CDCl$_3$) 1.85-1.91 and 2.05-2.11 (2H total, m, CH$_2$CH$_2$OMs), 3.00 (3H, s, SCH$_3$), 4.33-4.36, 4.58-4.68 and 4.92-4.97 (5H total, m, OCH$_2$CH=CH, OCHCH$_2$CH$_2$OMs), 5.78-5.81 and 5.92-5.95 (2H total, m, CH$_2$C=CH); δ$_C$ (125 MHz, CDCl$_3$) 35.177 (CH$_2$CH$_2$OMs), 37.235 (OSO$_2$CH$_3$), 67.078 (CH$_2$OMs), 75.202 (OCH$_2$CH=CH), 82.123 (OCHCH=CH), 127.336 and 128.677 (OCH$_2$CH=CH).

(ii) Preparation of (R)-Benzyl 2-(2,5-dihydrofuran-2-yl)ethyl carbamate (23). Sodium azide (218 mg, 3.35 mmol) was added to a stirred solution of mesylate (20) (585 mg, 3.05 mmol) in dimethylformamide (5.0 mL) then the mixture heated at 60° C. under an atmosphere of argon for 2 hours before allowing to cool to ambient temperature. Water (0.5 mL) then triphenylphosphine (1.20 g, 4.57 mmol) were added then the mixture stirred at ambient temperature for 2 hours and heated at 45° C. for 2 hours. The reaction was diluted with 1,4-dioxane (25 mL) then a solution of sodium carbonate (0.68 g, 6.4 mmol) in water (12.5 mL) was added. The mixture was cooled to 0° C. then a solution of benzylchloroformate (0.54 mL, 3.81 mmol) in 1,4-dioxane (5 mL) added dropwise over 30 minutes. The reaction was stirred for 30 minutes then diluted with water (75 mL). The product was extracted into dichloromethane (3×40 mL) then the organic layer was washed a mixture of brine and water (1:1, 50 mL), then dried (Na$_2$SO$_4$), filtered and reduced in vacuo to leave a residue (2.4 g). Flash chromatography over silica, eluting with ethyl acetate:heptane mixtures 5:95 to 30:60 gave alkene (23) (0.46 g, 61%) as a colourless oil. TLC (R$_f$=0.50, EtOAc:heptane 1:1), analytical HPLC main peak, R$_t$=14.223 min., HPLC-MS 248.1 [M+H]$^+$, 517.2 [2M+Na]$^+$; [α]$_D^{19}$ –47.1° (c=4.458, CHCl$_3$; δH (500 MHz, CDCl$_3$) 1.62-1.70 and 1.80-1.88 (2H total, m, CH$_2$CH$_2$NH), 3.26-3.38 (2H, m, CH$_2$CH$_2$NH), 4.56-4.68 (2H, m, OCH$_2$CH=CH), 4.91 (1H, brs, OCHCH$_2$), 5.08 (2H, s, CH$_2$Ph), 5.27 (1H, brs, NH), 5.73-5.77 and 5.83-5.91 (2H total, m, CH$_2$CH=CH), 7.28-7.36 (5H, aromatic Ch); δ$_c$ (125 MHz, CDCl$_3$) 34.997 (CH$_2$CH$_2$NH), 38.379 (CH$_2$CH$_2$NH), 66.508 (CH$_2$Ph), 75.148 (OCH$_2$CH=CH), 85.033 (OCHCH=CH), 127.000, 128.027, 128.107, 128.469, 128.512 and 129.177 (OCH$_2$CH=CH and aromatic CH), 136.696 (Cbz quaternary), 156.376 (Cbz C=O).

(iii) Epoxidation studies with (R)-Benzyl 2-(2,5-dihydrofuran-2-yl)ethyl carbamate (23).

(a) Acetonitrile (0.1 mL, 1.9 mmol), then hydrogen peroxide (30% in water, 0.115 mL) then sodium bicarbonate (30 mg) were added to a stirred solution of alkene (23) (50 mg, 0.20 mmol) in methanol (1 mL). The mixture was stirred for 1 day before adding acetonitrile (0.1 mL, 1.9 mmol), then hydrogen peroxide (30% in water, 0.115 mL) then sodium bicarbonate (30 mg). The mixture was stirred for an additional 3 days then reduced in vacuo, then the residue partitioned between water and ethyl acetate. The organic phase was dried ($MgSO_4$), filtered and reduced in vacuo. $^1H$ nmr analysis of the residue indicated a 2:1 mixture of anti-(24a): syn-(24b) respectively. A sample of this residue prepared as above was purified by flash chromatography over silica, eluting with ethyl acetate:heptane mixtures 5:95 to 40:60 to give a partially separated mixture of the two epoxide diastereoisomers for spectroscopic analysis. Analytical HPLC two main peaks, $R_t$=11.286 and 11.443 min., HPLC-MS 264.1 $[M+H]^+$, 286.1 $[M+Na]^+$, 549.2 $[2M+Na]^+$. Data for anti-(24a); TLC ($R_f$=0.25, EtOAc:heptane 1:1); $\delta_H$ (500 MHz, $CDCl_3$) 1.46-1.55 (1H, m, $CH_2CH_2NH$), 1.66-1.75 (1H, m, $CH_2CH_2NH$), 3.28-3.43 (2H, m, $CH_2NH$), 3.57 (1H, d, J=2.67 Hz, epoxide CH), 3.69 (1H, d, J=10.62 Hz, $OCH_2CH$), 3.75 (1H, d, J=2.77 Hz, epoxide CH), 3.96 (1H, d, J=10.66 Hz, $OCH_2CH$), 4.11-4.16 (1H, m, $OCHCH_2CH_2$), 5.08 (2H, s, $CH_2Ph$), 5.16 (1H, brs, NH), 7.29-7.36 (5H, m, aromatic CH); $\delta_C$ (125 MHz, $CDCl_3$) 30.331 ($CH_2CH_2NH$), 38.309 ($CH_2NHCbz$), 55.703 and 58.742 ($OCH_2CHCH$), 65.898 ($OCH_2CH$), 66.658 ($CH_2Ph$), 76.220 ($OCHCH_2CH_2$), 128.044, 128.121, and 128.511 (aromatic CH) 136.501 (Cbz quaternary), 156.376 (Cbz C=O). Data for syn-(24b); TLC ($R_f$=0.25, EtOAc:heptane 1:1), analytical HPLC single main peak, $R_t$=11.626 min., HPLC-MS 264.1 $[M+H]^+$, 286.1 $[M+Na]^+$, 549.2 $[2M+Na]^+$; $\delta_H$ (500 MHz, $CDCl_3$) 1.80-1.97 (2H, m, $CH_2CH_2NH$), 3.28-3.43 (2H, m, $CH_2NH$), 3.64 (1H, d, J=10.58 Hz, $OCH_2CHCH$), 3.65 (1H, brs, epoxide CH), 3.71 (1H, d, J=3.00 Hz, epoxide CH), 3.84-3.88 (1H, m, $OCHCH_2CH_2$), 4.02 (1H, d, J=10.68 Hz, $OCH_2CH$), 5.08 (2H, s, $CH_2Ph$), 5.16 (1H brs, NH), 7.29-7.36 (5H, m, aromatic CH); $\delta_C$ (125 MHz, $CDCl_3$) 30.248 ($CH_2CH_2NH$), 38.309 ($CH_2NHCbz$), 55.783 and 57.508 ($OCH_2CHCH$), 66.560 ($CH_2Ph$), 67.539 ($OCH_2CH$), 76.005 ($OCHCH_2CH_2$), 128.044, 128.121, and 128.479 (aromatic CH) 136.501 (Cbz quaternary), 156.376 (Cbz C=O).

(b) 3-Chloroperbenzoic acid (186 mg, ≦77%, 0.83 mmol) was added to a stirred solution of alkene (23) (100 mg, 0.40 mmol) in dichloromethane (4 mL). The mixture was stirred for 1.5 hours then 3-chloroperbenzoic acid (300 mg, ≦77%, 1.34 mmol) was added. The mixture was stirred for 3 hours then 3-chloroperbenzoic acid (410 mg, ≦77%, 1.83 mmol) was added. The mixture was stirred diluted with dichloromethane and aqueous sodium hydroxide solution (10%) then stirred for 30 minutes. The organic phase was washed with aqueous sodium hydroxide solution (10%) then dried ($MgSO_4$) and reduced in vacuo. $^1H$ nmr analysis of the residue indicated a 17:19 mixture of anti-(24a): syn-(24b) respectively.

(c) To a solution of alkene (23) (64 mg, 0.26 mmol) in acetonitrile (1.5 mL) and aqueous $Na_2.EDTA$ (1.5 mL, 0.4 mmol solution) at 0° C. was added 1,1,1-trifluoroacetone (0.28 mL, 3.12 mmol) via a pre-cooled syringe. To this solution was added in portions a mixture of sodium bicarbonate (185 mg, 2.18 mmol) and OXONE® (0.50 g, 0.81 mmol) over a period of 1 hour. The mixture was stirred for 55 minutes then diluted with water (10 mL) and the product extracted into dichloromethane (3×5 mL). The combined organic layers were washed with water (10 mL), aqueous sodium hydrogen sulphite solution (5%, 7.5 mL), water (5 mL), brine (12.5 mL), then dried ($Na_2SO_4$), filtered and reduced in vacuo. $^1H$ nmr analysis of the residue indicated a 5:4 mixture of anti-(24a): syn-(24b) respectively, together with over oxidation products.

(d) 3-Chloroperbenzoic acid (18 g, ≦77%, 80.3 mmol) was added in portions to a stirred solution of alkene (23) (1.98 g, 8.02 mmol) in dichloromethane (40 mL) over 30 minutes. The mixture was stirred for 18 hours at ambient temperature then diluted with dichloromethane (150 mL). The organic phase was washed with aqueous sodium hydroxide solution (10%, 2×200 mL), then dried ($Na_2SO_4$), filtered and reduced in vacuo to leave a colourless oil (2.12 g). Flash chromatography over silica, eluting with ethyl acetate:heptane mixtures 5:95 to 30:70 gave a 5:6 mixture of anti-(24a):syn-(24b) respectively as a colourless oil (1.65 g, 78%) which was used without further purification.

(iv) Preparation of (3R,3aR,6aR)-(9H-fluoren-9-yl)methyl 3-hydroxytetrahydro-2H-furo[3,2-b]pyrrole-4(5H)-carboxylate (2b). A suspension of 10% palladium on charcoal (150 mg) and the mixture of epoxides (24a, 24b) in ethanol (40 mL) was stirred under an atmosphere of hydrogen for 75 minutes before filtering the mixture through celite in vacuo. The filter cake was washed with ethanol (60 mL) then the solvents removed in vacuo from the filtrate to obtain a colourless oil (1.0 g) which was used without further purification. A solution of sodium carbonate (1.67 g, 15.75 mmol) in water (30 mL) was added whilst stirring to a solution of the hydrogenation residue in 1,4-dioxane (20 mL). The solution was cooled to 0° C. then a solution of 9-fluorenylmethoxycarbonyl chloride (1.96 g, 7.56 mmol) in 1,4-dioxane (10 mL) was added dropwise over 20 minutes. The mixture stirred for 40 minutes then water (100 mL) was added and the product extracted into dichloromethane (2×100 mL). The organic layer was washed with brine (200 mL), then dried ($Na_2SO_4$), filtered and reduced in vacuo to leave an oily residue (3.6 g). Flash chromatography over silica, eluting with ethyl acetate:heptane mixtures 5:95 to 35:65 gave two batches of alcohol (2b) contaminated with (9H-fluoren-9-yl)methyl 2-((1S, 2R,5R)-3,6-dioxabicyclo[3.1.0]hexan-2-yl)ethyl carbamate as white solids (0.660 g and 0.720 g). From analytical HPLC the estimated purity of alcohol (2b) in each batch was 90% and 40% respectively (i.e. 594 mg and 288 mg, 31%). Data for alcohol (2b). TLC ($R_f$=0.15, EtOAc:heptane 1:1), analytical HPLC single main peak, $R_t$=15.81 min., HPLC-MS 352.1 $[M+H]^+$, 374.1 $[M+Na]^+$, 725.1 $[2M+Na]^+$. Data for (9H-fluoren-9-yl)methyl 2-((1S,2R,5R)-3,6-dioxabicyclo[3.1.0]hexan-2-yl)ethyl carbamate. TLC ($R_f$=0.20, EtOAc:heptane 1:1), analytical HPLC single main peak, $R_t$=16.68 min., HPLC-MS 352.1 $[M+H]^+$, 374.1 $[M+Na]^+$; $[\alpha]_D^{16}$ −19.8° (c=2.65, $CHCl_3$); $\delta_H$ (500 MHz, $CDCl_3$) 1.82-1.99 (2H, m, $CH_2CH_2NH$), 3.30-3.45 (2H, m, $CH_2NH$), 3.65-3.70 (2H, m, 1× epoxide CH and 1×$OCH_2CH$), 3.74 (1H, d, J=2.79 Hz, epoxide CH), 3.84-3.88 (1H, m, $OCHCH_2CH_2$), 4.05 (1H, d, J=10.69 Hz, $OCH_2CH$), 4.22 (1H, t, J=7.02 Hz, Fmoc CH), 4.38 (2H, d, J=7.10 Hz, Fmoc $CH_2$), 5.20 (1H brs, NH), 7.29-7.76 (8H, aromatic CH); $\delta_C$ (125 MHz, $CDCl_3$) 30.269 ($CH_2CH_2NH$), 38.223 ($CH_2NH$), 47.275 (Fmoc CH), 55.842 and 57.521 ($OCH_2CHCH$), 66.566 (Fmoc $CH_2$), 67.567 ($OCH_2CH$), 75.915 ($OCHCH_2CH_2$), 119.930, 125.084, 126.996 and 127.622 (aromatic CH), 141.284 and 144.008 (Fmoc quaternary), 156.454 (Cbz C=O).

(v) Oxidation of alcohol (2b) to ketone (2c). Dess-Martin periodinane (1.52 g, 3.6 mmol) was added to a stirred solution of alcohol (2b) (660 mg of approximately 90% purity, 1.7 mmol) in dichloromethane (25 mL) under an atmosphere of nitrogen. The mixture was stirred for 1.25 hours then diluted with dichloromethane (50 mL). The organic phase was washed with a mixture of saturated aqueous sodium bicarbonate and 0.25M sodium thiosulphate solution (1:1), then saturated aqueous sodium bicarbonate then brine, then dried ($Na_2SO_4$), filtered and reduced in vacuo. Flash chromatography over silica, eluting with ethyl acetate:heptane mixtures 10:90 to 40:60 gave ketone (2c) (611 mg, quantitative) as a white solid. TLC ($R_f$=0.30, EtOAc heptane 1:1), analytical HPLC broad main peak, $R_t$=15.311-17.960 min., HPLC-MS 350.2 [M+H]$^+$, 372.2 [M+Na]$^+$, 390.2 [M+H$_2$O+Na]$^+$, 721.3 [2M+Na]$^+$; $[\alpha]_D^{16}$=−133.2° (c=1.84, CHCl$_3$). Analysis by $^1$H and $^{13}$C NMR showed the presence of rotamers around the 3° amide bond. $^1$H NMR $\delta_H$ (400 MHz, CDCl$_3$) 1.61-1.97/2.10-2.15 (2H, m, NCH$_2$CH$_2$), 3.32-3.45 (1H, m, NCH$_2$CH$_2$), 3.66-3.75/3.85-3.95 (2×0.5H, m, NCH$_2$CH$_2$), 3.95/4.10 (2H, m, COCH$_{2A}$+COCH$_{2B}$), 4.15-4.30 (3H, m, Fmoc H-9+Fmoc CH$_2$), 4.40-4.60/4.80-4.92 (2H, complex, FmocNCH+OCHCH$_2$), 7.20-7.30 (2H, Fmoc H-2 and H-7), 7.31-7.42 (2H, Fmoc H-3 and H-6), 7.50-7.57/7.60-7.66 (2H, Fmoc H-1 and H-8), 7.68-7.76 (2H, Fmoc H-4 and H-5); $\delta_C$ (100 MHz, CDCl$_3$) 31.76/32.28 (NCH$_2$CH$_2$), 45.59/45.95 (NCH$_2$CH$_2$), 47.64 (Fmoc C-9), 62.26/62.77 (C$_\alpha$), 68.03/68.65 (Fmoc CH$_2$), 71.28 (COCH$_2$), 82.17/83.11 (C$_\beta$), 120.38 (Fmoc C-4 and C-5), 125.41/125.59/125.88 (Fmoc C-1 and C-8), 127.45/127.49 (Fmoc C-2 and C-7), 128.13 (Fmoc C-3 and C-6), 141.73 (Fmoc C-4' and C-5'), 144.16/144.37/144.88 (Fmoc C-1' and C-8), 155.33 (OCON), 209.32 (COCH$_2$).

Epoxidation Studies with (R)-2-(Benzyloxycarbonylamino)-1-((S)-2,5-dihydro furan-2-yl)ethyl 4-methylbenzenesulfonate (32b)

(a) 3-Chloroperbenzoic acid (97 mg, ≦77%, 0.43 mmol) was added to a stirred solution of alkene (32b) (36 mg, 0.086 mmol) in dichloromethane (1.5 mL). The mixture was stirred for 20 hours at ambient temperature then 3-chloroperbenzoic acid (97 mg, ≦77%, 0.43 mmol) was added and stirring continued for 1 day at 24° C. then diluted with dichloromethane (15 mL). The organic phase was washed with aqueous sodium hydroxide solution (5%, 10 mL), water (10 mL), then dried (Na$_2$SO$_4$), filtered and reduced in vacuo to leave a residue (0.038 mg). Flash chromatography over silica, eluting with ethyl acetate:heptane mixtures 10:90 to 50:50 gave (in order of elution) anti-(33b) (16 mg, 43%) as a colourless viscous oil and syn-epoxide (9 mg, 24%) as a white solid. Data for anti-(33b); TLC ($R_f$=0.50, EtOAc:heptane 1:1), analytical HPLC single main peak, $R_t$=17.999 min., HPLC-MS 434.1 [M+H]$^+$, 456.1 [M+Na]$^+$, 889.2 [2M+Na]$^+$; $[\alpha]_D^{17}$+25.6° (c=2.54, CHCl$_3$); $\delta_H$ (500 MHz, CDCl$_3$) 2.41 (3H, s, aryl-CH$_3$), 3.31-3.38 and 3.60-3.66 (2H total, m, CH$_2$NH), 3.67 (1H, d, J=10.46 Hz, OCH$_2$CH), 3.75 and 3.81 (each 1H, d, J=2.50 and 2.75 Hz respectively, OCH$_2$CHCH), 3.94 (1H, d, J=10.57 Hz, OCH$_2$CH), 4.07 (1H, d, J=6.90 Hz, OCHCHOTs), 4.60-4.64 (1H, m, CHOTs), 4.97-5.01 (1H brt, NH), 5.08 (2H, brs, CH$_2$Ph), 7.29-7.37 (7H, aromatic CH$_3$CCH and phenyl CH), 7.78 (2H, d, J=8.18 Hz, aromatic OSO$_2$CCH); $\delta_C$ (125 MHz, CDCl$_3$) 21.665 (aryl-CH$_3$), 42.054 (CH$_2$NHCbz), 56.175 and 57.048 (OCH$_2$CHCH), 67.031 (CH$_2$Ph), 67.672 (OCH$_2$CH), 76.732 (OCHCHOTs), 79.388 (CHOTs), 127.776, 128.108, 128.222, 128.544 and 130.043 (aromatic CH), 133.249 (CHOSO$_2$C quaternary), 136.192 (Cbz quaternary), 145.487 (CH$_3$C quaternary), 156.224 (Cbz C=O). Data for syn-epoxide; TLC ($R_f$=0.42, EtOAc:heptane 1:1), analytical HPLC single main peak, $R_t$=18.009 min., HPLC-MS 434.1 [M+H]$^+$, 889.2 [2M+Na]$^+$; $\delta_H$ (500 MHz, CDCl$_3$) 2.40 (3H, s, aryl-CH$_3$), 3.40-3.47 and 3.58-3.63 (2H total, m, CH$_2$NH), 3.62 and 3.72 (each 1H, d and dd respectively, J=2.84 and 3.01, 0.60 Hz respectively, OCH$_2$CHCH), 3.67 (1H, d, J=10.68 Hz, OCH$_2$CH), 3.92 (1H, d, J=7.07 Hz, OCHCHOTs), 3.97 (1H, d, J=10.67 Hz, OCH$_2$CH), 4.65-4.70 (1H, m, CHOTs), 5.00-5.04 (1H brt, NH), 5.05 (2H, brs, CH$_2$Ph), 7.29-7.37 (7H, aromatic CH$_3$CCH and phenyl CH), 7.83 (2H, d, J=8.11 Hz, aromatic OSO$_2$CCH); $\delta_C$ (125 MHz, CDCl$_3$) 21.664 (aryl-CH$_3$), 41.958 (CH$_2$NHCbz), 55.948 and 56.425 (OCH$_2$CHCH), 66.823 (CH$_2$Ph), 68.008 (OCH$_2$CH), 76.498 (OCHCHOTs), 78.395 (CHOTs), 127.986, 128.072, 128.110, 128.493 and 129.928 (aromatic CH), 133.189 (CHOSO$_2$C quaternary), 136.383 (Cbz quaternary), 145.177 (CH$_3$C quaternary), 156.202 (Cbz C=O).

(b) To a solution of alkene (32b) (262 mg, 0.63 mmol) in acetonitrile (4 mL) and aqueous Na$_2$.EDTA (4 mL, 0.4 mmol solution) at 0° C. was added 1,1,1-trifluoroacetone (0.67 mL, 7.54 nmol) via a pre-cooled syringe. To this solution was added in portions a mixture of sodium bicarbonate (0.44 g, 5.28 mmol) and OXONE® (1.20 g, 1.95 mmol) over a period of 55 minutes. The mixture was stirred for 2.5 hours then diluted with water (25 mL) and the product extracted into dichloromethane (2×25 mL). The combined organic layers were washed with brine (12.5 mL) then dried (Na$_2$SO$_4$), filtered and reduced in vacuo to leave a residue (310 mg). Flash chromatography over silica, eluting with ethyl acetate:heptane mixtures 15:85 to 50: 50 gave anti-(33b) as a viscous white oil (216 mg, 79%).

(c) To a solution of alkene (32b) (4.74 g, 11.35 mmol) in acetonitrile (260 mL) and aqueous Na$_2$.EDTA (80 mL, 0.4 mM solution) at 0° C. was added 1,1,1-trifluoroacetone (12.19 mL, 136.24 mmol) via a pre-cooled syringe. To this solution was added in portions a mixture of sodium bicarbonate (8.01 g, 95.37 mmol) and OXONE® (21.64 g, 35.19 mmol) over a period of 1 hour. The mixture was stirred for 1 hour then diluted with water (500 mL) and the product extracted into dichloromethane (3×200 mL). The combined organic layers were washed with aqueous sodium hydrogen sulphite solution (5%, 200 mL) then dried (Na$_2$SO$_4$), filtered and reduced in vacuo to leave a residue that was recrystallised from ethanol (20 mL) to give anti-(33b) as a white solid (0.68 g, 14%). $[\alpha]_D^{16}$+30.1° (c=7.14, CHCl$_3$).

(d) To a solution of alkene (32b) (1.48 g, 3.54 mmol) in acetonitrile (85 mL) and aqueous Na$_2$.EDTA (25 mL, 0.4 mM solution) at 0° C. was added 1,1,1-trifluoroacetone (3.81 mL, 42.54 mmol) via a pre-cooled syringe. To this solution was added in portions a mixture of sodium bicarbonate (2.5 g, 29.8 mmol) and OXONE® (6.76 g, 10.99 mmol) over a period of 1 hour. The mixture was stirred for 1 hour then diluted with water (150 mL) and the product extracted into dichloromethane (3×60 mL). The combined organic layers were washed with aqueous sodium hydrogen sulphite solution (5%, 60 mL) then dried (Na$_2$SO$_4$), filtered and reduced in vacuo to leave a residue that was recrystallised from propan-2-ol (15 mL) to give anti-(33b) as an off-white solid (0.54 g, 35%). The mother liquor was concentrated in vacuo to leave a residue (0.98 g). Flash chromatography over silica, eluting with ethyl acetate:heptane 1:2 gave anti-(33b) (0.555 g, 36%).

(e) Acetonitrile (0.2 mL, 3.8 mmol), then hydrogen peroxide (30% in water, 0.271 mL), then sodium bicarbonate (50 mg) were added to a stirred solution of alkene (32b) (100 mg, 0.24 mmol) in methanol (3 mL). The mixture was stirred for 5 days before adding acetonitrile (0.2 mL, 3.8 mmol), then hydrogen peroxide (30% in water, 0.271 mL), then sodium bicarbonate (50 mg). The mixture was stirred for an additional 2 days before adding acetonitrile (0.2 mL, 3.8 mmol), then hydrogen peroxide (30% in water, 0.271 mL), then sodium bicarbonate (50 mg). The mixture was stirred for 1 day then reduced in vacuo, then the residue partitioned between water (10 mL) and ethyl acetate (2×15 mL). The organic phase was dried ($MgSO_4$), filtered and reduced in vacuo. $^1H$ nmr analysis of the residue indicated an approximate ratio of 10:1:3 of anti-(33b): syn-epoxide: starting material alkene (32b) respectively to be present.

(f) To a solution of alhene (32b) (21.26 g, 50.9 mmol) in acetonitrile (600 mL) and aqueous $Na_2.EDTA$ (400 mL, 0.4 mmol solution) at 0° C. was added 1,1,1-trifluoroacetone (54 mL, 604 mmol). To this solution was added in portions a mixture of sodium bicarbonate (35 g, 417 mmol) and OXONE® (93 g, 151 mmol) over a period of 1 hour. The mixture was stirred for 0.5 hours then diluted with dichloromethane (500 mL) and water (2 L). The organic layer was separated then the aqueous extracted with dichloromethane (500 mL then 1 L). The combined organic layers were washed with water (1 L), aqueous sodium hydrogen sulphite solution (5%, 1 L), then water (1 L), then dried ($Na_2SO_4$), filtered and reduced in vacuo to leave a residue. Flash chromatography over silica, eluting with ethyl acetate:heptane mixtures 0:100 to 50:50 gave anti-(33b) as a viscous white oil (18.02 g, 82%).

Epoxidation Studies with (S)-2-(Benzloxycarbonylamino)-1-((S)-2,5-dihydro furan-2-yl)ethyl 4-methylbenzenesulfonate (32)

(a) To a solution of alkene (32) (765 mg, 1.83 mmol) in acetonitrile (10 mL) and aqueous $Na_2.EDTA$ (10 mL, 0.4 mmol solution) at 0° C. was added 1,1,1-trifluoroacetone (1.98 mL, 22.0 mmol). To this solution was added in portions a mixture of sodium bicarbonate (1.29 g, 15.4 mmol) and OXONE® (3.49 g, 5.68 mmol) over a period of 1.5 hours. The mixture was stirred for 1.5 hours then diluted with water (30 mL) and the product extracted into dichloromethane (3×30 mL). The combined organic layers were washed with brine (50 mL) then dried ($MgSO_4$), filtered and reduced in vacuo. Flash chromatography over silica, eluting with ethyl acetate heptane mixtures 10:90 to 30:70 gave (in order of elution) anti-(33) as a white solid (597 mg, 75%) and syn-epoxide (35 mg, 4%) as a white solid. Data for anti-(33); TLC ($R_f$=0.50, EtOAc:heptane 1:1), analytical HPLC single main peak, $R_t$=17.989 min., HPLC-MS 434.2 $[M+H]^+$, 889.3 $[2M+Na]^+$; $[\alpha]_D^{11.5}$ –49.08° (c=1.630, $CHCl_3$); 8H (500 MHz, $CDCl_3$) 2.38 (3H, s, aryl-$CH_3$), 3.30-3.37 and 3.44-3.50 (2H, m, $CH_2NH$), 3.73 and 2.74 (2H, each d, J=2.78 and 2.73 Hz respectively, $OCH_2CHCH$), 3.81 (1H, d, J=10.08 Hz, $OCH_2CH$), 3.91 (1H, d, J=10.12 Hz, $OCH_2CH$), 4.13 (1H, d, J=2.04 Hz, OCHCHOTs), 4.83-4.86 (1H, m, CHOTS), 4.89-5.00 (1H brt, J=5.39 Hz, NH), 5.02-5.09 (2H, m, $CH_2Ph$), 7.28 (2H, d, J=8.10 Hz, aromatic $CH_3CCH$), 7.31-7.38 (5H, phenyl CH), 7.76 (2H, d, J=8.22 Hz, aromatic $OSO_2CCH$); $\delta_C$ (125 MHz, $CDCl_3$) 21.636 (aryl-$CH_3$), 42.085 ($CH_2NHCbz$), 56.414 and 57.217 ($OCH_2CHCH$), 66.977 ($CH_2Ph$), 68.582 ($OCH_2CH$), 76.846 (OCHCHOTs), 79.979 (CHOTs), 127.668, 128.073, 128.241, 128.551 and 130.001 (aromatic CH), 133.489 ($CHOSO_2C$ quaternary), 136.172 (Cbz quaternary), 145.322 ($CH_3C$ quaternary), 156.247 (Cbz C=O). Data for syn-epoxide; TLC ($R_f$=0.45, EtOAc:heptane 1:1), analytical HPLC main peak, $R_t$=17.902 min., HPLC-MS 434.2 $[M+H]^+$, 889.3 $[2M+Na]^+$; $[\alpha]_D^{12.5}$ –38.4° (c=2.277, $CHCl_3$); $\delta_H$ (500 MHz, $CDCl_3$) 2.39 (3H, s, aryl-$CH_3$), 3.49-3.58 and 3.58-3.66 (2H total, m, $CH_2NH$), 3.62 (1H, d, J=10.27 Hz $OCH_2CH$), 3.71 (1H, d, J=3.01 Hz, epoxide CH), 3.88 (1H, brd, J=10.62 Hz, $OCH_2CH$), 3.88 (1H, brs, epoxide CH), 3.97 (1H, d, J=6.11 Hz, OCHCHOTs), 4.69-4.74 (1H, m, CHOTS), 5.02-5.11 (3H, m, NH and $CH_2Ph$), 7.28-7.38 (7H, aromatic $CH_3CCH$ and phenyl CH), 7.80 (2H, brd, J=8.22 Hz, aromatic $OSO_2CCH$); $\delta_C$ (125 MHz, $CDCl_3$) 21.634 (aryl-$CH_3$), 41.450 ($CH_2NHCbz$), 55.391 and 55.741 ($OCH_2CHCH$), 66.828 ($CH_2Ph$), 67.724 ($OCH_2CH$), 76.526 (OCHCHOTs), 79.632 (CHOTs), 127.805, 128.958, 128.102, 128.117, 128.504, 128.550, 128.596, 129.742, 130.002 and 130.177 (aromatic CH), 133.093 ($CHOSO_2C$ quaternary), 136.330 (Cbz quaternary), 144.990 ($CH_3C$ quaternary), 156.344 (Cbz C=O).

(b) 3-Chloroperbenzoic acid (268 mg, ≦77%, 1.2 mmol) was added to a stirred solution of alkene (32) (50 mg, 0.12 mmol) in dichloromethane (2.0 mL). The mixture was stirred for 20 hours at ambient temperature then at 24° C. for 26 hours. The mixture was partitioned between dichloromethane (10 mL) and aqueous sodium hydroxide solution (10%, 10 mL). The aqueous phase was extracted with dichloromethane (2×15 mL) then the combined organic phase dried ($Na_2SO_4$), filtered and reduced in vacuo. $^1H$ (500 MHz, $CDCl_3$) nrnir analysis of the residue indicated that a 3:1 mixture of anti-(33) and syn-epoxide respectively.

Epoxidation Studies with (S)-2-(Benzloxycarbonylamino)-1-((S)-2,5-dihydro furan-2-yl)ethyl 4-methanesulfonate (51)

(i) Preparation of (S)-2-(Benzyloxycarbonylamino)-1-((S)-2,5-dihydrofuran-2-yl)ethyl methane sulfonate (51). Triethylamine (0.594 mL, 4.25 mmol) then methanesulfonyl chloride (0.309 mL, 3.99 mmol) were added to a stirred solution of (alcohol (17) (700 mg, 2.66 mmol) in dichloromethane (15 mL). The mixture was stirred for 2 hours then diluted with water (20 mL). The product was extracted into dichloromethane (2×25 mL) then dried ($MgSO_4$), filtered and reduced in vacuo. Flash chromatography over silica, eluting with ethyl acetate:heptane mixtures 10:90 to 40:60 gave mesylate (51) (584 mg, 64%) as a white solid. TLC ($R_f$=0.35, EtOAc:heptane 1:1), analytical HPLC single main peak, $R_t$=14.21 min., HPLC-MS 342.1 $[M+H]^+$, 364.1 $[M+Na]^+$, 705.2 $[2M+Na]^+$; $[\alpha]_D^{12.5}$ –67.0° (c=1.034, $CHCl_3$); $\delta_H$ (500 MHz, $CDCl_3$) 3.02 (3H, s, $OSO_2CH_3$), 3.48 (1H, dt, J=14.80 and 6.40 Hz, $CH_2NH$), 3.62 (1H, dt, J=14.71 and 6.24 Hz, $CH_2NH$), 4.61-4.71 (3H, m, $OCH_2CH$=CH and OCHCH=CH), 4.93-4.97 (1H, m, CHOMs), 5.10 (2H, brs, $OCH_2Ph$), 5.26 (1H, brs, NH), 5.82-5.87 and 6.06-6.11 (2H total, m, $CH_2CH$=CH), 7.28-7.37 (5H, m, aromatic CH); $\delta_C$ (125 MHz, $CDCl_3$) 38.487 ($OSO_2CH_3$), 42.063 ($CH_2NHCbz$), 67.002 ($CH_2Ph$), 75.768 ($OCH_2CH$=CH), 81.235 (CHOMs), 85.485 (OCHCH=CH), 124.835, 128.096, 128.177, 1283519, and 130.104 ($OCH_2CH$=CH and aromatic CH), 136.275 (Cbz quaternary), 156.500 (Cbz C=O).

(ii) Preparation of (S)-2-(Benzyloxycarbonylamino)-1-((1S,2S,5s)-3,6-dioxabicyclo[3.1.0]hexan-2-yl)ethyl methanesulfonate anti-(52). To a solution of mesylate (51) (439 mg, 1.29 mmol) in acetonitrile (7 mL) and aqueous $Na_2.EDTA$ (7 mL, 0.4 mmol solution) at 0° C. was added 1,1,1-trifluoroacetone (1.38 mL, 15.4 mmol). To this solution was added in portions a mixture of sodium bicarbonate (0.907 g, 10.8 mmol) and OXONE® (2.45 g, 3.99 mmol) over a period of 80 minutes. The mixture was stirred for 30 minutes then diluted with water (10 mL) and the product extracted into dichloromethane (1×10 mL and 2×20 mL). The combined organic layers were washed with brine (30 mL) then dried (MgSO$_4$), filtered and reduced in vacuo. Flash chromatography over silica, eluting with ethyl acetate:heptane mixtures 10:90 to 50:50 gave (in order of elution) anti-(52) (271 mg, 59%) and syn-epoxide (71 mg, 15%) as colourless oils. Data for anti-(52); TLC (R$_f$=0.41, EtOAc:heptane 3:2), analytical HPLC single main peak, R$_t$=13.556 min., HPLC-MS 358.2 [M+H]$^+$, 380.2 [M+Na]$^+$, 737.3 [2M+Na]$^+$; [α]$_D^{12.5}$−28.8° (c=1.910, CHCl$_3$); δ$_H$ (500 MHz, CDCl$_3$) 2.99 (3H, s, OSO$_2$CH$_3$), 3.47 and 3.50 (1H total, each brt, J=6.24 Hz, CH$_2$NH), 3.60 and 3.63 (1H total, each brt, J=5.59 and 5.63 respectively, CH$_2$NH), 3.86-3.90 (3H, m, OCH$_2$CHCH), 3.98 (1H, d, J=10.27 Hz, OCH$_2$CH), 4.17 (1H, d, J=2.70 Hz, OCH-CHOMs), 4.83-4.87 (1H, m, CHOMs), 5.08-5.14 (2H m, CH$_2$Ph), 5.23 (1H, brs, NH), 7.30-7.36 (5H, m, aromatic CH); δ$_C$ (125 MHz, CDCl$_3$) 38.570 (OSO$_2$CH$_3$), 42.217 (CH$_2$NHCbz), 56.231 and 57.062 (OCH$_2$CHCH), 67.176 (CH$_2$Ph), 68.353 (OCH$_2$CH), 77.063 (OCHCHOMs), 79.435 (CHOMs), 128.209, 128.343 and 128.587 (aromatic CH), 136.089 (Cbz quaternary), 156.528 (Cbz C=O). Data for syn-epoxide; TLC (R$_f$=0.29, EtOAc:heptane 3:2), analytical HPLC main peak, R$_t$=13.639 min., HPLC-MS 358.1 [M+H]$^+$, 737.2 [2M+Na]$^+$; [α]$_D^{12.5}$−9.2° (c=3.543, CHCl$_3$); δ$_H$ (500 MHz, CDCl$_3$) 3.04 (3H, s, OSO$_2$CH$_3$), 3.60-3.80 (2H, m, CH$_2$NH), 3.72 (1H, d, J=10.54 Hz, OCH$_2$CHCH), 3.79 (1H, d, J=2.90 Hz, epoxide CH), 3.96 (1H, d, J=2.84 Hz, epoxide CH), 3.99 (1H, d, J=7.36 Hz, OCHCHOMs) 4.06 (1H, d, J=10.68 Hz, OCH$_2$CHCH), 4.78 (1H, dt, J=7.25 and 4.25 Hz, CHOMs), 5.07-5.14 (2H, m, CH$_2$Ph), 5.29 (1H, brs, NH), 7.29-7.37 (5H, m, aromatic CH); δ$_C$ (125 MHz, CDCl$_3$) 38.234 (OSO$_2$CH$_3$), 42.241 (CH$_2$NHCbz), 55.571 and 56.081 (OCH$_2$CHCH), 67.047 (CH$_2$Ph), 67.852 (OCH$_2$CH), 76.662 (OCHCHOMs), 80.615 (CHOMs), 128.023, 128.195 and 128.531 (aromatic CH), 136.212 (Cbz quaternary), 156.653 (Cbz C=O).

Preparation of (3aS,6aR)-(9H-Fluoren-9-yl)methyl 3-oxotetrahydro-2H-furo[3,2-b]pyrrole-4(5H)-carboxylate (2c); Route 2.

(i) Preparation (3R,3aR,6R,6aS)- tert-Butyl 3-hydroxy-6-(tosyloxy)tetrahydro-2H -furo[3,2-b]pyrrole-4(5H)-carboxylate (35b). Ethanol (1.5 mL) was added dropwise to a mixture of 10% palladium on charcoal (20 mg) and anti-(33b) (100 mg, 0.25 mmol) under an atmosphere of argon. The argon was replaced by hydrogen then the suspension was stirred for 4.5 hours before filtering the mixture through celite in vacuo. The filter cake was washed with ethanol (10 mL) then the solvents removed in vacuo from the filtrate. The residue was azeotroped with toluene (2×3 mL) to obtain (3R, 3a, 6R,6aS)-3-hydroxyhexahydro-2H-furo[3,2-b]pyrrol-6-yl 4-methylbenzenesulfonate (74) which was used without further purification.

A solution of sodium carbonate (56 mg, 0.275 mmol) in water (0.75 mL) was added whilst stirring to a solution of aminoalcohol (74) in 1,4-dioxane (0.75 mL). A solution of di-tert-butyl dicarbonate (60 mg, 0.275 mmol) in 1,4-dioxane (0.5 mL) was added dropwise over 5 minutes then the mixture stirred for 1 hour before adding an additional aliquot of di-tert-butyl dicarbonate (40 mg, 0.184 mmol) in 1,4-dioxane (0.25 mL) dropwise over 1 minute. The mixture was stirred for 70 minutes then water (5 mL) was added and the product extracted into dichloromethane (3×5 mL). The organic layer was washed with brine (5 mL), then dried (Na$_2$SO$_4$), filtered and reduced in vacuo to leave a residue (132 mg). Flash chromatography over silica, eluting with ethyl acetate:heptane mixtures 15:85 to 45:55 gave bicyclic alcohol (35b) (58.9 mg, 60%) as a white solid. TLC (R$_f$=0.30, EtOAc:heptane 1:1), analytical HPLC single main peak, R$_t$=16.54 min., HPLC-MS 344.1 [M+2H-$^t$Bu]$^+$, 821.3 [2M+Na]$^+$; [α]$_D^{18.5}$−30.3° (c=6.10, CHCl$_3$); δ$_H$ (500 MHz, CDCl$_3$) mixture of rotamers major:minor 2:1; 1.44 (6H, brs, (CH$_3$)$_3$C, major), 1.46 (3H, brs, (CH$_3$)$_3$C, minor), 1.98 (0.33H, d, J=4.00 Hz, OH minor), 2.44 (3H, s, aryl-CH$_3$), 2.69 (0.66H, d, J=2.88 Hz, OH major), 3.08-3.15 (0.33H, m, BocNCH$_2$ minor), 3.26-3.32 (0.66H, m, BocNCH$_2$ major), 3.75-3.87 (2H, m, 1×OCH$_2$CHOH and 1×BocNCH$_2$), 3.94-4.02 (1H, m, OCH$_2$CHOH), 4.07 (1H, brs, BocNCH), 4.35 (0.33H, brs, OCH$_2$CHOH minor), 4.41 (0.66H, brs, OCH$_2$CHOH major), 4.52 (0.66H, t, J=4.75 Hz, TsOCHCH major), 4.65 (0.33H, t, J=3.95 Hz, TsOCHCH minor), 4.72-4.78 (11H, m, TsOCHCH), 7.34 (2H, brd, J=7.82 Hz, aromatic CH$_3$CCH), 7.82 (2H, brd, J=8.01 Hz, aromatic OSO$_2$CCH); δ$_C$ (125 MHz, CDCl$_3$) 21.681 (aryl-CH$_3$), 28.294/28.386 ((CH$_3$)$_3$C), 46.810/48.177 (BocNCH$_2$), 68.153/68.484 (BocNCH), 75.484/75.697 (OCH$_2$CHOH), 76.228/76.980 (OCH$_2$CHOH), 76.269/76.585 (TsOCHCH), 79.391/80.233 (TsOCHCH), 81.079/81.139 ((CH$_3$)$_3$C quarternary), 127.973, 129.911, 129.966 and 130.125 (aromatic CH), 133.144 (CHOSO$_2$C quaternary), 145.247 (CH$_3$C quaternary), 153.161/154,244 (Boc C=O).

(ii) Alternative preparation (3R,3aR,6R,6aS)- tert-Butyl 3-hydroxy-6-(tosyloxy)tetrahydro-2H-furo[3,2-b]pyrrole-4(5H)-carboxylate (35b). 10% Palladium on charcoal (2 g) was added in portions to a solution of anti-(33b) (18.02 g, 41.62 mmol) in ethanol (300 mL) at 0° C. The mixture was stirred under an atmosphere of hydrogen at ambient temperature for 16 hours before filtering through celite in vacuo. The filter cake was washed with ethyl acetate then the solvents removed in vacuo from the filtrate. The residue was azeotroped with toluene (2×100 mL) to obtain (3R,3aR,6R,6aS)-3-hydroxyhexahydro-2H-furo[3,2-b]pyrrol-6-yl 4-methylbenzenesulfonate (74) which was used without further purification. δ$_H$ (500 MHz, CDCl$_3$) 2.43 (3H, s, aryl-CH$_3$), 2.49 (2H, brs, OH and NH), 2.83 (1H, dd, J=11.63 and 8.17 Hz, 1×CH$_2$NH), 3.08 (1H, dd, J=11.62 and 6.62 Hz, 1×CH$_2$NH), 3.73 (1H, d, J=5.19 Hz, CHNH), 3.81 (1H, d, J=10.15 Hz, 1×OCH$_2$CHOH), 3.90 (1H, dd, J=10.15 and 3.45 Hz, 1×OCH$_2$CHOH), 4.13-4.15 (1H, m, OCH$_2$CHOH), 4.54 (1H, t, J=4.95 Hz, TsOCHCH), 4.67-4.72 (1H, m, TsOCH), 7.33 (2H, brd, J=8.24 Hz, aromatic CH$_3$CCH), 7.82 (2H, brd, J=8.52 Hz, aromatic OSO$_2$CCH); δ$_C$ (125 MHz, CDCl$_3$) 21.660 (aryl-CH$_3$), 48.607 (CH$_2$NH), 68.530 (CHNH), 75.968 (OCH$_2$CHOH), 78.397, 79.960 and 80.158 (OCH$_2$CHOH and TsOCHCH), 127.924 and 129.848 (aromatic CH), 133.400 (CHOSO$_2$C quaternary), 144.983 (CH$_3$C quaternary); [α]$_D^{22}$+48.0° (c=1.98, CHCl$_3$).

Di-tert-butyl dicarbonate (9.1 g, 41.62 mmol) was added a solution of aminoalcohol (74) (assumed to be 41.62 mmol) in ethyl acetate (300 mL). The mixture was stirred for 40 minutes at 25° C. then reduced in vacuo to leave a yellow oil. Flash chromatography over silica, eluting with ethyl acetate: heptane mixtures 0:100 to 50:50 gave (3R,3aR,6R,6aS)-tert-butyl 3-hydroxy-6-(tosyloxy)tetrahydro-2H-furo[3,2-b]pyrrole-4(5H)-carboxylate (13.38 g, 81%) as a white solid.

(iii) Alternative preparation of (3R,3aR,6R,6aS)-tert-Butyl 3-hydroxy-6-(tosyloxy)tetrahydro-2H-furo[3,2-b]pyrrole-4(5H)-carboxylate (35b). Potassium tert-butoxide (9.0 mg, 0.080 mmol) was added to anti-epoxide (82) (29.1 mg, 0.073 mmol) followed by tetrahydrofuran (0.5 mL) under an atmosphere of argon. The suspension was stirred for 5 minutes then sonicated for 30 seconds. Stirring was continued for 30 minutes. HPLC-MS indicated the appearance of a new peak corresponding to bicycle (35b) together with other products. Data for bicycle (35b): analytical HPLC, $R_t$=14.5 min., HPLC-MS 344.0 [M+2H–$^t$Bu]$^+$, 821.2 [2M+Na]$^+$.

(iv) Preparation of (3R,3aR,6aR)- tert-Butyl 3-hydroxytetrahydro-2H-furo[3,2-b]pyrrole-4(5H)-carboxylate (2f). A solution of Super-Hydride® (12.5 mL, IM in tetrahydrofuran, 12.5 mmol) was added dropwise over 2 minutes to a stirred solution of bicyclic alcohol (35b) (1 g, 2.51 mmol) in tetrahydrofuran (20 mL) under an atmosphere of argon. The mixture was heated for 1 hour at 40° C. then an additional aliquot of Super-Hydride® (12.5 mL, IM in tetrahydrofuran, 12.5 mmol) was added. The mixture was heated at 40° C. for 1 hour then cooled to 0° C. Water (100 mL) was cautiously added and the product extracted into dichloromethane (3×100 mL). The organic phase was washed with a mixture of brine and water (1:1, 500 mL), then dried (Na$_2$SO$_4$), filtered and reduced in vacuo to leave an oil. Flash chromatography over silica, eluting with ethyl acetate:heptane mixtures 0:100 to 50:50 gave bicyclic alcohol (2f) (416 mg, 72%) as a viscous colourless oil. TLC (R$_f$=0.25, EtOAc:heptane 2:1); HPLC-MS 174.1 [M+2H–$^t$Bu]$^+$, 252.1 [M+Na]$^+$, 481.3 [2M+Na]$^+$; $[\alpha]_D^{13}$ –72.8° (c=4.26, CHCl$_3$); $\delta_H$ (500 MHz, CDCl$_3$) mixture of rotamers major minor 5:3; 1.45 and 1.49 (9H total, each s, (CH$_3$)$_3$C), 1.83-1.93 and 1.98-2.05 (2H total, m, BocNCH$_2$CH$_2$), 2.08 (0.38H, d, J=4.00 Hz, OH minor), 2.85 (0.62H, d, J=2.37 Hz, OH major), 3.18-3.28, 3.53-3.58 and 3.67-3.73 (3H total, m, BocNCH$_2$CH$_2$ and BocNCH), 3.92-3.96 (0.38H, m, OCH$_2$CHOH minor), 3.99-4.10 (1.62H, m, OCH$_2$CHOH), 4.34 (0.38H, brs, OCH$_2$CHOH minor), 4.37 (0.68H, brs, OCH$_2$CHOH major), 4.71 (0.62H, brt, J=4.78 Hz, OCHCHN major), 4.75 (0.38H, brt, J=4.78 Hz, OCHCHN minor); $\delta_C$ (125 MHz, CDCl$_3$) 28.433/28.533 ((CH$_3$)$_3$C), 31.273/31.557 (BocNCH$_2$CH$_2$), 44.866/45.260 (BocNCH$_2$), 69.777/70.392 (BocNCH), 74.116/74.375 (OCH$_2$CHOH), 77.092/77.708 (OCH$_2$CHOH), 80.113/80.154 ((CH$_3$)$_3$C quarternary), 81.803/82.634 (OCHCHN), 153.690/154.798 (Boc C=O).

(v) Alternative preparation of (3R, 3aR, 6aR)- tert-Butyl 3-hydroxytetrahydro-2H-furo[3,2-b]pyrrole-4(5H)-carboxylate (2f). A solution of Super-Hydrides (61.65 mL, 1M in tetrahydrofuran, 61.65 mmol) was added dropwise over 15 minutes to a stirred solution of (3R, 3aR, 6R, 6aS)-tert-butyl 3-hydroxy-6-(tosyloxy)tetrahydro-2H-furo[3,2-b]pyrrole-4(5H)-carboxylate (4.92 g, 12.33 mmol) in tetrahydrofuran (50 mL) under an atmosphere of argon. The mixture was heated for 3 hour at 40° C. then cooled to 0° C. Water (150 mL) was cautiously added and the product extracted into dichloromethane (3×150 mL). The organic phase was washed with a mixture of brine and water (1:1, 100 mL), then dried (Na$_2$SO$_4$), filtered and reduced in vacuo to leave an oil. Flash chromatography over silica, eluting with ethyl acetate:heptane mixtures 0:100 to 50:50 gave (3R, 3aR, 6aR)-tert-butyl 3-hydroxytetrahydro-2H-furo[3,2-b]pyrrole-4(5H)-carboxylate (1.72 g, 61%) as a white solid. In addition, fractions containing less pure (3R, 3aR, 6aR)-tert-butyl 3-hydroxytetrahydro-2H-furo[3,2-b]pyrrole-4(5H)-carboxylate were collected, reduced in vacuo then the residue dissolved in dichloromethane (20 mL). The solution was washed with aqueous sodium hydroxide solution (1M, 15 mL), then water (15 mL), then dried (Na$_2$SO$_4$), filtered and reduced in vacuo to leave pure (3R, 3aR, 6aR)-tert-butyl 3-hydroxytetrahydro-2H-furo[3,2-b]pyrrole-4(5H)-carboxylate (0.697 g, 25%).

(vi) Alternative preparation of (3R, 3aR, 6aR)-tert-Butyl 3-hydroxytetrahydro-2H-furo[3,2-b]pyrrole-4(5H)-carboxylate (2f). A suspension of (3R, 3aR, 6R, 6aS)-tert-butyl 3-hydroxy-6-(tosyloxy)tetrahydro-2H-furo[3,2-b]pyrrole-4(5H)-carboxylate (35b) (250 mg, 0.63 mmol) in diethyl ether (1.5 mL) and tetrahydrofuran (1 mL) was added to a stirred suspension of lithium aluminium hydride (48 mg, 1.25 mmol) in diethyl ether (1.5 mL) under an atmosphere of argon. The mixture was stirred for 1 hour at ambient temperature then heated at 35° C. for 2.75 hours. HPLC-MS analysis of the reaction indicated starting tosylate (35b) together with small amounts of both (3R, 3aR, 6aR)-tert-butyl 3-hydroxytetrahydro-2H-furo[3,2-b]pyrrole-4(5H)-carboxylate (2f) and (3R, 3aR, 6aR)-hexahydro-2H-furo[3,2-b]pyrrol-3-ol (2g) to be present.

(vii) Preparation of (3R, 3aR, 6aR)-(9H-fluoren-9-yl)methyl 3-hydroxytetrahydro-2H-furo[3,2-b]pyrrole-4(5H)-carboxylate (2b). Alcohol (2f) (558 mg, 2.43 mmol) was dissolved in 4M HCl in dioxane (14.06 mL) and left to stand at ambient temperature for 1 h. The solvent was removed in vacuo and the residue azeotroped from toluene (3×20 mL) to give hydrochloride salt of (3R,3aR,6aR)-hexahydro-2H-furo[3,2-b]pyrrol-3-ol (2g) used directly in the following step.

A solution of sodium carbonate (0.54 g, 5.11 mmol) in water (4 mL) was added whilst stirring to a solution of the HCl salt of aminoalcohol (2g) in 1,4-dioxane (10 mL). The solution was cooled to 0° C. then a solution of 9-fluorenylmethoxycarbonyl chloride (0.66 g, 2.56 mmol) in 1,4-dioxane (10 mL) was added dropwise over 30 minutes. The mixture stirred for 2 h then water (50 mL) was added and the product extracted into dichloromethane (2×50 mL). The organic layer was washed with brine (50 mL), then dried (Na$_2$SO$_4$), filtered and reduced in vacuo to leave an oily residue. Flash chromatography over silica, eluting with ethyl acetate:heptane mixtures 15:85 to 50:50 gave alcohol (2b) as a white solid (0.324 g, 0.93 mmol). Data for alcohol (2b). TLC (R$_f$=0.15, EtOAc:heptane 1:1), analytical HPLC single main peak, R$_t$=15.81 min., HPLC-MS 352.1 [M+H]$^+$, 374.1 [M+Na]$^+$, 725.1 [2M+Na]$^+$.

(viii) Alternative preparation of (3R,3aR,6aR)-hexahydro-2H-furo[3,2-b]pyrrol-3-ol (2 g). A solution of Super-Hydride® (1.0 mL, IM in tetrahydrofuran, 1.0 mmol) was added dropwise over 2 minutes to a stirred solution of (3R, 3aR, 6R,6aS) 3-hydroxyhexahydro-2H-furo[3,2-b]pyrrol-6-yl 4-methylbenzenesulfonate (74) (100 mg, 0.33 mmol) in tetrahydrofuran (1 mL) under an atmosphere of argon. The mixture was heated for 1.5 hours at 40° C. then chilled with iced water to provide a solution containing aminoalcohol (2 g) used directly in the next step.

(ix) Alternative preparation of (3R,3aR,6aR)-hexahydro-2H-furo[3,2-b]pyrrol-3-ol (2 g). A suspension of (3R,3aR,6R, 6aS) 3-hydroxyhexahydro-2H-furo[3,2-b]pyrrol-6-yl 4-methylbenzenesulfonate (74) (100 mg, 0.33 mmol) in diethyl ether (1 mL) and tetrahydrofuran (0.5 mL) was added to a stirred suspension of lithium aluminium hydride (25.4 mg, 0.67 mmol) in diethyl ether (1 mL) under an atmosphere of argon. The mixture was stirred for 1 hour at ambient temperature then heated at 35° C. for 2 hours.

Tetrahydrofuran (1.5 mL) was added then heating at 35° C. continued for 45 minutes. The mixture was stirred at ambient temperature for 16 hours then lithium aluminium hydride (25.4 mg, 0.67 mmol) added. The mixture was stirred for 1 hour 35 minutes then tetrahydrofuran (1 mL) was added and the solution containing aminoalcohol (2 g) used directly in the next step.

Preparation of (3R,3aR,6aR)-Benzyl 3-hydroxytetrahydro-2H-furo[3,2-b]pyrrole-4(5H)-carboxylate (83). A solution of Super-Hydride® (1.0 mL, 1M in tetrahydrofuran, 1.0 mmol) was added dropwise over 2 minutes to a stirred solution of (3R,3aR,6R,6aS) 3-hydroxyhexahydro-2H-furo[3,2-b]pyrrol-6-yl 4-methylbenzenesulfonate (74) (100 mg, 0.33 mmol) in tetrahydrofuran (1 mL) under an atmosphere of argon. The mixture was heated for 1.5 hours at 40° C. then chilled with iced water to provide a solution containing aminoalcohol (2 g). A solution of sodium carbonate (89 mg, 0.84 mmol) in water (1.5 mL) was added cautiously followed by benzylchloroformate (0.105 mL, 0.74 mmol). The mixture was stirred at ambient temperature for 1 hour then dichloromethane (10 mL) and water (15 mL) added. The organic phase was separated and the aqueous extracted with dichloromethane (2×5 mL). The combined organic phase was washed with brine (5 mL), then dried ($Na_2SO_4$), filtered and reduced in vacuo to leave a colourless oil (143 mg). Flash chromatography over silica, eluting with ethyl acetate:heptane mixtures 10:90 to 60:40 gave (3R,3aR,6aR)-benzyl 3-hydroxytetrahydro-2H-furo[3,2-b]pyrrole-4(5H)-carboxylate (83) (43 mg, 50%) as a viscous colourless oil and a less pure sample of alcohol (83) (22 mg) contaminated with 10% of (3R,3aR,6R,6aS)-benzyl 3-hydroxy-6-(tosyloxy)tetrahydro-2H-furo[3,2-b]pyrrole-4(5H)-carboxylate (34b). Data for bicycle (83): TLC ($R_f$=0.20, EtOAc:heptane 3:2); HPLC-MS 264.1 [M+H]$^+$, 286.1 [M+Na]$^+$, 549.2 [2M+Na]$^+$; $[\alpha]_D^{22}$ –63.8° (c=0.94, $CHCl_3$); $\delta_H$ (500 MHz, $CDCl_3$) mixture of rotamers major:minor 2:1; 1.83-1.93 and 2.03-2.09 (2H total, m, $CbzNCH_2CH_2$), 2.56 (1H, brs, OH), 3.25-3.34 (1H, m, 1×$CbzNCH_2CH_2$), 3.65-3.80 (2H, m, 1×$OCH_2CHOH$ and 1×$CbzNCH_2CH_2$), 3.91 (0.33H, dd, J=9.96 and 4.33 Hz, 1×$OCH_2CHOH$ minor), 3.98 (0.66H, dd, J=9.78 and 4.91 Hz, 1×$OCH_2CHOH$ major), 4.12-4.16 (1H, m, CbzNCH), 4.33 (0.33H, brs, $OCH_2CHOH$ minor), 4.43 (0.66H, brt, J=3.78 Hz $OCH_2CHOH$ major), 4.73-4.78 (1H, m, OCHCHCHOH), 5.08-5.22 (2H, m, $CH_2Ph$), 7.30-7.39 (5H, m, aromatic CH); $\delta_C$ (125 MHz, $CDCl_3$) 31.359/31.671 ($CbzNCH_2CH_2$), 45.187/45.506 ($CbzNCH_2$), 67.159/67.277 ($CH_2Ph$), 69.566/70.679 (CbzNCH), 74.378/74.451 ($OCH_2CHOH$), 76.516/77.382 ($OCH_2CHOH$), 81.686/82.622 (OCHCHN), 127.892, 127.992, 128.131, 128.283, 128.523 and 128.697 (aromatic CH), 136.368/136.414 (Cbz quaternary), 154.228/155.090 (Cbz C=O).

Alternative preparation of (3R,3aR,6aR)-Benzyl 3-hydroxytetrahydro-2H-furo[3,2-b]pyrrole-4(5H)-carboxylate (83). A suspension of (3R,3aR,6R,6aS) 3-hydroxyhexahydro-2H-furo[3,2-b]pyrrol-6-yl 4-methylbenzenesulfonate (74) (100 mg, 0.33 mmol) in diethyl ether (1 mL) and tetrahydrofuran (0.5 mL) was added to a stirred suspension of lithium aluminium hydride (25.4 mg, 0.67 mmol) in diethyl ether (1 mL) under an atmosphere of argon. The mixture was stirred for 1 hour at ambient temperature then heated at 35° C. for 2 hours. Tetrahydrofuran (1.5 mL) was added then heating at 35° C. continued for 45 minutes. The mixture was stirred at ambient temperature for 16 hours then lithium aluminium hydride (25.4 mg, 0.67 mmol) added. The mixture was stirred for 1 hour 35 minutes then tetrahydrofuran (1 mL) was added. After stirring for 30 minutes a solution of sodium carbonate (89 mg, 0.84 mmol) in water (1.5 mL) was added cautiously. The thick suspension was stirred for 5 minutes then benzylchloroformate (0.105 mL, 0.74 mmol) was added. The mixture was stirred for 20 minutes then dichloromethane (10 mL) and water (15 mL) were added. The organic phase was separated and the aqueous reextracted with dichloromethane (2×5 mL). The combined organic phase was washed with brine (5 mL), then dried ($Na_2SO_4$), filtered and reduced in vacuo to leave a residue (95 mg). Flash chromatography over silica, eluting with ethyl acetate:heptane mixtures 10:90 to 50:50 gave bicycle alcohol (83) (23.3 mg, 16%) as a viscous colourless oil and a less pure sample of bicycle alcohol (83) (13.8 mg) contaminated with 8% of (3R,3aR,6R,6aS)-benzyl 3-hydroxy-6-(tosyloxy)tetrahydro-2H-furo[3,2-b]pyrrole-4(5H)-carboxylate (34b).

Preparation of tert-Butyl (S)-1-cyclopentyl-2-((3R,3aR,6aR)-3-hydroxydihydro-2H-furo[3,2-b]pyrrol-4(5H,6H, 6aH)-yl)-2-oxoethylcarbamate (84). A solution of (3R,3aR,6R,6aS) 3-hydroxyhexahydro-2H-furo[3,2-b]pyrrol-6-yl 4-methylbenzenesulfonate (74) (100 mg, 0.33 mmol) in tetrahydrofuran (1.5 mL) was added dropwise to a stirred suspension of lithium aluminium hydride (51 mg, 1.34 mmol) in tetrahydrofuran (1 mL) under an atmosphere of argon over 2 minutes. The mixture was stirred for 3 hours then hydrochloric acid (1M then 5M) added carefully until pH=1. Sodium hydroxide solution (1M) was added until pH=14 followed by hydrochloric acid (1M) until pH=2. The solvents were removed in vacuo then the residue azeotroped with toluene (3×5 mL) to leave aminoalcohol (2 g) which was used without further purification.

4-Methylmorpholine (0.077 mL, 0.70 mmol) was added to a suspension of 2-(1H-benzotriazole-1-yl)-1,1,3,3-tetramethyluronium hexafluorophosphate (HBTU, 133 mg, 0.35 mmol), 1-hydroxybenzotriazole monohydrate (54 mg, 0.35 mmol) and (S)-2-(tert-butoxycarbonylamino)-2-cyclopentyl acid (85 mg, 0.35 mmol) in dimethylformide (0.75 mL). The suspension was agitated for 5 minutes before adding to a stirred suspension of aminoalcohol (2 g) (assume 0.33 mmol) in dimethylformamide (1 mL). After 2.25 hours 4-methylmorpholine (0.077 mL, 0.70 mmol) was added to a suspension of 2-(1H-benzotriazole-1-yl)-1,1,3,3-tetramethyluronium hexafluorophosphate (HBTU, 133 mg, 0.35 mmol), 1-hydroxybenzotriazole monohydrate (54 mg, 0.35 mmol) and (S)-2-(tert-butoxycarbonylamino)-2-cyclopentyl acid (85 mg, 0.35 mmol) in dimethylformamide (0.75 mL). The suspension was agitated for 5 minutes then added to the reaction mixture. The reaction was stirred for 1 hour then the solvents removed in vacuo. The residue was partitioned between dichloromethane (10 mL) and saturated sodium hydrogen carbonate solution (10 mL). The aqueous phase was reextracted with dichloromethane (2×5 mL) then the combined organic layers washed with brine (5 mL), then dried ($Na_2SO_4$), filtered and reduced in vacuo to give a brown oil (141 mg). Flash chromatography over silica, eluting with ethyl acetate:heptane mixtures 25:75 to 80:20 gave tert-butyl (S)-1-cyclopentyl-2-((3R,3aR,6aR)-3-hydroxydihydro-2H-furo[3,2-b]pyrrol-4(5H, 6H, 6aH)-yl)-2-oxoethylcarbamate (84) contaminated with approximately 15% of by-products as a colourless oil (28.7 mg). TLC ($R_f$=0.10, EtOAc:heptane 4:1); analytical HPLC main peak, $R_t$=11.54 min., HPLC-MS 299.1 [M+2H–$^t$Bu]$^+$, 355.1 [M+H]$^+$, 377.1 [M+Na]$^+$, 731.2 [2M+Na]$^+$.

Preparation (3R,3aR,6S,6aS)-tert-Butyl 3-hydroxy-6-(tosyloxy)tetrahydro-2H-furo[3,2-b]pyrrole-4(5H)-carboxylate (35). Ethanol (20 mL) was added dropwise to a mixture of 10% palladium on charcoal (50 mg) and anti-(33) (578 mg, 1.33 mmol) under an atmosphere of argon. The argon was replaced by hydrogen then the suspension was stirred for 1.5 hours before filtering the mixture through celite in vacuo. The filter cake was washed with ethanol then the solvents removed in vacuo from the filtrate to obtain (3R,3aR,6S,6aS)-3-hydroxyhexahydro-2H-furo[3,2-b]pyrrol-6-yl 4-methylbenzenesulfonate which was used without further purification.

A solution of sodium carbonate (297 mg, 2.80 mmol) in water (10 mL) was added whilst stirring to a solution of (3R,3aR,6S,6aS)-3-hydroxyhexahydro-2H-furo[3,2-b]pyrrol-6-yl 4-methylbenzenesulfonate in 1,4-dioxane (7 mL). A solution of di-tert-butyl dicarbonate (320 mg, 1.47 mmol) in 1,4-dioxane (3 mL) was added then the mixture stirred for 2 hours then stored at 4° C. for 16 hours then water (30 mL) was added and the product extracted into dichloromethane (3×30 mL). The organic layer was washed with brine (30 mL), then dried ($MgSO_4$), filtered and reduced in vacuo to leave a residue. Flash chromatography over silica, eluting with ethyl acetate:heptane mixtures 20:80 to 40:60 gave bicyclic alcohol (35) (292 mg, 55%) as a white solid. TLC ($R_f$=0.38, EtOAc:heptane 3:2), analytical HPLC single main peak, $R_t$=16.80 min., HPLC-MS 344.1 [M+2H–$^t$Bu]$^+$, 821.3 [2M+Na]$^+$; $[\alpha]_D^{15}$–36.5° (c=3.42, $CHCl_3$); $\delta_H$ (500 MHz, $CDCl_3$) mixture of rotamers major:minor 2:1; 1.43 (6H, brs, $(CH_3)_3C$, major), 1.47 (3H, brs, $(CH_3)_3C$, minor), 2.19 (0.33H, d, J=4.06 Hz, OH minor), 2.80 (0.66H, d, J=3.10 Hz, OH major), 2.45 (3H, s, aryl-$CH_3$), 3.27 (0.33H, dd, J=13.48 and 3.65 Hz, $BocNCH_2$ minor), 3.35 (0.66H, dd, J=13.37 and 3.83 Hz, $BocNCH_2$ major), 3.72-3.82 (3H, m, 2×$OCH_2CHOH$ and 1×$BocNCH_2$), 4.21-4.24 (1H, brs, BocNCH), 4.37 (0.33H, brs, $OCH_2CHOH$ minor), 4.44 (0.66H, brs, $OCH_2CHOH$ major), 4.46 (0.66H, brd, J=4.62 Hz, TsOCHCH major), 4.64 (0.33H, brd, J=4.18 Hz, TsOCHCH minor), 4.74 (0.33H, brd, J=3.09 Hz, TsOCH minor), 4.77 (0.66H, brd, J=3.43 Hz, TsOCH major), 7.35 (2H, brd, J=7.95 Hz, aromatic $CH_3CCH$), 7.78 (2H, brd, J=8.24 Hz, aromatic $OSO_2CCH$); $\delta_C$ (125 MHz, $CDCl_3$) 21.679 (aryl-$CH_3$), 28.308/28.434 (($CH_3)_3C$), 50.487/51.186 ($BocNCH_2$), 68.000/68.553 (BocNCH), 74.330/74.458 ($OCH_2CHOH$), 75.499/76.335 ($OCH_2CHOH$), 80.187/80.914 (TsOCHCH), 80.849 (($CH_3)_3C$ quaternary), 83.599/84.662 (TsOCHCH), 127.816, 127.852 and 130.125 (aromatic CH), 133.081/133.268 ($CHOSO_2C$ quaternary), 145.371 ($CH_3C$ quaternary), 153.259/154.119 (Boc C=O).

Preparation of (3R,3aR,6S,6aS) tert-Butyl 3-hydroxy-6-(methylsulfonyloxy)tetrahydro-2H-furo[3,2-b]pyrrole-4(5H)-carboxylate (53). Ethanol (3 mL) was added dropwise to a mixture of 10% palladium on charcoal (5 mg) and anti-(52) (60 mg, 0.17 mmol) under an atmosphere of argon. The argon was replaced by hydrogen then the suspension was stirred for 1 hour before filtering the mixture through celite in vacuo. The filter cake was washed with ethanol then the solvents removed in vacuo from the filtrate to obtain (3R,3aR,6S,6aS)- 3-hydroxyhexahydro-2H-furo[3,2-b]pyrrol-6-yl methanesulfonate which was used without further purification.

A solution of sodium carbonate (37 mg, 0.35 mmol) in water (2 mL) was added whilst stirring to a solution of (3R,3aR,6S,6aS)-3-hydroxyhexahydro-2H-furo[3,2-b]pyrrol-6-yl methanesulfonate in 1,4-dioxane (1 mL). A solution of di-tert-butyl dicarbonate (40 mg, 0.18 mmol) in 1,4-dioxane (1 mL) was added then the mixture stirred for 3 hours before adding di-tert-butyl dicarbonate (40 mg, 0.18 mmol). The mixture was stirred for 16 hours then water (10 mL) was added and the product extracted into dichloromethane (1×10 mL and 2×15 mL). The organic layer was washed with brine (15 mL), then dried ($MgSO_4$), filtered and reduced in vacuo to leave a residue. Flash chromatography over silica, eluting with ethyl acetate:heptane mixtures 20:80 to 50:50 gave bicyclic alcohol (53) (27 mg, 49%) as a white solid. TLC ($R_f$=0.15, EtOAc heptane 1:1), HPLC-MS 268.1 [M+2H–Bu]$^+$, 346.1 [M+Na]$^+$, 669.3 [2M+Na]$^+$; $[\alpha]_D^{12.5}$–46.1° (c=2.820, $CHCl_3$); $\delta_H$ (500 MHz, $CDCl_3$) mixture of rotamers major minor 2:1; 1.45 (6H, brs, $(CH_3)_3C$ major), 1.49 (3H, brs, $(CH_3)_3C$ minor), 2.20 (1H, brs, OH), 3.05 (1H, s, $OSO_2CH_3$ minor), 3.06 (2H, S, $OSO_2CH_3$ major), 3.43 (0.33H, dd, J=13.56 and 2.70 Hz, $BocNCH_2$ minor), 3.50 (0.66H, dd, J=13.36 and 3.75 Hz, $BocNCH_2$ major), 3.82-3.87 (2H, m, 1.33×$OCH_2CHOH$ and 0.66×$BocNCH_2$ major), 3.90 (0.66H, dd, J=9.46 and 2.77 Hz, $OCH_2CHOH$ major), 3.96 (0.33H, brd, J=13.48 Hz, $BocNCH_2$ minor), 4.26 (0.33H, d, J=3.92 Hz, BocNCH minor), 4.30 (0.66H, d, J=3.58 Hz, BocNCH major), 4.42 (0.33H, brs, $OCH_2CHOH$ minor), 4.50 (0.66H, brs, $OCH_2CHOH$ major), 4.72 (0.66H, d, J=2.87 Hz, MsOCHCH major), 4.80 (0.33H, d, J=3.54 Hz, MsOCHCH minor), 5.00 (1H, brs, MsOCH); $\delta_C$ (125 MHz, $CDCl_3$) 28.352/28.446 (($CH_3)_3C$ quaternary), 38.644/38.711 ($OSO_2CH_3$), 50.675/51.401 ($BocNCH_2$), 68.078/68.631 (BocNCH), 74.505/74.590 ($OCH_2CHOH$), 75.662/76.402 ($OCH_2CHOH$), 79.776/80.274 (MsOCHCH), 81.013/81.181 (C$(CH_3)_3$ quaternary), 83.872/84.785 (MsOCHCH), 153.452/154.266 (Boc C=O).

Preparation of (3aS,6S,6aS)-(9H-fluoren-9-yl)methyl 6-tert-butoxy-3-oxotetrahydro-2H-furo[3,2-b]pyrrole-4(5H)-carboxylate (4c)

(i) Preparation of Benzyl (S)-2-tert-butoxy-2-((S)-2,5-dihydrofuran-2-yl)ethylcarbamate (26). Alcohol (17) (270 mg, 1.02 mmol) was dissolved in anhydrous dichloromethane (8 mL) in a 50 mL glass pressure tube and cooled to –78° C. Isobutene (~3 mL) was condensed into the solution and conc. $H_2SO_4$ (25 µL) added. The tube was sealed and stirred at ambient temperature overnight. The sealed tube was cooled to –78° C., N-methylmorpholine (60 µL, 1 eq. w.r.t. conc. $H_2SO_4$) added and allowed to warm to ambient temperature, unsealed, with stirring over 2 h. Dichloromethane (25 mL) was added and the organics washed with pH 3 HCl (25 mL), $NaHCO_3$ (25 mL) then brine (25 mL) and dried ($Na_2SO_4$). The solvents were removed in vacuo to give a tan oil. The crude oil was purified on a 5 g Flash silica cartridge eluting with a gradient of heptane:ethyl acetate 9:1→6:1. Desired fractions were combined and reduced in vacuo to provide ether (26) as a clear gum (222 mg, 68%). TLC ($KMnO_4$ stain, $R_f$=0.46, heptane:ethyl acetate 1:2), analytical HPLC $R_t$=17.10 min, HPLC-MS (single main UV peak with $R_t$=2.91 min, 264.1 [M+2H–Bu]$^+$, 342.2 [M+Na]$^+$, 661.3 [2M+Na]$^+$); $[\alpha]_D^{18}$–94.3° (c=1.962, $CHCl_3$).

(ii) Preparation of epoxide mixture Benzyl (S)-2-((1R,2R,5R)-3,6-dioxabicyclo[3.1.0]hexan-2-yl)-2-tert-butoxyethylcarbamate syn-(27) and Benzyl (S)-2-((1S,2R,5S)-3,6-dioxabicyclo[3.1.0]hexan-2-yl)-2-tert-butoxyethylcarbamate anti-(28). Method 1; meta-Chloroperbenzoic acid. Ether (26) (210 mg, 0.66 mmol) was dissolved in anhydrous dichloromethane (10 mL) with stirring and meta-chloroperoxybenzoic acid (1.48 g, 77% reagent, 6.6 mmol) added. The mixture was stirred at ambient temperature under argon for 16 h. Dichloromethane (20 mL) was added and the organic phase washed with 10% aqueous w/v solution of sodium hydroxide (2×20 mL), then dried ($Na_2SO_4$), filtered and reduced in vacuo to leave a clear gum (200 mg). The crude gum was purified on a 5 g Flash silica cartridge eluting with a gradient of heptane:ethyl acetate 9:1→7:1. Desired fractions containing the co-eluting epoxides were combined and reduced in vacuo to provide a viscous oil (183 mg, 82.7%). TLC ($R_f$=0.30

(figure of eight mixture of syn and anti epoxides), EtOAc:heptane 2:1), HPLC-MS 236.1, 280.1 [M+2H–Bu]+, 358.2 [M+Na]+, 693.2 [2M+Na]+.

(iii) Alternative preparation of epoxide mixture Benzyl (S)-2-((1R,2R,5R)-3,6-dioxabicyclo[3.1.0]hexan-2-yl)-2-tert-butoxyethylcarbamate syn-(27). and Benzyl (S)-2-((1S,2R,5S)-3,6-dioxabicyclo[3.1.0]hexan-2-yl)-2-tert-butoxyethylcarbamate anti-(28). Method 2; Oxone. To a solution of ether (26) (9.5 mg, 0.030 mmol) in acetonitrile (0.15 mL) and aqueous $Na_2$.EDTA (0.15 mL, 0.4 mmol solution) at 0° C. was added 1,1,1-trifluoroacetone (0.032 mL, 0.36 mmol). To this solution was added in portions a mixture of sodium bicarbonate (21 mg, 0.25 mmol) and OXONE® (57 mg, 0.092 mmol) over a period of 1 hour. The mixture was stirred for 50 minutes then diluted with water (5 mL) and the product extracted into dichloromethane (2×50 mL). The combined organic layers were washed with brine (5 mL) then dried ($Na_2SO_4$), filtered and reduced in vacuo. $^1H$ nmr analysis of the residue indicated a 10:1 mixture benzyl anti-(28) and syn-(27) respectively (6.7 mg).

(iv) Preparation of Benzyl (S)-2-((1R,2R,5R)-3,6-dioxabicyclo[3.1.0]hexan-2-yl)-2-tert-butoxyethylcarbamate syn-(27) and (3R,3aR,6S,6aS)-benzyl 6-tert-butoxy-3-hydroxytetrahydro-2H-furo[3,2-b]pyrrole-4(5H)-carboxylate (29). Epoxide mixture (27, 28) (175 mg, 0.52 mmol) was dissolved in anhydrous THF (3 mL), cooled to 0° C. and sodium hydride (60% dispersion in oil) (26.2 mg, 0.65 mmol) added. The mixture was stirred at ambient temperature for 3 h. Dichloromethane (25 mL) was added and the organic phase washed with brine (1×25 mL), then dried ($Na_2SO_4$), filtered and reduced in vacuo to leave an opaque gum (~150 mg). The crude gum was purified on a 5 g Flash silica cartridge eluting with a gradient of heptane:ethyl acetate 9:1→5:1 to provide two products:

(a) Syn-epoxide (27) as a viscous oil (39.2 mg, 0.12 mmol, 22.4%), TLC ($R_f$=0.37, EtOAc:heptane 1:1), analytical HPLC $R_t$=15.61 min, HPLC-MS 280.1 [M+2H–Bu]+, 358.2 [M+Na]+, 693.2 [2M+Na]+.

(b) Bicycle alcohol (29) as a viscous oil (80.4 mg, 0.24 mmol, 46%), TLC ($R_f$=0.31, EtOAc:heptane 1:1), analytical HPLC $R_t$=15.17 min, HPLC-MS 236.1, 280.1 [M+2H–Bu]+, 358.2 [M+Na]+, 693.2 [2M+Na]+; $[\alpha]_D^{18}$=–46.0° (c=8.04, $CHCl_3$); $^1H$ NMR (500 MHz, $CDCl_3$ at 300K): δ 1.18 (s, $C(CH_3)_3$, 9H), 1.98 (d, J=4.0 Hz, OH, 0.4H), 2.76 (d, J=2.6 Hz, OH, 0.6H), 3.36-3.44 (m, $CbzNCH_2$, 0.6H), 3.45-3.52 (m, $CbzNCH_2$, 1H), 3.62 (d, J=11.8 Hz, $CbzNCH_2$, 0.4H), 3.70-3.92 (m, $OCH_2CHOH$, 2H), 4.04 (b, CHOBUt, 1H), 4.26 (b, NCHCHOH, 1H), 4.36 (b, $OCH_2CHOH$, 0.4H), 4.45 (d, J=4.6 Hz, ButOCHCHO, 1H), 4.48 (b, $OCH_2CHOH$, 0.6H), 5.09-5.26 (m, $OCH_2Ph$, 2H), 7.34-7.37 (bm, 5H aromatic); $^{13}C$ NMR (125 MHz, $CDCl_3$ at 300K): δ 28.08/28.12 ($C(CH_3)_3$), 53.48/53.71 ($CbzNCH_2$), 67.11/67.29 ($OCH_2Ph$), 68.31/69.27 (NCHCHOH), 72.51/73.29 ($CHOBu^t$), 73.88 ($OCH_2CHOH$), 74.72/74.78 ($C(CH_3)_3$), 75.80±76.62 ($OCH_2CHOH$), 86.89/87.52 (ButOCHCHO), 127.81/127.93/128.06/128.23/128.50/128.68 (aromatic CH), 136.43 (aromatic quarternary), 154.51/155.26 (NHC(O)O).

(v) Preparation of (3R,3aR,6S,6aS)-(9H-fluoren-9-yl)methyl 6-tert-butoxy-3-hydroxytetrahydro-2H-furo[3,2-b]pyrrole-4(5H)-carboxylate (4b). Bicycle alcohol (29) (75 mg, 0.22 mmol) was dissolved in methanol (5 mL), cooled to 0° C. and 10% palladium on charcoal (20 mg) added. The mixture was stirred, then evacuated and flushed with hydrogen. The mixture was warmed to ambient temperature and after 1 h. filtered through celite. The filter cake was washed with ethanol (3×5 mL) and the combined filtrates reduced in vacuo to provide the crude amine (~45 mg). HPLC-MS 146.1 [M+2H–Bu]+, 202.1 [M+H]+, 425.2 [M+Na]+. The crude amine was dissolved in 1,4-dioxane (3.5 mL) with stirring, ice-cooled and a solution of sodium carbonate (50 mg, 0.47 mmol) in water (3.5 mL) was added. 9-Fluorenylmethyl chloroformate (61 mg, 0.234 mmol) in 1,4-dioxane (2.5 mL) was added dropwise over 30 minutes and the mixture stirred for a further 1 h. $CHCl_3$ (25 mL) was then added and the organic phase washed with 0.1N HCl (25 mL), sat. $NaHCO_3$ (25 mL), then brine (25 mL) and dried ($Na_2SO_4$). The organic layer was filtered and reduced in vacuo to leave a clear film (~100 mg). The crude film was purified on a 5 g Flash silica cartridge eluting with a gradient of heptane:ethyl acetate 8:1→2:1 to provide alcohol (4b) as a white solid (74.4 mg, 0.175 mmol, 78%). TLC ($R_f$=0.33, EtOAc:heptane 1:1), analytical HPLC $R_t$=18.78 min, HPLC-MS 368.1 [M+2H–Bu]+, 424.2 [M+H]+, 446.2 [M+Na]+, 869.4 [2M+Na]+; $[\alpha]_D^{18}$=–34.8° (c=6.9, $CHCl_3$).

(vi) Preparation of (3aS,6S,6aS)-(9H-fluoren-9-yl)methyl 6-tert-butoxy-3-oxotetrahydro-2H-furo[3,2-b]pyrrole-4(5H)-carboxylate (4c). Alcohol (4b) (70 mg, 0.165 mmol) was dissolved in anhydrous dichloromethane (5 mL) with stirring under argon. Dess-Martin periodinane (141 mg, 0.33 mmol) was added and the mixture stirred for 2 h. The mixture was diluted with DCM (20 mL) and washed with sat. $NaHCO_3$/0.25M $Na_2S_2O_3$, sat. $NaHCO_3$, brine (25 mL each) and dried ($Na_2SO_4$)—. The organic layer was filtered and reduced in vacuo to leave a clear film (~110 mg). The crude film was purified on a 5 g Flash silica cartridge eluting with a gradient of heptane:ethyl acetate 7:1→2:1 to provide ketone (4c) as a colourless gum (70.5 mg, 0.165 mmol, 99.8%). TLC ($R_f$=0.50, EtOAc:heptane 1:1), analytical HPLC broad peak with $R_t$=18.58-20.92 min, HPLC-MS 366.1 [M+2H–Bu]+, 422.2 [M+H]+, 444.2 [M+Na]+, 865.4 [2M+Na]+; $[\alpha]_D^{18}$=–100.8° (c=6.5, $CHCl_3$); $^1H$ NMR (500 MHz, $CDCl_3$ at 300K): δ 1.22 (s, $C(CH_3)_3$, 9H), 3.55-3.67 (m, $FmocNCH_2$, 1.6H), 3.78-3.83 (m, $FmocNCH_2$, 0.4H), 3.90-3.96 (m, $OCH_2C(O)$, 1H), 4.10-4.19 (m, $OCH_2C(O)$+$CHOBu^t$, 2H), 4.25-4.42 (m, 0.4+0.6 FmocCH+1×$FmocCH_2$+. NCHC(O), 3H), 4.50 (q, J=6.7, 3.7 Hz, $FmocCH_2$), 4.59/4.64 (b, $Bu^tOCH$-CHO, 1H), 7.30 (d, J=6.65 Hz, Fmoc H-2 and H-7), 7.39 (t, J=7.5 Hz, Fmoc H-3 and H-6), 7.57 (d, J=7.2 Hz, 1.2 Fmoc H-1 and H-8), 7.66 (d, J=7.1 Hz, 0.8 Fmoc H-1 or H-8), 7.76 (d, J=7.55 Hz, Fmoc H-4 and H-5); $^{13}C$ NMR (125 MHz, $CDCl_3$ at 300K): δ 28.10 ($C(CH_3)_3$), 47.13 (FmocCH), 53.40/53.84 ($FmocNCH_2$), 61.12/61.56 (NCHC(O)), 67.63/68.38 ($FmocCH_2$), 69.99 ($OCH_2C$(O)), 72.54/73.21 ($CHOBu^t$), 75.05/75.13 ($C(CH_3)_3$), 86.36/87.37 ($Bu^tOCHCHO$), 119.89/119.96 (Fmoc C-4 and C-5), 124.97/125.03/125.25/125.59 (Fmoc C-1 and C-8), 126.99/127.04 (Fmoc C-2 and C-7), 127.67 (Fmoc C-3 and C-6), 141.22/141.33/143.71/143.87/144.47 (Fmoc quaternary aromatics), 155.17 (FmOC(O)N), 208.02/208.31 (C═O).

Preparation of (3aS,6R,6aS)-(9H-fluoren-9-yl)methyl 6-tert-butoxy-3-oxotetrahydro-2H-furo[3,2-b]pyrrole-4(5H)-carboxylate (3c)

(i) Preparation of Benzyl (R)-2-tert-butoxy-2-((S)-2,5-dihydrofuran-2-yl)ethylcarbamate (26b). Alcohol (18) (400 mg, 1.52 mmol) was dissolved in anhydrous dichloromethane (8 mL) in a 50 mL glass pressure tube and cooled to –78° C. Isobutene (~4 mL) was condensed into the solution and conc. $H_2SO_4$ (35 μL) added. The tube was sealed and stirred at ambient temperature for 6 h. The sealed tube was cooled to −78° C., N-methylmorpholine (75 μL, 1 eq. w.r.t. conc. H$_2$SO$_4$) added and allowed to warm to ambient temperature, unsealed, with stirring over 2 h. Dichloromethane (20 mL) was added and the organics washed with pH 3HCl (25 mL), NaHCO$_3$ (25 mL) then brine (25 mL) and dried (Na$_2$SO$_4$). The solvents were removed in vacuo to give an opaque gum (350 mg). The crude gum was purified on a 5 g Flash silica cartridge eluting with a gradient of heptane:ethyl acetate 7:1→2:1. Desired fractions were combined and reduced in vacuo to provide ether (26b) as a thick clear oil (204 mg, 42%) and recovered starting alcohol (108 mg, 27%). TLC (KMnO$_4$ stain, R$_f$=0.70, heptane:ethyl acetate 2:1), analytical HPLC R$_t$=16.85 min, HPLC-MS (single main UV peak with R$_t$=2.85 min, 264.1 [M+2H−Bu]$^+$, 342.2 [M+Na]$^+$, 661.3 [2M+Na]$^+$); [α]$_D^{18}$−56.8° (c=2.068, CHCl$_3$).

(ii) Preparation of epoxide mixture Benzyl (R)-2-((1R,2R,5R)-3,6-dioxabicyclo[3.1.0]hexan-2-yl)-2-tert-butoxyethylcarbamate syn-(27b). and Benzyl (R)-2-((1S,2R,5S)-3,6-dioxabicyclo[3.1.0]hexan-2-yl)-2-tert-butoxyethylcarbamate anti-(28b). Method 1; meta-Chloroperbenzoic acid. Ether (26b) (175 mg, 0.55 mmol) was dissolved in anhydrous dichloromethane (7.5 mL) with stirring and meta-chloroperoxybenzoic acid (1.22 g, 77% reagent, 5.5 mmol) added. The mixture was stirred at ambient temperature under argon for 16 h. Dichloromethane (20 mL) was added and the organic phase washed with 10% aqueous w/v solution of sodium hydroxide (2×50 mL), then dried (Na$_2$SO$_4$), filtered and reduced in vacuo to leave a clear oil (180 mg). The crude oil was purified on a 5 g Flash silica cartridge eluting with a gradient of heptane:ethyl acetate 8:1→2:1. Desired fractions containing the co-eluting epoxides were combined and reduced in vacuo to provide a clear gum (171 mg, 92.7%). TLC (R$_f$=0.28 (mixture of syn and anti epoxides), EtOAc:heptane 1:2), HPLC-MS 236.1, 280.1 [M+2H−Bu]$^+$, 358.2 [M+Na]$^+$, 693.2 [2M+Na]$^+$.

(iii) Alternative preparation of epoxide mixture Benzyl (R)-2-((1R,2R,5R)-3,6-dioxabicyclo[3.1.0]hexan-2-yl)-2-tert-butoxyethylcarbamate syn-(27b). and Benzyl (R)-2-((1S,2R,5S)-3,6-dioxabicyclo[3.1.0]hexan-2-yl)-2-tert-butoxyethylcarbamate anti-(28b). Method 2; Oxone. To a solution of ether (26b) (9.5 mg, 0.030 mmol) in acetonitrile (0.15 mL) and aqueous Na$_2$.EDTA (0.15 mL, 0.4 mmol solution) at 0° C. was added 1,1,1-trifluoroacetone (0.032 mL, 0.36 mmol). To this solution was added in portions a mixture of sodium bicarbonate (21 mg, 0.25 mmol) and OXONE® (57 mg, 0.092 mmol) over a period of 1 hour. The mixture was stirred for 50 minutes then diluted with water (5 mL) and the product extracted into dichloromethane (2×50 mL). The combined organic layers were washed with brine (5 mL) then dried (Na$_2$SO$_4$), filtered and reduced in vacuo. 1H nmr analysis of the residue indicated a 10:1 mixture of anti-(28b) and syn-(27b) respectively (8.9 mg).

(iv) Preparation of Benzyl (R)-2-((1R,2R,5R)-3,6-dioxabicyclo[3.1.0]hexan-2-yl)-2-tert-butoxyethylcarbamate syn-(27b) and (3R,3aR,6R,6aS)-benzyl 6-tert-butoxy-3-hydroxytetrahydro-2H-furo[3,2-b]pyrrole-4(5H)-carboxylate (29b). Epoxide mixture (27b, 28b) (165 mg, 0.49 mmol) was dissolved in anhydrous THF (3 mL), cooled to 0° C. and sodium hydride (60% dispersion in oil) (24.6 mg, 0.615 mmol) added. The mixture was stirred at ambient temperature overnight. Dichloromethane (25 mL) was added and the organic phase washed with brine (1×25 mL), then dried (Na$_2$SO$_4$), filtered and reduced in vacuo to leave a colourless gum (~200 mg). The crude gum was purified on a 5 g Flash silica cartridge eluting with a gradient of heptane:ethyl acetate 6:1→1:2 to provide two products:

(c) Syn-epoxide (27b) as a viscous oil (88 mg, 0.26 mmol, 53.4%), TLC (R$_f$=0.42, EtOAc:heptane 1:1), analytical HPLC R$_t$=15.64 min, HPLC-MS 280.1 [M+2H−Bu]$^+$, 358.2 [M+Na]$^+$, 693.2 [2M+Na]$^+$; [α]$_D^{18}$−36.9° (c 8.8, CHCl$_3$); $^1$H NMR (500 MHz, CDCl$_3$ at 300K): δ 1.25 (s, C(CH$_3$)$_3$, 9H), 3.20-3.25 (dq, CbzNHCH$_2$, 1H), 3.57-3.64 (m, CbzNHCH$_2$, 1H), 3.67-3.71 (b, CH$_2$OCHCHOBu$^t$+CH$_2$OCHCHOBu$^t$, 3H), 3.73-3.77 (m, CHOCH+CHOCH, 2H), 4.08 (d, J=10.70 Hz, CH$_2$OCHCHOBUt, 1H), 5.03-5.14 (dd, J=12.2 Hz, OCH$_2$Ph, 2H), 5.22 (d, J=5.5 Hz, NH, 1H), 7.35 (bm, 5H aromatic); $^{13}$C NMR (125 MHz, CDCl$_3$ at 300K): δ 28.38 (C(CH$_3$)$_3$), 44.22 (CbzNHCH$_2$), 56.71/56.83 (CHOCH+CHOCH), 66.63 (OCH$_2$Ph), 68.03 (CH$_2$OCHCHOBu$^t$), 68.23 (CH$_2$OCHCHOBu$^t$), 75.30 (C(CH$_3$)$_3$), 78.71 (CH$_2$OCHCHOBu$^t$), 128.05/128.20/128.47 (aromatic CH), 136.67 (aromatic quarternary), 156.53 (NHC(O)O).

(d) Bicycle alcohol (29b) as a viscous oil (33 mg, 0.10 mmol, 20.0%), TLC (R$_f$=0.13, EtOAc:heptane 1:1), analytical HPLC R$_t$=13.66 min, HPLC-MS 236.1, 280.1 [M+2H−Bu]$^+$, 358.2 [M+Na]$^+$, 693.2 [2M+Na]$^+$; [α]$_D^{18}$−22.7° (c=3.3, CHCl$_3$); $^1$H NMR (500 MHz, CDCl$_3$ at 300K): δ 1.23 (s, C(CH$_3$)$_3$, 9H), 1.91/2.56 (b, OH, 0.4/0.6H), 3.06-3.14 (m, CbzNCH$_2$, 1H), 3.68-3.75/3.81-3.86 (dq, J=7.7 Hz, CbzNCH$_2$, 0.6+0.4H), 3.75-3.80 (m, OCH$_2$CHOH, 1H), 4.00-4.06 (m, CHOBu$^t$+0.4 OCH$_2$CHOH, 1.4H), 4.09-4.14 (m, NCHCHOH+0.6 OCH$_2$CHOH, 1.6H), 4.35 (b, OCH$_2$CHOH, 0.4H), 4.45-4.48 (m, OCH$_2$CHOH, 0.6H), 4.48-4.51 (m, Bu$^t$OCHCHO, 1H), 5.08-5.20 (m, OCH$_2$Ph, 2H), 7.35 (bm, 5H aromatic); $^{13}$C NMR (125 MHz, CDCl$_3$ at 300K): δ 28.15 (C(CH$_3$)$_3$), 48.97/49.09 (CbzNCH$_2$), 67.23/67.39 (OCH$_2$Ph), 68.23/69.23 (NCHCHOH), 70.81/71.04 (CHOBu$^t$), 74.53/74.57 (C(CH$_3$)$_3$), 74.98/75.25 (OCH$_2$CHOH), 77.19/77.32 (OCH$_2$CHOH), 81.47/82.29 (Bu$^t$OCHCHO), 127.99/128.04/128.18/128.36/128.54/128.72 (aromatic CH), 136.28 (aromatic quarternary), 154.21/155.06 (NHC(O)O).

(v) Preparation of (3R,3aR,6R,6aS)-(9H-fluoren-9-yl)methyl 6-tert-butoxy-3-hydroxytetrahydro-2H-furo[3,2-b]pyrrole-4(5H)carboxylate (3b). Alcohol (29b) (33 mg, 0.1 mmol) was dissolved in methanol (5 mL), cooled to 0° C. and 10% palladium on charcoal (15 mg) added. The mixture was stirred, then evacuated and flushed with hydrogen. The mixture was warmed to ambient temperature and after 1 h. filtered through celite. The filter cake was washed with ethanol (3×5 mL) and the combined filtrates reduced in vacuo to provide the crude amine (~15 mg). HPLC-MS 146.1 [M+2H−Bu]$^+$, 202.1 [M+H]$^+$, 425.2 [M+Na]$^+$. The crude amine was dissolved in 1,4-dioxane (2.5 mL) with stirring, ice-cooled and a solution of sodium carbonate (22 mg, 0.21 mmol) in water (2.5 mL) was added. 9-Fluorenylmethyl chloroformate (27 mg, 0.10 mmol) in 1,4-dioxane (2.5 mL) was added dropwise over 30 minutes and the mixture stirred for a further 1 h. CHCl$_3$ (25 mL) was then added and the organic phase washed with 0.1N HCl (25 mL), sat. NaHCO$_3$ (25 mL), then brine (25 mL) and dried (Na$_2$SO$_4$). The organic layer was filtered and reduced in vacuo to leave a clear film (~40 mg). The crude film was purified on a 5 g Flash silica cartridge eluting with a gradient of heptane:ethyl acetate 8:1→1:1 to provide alcohol (3b) as a white solid (27.3 mg, 0.065 mmol, 65.8%). TLC (R$_f$=0.16, EtOAc:heptane 1:1), analytical HPLC R$_t$=17.39 min., HPLC-MS 368.2 [M+2H−Bu]$^+$, 424.2 [M+H]$^+$, 446.2 [M+Na]$^+$, 869.4 [2M+Na]$^+$; [α]$_D^{18}$−120.2° (c=2.45, CHCl$_3$).

(vi) Preparation of (3aS,6R,6aS)-(9H-fluoren-9-yl)methyl 6-tert-butoxy-3-oxotetrahydro-2H-furo[3,2-b]pyrrole-4(5H)-carboxylate (3c). Bicycle alcohol (3b) (25 mg, 0.06 mmol) was dissolved in anhydrous dichloromethane (3 mL) with stirring under argon. Dess-Martin periodinane (50 mg, 0.12 mmol) was added and the mixture stirred overnight. The mixture was diluted with DCM (20 mL) and washed with sat. NaHCO$_3$/0.25M Na$_2$S$_2$O$_3$, sat. NaHCO$_3$, brine (25 mL each) and dried (Na$_2$SO$_4$). The organic layer was filtered and reduced in vacuo to leave a tan gum (~40 mg). The crude gum was purified on a 5 g Flash silica cartridge eluting with a gradient of heptane:ethyl acetate 6:1→3:1 to provide ketone (3c) as a white solid (21.9 mg, 0.052 mmol, 88.1%). TLC (R$_f$=0.57, EtOAc:heptane 2:1), analytical HPLC broad peak with R$_t$=17.15-19.96 min, HPLC-MS 366.1 [M+2H−Bu]$^+$, 422.2 [M+H]$^+$, 444.2 [M+Na]$^+$, 865.4 [2M+Na]$^+$; [α]$_D^{18}$−870.5° (c=1.6, CHCl$_3$); $^1$H NMR (500 MHz, CDCl$_3$ at 300K): δ 1.25 (s, C(CH$_3$)$_3$, 9H), 3.30-3.40 (m, FmocNCH$_2$, 1H), 3.61-3.66 (m, FmocNCH$_2$, 0.4H), 3.76-3.80 (m, FmocNCH$_2$, 0.6H), 4.01-4.17 (m, OCH$_2$C(O), 2H), 4.22-4.35 (m, NCHC(O)+CHOBu$^t$+FmocCH+0.6 FmocCH$_2$, 3.6H), 4.37-4.43 (bt, 0.4 FmocCH$_2$), 4.49-4.54/4.56-4.63 (m, 0.4 FmocCH$_2$+0.6 FmocCH$_2$), 4.69-4.72/4.72-4.77 (m, ButOCHCHO, 1H), 7.29-7.33 (m, Fmoc H-2 and H-7), 7.38 (t, J=7.45 Hz, Fmoc H-3 and H-6), 7.56 (d, J=8.7 Hz, 1.0 Fmoc H-1 or H-8), 7.65 (d, J=7.3 Hz, 0.5 Fmoc H-1 or H-8), (d+m, J=7.55 Hz, Fmoc H-4 and H-5+0.5H-1 or H-8); $^{13}$C NMR (125 MHz, CDCl$_3$ at 300K): δ 28.11 (C(CH$_3$)$_3$), 47.19 (FmocCH), 50.48/50.94 (FmocNCH$_2$), 60.45/60.83 NCHC(O)), 67.64/68.23 (FmocCH$_2$), 71.32/71.45 (OCH$_2$C(O)), 71.50 (CHOBu$^t$), 75.22 (C(CH$_3$)$_3$), 80.78/81.49 (ButOCHCHO), 119.88/119.95 (Fmoc C-4 and C-5), 124.98/125.01/125.20/125.43 (Fmoc C-1 and C-8), 127.03 (Fmoc C-2 and C-7), 127.65/127.71 (Fmoc C-3 and C-6), 141.22/141.33/143.63/143.97/144.38 (Fmoc quaternary aromatics), 155.10 (CH$_2$OC(O)N), 208.56/208.66 (C=O).

Preparation of (3aS,6S,6aS)-(9H-Fluoren-9-yl)methyl 6-methoxy-3-oxotetrahydro-2H-furo[3,2-b]pyrrole-4(5H)-carboxylate (6c)

(i) Preparation of Benzyl (S)-2-((S)-2,5-dihydrofuran-2-yl)-2-methoxyethyl carbamate (30). Methyl iodide (1.18 mL, 19.0 mmol) was added to a stirred mixture of alcohol (17) (1.0 g, 3.80 mmol) and silver (1) oxide (1.32 g, 5.70 mmol) in acetonitrile (15 mL). The mixture was heated at 75° C. for 3 hours then at 80° C. for 3.5 hours. Silver (I) oxide (0.20 g, 0.86 mmol) and methyl iodide (0.25 mL, 4.0 mmol) were added and heating continued for 4 hours then allowed to cool to ambient temperature, filtered and reduced in vacuo. Flash chromatography over silica, eluting with ethyl acetate:heptane mixtures 10:90 to 30:70 gave methyl ether (30) (731 mg, 69%) as a colourless oil. TLC (R$_f$=0.40, EtOAc:heptane 1:1), analytical HPLC single main peak, R$_t$=13.107 min., HPLC-MS 278.1 [M+H]$^+$, 577.2 [2M+Na]$^+$; [α]$_D^{19}$−100.4° (c=2.888, CHCl$_3$); δ$_H$ (500 MHz, CDCl$_3$) 3.20 (1H, dt, J=13.85 and 5.67 Hz, CH$_2$N), 3.32-3.36 (1H, m, CHOCH$_3$), 3.44 (3H, s, CHOCH$_3$), 3.42-3.49 (1H, m, CH$_2$N), 4.57-4.71 (2H, m, OCH$_2$CH=CH), 4.88-4.92 (1H, m, OCHCH=CH), 5.09 (2H, s, OCH$_2$Ph), 5.16 (1H, brs, NH), 5.79-5.83 and 5.95-5.99 (2H total, m, CH$_2$CH=CH), 7.29-7.36 (5H, aromatic CH); δ$_C$ (125 MHz, CDCl$_3$) 40.952 (CH$_2$NHCbz), 58.752 (OCH$_3$), 66.705 (CH$_2$Ph), 75.589 (OCH$_2$CH=CH), 81.184 (CHOCH$_3$), 86.559 (OCHCH=CH), 126.033, 128.097 and 128.497 (OCH$_2$CH=CH and Cbz aromatic CH), 136.555 (Cbz quaternary), 156.441 (Cbz C=O).

(ii) Alternative preparation of Benzyl (R)-2-((S)-2,5-dihydrofuran-2-yl)-2-methoxyethylcarbamate (30). Trimethyloxonium fluoroborate (19.12 g, 129.3 mmol) was added to a stirred mixture of benzyl (S)-2-((S)-2,5-dihydrofuran-2-yl)-2-hydroxyethylcarbamate (17) (20.0 g, 76.0 mmol), 4 Å molecular sieves (66 g), 1,8-bis(dimethylamino)naphthalene (97.8 g, 456.2 mmol) and dichloromethane (500 mL) under an atmosphere of argon. The mixture was stirred for 2 hours then filtered through celite in vacuo. The filter cake was washed with dichloromethane (750 mL) then the solvents removed in vacuo from the filtrate. The residue was triturated with TBME (250 mL) then the granular solid removed by filtration in vacuo. The solid was washed with TBME (3×100 mL) then the combined filtrates washed with hydrochloric acid (2.5M, 1×100 mL then 2×50 mL), brine (50 mL) then dried (Na$_2$SO$_4$), filtered and reduced in vacuo to leave a pale yellow oil. Flash chromatography over silica, eluting with ethyl acetate:heptane mixtures 10:90 to 50:50 gave methylether (30) as a colourless oil (17.2 g, 82%).

(iii) Preparation of Benzyl (S)-2-((1S,2R,5S)-3,6-dioxabicyclo[3.1.0]hexan-2-yl)-2-methoxyethyl carbamate anti-(31). To a solution of methyl ether (30) (731 mg, 2.64 mmol) in acetonitrile (15 mL) and aqueous Na$_2$.EDTA (15 mL, 0.4 mmol solution) at 0° C. was added 1,1,1-trifluoroacetone (2.84 mL, 31.7 mmol). To this solution was added in portions a mixture of sodium bicarbonate (1.87 g, 22.2 mmol) and OXONE® (5.04 g, 8.19 mmol) over a period of 1.5 hours. The mixture was stirred for 15 minutes then diluted with water (50 mL) and the product extracted into dichloromethane (3×50 mL). The combined organic layers were washed with brine (75 mL) then dried (MgSO$_4$), filtered and reduced in vacuo. Flash chromatography over silica, eluting with ethyl acetate:heptane mixtures 10:90 to 30:70 gave anti-(31) (323 mg, 42%) as a colourless oil. TLC (R$_f$=0.25, EtOAc:heptane 1:1), analytical HPLC single main peak, R$_t$=10.901 min., HPLC-MS 294.2 [M+H]$^+$, 609.3 [2M+Na]$^+$; [α]$_D^{15}$+12.1° (c=2.890, CHCl$_3$); δ$_H$ (500 MHz, CDCl$_3$) 3.27-3.55 (6H, m, CH$_2$NH, CHOCH$_3$), 3.72 and 3.78 (2H, each d, J=2.88 and 2.49 Hz respectively, OCH$_2$CHCH), 3.84 (1H, d, J=9.98 Hz, OCH$_2$CH), 3.94 (1H, d, J=10.02 Hz, OCH$_2$CH), 4.12 (1H, d, J=2.76 Hz, OCHCHOCH$_3$), 5.10 (2H, s, CH$_2$Ph), 5.27 (1H, brs, NH), 7.28-7.37 (5H, m, phenyl CH); δ$_C$ (125 MHz, CDCl$_3$) 40.819 (CH$_2$NHCbz), 56.769 and 57.700 (OCH$_2$CHCH), 58.442 (OCH$_3$), 66.784 (CH$_2$Ph), 68.446 (OCH$_2$CH), 78.631 (OCHCHOCH$_3$), 79.264 (CHOCH$_3$), 128.079, 128.160 and 128.521 (aromatic CH), 136.451 (Cbz quaternary), 156.532 (Cbz C=O).

(iv) (3R,3aR,6S,6aS)-(9H-Fluoren-9-yl)methyl 3-hydroxy-6-methoxytetrahydro-2H-furo[3,2-b]pyrrole-4(5H)-carboxylate (6b). Ethanol (15 mL) was added dropwise to a mixture of 10% palladium on charcoal (30 mg) and anti-(31) (315 mg, 1.07 mmol) under an atmosphere of argon. The argon was replaced by hydrogen then the suspension was stirred for 1.5 hours then 10% palladium on charcoal (30 mg) was added. The mixture was stirred for 2 hours then 10% palladium on charcoal (50 mg) was added. The mixture was stirred for 4.5 hours then filtered through celite in vacuo. The filter cake was washed with ethanol then the solvents removed in vacuo from the filtrate to obtain the crude (3R,3aR,6S,6aS)-6-methoxyhexahydro-2H-furo[3,2-b]pyrrol-3-ol which was used without further purification.

A solution of sodium carbonate (239 mg, 2.26 mmol) in water (10 mL) was added whilst stirring to a solution of (3R,3aR,6S,6aS)-6-methoxyhexahydro-2H-furo[3,2-b]pyrrol-3-ol in 1,4-dioxane (7 mL). A solution of 9-fluorenylmethoxycarbonyl chloride (319 mg, 1.23 mmol) in 1,4-dioxane (3 mL) was added then the mixture stirred for 40 minutes then water (30 mL) was added and the product extracted into dichloromethane (1×40 mL then 2×30 mL). The organic layer was washed with brine (50 mL), then dried (MgSO$_4$), filtered and reduced in vacuo to leave a residue. Flash chromatography over silica, eluting with ethyl acetate:heptane mixtures 7:93 to 45:55 gave bicyclic alcohol (6b) (270 mg, 66%) as a white solid. TLC (R$_f$=0.34, EtOAc:heptane 3:2), analytical HPLC single main peak, R$_t$=15.990 min., HPLC-MS 382.1 [M+H]$^+$, 404.1 [M+Na]$^+$, 785.3 [2M+Na]$^+$; [α]$_D^{18.5}$ −35.4° (c=2.758, CHCl$_3$); δ$_H$ (500 MHz, CDCl$_3$) mixture of rotamers major:minor 3:2; 1.02 (0.6H, d, J=3.55 Hz, OH major), 2.59 (0.40H, d, J=3.19 Hz, OH minor), 3.10 (0.6H, dd, J=12.54 and 3.89 Hz, FmocNCH$_2$ major), 3.26 (1.8H, s, OCH$_3$ major), 3.30 (0.4H, dd, J=12.21 and 4.19 Hz, FmocNCH$_2$ minor), 3.35 (1.2H, s, OCH$_3$ minor), 3.49 (0.6H, m, OCH$_2$CHOH major), 3.52 (0.6H, dd, J=10.04 and 1.81 Hz, OCH$_2$CHOH major), 3.55-3.59 (1.2H, m, OCH$_2$CHOH major and FmocNCH major), 3.64 (0.6H, d, J=3.69 Hz, CHOCH$_3$ major), 3.65-3.70 (1H, m, FmocNCH$_2$), 3.75-3.79 (0.8H, m, OCH$_2$CHOH minor and CHOCH$_3$ minor), 3.85 (0.4H, dd, J=9.85 and 4.46 Hz, OCH$_2$CHOH minor), 4.22-4.26 (1.4H, m, FmocNCH minor and Fmoc CH), 4.37 (0.6H, d, J=4.64 Hz, OCHCHOCH$_3$ major), 4.40-4.44 (1.2H, m, Fmoc CH$_2$ minor and OCH$_2$CHOH minor), 4.60 (0.4H, d, J=4.94 Hz, OCHCHOCH$_3$ minor), 4.70 (0.6H, dd, J=10.80 and 3.96 Hz, Fmoc CH$_2$ major), 4.82 (0.6H, dd, J=10.80 and 4.25 Hz, Fmoc CH$_2$ major), 7.29-7.80 (8H, Fmoc aromatic CH); δ$_C$ (125 MHz, CDCl$_3$) 47.248/47.378 (Fmoc CH), 49.754/50.177 (FmocNCH$_2$), 56.868/56.996 (OCH$_3$), 65.736/67.270 (Fmoc CH$_2$), 68.262/69.085 (FmocNCH), 73.760/74.008 (OCH$_2$CHOH), 75.812/76.145 (OCH$_2$CHOH), 81.509/82.286 (OCHCHOCH$_3$), 83.496/84.166 (OCHCHOCH$_3$), 119.805, 119.982, 120.003, 124.494, 124.576, 124.958, 124.975, 127.019, 127.034, 127.404, 127.488, 127.637, 127.726, 127.754 and 127.865 (Fmoc aromatic CH), 143.633, 143.909, 143.943 and 144.037 (Fmoc quaternary), 154.255/155.025 (Fmoc C=O).

(v) (3aS,6S,6aS)-(9H-Fluoren-9-yl)methyl 6-methoxy-3-oxotetrahydro-2H-furo[3,2-b]pyrrole-4(5H)-carboxylate (6c). Dess-Martin periodinane (600 mg, 1.42 mmol) was added to a stirred solution of bicyclic alcohol (6b) (270, 0.71 mmol) in dichloromethane (10 mL) at 0° C. under an atmosphere of argon. The mixture was allowed to warm to ambient temperature over 2 hours then Dess-Martin periodinane (300 mg, 0.71 mmol) added. The mixture was stirred for 4 hours then diluted with dichloromethane (20 mL). The organic phase was washed with a mixture of saturated aqueous sodium bicarbonate and 0.25M sodium thiosulphate solution (1:1, 15 mL), then saturated aqueous sodium bicarbonate (10 mL), then brine (10 mL), then dried (MgSO$_4$), filtered and reduced in vacuo. Flash chromatography over silica, eluting with ethyl acetate:heptane mixtures 15:85 to 40:60 gave bicyclic ketone (6c) (200 mg, 74%) as a white solid. TLC (R$_f$=0.45, EtOAc heptane 7:3), analytical HPLC broad main peak, R$_t$=15.676-16.668 min., HPLC-MS 380.2 [M+H]$^+$, 781.3 [2M+Na]$^+$; [α]$_D^{17}$ −105.6° (c=9.468, CHCl$_3$); δ$_H$ (500 MHz, CDCl$_3$) mixture of rotamers approx. 1:1; 3.33 (1.5H, s, OCH$_3$), 3.38 (1.5H, s, OCH$_3$), 3.42-3.49 (1H, m, FmocNCH$_2$), 3.82 (0.5H, d, J=12.07 Hz, FmocNCH$_2$), 3.89-4.01 (2H, m, OCHCHOMe and OCH$_2$C=O), 4.05-4.19 (1.5H, m, OCH$_2$C=O and FmocNCH$_2$), 4.21-4.34 (1.5H, m, Fmoc-CH$_2$ and Fmoc-CH), 4.37-4.40 (1H, m, FmocNCH), 4.42-4.56 (1.5H, m, Fmoc-CH$_2$), 4.74 (0.5H, d, J=4.33 Hz, OCHCHOCH$_3$), 4.79 (1H, d, J=4.14 Hz, OCHCHOCH$_3$), 7.28-7.76 (8H, Fmoc aromatic CH); δ$_C$ (125 MHz, CDCl$_3$); 47.104/47.156 (Fmoc-CH), 49.957 (FmocNCH$_2$), 56.975/57.031 (OCH$_3$), 60.853/61.278 (FmocNCH), 67.649/68.476 (Fmoc-CH$_2$), 70.078 (OCH$_2$C=O), 81.701/82.335 (OCHCHOCH$_3$), 83.549/84.751 (OCHCHOCH$_3$), 119.894, 119.962, 124.963, 125.226, 125.524, 127.029, 127.065 and 127.695 (Fmoc aromatic CH), 141.238, 141.309, 143.654, 143.811 and 144.354 (Fmoc quaternary), 155.065/155.203 (Fmoc C=O), 207.830/207.992 (ketone C=O).

Preparation of (3R,3aR,6S,6aS)-Benzyl 3-hydroxy-methoxytetrahydro-2H-furo[3,2-b]pyrrole-4(5H)-carboxylate (72). Sodium hydride (60% dispersion in oil, 800 mg, 19.95 mmol) was added over 1 minute to a stirred solution consisting of a 4:1 mixture of anti-epoxide benzyl (S)-2-((1S,2R,5S)-3,6-dioxabicyclo[3.1.0]hexan-2-yl)-2-methoxyethyl carbamate (31) and syn-epoxide benzyl (S)-2-((1R,2R,5R)-3,6-dioxabicyclo[3.1.0]hexan-2-yl)-2-methoxyethyl carbamate (4.5 mg, 15.35 mmol total) in tetrahydrofuran (15 mL) at 0° C. under an atmosphere of argon. The mixture was stirred at 0° C. for 30 minutes then at ambient temperature overnight then dichloromethane (150 mL) added. The organic layer was washed with brine (75 mL), then dried (Na$_2$SO$_4$), filtered and reduced in vacuo to leave a residue (5.8 g). The residue was treated 4N HCl in dioxin (18 mL, 75 mmol) for 1 h then reduced in vacuo. Flash chromatography over silica, eluting with ethyl acetate:heptane mixtures 25:75 to 50:50 gave (3R,3aR,6S,6aS)-benzyl 3-hydroxy-6-methoxytetrahydro-2H-furo[3,2-b]pyrrole-4(5H)-carboxylate (72) as a straw coloured oil (2.20 g, 7.5 mmol). TLC (R$_f$=0.30, EtOAc:heptane 3:2), analytical HPLC single main peak, R$_t$=9.50 min.; HPLC-MS 294.1 [M+H]$^+$, 609.2 [2M+Na]$^+$; [α]$_D^{22.0}$ −49.6° (c=2.52, CHCl$_3$).

(vii) Alternative Preparation of (3R,3aR,6S,6aS)-Benzyl 3-hydroxy-6-methoxytetrahydro-2H-furo[3,2-b]pyrrole-4(5H)-carboxylate (72). Ethanol (100 mL) was added dropwise to a mixture of 10% palladium on charcoal (400 mg) and benzyl (S)-2-((1S,2R,5S)-3,6-dioxabicyclo[3.1.0]hexan-2-yl)-2-methoxyethyl carbamate (31) (4.0 g, 13.65 mmol) under an atmosphere of argon. The argon was replaced by hydrogen then the suspension was stirred for 15 hours then filtered through celite in vacuo. The filter cake was washed with ethanol then the solvents removed in vacuo from the filtrate to obtain the crude (3R,3aR,6S,6aS)-6-methoxyhexahydro-2H-furo[3,2-b]pyrrol-3-ol which was used without further purification.

A solution of sodium carbonate (3.04 g, 28.7 mmol) in water (20 mL) was added whilst stirring to a solution of (3R,3aR,6S,6aS)-6-methoxyhexahydro-2H-furo[3,2-b]pyrrol-3-ol (prepared as above, assumed to be 13.65 mmol) in 1,4-dioxane (50 mL). Benzyl chloroformate (2.88 mL, 20.48 mmol) was added dropwise then the mixture stirred for 6 hours, then water (200 mL) was added and the product extracted into dichloromethane (3×75 mL). The organic layer was dried (Na$_2$SO$_4$), filtered and reduced in vacuo to leave a colourless oil (4.95 g). Flash chromatography over silica, eluting with ethyl acetate:heptane mixtures 15:85 to 75:25 gave (3R,3aR,6S,6aS)-benzyl 3-hydroxy-6-methoxytetrahydro-2H-furo[3,2-b]pyrrole-4(5H)-carboxylate (72) (2.98 g, 74%) as a colourless oil. TLC (R$_f$=0.47, EtOAc:heptane 2:1), analytical HPLC single main peak, $R_t$=9.78 min., HPLC-MS 294.1 [M+H]$^+$, 316.1 [M+Na]$^+$, 609.2 [2M+Na]$^+$; $\delta_H$ (500 MHz, CDCl$_3$) mixture of rotamers major:minor 3:2; 3.29 (0.4H, dd, J=12.54 and 3.87 Hz, 1×CbzNCH$_2$ minor), 3.34 (3H, s, OCH$_3$), 3.34-3.38 (0.6H, m, 1×CbzNCH$_2$ major), 3.69-3.97 (4H, m, 1×CbzNCH$_2$, OCH$_2$CHOH and CHOMe), 4.26 (1H, brt, J=5.55 Hz, OCHCHOCH$_3$), 4.37 (0.4H, brs, OCH$_2$CHOH minor), 4.49 (0.6H, brs, OCH$_2$CHOH major), 4.61 (1H, d, J=4.89 Hz, CbzNCH), 5.09-5.24 (2H, m, CH$_2$Ph), 7.30-7.40 (5H, m, aromatic CH); $\delta_C$ (125 MHz, CDCl$_3$) 50.14/50.41 (CbzNCH$_2$), 56.97/57.03 (OCH$_3$), 67.26/67.38 (CH$_2$Ph), 68.15/69.14 (CbzNCH), 74.05/74.34 (OCH$_2$CHOH), 75.79/76.59 (OCH$_2$CHOH), 81.64/82.34 (OCHCHOCH$_3$), 83.47/84.59 (OCHCHOCH$_3$), 127.91, 127.96, 128.13/128.26/128.52/128.56/128.67 and 128.80 (aromatic CH), 136.26/136.32 (aromatic quaternary), 154.50/155.13 (Cbz C=O).

Preparation of (3aS,6R,6aS)-(9H-Fluoren-9-yl)methyl 6-methoxy-3-oxotetrahydro-2H-furo[3,2-b]pyrrole-4(5H)-carboxylate (5c)

(i) Preparation of Benzyl (R)-2-((S)-2,5-dihydrofuran-2-yl)-2methoxyethyl carbamate (30b). Methyl iodide (1.89 mL, 30.4 mmol) was added to a stirred mixture of alcohol (18) (2.0 g, 7.59 mmol) and silver (I) oxide (2.64 g, 11.4 mmol) in acetonitrile (32 mL). The mixture was heated at 72° C. for 3 hours then stood at ambient temperature for 16 hours. Heating was continued for 1.5 hours at 72° C. then the mixture allowed to cool to ambient temperature, filtered and reduced in vacuo. Flash chromatography over silica, eluting with an ethyl acetate:heptane mixture 1:1 to give methyl ether (30b) (1.05 g, 50%) with an estimated purity of 93%, as a colourless oil together with recovered alcohol (18) (694 mg, 35%). Data for methyl ether (30b); TLC (R$_f$=0.35, EtOAc:heptane 1:1), analytical HPLC main peak, R$_t$=13.082 min., HPLC-MS 278.1 [M+H]$^+$, 577.2 [2M+Na]$^+$; $[\alpha]_D^{18}$ -54.5° (c=3.487, CHCl$_3$); $\delta_H$ (500 MHz, CDCl$_3$) 3.22-3.27, (2H, m, CH$_2$N and CHOCH$_3$), 3.42 (3H, s, CHOCH$_3$), 3.44-3.53 (1H, m, CH$_2$N), 4.58-4.67 (2H, m, OCH$_2$CH=CH), 4.88 (1H, m, OCHCH=CH), 5.09 (2H, s, OCH$_2$Ph), 5.18 (1H, brs, NH), 5.80-5.84 and 5.97-6.00 (2H total, m, CH$_2$CH=CH), 7.29-7.36 (5H, m, aromatic CH); $\delta_C$ (125 MHz, CDCl$_3$) 60.634 (CH$_2$NHCbz), 58.141 (OCH$_3$), 66.697 (CH$_2$Ph), 75.621 (OCH$_2$CH=), 81.912 (CHOCH$_3$), 86.193 (OCHCH=), 126.506, 128.084, 128.100, 128.328, and 128.491 (OCH$_2$CH=CH and Cbz aromatic CH), 136.563 (Cbz quaternary), 156.481 (Cbz C=O).

(ii) Alternative preparation of Benzyl (R)-2-((S)-2,5-dihydrofuran-2-yl)-2-methoxyethylcarbamate (30b). Trimethyloxonium fluoroborate (2.16 g, 14.61 mmol) was added to a stirred mixture of benzyl (R)-2-((S)-2,5-dihydrofuran-2-yl)-2-hydroxyethylcarbamate (18) (2.26 g, 8.59 mmol), 4 Å molecular sieves (7.1 g), 1,8-bis(dimethylamino)naphthalene (11.0 g, 51.6 mmol) and dichloromethane (55 mL) under an atmosphere of argon. The mixture was stirred for 2 hours then filtered through celite in vacuo. The filter cake was washed with dichloromethane (300 mL) then the solvents removed in vacuo from the filtrate. The residue was triturated with diethyl ether (100 mL) then the yellow solid removed by filtration in vacuo. The solid was washed with diethyl ether (100 mL) then the combined filtrates washed with hydrochloric acid (2.5M, 1×50 mL then 2×25 mL), brine (50 mL) then dried (Na$_2$SO$_4$), filtered and reduced in vacuo to leave a pale yellow oil (1.93 g). Flash chromatography over silica, eluting with ethyl acetate:heptane mixtures 5:95 to 50:50 gave methylether (30b) as a colourless oil (1.42 g, 60%).

(iii) Preparation of Benzyl (R)-2-((1S,2R,5S)-3,6-dioxabicyclo[3.1.0]hexan-2-yl)-2-methoxyethyl carbamate anti-(31b). To a solution of methyl ether (30b) (1.0 g, 3.61 mmol) in acetonitrile (20 mL) and aqueous Na$_2$.EDTA (20 mL, 0.4 mmol solution) at 0° C. was added 1,1,1-trifluoroacetone (3.87 mL, 43.3 mmol). To this solution was added in portions a mixture of sodium bicarbonate (2.54 g, 30.3 mmol) and OXONE® (6.87 g, 11.2 mmol) over a period of 1.5 hours. The mixture was stirred for 30 minutes then diluted with water (50 mL) and the product extracted into dichloromethane (3×50 mL). The combined organic layers were washed with brine (60 mL) then dried (Na$_2$SO$_4$), filtered and reduced in vacuo. Flash chromatography over silica, eluting with ethyl acetate:heptane mixtures 7:93 to 50:50 gave a 3:1 mixture of anti-(31b) and syn-epoxide benzyl (R)-2-((1R,2R,5R)-3,6-dioxabicyclo[3.1.0]hexan-2-yl)-2-methoxyethyl carbamate respectively (611 mg, 58%) as a colourless oil. TLC (R$_f$=0.25, EtOAc:heptane 1:1), analytical HPLC two main peaks, R$_t$=11.792 and 12.132 min. (approx. 3:1 respectively). HPLC-MS 294.2 [M+H]$^+$, 316.1 [M+Na]$^+$, 609.3 [2M+Na]$^+$.

(iv) (3R,3aR,6R,6aS)-(9H-Fluoren-9-yl)methyl 3-hydroxy-6-methoxytetrahydro-2H-furo[3,2-b]pyrrole-4(5H)-carboxylate (5b). Ethanol (30 mL) was added dropwise to a mixture of 10% palladium on charcoal (200 mg) and syn-/anti-epoxides respectively (605 mg, 2.06 mmol) under an atmosphere of argon. The argon was replaced by hydrogen then the suspension was stirred for 2.5 hours then filtered through celite in vacuo. The filter cake was washed with ethanol then the solvents removed in vacuo from the filtrate to obtain the crude (3R,3aR,6R,6aS)-6-methoxyhexahydro-2H-furo[3,2-b]pyrrol-3-ol which was used without further purification.

A solution of sodium carbonate (459 mg, 4.33 mmol) in water (20 mL) was added whilst stirring to a solution of (3R,3aR,6R,6aS)-6-methoxyhexahydro-2H-furo[3,2-b]pyrrol-3-ol in 1,4-dioxane (20 mL). A solution of 9-fluorenylmethoxycarbonyl chloride (614 mg, 2.37 mmol) in 1,4-dioxane (3 mL) was added then the mixture stirred for 1.5 hours then water (30 mL) was added and the product extracted into dichloromethane (3×50 mL). The organic layer was washed with brine (70 mL), then dried (Na$_2$SO$_4$), filtered and reduced in vacuo to leave a residue. Flash chromatography over silica, eluting with ethyl acetate:heptane mixtures 10:90 to 80:20 gave (in order of elution) syn-epoxide (9H-fluoren-9-yl)methyl (R)-2-((1R,2R,5R)-3,6-dioxabicyclo[3.1.0]hexan-2-yl)-2-methoxyethyl carbamate (111 mg, 14%) as a colourless oil and bicyclic alcohol (5b) (453 mg, 58%) as a white solid. Data for syn-epoxide; TLC (R$_f$=0.22, EtOAc:heptane 1:1), analytical HPLC single main peak, R$_t$=17.108 min.; HPLC-MS 382.2 [M+H]$^+$, 404.2 [2M+Na]$^+$; $[\alpha]_D^{19}$ -24.5° (c=6.120, CHCl$_3$); $\delta_H$ (500 MHz, CDCl$_3$) 3.37-3.56 (3H, m, CHOCH$_3$ and CH$_2$NH), 3.49 (3H, s, OCH$_3$ major), 3.71 (1H, d, J=10.63 Hz, OCH$_2$CH), 3.75 (1H, d, J=7.48 Hz, OCHCHOCH$_3$), 3.79-3.84 (2H, m, OCH$_2$CHCH), 4.04 (1H, d, J=10.67 Hz, OCH$_2$CH), 4.23 (1H, t, J=6.97 Hz, Fmoc CH), 4.38 (2H, d, J=7.12 Hz, Fmoc CH$_2$), 5.16 (1H brs, NH), 7.29-7.76 (8H, Fmoc aromatic CH); $\delta_C$ (125 MHz, CDCl$_3$) 40.837 (CH$_2$NHFmoc), 47.259 (Fmoc CH), 56.424/56.648 (OCH$_2$CHCH), 58.047 (OCH$_3$), 66.688 (Fmoc CH$_2$), 67.700 (OCH$_2$CH), 77.573 (OCHCHOCH$_3$), 78.238 (CHOCH$_3$), 119.932, 125.088, 126.998 and 127.617 (Fmoc aromatic CH), 141.277, 143.021 and 144.021 (Fmoc quaternary), 156.521 (Cbz C=O). Data for bicyclic alcohol (5b); TLC (R$_f$=0.05, EtOAc:heptane 1:1), analytical HPLC single main peak, R$_t$=15.004 min., HPLC-MS 382.2 [M+H]$^+$, 404.2

[M+Na]$^+$, 785.3 [2M+Na]$^+$; [α]$_D^{16}$ –10.0° (c=4.016, CHCl$_3$); δ$_H$ (500 MHz, CDCl$_3$) mixture of rotamers major:minor 4:3; 0.96 (0.57H, d, J=3.54 Hz, OH major), 2.51 (0.43H, d, J=3.50 Hz, OH minor), 2.93 (0.57H, t, J=10.12 Hz, FmocNCH$_2$ major), 3.07-3.15 (0.43H, m, FmocNCH$_2$ minor), 3.36 (1.71H, s, OCH$_3$ major), 3.41 (1H, brd, J=4.63 Hz, Fmoc-NCH major), 3.46 (1.29H, s, OCH$_3$ minor), 3.48-3.52 (0.57H, m, OCH$_2$CHOH major), 3.56-3.64 (1.14H, m, CHOCH$_3$ major and OCH$_2$CHOH major), 3.73-3.86 (2.43H, m, OCH$_2$CHOH, FmocNCH$_2$ and CHOCH$_3$ minor), 4.00 (0.43H, dd, J=4.65 and 9.90 Hz, OCH$_2$CHOH minor), 4.16 (1H, dd, J=4.85 and 1.09 Hz, FmocNCH minor), 4.20-4.25 (1H, m, Fmoc CH), 4.38-4.43 (0.86H, m, OCHOH minor and 1×Fmoc CH$_2$ minor), 4.45 (0.57H, t, J=4.29 Hz, CHCHOCH$_3$ major), 4.49 (0.43H, dd, J=10.64 and 6.82 Hz, Fmoc CH$_2$ minor), 4.69-4.73 (0.43H, m, OCHCHOCH$_3$ minor), 4.75 (0.57H, dd, J=10.83 and 3.74 Hz, Fmoc CH$_2$ major), 4.81 (0.57H, dd, J=10.83 and 4.01 Hz, Fmoc CH$_2$ major), 7.28-7.81 (8H, Fmoc aromatic CH); δ$_C$ (125 MHz, CDCl$_3$) 47.276/47.369 (Fmoc CH), 47.504/47.898 (FmocNCH$_2$), 57.788/57.839 (OCH$_3$), 65.761/67.333 (Fmoc CH$_2$), 68.812/69.338 (FmocNCH), 74.940/75.145 (OCH$_2$CHOH), 76.276/76.746 (OCH$_2$CHOH), 78.834/79.335 (OCHiCHOCH$_3$), 78.994/79.507 (OCHCHOCH$_3$), 119.859, 119.895, 120.036, 124.389, 124.442, 124.877, 124.960, 127.035, 127.059, 127.451, 127.494, 127.803, 127.89 and 127.941 (Fmoc aromatic CH), 141.348, 141.373, 141.434, 143.585, 143.585, 143.729, 143.911 and 143.947 (Fmoc quaternary), 153.937/154.896 (Fmoc C=O).

(v) (3aS,6R,6aS)-(9H-Fluoren-9-yl)methyl 6-methoxy-3-oxotetrahydro-2H-furo[3,2-b]pyrrole-4(5H)-carboxylate (5c). Dess-Martin periodinane (985 mg, 2.32 mmol) was added to a stirred solution of bicyclic alcohol (5b) (443 mg, 1.16 mmol) in dichloromethane (17 mL) at 0° C. under an atmosphere of argon. The mixture was stirred for 2 hours then allowed to warm to ambient temperature then stirred for 2 hours, then diluted with dichloromethane (30 mL). The organic phase was washed with a mixture of saturated aqueous sodium bicarbonate and 0.5M sodium thiosulphate solution (1:1, 30 mL), then saturated aqueous sodium bicarbonate (20 mL), then brine (20 mL), then dried (Na$_2$SO$_4$), filtered and reduced in vacuo. Flash chromatography over silica, eluting with ethyl acetate:heptane mixtures 20:80 to 40:60 gave bicyclic ketone (5c) (305 mg, 69%) as a white solid. TLC (R$_f$=0.50, EtOAc:heptane 3:1), analytical HPLC broad main peak, R$_t$=14.547-17.583 min., HPLC-MS 380.2 [M+H]$^+$, 781.3 [2M+Na]$^+$; [α]$_D^{16.5-95.5o}$ (c=2.565, CHCl$_3$); δ$_H$ (500 MHz, CDCl$_3$) mixture of rotamers approx. 1:1; 3.46 (3H, s, OCH$_3$), 3.42-3.53 (1H, m, FmocNCH$_2$), 3.64-3.70 (0.5H, m, FmocNCH$_2$), 3.75-3.81 (0.5H, m, FmocNCH$_2$), 3.90-3.95 (1H, m, OCHCHOMe), 4.09-4.15 (1H, m, OCH$_2$C=O), 4.20-4.35 (3H, m, 1×Fmoc CH, 1×OCH$_2$C=O, 0.5×Fmoc-NCH, and 0.5×Fmoc CH$_2$), 4.38-4.44 (1H, m, FmocNCH and Fmoc CH$_2$), 4.50-4.61 (1H, m, Fmoc CH$_2$), 4.88-4.91 (1H, m, OCHCHOCH$_3$), 7.28-7.77 (8H, Fmoc aromatic CH); δ$_C$ (125 MHz, CDCl$_3$); 46.944/47.188 (Fmoc CH), 48.972/49.088 (FmocNCH$_2$), 58.036 (OCH$_3$), 60.295/60.704 (FmocNCH), 67.746/68.277 (Fmoc CH$_2$), 71.427 (OCH$_2$C=O), 79.339/80.093 (OCHCHOCH$_3$), 79.424/80.241 (OCHCHOCH$_3$), 119.904, 119.993, 120.191, 124.990, 125.190, 125.380, 127.053, 127.094, 127.734, 127.848 and 128.038 (Fmoc aromatic CH), 141.302, 143.604, 143.910 and 144.285 (Fmoc quaternary), 155.141 (Fmoc C=O), 208.397/208.594 (ketone C=O).

Preparation of (3R,3aR,6R,6aS)-Benzyl 3-hydroxy-6-methoxytetrahydro-2H-furo[3,2-b]pyrrole-4(5H)-carboxylate (73). Sodium hydride (60% dispersion in oil, 164 mg, 4.11 mmol) was added over 1 minute to a stirred solution consisting of an ~4:1 mixture of anti-epoxide benzyl (R)-2-((1S,2R,5S)-3,6-dioxabicyclo[3.1.0]hexan-2-yl)-2-methoxyethyl carbamate (31b) and syn-epoxide benzyl (R)-2-((1S,2R,5R)-3,6-dioxabicyclo[3.1.0]hexan-2-yl)-2-methoxyethyl carbamate (963 mg, 3.29 mmol total) in tetrahydrofuran (10 mL) at 0° C. under an atmosphere of argon. The mixture was stirred at 0° C. for 30 minutes then at ambient temperature for 2.75 hours then dichloromethane (150 mL) added. The organic layer was washed with brine (75 mL), then dried (Na$_2$SO$_4$), filtered and reduced in vacuo to leave a residue (1.0 g). Flash chromatography over silica, eluting with ethyl acetate:heptane mixtures 30:70 to 90:10 gave (3R,3aR,6R,6aS)-benzyl 3-hydroxy-6-methoxytetrahydro-2H-furo[3,2-b]pyrrole-4(5H)-carboxylate (73) as a colourless oil (657 mg, 85% based on anti-epoxide). TLC (R$_f$=0.30, EtOAc:heptane 2:1), analytical HPLC single main peak, R$_t$=8.70 min.; HPLC-MS 294.1 [M+H]$^+$, 609.2 [2M+Na]$^+$; [α]$_D^{30}$ -29.4° (c=2.38, CHCl$_3$); δ$_C$ (125 MHz, CDCl$_3$) 47.93/48.02 (CbzNCH$_2$), 57.87/57.90 (OCH$_3$), 67.39/67.46 (CH$_2$Ph), 68.43/69.40 (CbzNCH), 75.24/75.41 (OCH$_2$CHOH), 76.07 (OCH$_2$CHOH), 78.88/79.22/79.56/79.72 (OCHCHOCH$_3$)+(OCHCHOCH$_3$), 127.96/128.03/128.17/128.24/128.35/128.55/128.69 (aromatic CH), 136.06/136.18 (aromatic quaternary), 154.19/155.02 (Cbz C=O).

Preparation of (3aS,6S,6aR)-(9H-fluoren-9-yl)methyl 6-(tert-butoxycarbonylamino)-3-oxotetrahydro-2H-furo[3,2-b]pyrrole-4(5H)-carboxylate (8c)

(i) Preparation of (3R,3aR,6R,6aS)- Benzyl 3-hydroxy-6-(tosyloxy)tetrahydro-2H-furo[3,2-b]pyrrole-4(5H)-carboxylate (34b). Ethanol (1.5 mL) was added dropwise to a mixture of 10% palladium on charcoal (10 mg) and anti-(33b) (12.0 mg, 0.028 mmol) under an atmosphere of argon. The argon was replaced by hydrogen then the suspension was stirred for 1.75 hours before filtering the mixture through celite in vacuo. The filter cake was washed with ethanol (7.5 mL) then the solvents removed in vacuo from the filtrate. The residue was azeotroped with toluene (2 mL) to obtain (3R,3aR,6R,6aS)-3-hydroxyhexahydro-2H-furo[3,2-b]pyrrol-6-yl 4-methylbenzenesulfonate (7.6 mg, 89%) as a pale yellow oil which was used without further purification. TLC (R$_f$=0.01, EtOAc:heptane 1:1), HPLC-MS 300.1 [M+H]$^+$, 621.2 [2M+Na]$^+$.

A solution of sodium carbonate (6.2 mg, 0.058 mmol) in water (0.15 mL) was added whilst stirring to a solution of (3R,3aR,6R,6aS)-3-hydroxyhexahydro-2H-furo[3,2-b]pyrrol-6-yl 4-methylbenzenesulfonate in 1,4-dioxane (0.3 mL). Benzylchloroformate (5.9 µL, 0.042 mmol) was added then the mixture stirred for 2 hours. Water (5 mL) was added and the product extracted into dichloromethane (2×5 mL). The organic layer was washed with brine (5 mL), then dried (Na$_2$SO$_4$), filtered and reduced in vacuo to leave a residue (10.6 mg). Flash chromatography over silica, eluting with ethyl acetate:heptane mixtures 20:80 to 50:50 gave bicyclic alcohol (34b) (6.6 mg, 54%) as a white solid. TLC (R$_f$=0.20, EtOAc:heptane 1:1), analytical HPLC single main peak, R$_t$=17.32 min., HPLC-MS 434.1 [M+H]$^+$, 889.2 [2M+Na]$^+$; [α]$_D^{20}$ -25.7° (c=2.53, CHCl$_3$); δ$_H$(500 MHz, CDCl$_3$) mixture of rotamers majo:minor 2:1; 2.01 (0.33H, brs, OH minor), 2.43 (3H, s, aryl-CH$_3$), 2.77 (0.66H, brs, OH major), 3.18-3.24 (0.33H, m, CbzNCH$_2$ minor), 3.33-3.38 (0.66H, m, CbzNCH$_2$ major), 3.79-3.85 (1H, m, OCH$_2$CHOH), 3.86-3.91 (1H, m, CbzNCH$_2$), 3.92-3.96 (0.33H, m, OCH$_2$CHOH minor), 3.96-4.01 (0.66H, m, OCH$_2$CHOH major), 4.13-4.16 (1H, m, CbzNCH), 4.35 (0.33H, m, OCH$_2$CHOH minor), 4.45 (0.66H, m, OCH$_2$CHOH major), 4.56 (0.33H, t, J=4.64 Hz, TsOCHCH, minor), 4.64 (0.66H, t, J=4.36 Hz, TsOCHCH, major), 4.71-4.78 (1H, m, TsOCHCH), 5.06-5.17 (2H, m, CH$_2$Ph), 7.31-7.38 (7H, m, phenyl CH and aromatic CH$_3$CCH), 7.80 (2H, d, J=8.33 Hz, aromatic OSO$_2$CCH); δ$_C$ (125 MHz, CDCl$_3$) 21.683 (aryl-CH$_3$), 47.38447.855 (CbzNCH$_2$), 67.636/67.717 (CH$_2$Ph), 68.042/68.817 (CbzNCH), 75.525/75.967 (OCH$_2$CHOH), 75.967/76.836 (OCH$_2$CHOH), 76.068/76.401 (TsOCHCH), 79.342/80.208 (TsOCHCH), 127.965, 128.107, 128.382, 128.510, 128.605, 128.753, 129.940 and 129.997 (aromatic CH), 132.991 (CHOSO$_2$C quaternary), 135.779/135.869 (Cbz quaternary), 145.319 (CH$_3$C quaternary), 153.862/154.751 (Cbz C=O).

(ii) Preparation of (3R,3aR,6S,6aS)-benzyl 6-azido-3-hydroxytetrahydro-2H-furo[3,2-b]pyrrole-4(5H)-carboxylate (36b). Sodium azide (15 mg, 0.231 mmol) was added to a stirred solution of bicyclic alcohol (34b) (50 mg, 0.115 mmol) in dimethylformamide (1 mL) under an atmosphere of argon. The mixture was heated at 70° C. for 18 hours then sodium azide (10 mg, 0.154 mmol) was added and heating continued at 105° C. for 21 hours. Water (6 mL) was added and the product extracted into tert-butyl methyl ether (3×3 mL). The organic layer was washed with brine (9 mL), then dried (Na$_2$SO$_4$), filtered and reduced in vacuo to leave a residue (56 mg). Flash chromatography over silica, eluting with ethyl acetate:pentane mixtures 1:2 gave bicyclic azidoalcohol (36b) (28 mg, 80%) as a (viscous) colourless oil. TLC (R$_f$=0.25, EtOAc:heptane 1:1), analytical HPLC single main peak, R$_t$=13.43 min., HPLC-MS 277.2 [M-N$_2$+H]$^+$, 327.2 [M+Na]$^+$, 631.3 [2M+Na]$^+$; [α]$_D^{17}$-22.4° (c=1.56, CHCl$_3$); δ$_H$ (500 MHz, CDCl$_3$) mixture of rotamers major:minor 2:1; 1.9 and 3.2 (approx. 1H total, each brs, OH), 3.39-3.45 (1H, m, CbzNCH$_2$), 3.74 (0.66H, d, J=12.37 Hz, CbzNCH$_2$, major), 3.78-3.91 (2H, m, OCH$_2$CHOH), 3.87 (0.33H, J=12.24 Hz, CbzNCH$_2$, minor), 4.02 (1H, d, J=4.21 Hz, CHN$_3$), 4.28 (0.33H, d, J=4.45 Hz, CbzNCH minor), 4.30 (0.66H, d, J=4.58 Hz, CbzNCH major), 4.39 (0.33H, brs, OCH$_2$CHOH minor), 4.50 (0.66H, brs, OCH$_2$CHOH major), 4.61 (1H, d, J=4.56 Hz, CHCHN$_3$), 5.13 (0.33H, d, J=12.08 Hz, CH$_2$Ph minor), 5.13 (1.32H, s, CH$_2$Ph major), 5.23 (0.33H, d, J=12.27 Hz, CH$_2$Ph minor), 7.30-7.38 (5H, m, phenyl CH); 8c (125 MHz, CDCl$_3$) 50.000/50.282 (CbzNCH$_2$), 62.823/63.317 (CHN$_3$), 67.601 (CH$_2$Ph), 68.013/68.998 (CbzNCH), 74.633/74.660 (OCH$_2$CHOH), 75.378/76.251 (OCH$_2$CHOH), 84.223/85.159 (CHCHN$_3$), 127.959, 127.976, 128.292, 128.368, 128.587 and 128.715 (aromatic CH), 135.933/136.109 (Cbz quaternary), 154.172/154.808 (Cbz C=O).

(iii) Preparation of (3R,3aR,6S,6aS)-benzyl 6-(tert-butoxycarbonylamino)-3-hydroxytetrahydro-2H-furo[3,2-b]pyrrole-4(5H)-carboxylate (37b).

(a) Reduction of azide. Azide (36b) (54 mg, 0.177 mmol) was dissolved in THF (6 mL) with stirring and water (32 μL, 1.77 mmol) added followed by triphenylphosphine (70 mg, 0.266 mmol). The mixture was heated at 45° C. under nitrogen overnight. The mixture was reduced in vacuo to a syrup used directly in the next step. HPLC-MS 279.1 [M+H]$^+$, 301.1 [M+Na]$^+$, 557.2, 579.3 [2M+Na]$^+$.

(b) Amine protection. Crude amine (~0.18 mmol) was dissolved in 1,4-dioxan (2.5 mL) with stirring and ice-cooled and a solution of sodium carbonate (42 mg, 0.37 mmol) in water (2.5 mL) was added. Di-tert-butylcarbonate (46 mg, 0.27 mmol) in 1,4-dioxane (1.0 mL) was added dropwise over 30 minutes and the mixture stirred overnight at ambient temperature. DCM (20 mL) was then added and the organic phase washed with 0.1N HCl (20 mL), sat. NaHCO$_3$ (20 mL), then brine (20 mL) and dried (Na$_2$SO$_4$). The organic layer was filtered and reduced in vacuo to leave a clear gum. The crude gum was purified on a 5 g Flash silica cartridge eluting with a gradient of heptane:ethyl acetate 5:1→1:2 to provide alcohol (37b) as a white foam (65.5 mg) contaminated with triphenylphosphine oxide. TLC (R$_f$=0.43, EtOAc:heptane 2:1), analytical HPLC R$_t$=15.05 min (product 8.25% by UV) and 15.39 min (triphenylphosphine oxide 91.25% by UV), HPLC-MS 279.1 [M+H-Boc]$^+$, 323.1 [M+2H–Bu]$^+$, 401.1 [M+Na]$^+$, 557.2, 779.3 [2M+Na]$^+$.

(iv) Preparation of (3R,3aR,6S,6aR)-(9H-fluoren-9-yl)methyl 6-(tert-butoxycarbonylamino)-3-hydroxytetrahydro-2H-furo[3,2-b]pyrrole-4(5H)-carboxylate (8b). Bicycle alcohol (37b) (60 mg, ~0.16 mmol) was dissolved in methanol (5 mL), cooled to 0° C. and 10% palladium on charcoal (15 mg) added. The mixture was stirred, then evacuated and flushed with hydrogen. The mixture was warmed to ambient temperature and after 2 h. filtered through celite. The filter cake was washed with ethanol (3×5 mL) and the combined filtrates reduced in vacuo to provide the crude amine (~16 mg). HPLC-MS 245.2 [M+H]$^+$, 279.1, 511.3 [M+Na]$^+$, 557.2. The crude amine was dissolved in 1,4-dioxane (2.5 mL) with stirring, ice-cooled and a solution of sodium carbonate (35.5 mg, 0.333 mmol) in water (2.5 mL) was added. 9-Fluorenylmethyl chloroformate (43 mg, 0.166 mmol) in 1,4-dioxane (1.0 mL) was added dropwise over 30 minutes and the mixture stirred for a further 1 h. EtOAc (25 mL) was then added and the organic phase washed with 0.1N HCl (25 mL), sat. NaHCO$_3$ (25 mL), then brine (25 mL) and dried (Na$_2$SO$_4$). The organic layer was filtered and reduced in vacuo to leave a clear film (72.5 mg). The crude film was purified on a 5 g Flash silica cartridge eluting with a gradient of heptane:ethyl acetate 6:1→3:1 to provide alcohol (8b) as a white solid (40.0 mg) with triphenylphosphine oxide. TLC (R$_f$=0.23, EtOAc:heptane 1:1), analytical HPLC 15.39 min (triphenylphosphine oxide 63.8% by UV) and R$_t$=18.30 min (product 33.8% by UV), HPLC-MS 411.2 [M+2H–Bu]$^+$, 489.2 [M+Na]$^+$, 955.4 [2M+Na]+ and 279.1, 557.2.

(v) Preparation of (3aS,6S,6aR)-(9H-fluoren-9-yl)methyl 6-(tert-butoxycarbonylamino)-3-oxotetrahydro-2H-furo [3,2-b]pyrrole-4(5H)-carboxylate (8c). Bicycle alcohol (8b) (40 mg, ~0.08 mmol) was dissolved in anhydrous dichloromethane (3 mL) with stirring under argon. Dess-Martin periodinane (68 mg, 0.16 mmol) was added and the mixture stirred overnight. The mixture was diluted with DCM (20 mL) and washed with sat. NaHCO$_3$/0.25M Na$_2$S$_2$O$_3$, sat. NaHCO$_3$, brine (20 mL each) and dried (Na$_2$SO$_4$). The organic layer was filtered and reduced in vacuo to leave a colourless gum (~41 mg). The crude gum was purified on a 5 g Flash silica cartridge eluting with a gradient of heptane:ethyl acetate 5:1→2:1 to provide ketone (8c) as a white solid (17.3 mg, 0.037 mmol). TLC (R$_f$=0.36, EtOAc:heptane 1:1), analytical HPLC broad peak with R$_t$=18.14-20.32 min, HPLC-MS 409.2 [M+2H–Bu]$^+$, 465.2 [M+H]$^+$, 487.2 [M+Na]$^+$, 951.4 [2M+Na]$^+$; [α]$_D^{22}$-67.6° (c=0.74, CHCl$_3$).

Preparation of (3aS,6R,6aR)-(9H-fluoren-9-yl)methyl 6-(tert-butoxycarbonylamino)-3-oxotetrahydro-2H-furo[3,2-b]pyrrole-4(5H)-carboxylate (7c)

(i) Preparation of (3R,3aR,6S,6aS)- Benzyl 3-hydroxy-6-(tosyloxy)tetrahydro-2H-furo[3,2-b]pyrrole-4(5H)-carboxylate (34). Ethanol (6 mL) was added dropwise to a mixture of 10% palladium on charcoal (50 mg) and anti-(33) (547 mg, 1.26 mmol) under an atmosphere of argon. The argon was replaced by hydrogen then the suspension was stirred at 20° C. for 3.75 hours before filtering the mixture through celite in vacuo. The filter cake was washed with ethanol (40 mL) then the solvents removed in vacuo from the filtrate to obtain (3R,3aR,6S,6aS)-3-hydroxyhexahydro-2H-furo[3,2-b]pyrrol-6-yl 4-methylbenzenesulfonate which was used without further purification.

A solution of sodium carbonate (281 mg, 2.65 mmol) in water (5 mL) was added whilst stirring to a solution of (3R,3aR,6S,6aS)-3-hydroxyhexahydro-2H-furo[3,2-b]pyrrol-6-yl 4-methylbenzenesulfonate in 1,4-dioxane (5 mL). A solution of benzyl chloroformate (0.225 mL, 1.96 mmol) in 1,4-dioxane (2.5 mL) was added over 20 minutes then the mixture stirred for 35 minutes, then water (50 mL) was added and the product extracted into dichloromethane (2×50 mL). The organic layer was washed with brine (50 mL), then dried ($Na_2SO_4$), filtered and reduced in vacuo to leave a residue. Flash chromatography over silica, eluting with ethyl acetate:heptane mixtures 25:75 to 50:50 gave bicyclic alcohol (34) (518 mg, 95%) as a white solid. TLC ($R_f$=0.25, EtOAc:heptane 3:2), analytical HPLC single main peak, $R_t$=17.86 min., HPLC-MS 434.2 $[M+H]^+$, 456.1 $[M+Na]^+$, 889.3 $[2M+Na]^+$; $[\alpha]_D^{16.5}$–23.1° (c=1.190, $CHCl_3$); $\delta_H$ (500 MHz, $CDCl_3$) mixture of rotamers major:minor 3:2; 1.96 (0.4H, d, J=4.11 Hz, OH minor), 2.43 (1.8H, s, aryl-$CH_3$ major), 2.44 (1.2H, s, aryl-$CH_3$ minor), 2.59 (0.6H, d, J=3.42 Hz, OH major), 3.35 (0.4H, dd, J=13.43 and 3.71 Hz, CbzN$CH_2$ minor), 3.41 (0.6H, dd, J=13.31 and 3.80 Hz, CbzN$CH_2$ major), 3.74-3.88 (3H, m, 2×O$CH_2$CHOH and 1×CbzN$CH_2$), 4.29 (0.4H, s, CbzNCH minor), 4.31 (0.6H, s, CbzNHCH major), 4.37 (0.4H, brs, O$CH_2$CHOH minor), 4.49 (0.6H, brs, O$CH_2$CHOH major), 4.51 (0.6H, d, J=4.59 Hz, TsOCHCH major), 4.64 (0.4H, brd, J=4.44 Hz, TsOCHCH minor), 4.77 (0.4H, d, J=3.43 Hz, TsOCHCH minor), 4.79 (0.6H, d, J=3.53 Hz, TsOCHCH major), 5.06-5.13 (1.6H, m, $CH_2$Ph), 5.21 (0.4H, d, J=12.22 Hz, $CH_2$Ph minor), 7.30 (7H, m, aromatic-CH and $CH_3$CCH), 7.75-7.79 (2H, m, aromatic OSO$_2$CCH); $\delta_C$ (125 MHz, $CDCl_3$) 21.658 (aryl-$CH_3$), 51.015/51.082 (CbzN$CH_2$), 67.511/67.622 ($CH_2$Ph), 67.953/68.902 (CbzNCH), 74.375/74.420 (O$CH_2$CHOH), 75.322/76.156 (O$CH_2$CHOH), 79.944/80.600 (TsOCHCH), 83.537/84.651 (TsOCHCH), 127.791, 127.837, 127.942, 128.011, 128.382, 128.485, 128.558, 128.703 and 130.102 (aromatic CH), 133.021/133.087 (CHOSO$_2$C quaternary), 135.895/136.018 (Cbz quaternary), 145.441 ($CH_3$C quaternary), 153.976/154.591 (Cbz C=O).

(ii) Preparation of (3R,3aR,6R,6aS)-benzyl 6-azido-3-hydroxytetrahydro-2H-furo[3,2-b]pyrrole-4(5H)-carboxylate (36). Bicycle alcohol (34) (400 mg, 0.93 mmol) was dissolved in dimethylformamide (2 mL) in a glass pressure tube and sodium azide (120 mg, 1.85 mmol) added. The mixture was sealed and heated at 135° C. with stirring overnight. The viscous dark mixture was reduced in vacuo and the residue partitioned between DCM (25 mL) and brine (25 mL). The organic phase was washed with sat. NaHCO$_3$ (25 mL), brine (25 mL) and dried ($Na_2SO_4$). The organic layer was filtered and reduced in vacuo to leave a dark gum (105 mg). The crude gum was partially purified on a 5 g Flash silica cartridge eluting with a gradient of heptane:ethyl acetate 8:1→3:1 to provide azidoalcohol (36) as a thick tan oil (77 mg). TLC ($R_f$=0.50, EtOAc:heptane 2:1) plus an unidentified by-product ($R_f$=0.40, EtOAc:heptane 2:1), HPLC-MS 277.1 $[M+H-N_2]^+$, 305.1 $[M+H]^+$, 327.1 $[M+Na]^+$, 631.2 $[2M+Na]^+$.

(iii) Preparation of (3R,3aR,6S,6aR)-benzyl 6-(tert-butoxycarbonylamino)-3-hydroxytetrahydro-2H-furo[3,2-b]pyrrole-4(5H)-carboxylate (37).
(a) Reduction of azide. Azide (36) (77 mg, ~0.25 mmol) was dissolved in THF (8.5 mL) with stirring and water (46 μL, 2.53 mmol) added followed by triphenylphosphine (99 mg, 0.38 mmol). The mixture was heated at 45° C. under nitrogen overnight. The mixture was reduced in vacuo, the residue dissolved in DCM (10 mL) and washed with 0.1N HCl (2×5 mL). The aqueous layer was then adjusted to pH 11 with sat. NaCO$_3$ and back extracted with DCM (4×10 mL). The combined DCM back extracts were dried ($Na_2SO_4$), filtered and reduced in vacuo to leave a yellow oil (29.8 mg) used directly in the next step. HPLC-MS 279.1 $[M+H]^+$, 301.1 $[M+Na]^+$, 579.3 $[2M+Na]^+$.
(b) Amine protection. Crude amine (29.8 mg, ~0.11 mmol) was dissolved in 1,4-dioxan (1.5 mL) with stirring and ice-cooled and a solution of sodium carbonate (26 mg, 0.24 mmol) in water (1.5 mL) was added. Di-tert-butylcarbonate (28 mg, 0.16 mmol) in 1,4-dioxane (1.0 mL) was added dropwise over 30 minutes and the mixture stirred for a further 1 h at ambient temperature. DCM (20 mL) was then added and the organic phase washed with 0.1N HCl (20 mL), sat. NaHCO$_3$ (20 mL), then brine (20 mL) and dried ($Na_2SO_4$). The organic layer was filtered and reduced in vacuo to leave a clear gum (~44 mg). The crude gum was purified on a 5 g Flash silica cartridge eluting with a gradient of heptane:ethyl acetate 6:1→1:1 to provide alcohol (37) as a clear gum (30.0 mg, 0.08 mmol, 32% from azide). TLC ($R_f$=0.40, EtOAc:heptane 2:1), analytical HPLC $R_t$=15.25 min, HPLC-MS 279.1 $[M+H-Boc]^+$, 323.1 $[M+2H-Bu]^+$, 401.1 $[M+Na]^+$, 779.3 $[2M+Na]^+$.

(iv) Preparation of (3R,3aR,6S,6aR)-(9H-fluoren-9-yl)methyl 6-(tert-butoxycarbonylamino)-3-hydroxytetrahydro-2H-furo[3,2-b]pyrrole-4(5H)-carboxylate (7b). Bicycle alcohol (37) (30 mg, 0.08 mmol) was dissolved in methanol (3 mL), cooled to 0° C. and 10% palladium on charcoal (10 mg) added. The mixture was stirred, then evacuated and flushed with hydrogen. The mixture was warmed to ambient temperature and after 5 h. filtered through celite. The filter cake was washed with ethanol (3×5 mL) and the combined filtrates reduced in vacuo to provide the crude amine (~16 mg). HPLC-MS 245.2 $[M+H]^+$, 511.3 $[M+Na]^+$. The crude amine was dissolved in 1,4-dioxane (2.5 mL) with stirring, ice-cooled and a solution of sodium carbonate (18 mg, 0.165 mmol) in water (2.5 mL) was added. 9-Fluorenylmethyl chloroformate (22 mg, 0.084 mmol) in 1,4-dioxane (1.0 mL) was added dropwise over 30 minutes and the mixture stirred for a further 1 h. DCM (25 mL) was then added and the organic phase washed with 0.1N HCl (25 mL), sat. NaHCO$_3$ (25 mL), then brine (25 mL) and dried ($Na_2SO_4$). The organic layer was filtered and reduced in vacuo to leave a clear film. The crude film was purified on a 5 g Flash silica cartridge eluting with a gradient of heptane:ethyl acetate 6:1→1:1 to provide alcohol (7b) as a white solid (23.4 mg, 0.05 mmol, 63%). TLC ($R_f$=0.46, EtOAc:heptane 2:1), analytical HPLC $R_t$=18.52 min, HPLC-MS 367.2 $[M+H-Boc]^+$, 411.2 $[M+2H-Bu]^+$, 489.2 $[M+Na]^+$, 955.4 $[2M+Na]^+$; $[\alpha]_D^{18}$–17.1° (c=2.34, $CHCl_3$).

(v) Preparation of (3aS,6R,6aR)-(9H-fluoren-9-yl)methyl 6-(tert-butoxycarbonylamino)-3-oxotetrahydro-2H-furo[3,2-b]pyrrole-4(5H)-carboxylate (7c). Bicycle alcohol (7b) (23 mg, 0.05 mmol) was dissolved in anhydrous dichloromethane (3 mL) with stirring under argon. Dess-Martin periodinane (42 mg, 0.10 mmol) was added and the mixture stirred overnight. Additional Dess-Martin periodinane (21 mg, 0.05 mmol) was added and the mixture stirred for a further 2 h. The mixture was diluted with DCM (20 mL) and washed with sat. NaHCO$_3$/0.25M Na$_2$S$_2$O$_3$, sat. NaHCO$_3$, brine (25 mL each) and dried (Na$_2$SO$_4$). The organic layer was filtered and reduced in vacuo to leave a colourless film (~26 mg). The crude film was purified on a 5 g Flash silica cartridge eluting with a gradient of heptane:ethyl acetate 6:1→2:1 to provide ketone (7c) as a white solid (17.2 mg, 0.037 mmol, 74%). TLC (R$_f$=0.34, EtOAc:heptane 1:1), analytical HPLC broad peak with R$_t$=17.94-20.0 min, HPLC-MS 365.1 [M+H–Boc]$^+$, 409.1 [M+2H–Bu]$^+$, 465.2 [M+H]$^+$, 487.2 [M+Na]$^+$, 505.2 [M+18+Na]$^+$, 951.3 [2M+Na]$^+$; $[\alpha]_D^{18}$–84.3° (c=1.72, CHCl$_3$); $^1$H NMR (500 MHz, CD)Cl$_3$ at 300K): δ 1.45 (s, C(CH$_3$)$_3$, 9H), 3.05 (t, J=10.40 Hz, FmocNCH$_2$, 1H), 4.01 (d, J=16.90 Hz, OCH$_2$C(O), 1H), 4.03-4.08 (b, FmocNCH$_2$, 0.4H), 4.15-4.65 (bm, FmocNCH$_2$+FmocCH+OCH$_2$C(O)+NCHC(O)+FmocCH$_2$, 5.6H), 4.75 (b, BocNHCH-CHO, 1H), 5.07 (b, BocNHCH, 1H), 7.32 (dt, J=0.95, 8.4 Hz, Fmoc H-2 and H-7), 7.39 (t, J=7.50 Hz, Fmoc H-3 and H-6), 7.56 (bd, J=6.2 Hz, 1.0 Fmoc H-1 or H-8), 7.65 (bd, J=6.6 Hz, 0.25 Fmoc H-1 or H-8), 7.73-7.77 (d+m, J=7.40 Hz, Fmoc H-4 and H-5+0.75H-1 or H-8); $^{13}$C NMR (125 MHz, CDCl$_3$ at 300K): δ 28.30 (C(CH$_3$)$_3$), 47.17 (FmocCH), 48.21/48.36 (FmocNCH$_2$), 51.83/52.35 (CHNHBoc), 60.95/61.31 (NCHC(O)), 68.00/68.33 (FmocCH$_2$), 70.66 (OCH$_2$C(O)), 80.32/81.12 (BocNH-CHCHO), 119.91/120.02 (Fmoc C-4 and C-5), 124.95/125.01/125.13/125.36 (Fmoc C-1 and C-8), 127.10 (Fmoc C-2 and C-7), 127.75 (Fmoc C-3 and C-6), 141.27/141.33/143.52/143.69/144.30 (Fmoc quaternary aromatics), 154.37/154.66/155.10 (FmOC(O)N+ButOC(O)NH), 207.31/207.45 (C=O).

Preparation of (3R,3aR,6S,6aS)-tert-butyl 3-hydroxy-6-(methylthio)tetrahydro-2H-furo[3,2-b]pyrrole-4(5H)carboxylate (54) A stirred solution of tosylate (35b) (250 mg, 0.63 mmol) and sodium thiomethoxide [CAS 5188-07-8] (88 mg, 1.25 mmol) in 3 ml of DMA was heated under an atmosphere of argon in a sealed pressure vessel at 90° C. for 2 hours. The mixture was then allowed to cool to ambient temperature then an aqueous saturated solution of ammonium chloride (10 mL) was added. The aqueous phase was extracted with tert-butyl methyl ether (3×7 ml). The organic phase was dried (MgSO$_4$), filtered and reduced in vacuo to leave an oil. Flash chromatography over silica, eluting with diethyl ether:pentane 2:1 gave thiomethylether (54) as colourless oil (0.152 g, 88%). TLC (R$_f$=0.29, Et$_2$O:pentane 2:1), HPLC-MS 220.1 [M+2H–$^t$Bu]$^+$, 573.2 [2M+H]$^+$; δ$_H$ (500 MHz, CDCl$_3$) mixture of rotamers 1:1; 1.46 (4.5H, s, CCH$_3$), 1.49 (4.5H, s, CCH$_3$), 2.16 (3H, s, SCH$_3$), 3.20 (1H, brs, BocNCH$_2$), 3.47-4.05 (4H, m, OCH$_2$CHOH, BocNCH$_2$ and CHSCH$_3$), 4.24-4.45 (2H, m, BocNCH and OCH$_2$CHOH), 4.63 (1H, s, OCHCHSCH$_3$).

Preparation of (3R,3aR,6S,6aS)(9H-fluoren-9-yl)methyl 3-hydroxy-6-(methylthio)tetrahydro-2H-furo[3,2-b]pyrrole-4(5H)-carboxylate (55) A solution of HCl in 1,4-dioxane (4M, 5.5 mL) was added to thiomethylether (54) (152 mg, 0.55 mmol). The mixture stirred for 1 hour then the solvents removed in vacuo. The residue was azeotroped with CH$_3$CN (5 mL) to obtain (3R,3aR,6S,6aS)-6-(methylthio)hexahydro-2H-furo[3,2-b]pyrrol-3-ol which was used without further purification.

A solution of (3R,3aR,6S,6aS)-6-(methylthio)hexahydro-2H-furo[3,2-b]pyrrol-3-ol in 1,4-dioxane (5 mL) was added whilst stirring to a solution of sodium carbonate (123 mg, 1.16 mmol) in water (1.5 mL) at 0° C. A solution of 9-fluorenylmethoxycarbonyl chloride (150 mg, 0.58 mmol) in 1,4-dioxane (1.5 mL) was added dropwise over 5 minutes then the mixture allowed to warm to ambient temperature over 2 hours. Water (20 mL) was added and the product extracted into dichloromethane (3×10 mL). The organic layer was dried (Na$_2$SO$_4$), filtered and reduced in vacuo to leave a residue. Flash chromatography over silica, eluting with diethyl ether:pentane mixtures 2:1 gave alcohol (55) as a white solid (130 mg, 60%). TLC (R$_f$=0.19, Et$_2$O:pentane 2:1); HPLC-MS 398.2 [M+H]$^+$, 420.1 [M+Na]$^+$, 817.3 [2M+H]$^+$; analytical HPLC single main peak, R$_t$=16.096 min., $[\alpha]_D^{17}$–59.4° (c=2.78, CHCl$_3$); δ$_H$ (500 MHz, CDCl$_3$) mixture of rotamers major:minor 4:3; 1.06 (0.57H, d, J=3.63 Hz, OH major), 2.04 (1.71H, s, SCH$_3$ major), 2.14 (1.29H, s, SCH$_3$ minor), 2.57 (0.43H, d, J=2.83 Hz, OH minor), 3.10 (0.57H, d, J=5.40 Hz, FmocNCH$_2$ major), 3.21-3.24 (0.43H, m, FmocNCH$_2$ minor), 3.41 (0.57H, dd, J=12.18 and 5.57 Hz, OCH$_2$CHOH major), 3.52-3.82 (4.43H, m, FmocNCH, CHSCH$_3$ OCH$_2$CHOH minor, 1×FmocNCH$_2$ and 1×OCH$_2$CHOH), 3.92 (0.43H, dd, J=9.85 and 4.41 Hz, OCH$_2$CHOH minor), 4.23-4.84 (4.57H, m, Fmoc CH, OCHCHSCH$_3$, Fmoc CH$_2$ minor and 1×OCH$_2$CHOH major), 7.28-7.80 (8H, Fmoc aromatic CH); δ$_C$ (125 MHz, CDCl$_3$) 14.574/14.768 (SCH$_3$), 47.234, 47.445, 48.069 and 48.826 (Fmoc CH and CHSCH$_3$), 50.417/50.633 (FmocNCH$_2$), 65.752/67.282 (Fmoc CH$_2$), 68.555/69.282 (FmocNCH), 74.361/74.600 (OCH$_2$CHOH), 75.774/76.148 (OCH$_2$CHOH), 85.505/86.026 (OCHCHOCH$_3$), 119.848, 120.003, 120.029, 124.512, 124.593, 124.946, 127.030, 127.063, 127.427, 127.507, 127.755, 127.771 and 127.892 (Fmoc aromatic CH), 141.196, 141.320, 141.378, 141.428, 143.581, 143.818, 143.890 and 143.964 (Fmoc quaternary), 154.115/154.849 (Fmoc C=O).

Preparation of (3aS,6S,6aS)-(9H-Fluoren-9-yl)methyl 6-(methylthio)-3-oxotetrahydro-2H-furo[3,2-b]pyrrole-4(5H)-carboxylate (56). Dess-Martin periodinane (130 mg, 0.65 mmol) was added to a stirred solution of alcohol (55) (278 mg, 0.33 mmol) in dichloromethane (10 mL) under an atmosphere of argon. The mixture was stirred for 1 hour then diluted with dichloromethane (25 mL). The organic phase was washed with a mixture of saturated aqueous sodium bicarbonate and 10% aqueous sodium thiosulphate solution (1:1, 20 mL), then dried (Na$_2$SO$_4$), filtered and reduced in vacuo. Flash chromatography over silica, eluting with diethyl ether:pentane mixtures 60:40 to 65:35 gave ketone (56) (113 mg, 87%) as a white solid. TLC (R$_f$=0.24, Et$_2$O:pentane 2:1); analytical HPLC two main peaks, R$_t$=15.71 and 15.91 min.; HPLC-MS 396.1 [M+H]$^+$, 414.1 [M+H$_2$O+Na]$^+$, 813.2 [2M+H]$^+$; $[\alpha]_D^{18}$–137.3° (c=2.33, CHCl$_3$). δ$_H$(500 MHz, CDCl$_3$) mixture of rotamers approx. 1:1; 2.15 (1.5H, s, SCH$_3$), 2.19 (1.5H, s, SCH$_3$), 3.30-3.38 (1H, m, CHSMe), 3.68-3.80 (1.5H, m, FmocNCH$_2$), 3.93-4.05 (1.5H, m, 0.5× FmocNCH$_2$ and OCH$_2$C=O), 4.10-4.35 (2.5H, m, OCH$_2$C=O, Fmoc-CH, and 0.5×Fmoc-CH$_2$), 4.40-4.54 (2.5H, m 1.5×Fmoc-CH$_2$ and FmocNCH), 4.74-4.84 (1H, m, OCHCHSCH$_3$), 7.28-7.77 (8H, Fmoc aromatic CH); δ$_C$ (125 MHz, CDCl$_3$); 14.662 (SCH$_3$), 47.133 (Fmoc-CH), 48.449/48.954 (CHSCH$_3$), 50.539/53.419 (FmocNCH$_2$), 61.005/61.420 (FmocNCH), 67.710/68.437 (Fmoc-CH$_2$), 70.733 (OCH$_2$C=O), 85.174/86.042 (OCHCHSCH$_3$), 119.916, 119.987, 124.917, 124.964, 125.240, 125.448, 127.069, 127.712 and 127.969 (Fmoc aromatic CH), 141.255/141.317, 143.627, 143.778 and 144.264 (Fmoc quaternary), 154.942/155.049 (Fmoc C=O), 207.818/207.973 (ketone C=O).

Preparation of (3R,3aR,6S,6aR)benzyl 3-hydroxy-6-(methylamino)tetrahydro-2H-furo[3,2-b]pyrrole-4(5H)-carboxylate (57) A stirred solution of tosylate (34b) (200 mg, 0.46 mmol) and methylamine in ethanol (33% wt, 6 mL) was heated in a sealed pressure vessel at 150° C. for 72 hours. The mixture was then allowed to cool to ambient temperature then solvents removed in vacuo. The residue was dissolved in dichloromethane (20 mL), washed with water (15 mL) then dried (Na$_2$SO$_4$), filtered and reduced in vacuo. Flash chromatography over silica, eluting with dichloromethane:methanol mixtures 97:3 to 95:5 gave methylaminoalcohol (57) as a pale yellow solid (47 mg, 35%). TLC (R$_f$=0.22, DCM:MeOH 93:7), HPLC-MS 293.1 [M+H]$^+$, 315.2 [M+Na]$^+$, 607.3 [2M+Na]$^+$; δ$_H$(500 MHz, CDCl$_3$) mixture of rotamers major:minor 3:2; 2.42 (1.8H, s, NHCH$_3$ major), 2.3 (1.2H, s, NHCH$_3$ minor), 3.14-3.16 (1H, m, CHNHCH$_3$), 3.35-4.48 (7H, m, OCH$_2$CHOH, CHCHCHCH$_2$NCbz), 5.06 and 5.22 (0.8H total, each d, J=12.22 Hz, Cbz minor), 5.12 (1.2H, s, Cbz major), 7.27-7.37 (5H, m, aromatic CH).

Preparation of (3R,3aR,6S,6aR)-benzyl 6-(tert-butoxycarbonyl(methyl)amino)-3-hydroxytetrahydro-2H-furo[3,2-b]pyrrole-4(5H)-carboxylate (58) A solution of di-tert-butyl dicarbonate (48 mg, 0.22 mmol) and diisopropyl ethyl amine (30 mg, 0.23 mmol) in dichloromethane (1.5 mL) was added dropwise over 5 minutes to a solution of methylaminoalcohol (57) (47 mg, 0.161 mmol) dichloromethane (1.5 mL). The mixture was stirred for 16 hours then diluted with dichloromethane (10 mL), then washed with hydrochloric acid (1M, 5 mL), reduced in vacuo to leave Boc alcohol (58) as a yellow oil (72 mg). TLC (R$_f$=0.41, Et$_2$O), HPLC-MS 293.1 [M-Boc+H]$^+$, 337.1 [M+2H–$^t$Bu]$^+$, 415.2 [M+Na]$^+$, 807.3 [2M+Na]$^+$.

Preparation of (3R,3aR,6S,6aS)-tert-butyl 6-ethoxy-3-hydroxytetrahydro-2H-furo[3,2-b]pyrrole-4(5H)-carboxylate (59) A stirred mixture of tosylate (35b) (20 mg, 0.05 mmol), ethanol (1 mL) and sodium ethoxide solution in ethanol (21% wt, 94 µL, 0.25 mmol) was heated under an atmosphere of argon at 80° C. for 16 hours. The mixture was diluted with aqueous saturated sodium hydrogen carbonate solution (10 mL) then extracted with tert-butyl methyl ether (3×5 mL). The organic phase was dried (MgSO$_4$), filtered and reduced in vacuo to leave an oil. Flash chromatography over silica, eluting with diethyl ether:pentane mixtures 65:35 to 83:17 gave ethoxyalcohol (59) as a pale yellow solid (1 mg, 7%). TLC (R$_f$=0.50, Et$_2$O); analytical HPLC main peak, R$_t$=15.35 min., HPLC-MS 218.1 [M+2H–$^t$Bu], 296.1 [M+Na]$^+$, 569.3 [2M+Na]$^+$.

Preparation of (3R,3aR,6S,6aS)-Benzyl 6-fluoro-3-hydroxytetrahydro-2H-furo[3,2-b]pyrrole-4(5H)-carboxylate (60) A solution of potassium carbonate (5 mg, 0.034 mmol) in acetonitrile:water (95:5, 0.5 mL) was added to a mixture of Kryptofix®222 (66 mg, 0.175 mmol), oven dried potassium fluoride (13.1 mg, 0.225 mmol) in a pressure vessel. The mixture was stirred for 5 minutes then the solvent evaporated using a stream of argon. Acetonitrile (0.5 mL) was added then the solvent removed using a stream of argon. Acetonitrile (0.5 mL) was added three more times, removing the solvent each time using a stream of argon. A solution of tosylate (34b) (50 mg, 0.115 mmol) in acetonitrile (0.5 mL) was added then the vessel sealed and heated at 130° C. for 2 hours. HPLC-MS analysis showed the formation of 6-fluoro analogue; HPLC-MS 282.1 [M+H]$^+$, 304.1 [M+Na]$^+$, 585 [2M+Na]$^+$.

The Cbz analogue (60) may readily be converted to the corresponding Boc analogue (3R,3aR,6S,6aS)-tert-butyl 6-fluoro-3-hydroxytetrahydro-2H-furo[3,2-b]pyrrole-4(5H)-carboxylate (61) following standard Pd—C hydrogenation and treatment with di-tert-butyl dicarbonate and sodium carbonate in aqueous dioxane.

Alternative preparation of (3R,3aR,6S,6aS)-tert-Butyl 6-fluoro-3-hydroxytetrahydro-2H-furo[3,2-b]pyrrole-4(5H)-carboxylate (61). A solution of tetrabutylammonium fluoride (1M in tetrahydrofuran, 35 mL, 35 mmol) and (3R, 3aR,6R,6aS)-tert-butyl 3-hydroxy-6-(tosyloxy)tetrahydro-2H-furo[3,2-b]pyrrole-4(5H)-carboxylate (35b) (7.0 g, 17.5 mmol) in dimethylformamide (35 mL) was divided into seven portions then heated in sealed tubes under an atmosphere of argon at 140° C. for 1 hour 40 minutes then at 145° C. for 3 hours. The mixtures were stirred at ambient temperature for 19 hours then at 145° C. for 2.75 hours. The separate reaction mixtures were combined then the solvents were removed in vacuo. The residue was diluted with dichloromethane (400 mL) and water (200 mL). The organic layer was separated then the aqueous phase re-extracted with dichloromethane (100 mL). The combined organic layers were washed with water (2×200 mL), then dried (Na$_2$SO$_4$), filtered and reduced in vacuo to leave a brown-black residue (10.4 g). Flash chromatography over silica, eluting with ethyl acetate:heptane mixtures 0:100 to 40:60 gave crude 6-fluoroalcohol (61) (3.05 g) as brown oil. The oil was dissolved in dichloromethane (65 mL) then 3-chloroperoxybenzoic acid (supplied by Sigma-Aldrich 77% maximum purity, 2.77 g, 12.35 mmol) was added. The mixture was stirred for 1 hour then diluted with dichloromethane (300 mL), then washed with aqueous sodium hydroxide solution (1M, 2×150 mL), then water (150 mL), then dried (Na$_2$SO$_4$), filtered and reduced in vacuo to leave a residue (3.14 g). Flash chromatography over silica, eluting with ethyl acetate:heptane mixtures 0:100 to 50:50 gave 6-fluoroalcohol (61) (1.77 g, 41%) as a white solid. TLC (R$_f$=0.46, EtOAc:heptane 3:1), HPLC-MS 192.0 [M+2H–Bu]$^+$, 270.1 [M+Na]$^+$, 517.2 [2M+Na]$^+$; δ$_H$ (500 MHz, CDCl$_3$) mixture of rotamers major:minor 2:1; 1.45 (6H, s, (CH$_3$)$_3$C major), 1.49 (3H, s, (CH$_3$)$_3$C minor), 2.70 (1H, brs, OH), 3.30 (0.66H, dt, J=13.49 and 3.22 Hz, 1×Boc-NCH$_2$ major), 3.38 (0.33H, dt, J=13.26 and 3.22 Hz, 1×Boc-NCH$_2$ minor), 3.76-4.00 (3H, m, OCH$_2$CHOH and 1×CbzNCH$_2$), 4.27 (0.33H, d, J=4.51 Hz, BocNCH minor), 4.32 (0.66H, d, J=4.75 Hz, BocNCH major), 4.41 (0.33H, brd, J=2.69 Hz, OCH$_2$CHOH minor), 4.47 (0.66H, brs, OCH$_2$CHOH major), 4.69-4.76 (1H, m, CHCHF), 4.94 (0.33H, d, J=49.73 Hz, CHF minor), 4.95 (0.66H, d, J=49.71 Hz, CHF major); δ$_C$ (125 MHz, CDCl$_3$) 28.358/28.445 ((CH$_3$)$_3$C), 50.962/51.139 and 51.47/51.650 (BocNCH$_2$), 68.004/68.572 (BocNCH), 74.153/74.224 (OCH$_2$CHOH), 75.599/76.426 (OCH$_2$CHOH), 80.702/80.911 ((CH$_3$)$_3$C), 83.204/83.454 and 84.000/84.252 (CHCHF), 91.458/92.136 and 92.886/93.561 (CHF), 153.654/154.459 (Boc C=O).

Alternative Preparation of (3R,3aR,6S,6aS)-Benzyl 6-fluoro-3-hydroxytetrahydro-2H-furo[3,2-b]pyrrole-4 (5H)-carboxylate (60). A solution of tetrabutylammonium fluoride (1M in tetrahydrofuran, 8.2 mL, 8.2 mmol) and (3R, 3aR,6R,6aS)-benzyl 3-hydroxy-6-(tosyloxy)tetrahydro-2H-furo[3,2-b]pyrrole-4(5H)-carboxylate (34b) (1.77 g, 4.09 mmol) in acetonitrile (17 mL) was heated in a sealed tube under an atmosphere of argon at 135° C. for 16 hours. The solvents were removed in vacuo then residue was partitioned between EtOAc (150 mL) and 0.2N HCl (340 mL). The aqueous phase re-extracted with EtOAc (2×150 mL) then the combined organic layers were washed with saturated NaHCO$_3$ (300 mL), then brine (300 mL). The organic layer was then dried (Na$_2$SO$_4$), filtered and reduced in vacuo to leave a brown-black residue (1.07 g). Flash chromatography over silica, eluting with ethyl acetate:heptane mixtures 1:2 gave crude 6-fluoroalcohol (60) (780 mg) as a white solid. The crude alcohol was purified by on semi-preparative silica chromatography plates (EtOAc:DCM, 1:1) to give pure 6-fluoroalcohol (60) (379 mg, 33%) as a colourless oil. TLC (R$_f$=0.25, EtOAc:heptane 1:2), HPLC-MS 282.1 [M+H]$^+$, 304.1 [M+Na]$^+$, 585.2 [2M+Na]$^+$; [α]$_D^{26}$–51.8° (c=1.93, CHCl$_3$); δ$_C$ (125 MHz, CDCl$_3$) 51.32/51.50/51.53/51.71 (CbzNCH$_2$), 67.55/67.60 (PhCH$_2$O), 67.99/69.01

(CbzNCH), 73.47/74.19 (OCH$_2$CHOH), 75.45/76.29 (OCH$_2$CHOH), 83.13/83.38 and 84.02/84.28 (CHCHF), 91.34/91.98 and 92.77/93.41 (CHF), 127.98/128.03/128.29/128.38/128.58/128.72 (aromatic CH), 135.94/136.12 (aromatic quarternary), 154.31/154.96 (Cbz C=O).

Alternative Preparation of (3R,3aR,6S,6aS)-Benzyl 6-fluoro-3-hydroxytetrahydro-2H-furo[3,2-b]pyrrole-4(5H)-carboxylate (60). A solution of tetrabutylammonium fluoride (1M in tetrahydrofuran, 0.6 mL, 0.6 mmol) and (3R,3aR,6R,6aS)-benzyl 3-hydroxy-6-(tosyloxy)tetrahydro-2H-furo[3,2-b]pyrrole-4(5H)-carboxylate (34b) (130 mg, 0.30 mmol) in dimethylformamide (0.6 mL) was heated in a sealed tube under an atmosphere of argon at 135° C. for 3 hours. The solvents were removed in vacuo then residue was partitioned between dichloromethane (10 mL) and water (5 mL). The aqueous phase reextracted with dichloromethane (5 mL) then the combined organic layers were washed with water (5 mL), then dried (Na$_2$SO$_4$), filtered and reduced in vacuo to leave a brown-black residue (125 mg). Flash chromatography over silica, eluting with ethyl acetate:heptane mixtures 0:100 to 60:40 gave crude fluoroalcohol (60) (11 mg, 12%) as a white solid together with a contaminated sample of (60) (estimated 50% purity, 10 mg).

Alternative Preparation of (3R,3aR,6S,6aS)-Benzyl 6-fluoro-3-hydroxytetrahydro-2H-furo[3,2-b]pyrrole-4(5H)-carboxylate (60). A solution of tetrabutylammonium fluoride (1M in tetrahydrofuran, 0.66 mL, 0.66 mmol) was added to a solution of (3R,3aR,6R,6aS) 3-hydroxyhexahydro-2H-furo[3,2-b]pyrrol-6-yl 4-methylbenzenesulfonate (74) (100 mg, 0.33 mmol) in dimethylformamide (0.66 mL) under an atmosphere of argon. The mixture was heated at 125° C. for 5 hours then allowed to cool to ambient temperature. A solution of sodium carbonate (89 mg, 0.84 mmol) in water (1.5 mL) was added followed by benzylchloroformate (0.105 mL, 0.74 mmol). The mixture was stirred for 1 hour then dichloromethane (10 mL) and water (15 mL) added. The organic phase was separated and the aqueous extracted with dichloromethane (2×5 mL). The combined organic phase was washed with brine (5 mL), then dried (Na$_2$SO$_4$), filtered and reduced in vacuo to leave a brown oil. Flash chromatography over silica, eluting with ethyl acetate:heptane mixtures 5:95 to 40:60 gave fluoroalcohol (60) (23 mg, 25%) as a colourless oil. TLC (R$_f$=0.70, EtOAc heptane 3:1), analytical HPLC single main peak, R$_t$=9.641 min; HPLC-MS 282.1 [M+H]$^+$, 304.1 [M+Na]$^+$, 585.2 [M+H]$^+$; $[\alpha]_D^{23}$ –54.8° (c=2.28, CHCl$_3$).

Preparation of (3R,3aR,6S,6aS)-(9H-fluoren-9-yl)methyl 6-fluoro-3-hydroxytetrahydro-2H-furo-[3,2-b]pyrrole-4(5H)-carboxylate (63)

(i) Boc alcohol (61) (73 mg, 0.30 mmol) was dissolved in 1,4-dioxane (2 mL). A solution of hydrogen chloride in 1,4-dioxane (4M, 0.74 mL, 2.95 mmol) was added in a single portion then the mixture stirred for 18 hours. The solvent was removed in vacuo then the residue triturated with cold diethyl ether (10 mL) to afford a pale lilac powder (39 mg, 72%) which was used without further purification. Data for (3R,3aR,6S,6aS)-6-fluorohexahydro-2H-furo[3,2-b]pyrrol-3-ol hydrochloride TLC (R$_f$=0.0, EtOAc:heptane 2:3), HPLC-MS 148.1 [M+H]$^+$ $\delta_C$ (125 MHz, D6-DMSO) 49.521/49.697 (NCH$_2$), 68.088 (NCH), 72.738 (OCH$_2$CHOH), 74.944 (OCH$_2$CHOH), 83.813/84.057 (OCHCHF), 92/975/94.379 (CHF); $\delta_F$ (376 MHz, CDCl$_3$) –185.69.

(ii) Preparation of (3R,3aR,6S,6aS)-(9H-fluoren-9-yl)methyl 6-fluoro-3-hydroxytetrahydro-2H-furo[3,2-b]pyrrole-4(5H)-carboxylate (62). The crude (3R,3aR,6S,6aS)-6-fluorohexahydro-2H-furo[3,2-b]pyrrol-3-ol hydrochloride (34 mg, 0.19 mmol) was dissolved in aqueous sodium carbonate solution (39 mg in 2 mL) then 1,4-dioxane (1 mL) followed by 9-fluorenylmethoxycarbonyl chloride (50 mg, 0.19 mmol) added. The mixture was stirred for 24 hours then water (2 mL) added. The aqueous phase was extracted with chloroform (5×2 mL) then the combined organic phase was washed with brine (5 mL), then dried (Na$_2$SO$_4$), filtered and reduced in vacuo to obtain an opaque oil. Flash chromatography over silica, eluting with ethyl acetate:heptane mixtures 0:100 to 60:40 gave alcohol (62) as a colourless oil (64 mg, 94%). TLC (R$_f$=0.43, EtOAc:heptane 1:1), analytical HPLC single main peak, R$_t$=15.402 min., HPLC-MS 370.2 [M+H]$^+$, 392.2 [M+Na]$^+$, $[\alpha]_D^{19}$ =–43.1° (c=2.9, CHCl$_3$). $\delta_C$ (125 MHz, CDCl$_3$) 47.264, 47.373, 47.446 (Fmoc CH), 51.053, 51.160, 51.231 and 51.340 (FmocNCH$_2$), 65.862/65.916 (Fmoc CH$_2$), 68.235/68.865 (FmocNCH), 73.856/74.088 (OCH$_2$CHOH), 75.527, 75.559, 75.964 (OCH$_2$CHOH), 83.100, 83.349, 83.670, 83.921 (OCHCHF), 91.243, 91.931, 92.672, 93.360 (CHF), 119.797, 119.803, 120.003, 120.041, 124.483, 124.529, 124.866, 124.925, 127.047, 127.086, 127.441, 127.572, 127.799, 127.906 and 127.938 (Fmoc aromatic CH), 141.193, 141.313, 141.401, 141.491, 143.508, 143.769, 143.910 and 143.954 (Fmoc quaternary), 153.995/154.716 (Fmoc C=O). $\delta_F$(376 MHz, CDCl$_3$) –185.87 and –185.16.

(iii) Oxidation to ketone (63). Dess-Martin periodinane (135 mg, 0.32 mmol) was added in a single portion to a stirred solution of alcohol (62) (59 mg, 0.16 mmol) in dichloromethane (4 mL) under argon. The mixture was stirred for 4 hours then diluted with dichloromethane (5 mL). The organic phase was washed with a mixture of saturated aqueous sodium hydrogencarbonate and 10% sodium thiosulphate solution (1:1, 5 mL), then saturated aqueous sodium bicarbonate (5 mL), then dried (Na$_2$SO$_4$), filtered and reduced in vacuo to obtain a yellow solid. Flash chromatography over silica, eluting with ethyl acetate:heptane mixtures 0:100 to 60:40 gave ketone (63) as a white solid (47 mg, 80%). TLC (R$_f$=0.42, EtOAc:heptane 1:1), analytical HPLC single main peak, R$_t$=16.303 min., HPLC-MS 368.2 [M+H]$^+$, 390.1 [M+Na]$^+$, 757.3 [2M+Na]$^+$, $[\alpha]_D^{18}$=–126.8° (c=2.72, CHCl$_3$); $\delta_C$ (125 MHz, CDCl$_3$); 47.086/47.086 (Fmoc-CH), 51.292, 51.473, 51.581, 51.759 (FmocNCH$_2$), 60.578/61.016 (FmocNCH), 67.891/68.592 (Fmoc-CH$_2$), 69.937 (OCH$_2$C=O), 82.964, 83.214, 83.961 and 84.216 (OCHCHF), 91.431, 92.058, 92.864 and 93.490 CHF), 119.936, 120.005, 124.901, 125.147, 125.394, 127.101, 127.712 and 127.757 (Fmoc aromatic CH), 141.282, 141.331, 143.532, 143.637, 143.688 and 144.214 (Fmoc quaternary), 154.746/154.837 (Fmoc C=O), 206.614/206.744 (ketone C=O); $\delta_F$ (376 MHz, CDCl$_3$) –188.00 and –188.75.

Preparation of (3aS,6S,6aS)-(9H-Fluoren-9-yl)methyl 6-chloro-3-oxotetrahydro-2H-furo[3,2-b]pyrrole-4(5H)-carboxylate (71). Following Scheme 17.
(i) Preparation of (3R,3aR,6S,6aS)-Benzyl 6-chloro-3-hydroxytetrahydro-2H-furo[3,2-b]pyrrole-4(5H)-carboxylate (68).

(ii) (3R,3aR,6S,6aS)-(9H-Fluoren-9-yl)methyl 6-chloro-3-hydroxytetrahydro-2H-furo[3,2-b]pyrrole-4(5H)-carboxylate (70). Ethanol (8.5 mL) was added dropwise to a mixture of 10% palladium on charcoal (55 mg) and alcohol (68) (550 mg, 1.85 mmol) under an atmosphere of argon. The argon was replaced by hydrogen then the suspension

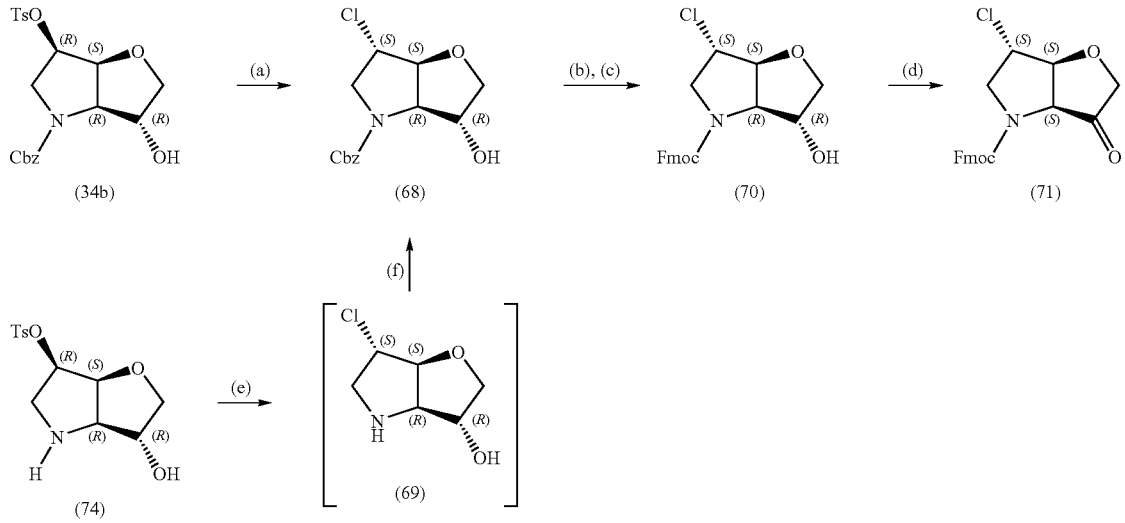

Scheme 17.

(a) LiCl, DMF, 130° C.; (b) Pd-C, H₂, ethanol; (c) Fmoc-Cl, Na₂CO₃, dioxane, H₂O; (d) Dess-Martin periodinane, anhydrous DCM; (e) LiCl, DMF, 130° C.; fb) Cbz-Cl, Na₂CO₃ dioxane, H₂O.

Lithium chloride (2.38 g, 56.2 mmol) was added to a stirred solution of (3R,3aR,6R,6aS)-benzyl 3-hydroxy-6-(tosyloxy) tetrahydro-2H-furo[3,2-b]pyrrole-4(5H)-carboxylate (34b) (2.435 g, 5.62 mmol) in dimethylformamide (75 mL) under an atmosphere of argon. The mixture was heated at 130° C. for 7 hours then allowed to cool to ambient temperature. The mixture was diluted with dichloromethane (100 mL), then water (50 mL) was added and the mixture filtered through celite (filter cake washed with dichloromethane). The filtrate was separated then the organic phase washed with water (2×50 mL), then dried (Na₂SO₄), filtered and reduced in vacuo to leave a residue (1.54 g). Flash chromatography over silica, eluting with ethyl acetate:heptane mixtures 20:80 to 60:40 gave alcohol (68) (1.28 g, 77%) as an orange-brown solid. TLC (R$_f$=0.40, EtOAc:heptane 2:1), analytical HPLC single main peak, R$_t$=11.47 min., HPLC-MS 298.1/300.1 [M+H]⁺, 617.1 [2M+Na]⁺; [α]$_D^{23.0}$ –72.8° (c=2.61, CHCl₃); δ$_H$ (500 MHz, CDCl₃) mixture of rotamers majo:minor 2:1; 1.78 and 2.24 (approx. 1H total, each brs, OH), 3.58-3.63 (1H, m, 1×CbzNCH₂), 3.83-3.88 (2H, m, OCH₂CHOH), 3.91 (0.66H, d, J=13.08 Hz, 1×CbzNCH₂, major), 4.02 (0.33H, J=13.09 Hz, 1×CbzNCH₂, minor), 4.24-4.26 (1H, m, CHCl), 4.39-4.42 (0.66H, m, CbzNCH minor and OCH₂CHOH minor), 4.43 (0.66H, d, J=4.33 Hz, CbzNCH major), 4.52 (0.66H, brs, OCH₂CHOH major), 4.72-4.75 (1H, m, CHCHCl), 5.11-5.16 (1.66H, m, 2×CH₂Ph major and 1×CH₂Ph minor), 5.24 (0.33H, d, J=12.29 Hz 1×CH₂Ph minor), 7.29-7.37 (5H, m, phenyl CH); δ$_C$ (125 MHz, CDCl₃) 53.57/53.74 (CbzNCH₂), 57.91/58.38 (CHCl), 67.53/67.58 (CH₂Ph), 67.69/68.64 (CbzNCH), 75.06/75.93 (OCH₂CHOH), 75.12/75.18 (OCH₂CHOH), 86.66/87.59 (CHCHCl), 127.85, 127.90, 128.24, 128.32, 128.56 and 128.69 (aromatic CH), 135.97/136.15 (Cbz quaternary), 154.41/154.96 (Cbz C=O).

was stirred for 1 hour 35 minutes before filtering the mixture through celite in vacuo. The filter cake was washed with ethanol (45 mL) then the solvents removed in vacuo from the filtrate. The residue was azeotroped with toluene (3×5 mL) to obtain (3R,3aR,6S,6aS)-6-chlorohexahydro-2H-furo[3,2-b]pyrrol-3-ol (69) which was used without further purification.

A solution of sodium carbonate (0.49 g, 4.63 mmol) in water (7.5 mL) followed by a solution of 9-fluorenylmethoxycarbonyl chloride (0.55 g, 2.13 mmol) in 1,4-dioxane (2.5 mL) was added dropwise over 15 minutes whilst stirring to a solution of aminoalcohol (69) in 1,4-dioxane (5 mL). The mixture was stirred for 60 minutes then water (50 mL) was added and the product extracted into dichloromethane (3×25 ml), then dried (Na₂SO₄), filtered and reduced in vacuo to leave a colourless oil. Flash chromatography over silica, eluting with ethyl acetate:heptane mixtures 10:90 to 45:55 gave alcohol (70) (623 mg, 87%) as a white solid. TLC (R$_f$=0.45, EtOAc:heptane 1:1), analytical HPLC single main peak, R$_t$=16.54 min., HPLC-MS 386.1/388.1 [M+H]⁺, 408.1/410.1 [M+Na]⁺; [α]$_D^{27.5}$ –51.9° (c=2.31, CHCl₃); (proton complex) δ$_c$ (125 MHz, CDCl₃) 47.21/47.41 (Fmoc CH), 53.30/53.43 (FmocNCH₂), 57.74/58.36 (CHCl), 66.04/67.42 (Fmoc CH₂), 67.87/68.52 (FmocNCH), 74.81/75.09 (OCH₂CHOH), 74.92/75.51 (OCH₂CHOH), 86.57/87.24 (CHCHCl), 119.80/119.82/120.00/120.64/124.55/124.63/124.90/127.04/127.08/127.40/127.51/127.78/127.80/127.87 and 127.91 (aromatic CH), 141.21/141.29/141.38/143.44/143.70/143.88 and 143.91 (aromatic quaternary), 154.13/154.79 (Fmoc C=O).

(iii) (3aS,6S,6aS)-(9H-Fluoren-9-yl)methyl 6-chloro-3-oxotetrahydro-2H-furo[3,2-b]pyrrole-4(5H)-carboxylate (71). Dess-Martin periodinane (1.32 g, 3.11 mmol) was added to a stirred solution of alcohol (70) (600 mg, 1.56 mmol) in dichloromethane (15 mL) under an atmosphere of argon. The mixture was stirred for 19 hours then diluted with dichloromethane (50 mL) then washed with a mixture of saturated aqueous sodium bicarbonate and 0.25M sodium thiosulphate solution (1:1, 30 mL), saturated aqueous sodium bicarbonate (25 mL), brine (25 mL), then dried (Na$_2$SO$_4$), filtered and reduced in vacuo to obtain a white solid (935 mg). Flash chromatography over silica, eluting with ethyl acetate:heptane mixtures 15:85 to 100:0 gave ketone (71) (506 mg, 85%) as a white solid contaminated with 2-iodosylbenzoic acid (<5%). TLC (R$_f$=0.35, EtOAc:heptane 1:1), analytical HPLC single main peak, R$_t$=15.81 min., HPLC-MS 384.1/386.1 [M+H]$^+$, 406.1/408.1 [M+Na]$^+$, 424.1/426.1 [M+H$_2$O+Na]$^+$, 789.1/791.2 [2M+Na]$^+$; [α]$_D^{25.5}$–1440.6° (c=2.18, CHCl$_3$); δ$_H$ (500 MHz, CDCl$_3$) mixture of rotamers majo:minor 0.55:0.45; 3.75-3.89 (1H, m, 1×FmocNCH$_2$), 3.93-4.03 (1.55H, m, 1×OCH$_2$C=O and 1×FmocNCH$_2$ major), 4.12-4.22 (1.45H, m, 1×OCH$_2$C=O and 1×FmocNCH$_2$ minor), 4.25 (0.55H, brt, J=6.72 Hz, Fmoc CH major), 4.30-4.44 (2.45H, m, CHCl, 1×FmocNCH$_2$ and Fmoc CH minor), 4.45 (0.45H, d, J=4.46 Hz, FmocNCH minor), 4.50-4.58 (1.55H, m, 1×Fmoc CH$_2$ and FmocNCH major), 4.85 (0.55H, d, J=4.44 Hz, CHCHCl major), 4.90 (0.45H, d, J=4.41 Hz, CHCHCl minor), 7.27-7.76 (8H, aromatic CH); 5c (125 MHz, CDCl$_3$) 47.09/47.13 (Fmoc CH), 53.43/53.66 (FmocNCH$_2$), 57.60/58.09 (CHCl), 60.47/60.87 (FmocNCH), 67.86/68.56 (Fmoc CH$_2$), 70.75 (OCH$_2$C=O), 86.32/87.32 (CHCHCl), 119.93/119.99/120.08/124.87/124.94/125.17/125.36/127.09/127.71 and 127.74 (aromatic CH), 141.28/141.32/143.51/143.63 and 144.16 (aromatic quaternary), 154.88/154.94 (Fmoc C=O), 206.45/206.64 (OCH$_2$C=O).

Alternative preparation of (3R,3aR,6S,6aS)-Benzyl 6-chloro-3-hydroxytetrahydro-2H-furo[3,2-b]pyrrole 4(5H)-carboxylate (68). Lithium chloride (142 mg, 3.34 mmol) was added to a stirred solution of (3R,3aR,6R,6aS) 3-hydroxyhexahydro-2H-furo[3,2-b]pyrrol-6-yl 4-methylbenzenesulfonate (74) (100 mg, 0.33 mmol) in dimethylformamide (3 mL) under an atmosphere of argon. The mixture was heated at 130° C. for 2.75 hours then allowed to cool to ambient temperature to give a solution containing 6-chloroaminoalcohol (69). A solution of sodium carbonate (89 mg, 0.84 mmol) in water (1.5 mL) was added followed by benzylchloroformate (0.105 mL, 0.74 mmol). The mixture was stirred for 35 minutes then dichloromethane (10 mL) and water (15 mL) added. The organic phase was separated and the aqueous extracted with dichloromethane (2×5 mL). The combined organic phase was washed with brine (5 mL), then dried (Na$_2$SO$_4$), filtered and reduced in vacuo to leave a black residue (97 mg). Flash chromatography over silica, eluting with ethyl acetate:heptane mixtures 5:95 to 50:50 gave 6-chloroalcohol (68) (48 mg, 48%) as a pale yellow oil. TLC (R$_f$=0.30, EtOAc heptane 3:2), analytical HPLC single main peak, R$_t$=11.47 min., HPLC-MS 298.0/300.0 [M+H]$^+$, 617.1/619.1 [2M+Na]$^+$; [α]$_D^{22}$–76.9° (c=4.81, CHCl$_3$).

Preparation of (3aS,6R,6aS)-(9H-Fluoren-9-yl)methyl 6-chloro-3-oxotetrahydro-2H-furo[3,2-b]pyrrole-4(5H)-carboxylate (79). Following Scheme 18.
(i) Preparation of (3R,3aR,6R,6aS)-Benzyl 6-chloro-3-hydroxytetrahydro-2H-furo[3,2-b]pyrrole-4(5H)-carboxylate (76).

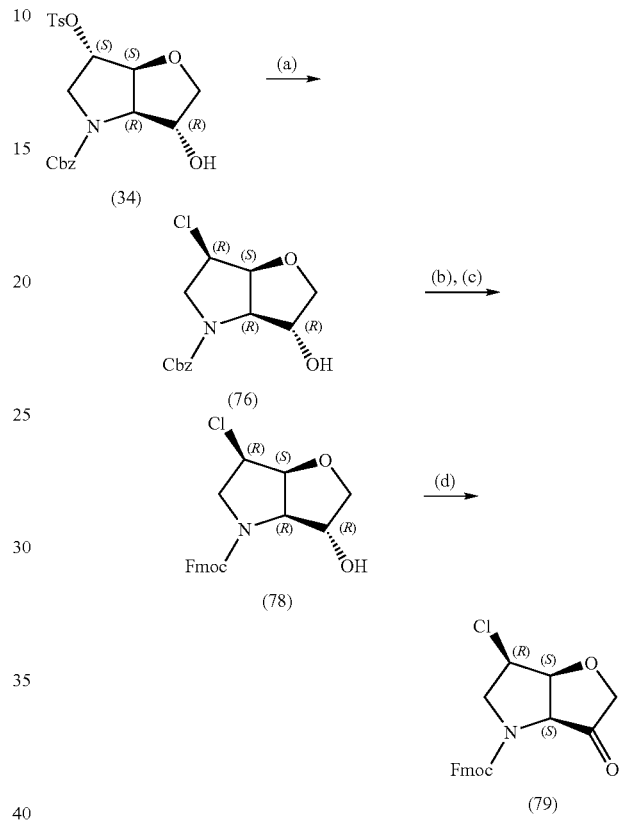

Scheme 18.

(a) LiCl, DMF, 140° C.; (b) Pd-C, H$_2$, ethanol; (c) Fmoc-Cl, Na$_2$CO$_3$, dioxane, H$_2$O; (d) Dess-Martin periodinane, anhydrous DCM.

Lithium chloride (1.37 g, 32.3 mmol) was added to a stirred solution of (3R,3aR,6S,6aS)-benzyl 3-hydroxy-6-(tosyloxy)tetrahydro-2H-furo[3,2-b]pyrrole-4(5H)-carboxylate (34) (2.435 g, 5.62 mmol) in dimethylformamide (25 mL) under an atmosphere of argon. The mixture was heated at 140° C. for 4.25 hours then allowed to cool to ambient temperature then diluted with dichloromethane (75 mL) and water (50 mL). The mixture was filtered through celite (filter cake washed with dichloromethane, 50 mL) then the filtrate separated. The organic phase was washed with water (2×75 mL), then water (75 mL) was added and the mixture filtered through celite (filter cake washed with dichloromethane, 50 mL). The filtrate was separated then the organic phase washed with water (75 mL), dried (Na$_2$SO$_4$), filtered and reduced in vacuo to leave a residue (0.34 g). Flash chromatography over silica, eluting with ethyl acetate:heptane mixtures 0:100 to 50:50 gave alcohol (76) (156 mg, 16%) as a green-black oil. TLC (R$_f$=0.35, EtOAc:heptane 2:1), analytical HPLC single main peak, R$_t$=11.01 min., HPLC-MS 298.1/300.1 [M+H]$^+$, 320.1/322.0 [M+Na]$^+$, 617.1/619.2 [2M+Na]$^+$; [α]$_D^{23.0}$–18.0° (c=4.16, CHCl$_3$); δ$_H$ (500 MHz, CDCl$_3$) mixture of rotamers majo:minor 2:1; 2.19 (0.33H, d, J=3.99 Hz, OH minor), 2.94 (0.66H, d, J=3.16 Hz, OH major), 3.22-3.35 (1H, m, 1×CbzNCH$_2$), 3.84-3.91 (1H, m, 1×OCH$_2$CHOH), 3.98-

4.16 (3H, m, 1×OCH$_2$CHOH, 1×CbzNCH$_2$ and CHCl), 4.23 (1H, d, J=4.68 Hz, CbzNCH), 4.42 (0.33H, brs, OCH$_2$CHOH minor), 4.53 (0.66H, brd, J=2.83 Hz, OCH$_2$CHOH major), 4.69 (1H, brt, J=4.37 Hz, CHCHCl), 5.08-5.22 (2H, m, CH$_2$Ph), 7.31-7.39 (5H, m, phenyl CH); δ$_C$ (125 MHz, CDCl$_3$) 51.09/51.14 (CbzNCH$_2$), 54.98/55.28 (CHCl), 67.62/67.68 (CH$_2$Ph), 68.82/69.65 (CbzNCH), 75.36/75.51 (OCH$_2$CHOH), 76.39/77.26 (OCH$_2$CHOH), 81.34/82.19 (CHCHCl), 128.07, 128.10, 128.38, 128.49, 128.61 and 128.75 (aromatic CH), 135.84/136.96 (Cbz quaternary), 153.67/154.46 (Cbz C=O).

(ii) Preparation of (3R,3aR,6R,6aS)-(9H-Fluoren-9-yl)methyl 6-chloro-3-hydroxytetrahydro-2H-furo[3,2-b]pyrrole-4(5H)-carboxylate (78). Ethanol (3.5 mL) was added dropwise to a mixture of 10% palladium on charcoal (25 mg) and (3R,3aR,6R,6aS)-benzyl 6-chloro-3-hydroxytetrahydro-2H-furo[3,2-b]pyrrole-4(5H)-carboxylate (198 mg, 0.67 mmol) under an atmosphere of argon. The argon was replaced by hydrogen then the suspension was stirred for 4.5 hours before filtering the mixture through celite in vacuo. The filter cake was washed with ethanol (20 mL) then the solvents removed in vacuo from the filtrate. The residue was azeotroped with toluene (3×5 mL) to obtain (3R,3aR,6R,6aS)-6-chlorohexahydro-2H-furo[3,2-b]pyrrol-3-ol (77) which was used without further purification.

A solution of sodium carbonate (155 mg, 1.46 mmol) in water (2.5 mL) then a solution of 9-fluorenylmethoxycarbonyl chloride (189 mg, 0.73 mmol) in 1,4-dioxane (1.5 mL) was added whilst stirring to a solution of aminoalcohol (77) in 1,4-dioxane (1 mL). The mixture was stirred for 65 minutes then water (20 mL) was added and the product extracted into dichloromethane (3×10 mL), then dried (Na$_2$SO$_4$), filtered and reduced in vacuo to leave a residue. Flash chromatography over silica, eluting with ethyl acetate:heptane mixtures 10:90 to 50:50 gave alcohol (78) (194 mg, 76%) as a white solid. TLC (R$_f$=0.45, EtOAc:heptane 1:1), analytical HPLC single main peak, R$_t$=15.51 min., HPLC-MS 386.1/388.1 [M+H]$^+$, 408.1/410.1 [M+Na]$^+$; [α]$_D^{23.0}$ -7.46° (c=2.01, CHCl$_3$); δH (500 MHz, CDCl$_3$) mixture of rotamers 1:1; 1.15 (0.5H, s, OH), 3.05 (0.5H, t, J=9.58 Hz, FmocNCH$_2$), 3.09 (0.5H, s, OH), 3.23 (0.5H, t, J=10.38 Hz, FmocNCH$_2$), 3.43 (0.5H, d, J=4.37 Hz, FmocNCH), 3.53 (0.5H, brs, OCH$_2$CHOH), 3.62 (0.5H, dd, J=10.20 and 1.92 Hz, OCH$_2$CHOH), 3.75 (0.5H, dd, J=10.21 and 4.53 Hz, OCH$_2$CHOH), 3.84-3.97 (2H, m, 1×FmocNCH$_2$, 0.5× OCH$_2$CHOH and 0.5×CHCl), 4.02 (0.5H, dd, J=9.96 and 4.65 Hz, OCH$_2$CHOH), 4.06-4.12 (0.5H, m, CHCl), 4.15-4.26 (1.5H, m, Fmoc CH and 0.5×FmocNCH), 4.39-4.46 (1.5H, m, 0.5×OCH$_2$CHOH, 0.5×Fmoc CH$_2$ and 0.5× CHCHCl), 4.50 (0.5H, dd, J=10.64 and 6.70 Hz, Fmoc CH$_2$), 4.67 (0.5H, t, J=4.29 Hz, CHCHCl), 4.75 (0.5H, dd, J=10.86 and 3.69 Hz, Fmoc CH$_2$), 4.82 (0.5H, dd, J=10.82 and 3.97 Hz, Fmoc CH$_2$), 7.30-7.81 (8H, aromatic CH); δ$_C$ (125 MHz, CDCl$_3$) 47.22/47.41 (Fmoc CH), 50.55/50.93 (FmocNCH$_2$), 54.60/55.28 (CHCl), 65.94/67.60 (Fmoc CH$_2$), 69.08/69.56 (FmocNCH), 75.00/75.35 (OCH$_2$CHOH), 76.23/76.86 (OCH$_2$CHOH), 81.27/81.84 (CHCHCl), 119.87/119.92/ 120.09/124.42/124.46/124.82/124.88/127.10/127.50/ 127.51/127.89/127.96/127.98/128.53 and 128.65 (aromatic CH), 141.24/141.36/141.44/143.44/143.57/143.83 and 143.84 (aromatic quaternary), 153.41/154.42 (Fmoc C=O).

(iii) Dess-Martin periodinane (383 mg, 0.90 mmol) was added to a stirred solution of alcohol (78) (174 mg, 0.45 mmol) in dichloromethane (4 mL) under an atmosphere of argon. The mixture was stirred for 19 hours then diluted with dichloromethane (20 mL) then washed with a mixture of saturated aqueous sodium bicarbonate and 0.25M sodium thiosulphate solution (1:1, 10 mL), saturated aqueous sodium bicarbonate (10 mL), brine (10 mL), then dried (Na$_2$SO$_4$), filtered and reduced in vacuo to obtain a white solid (310 mg). Flash chromatography over silica, eluting with ethyl acetate:heptane mixtures 20:80 to 40:60 gave ketone (79) (141 mg, 82%) as a white solid. TLC (R$_f$=0.35, EtOAc:heptane 1:1), analytical HPLC single main peak, R$_t$=15.04 min., HPLC-MS 384.1/386.1 [M+H]$^+$, 406.1/ 408.1 [M+Na]$^+$, 424.1/426.1 [M+H$_2$O+Na]$^+$, 789.1/791.2 [2M+Na]$^+$; [α]$_D^{23.5}$ -101.2° (c=2.03, CHCl$_3$); δH (500 z, CDCl$_3$) 3.49 (1H, brs, FmocNCH$_2$), 3.92 (0.5H, brs, FmocNCH$_2$), 4.09-4.13 (1H, m, OCH$_2$C=O), 4.13-4.49 (5.5H, m, 0.5×FmocNCH$_2$, 1×OCH$_2$C=O, FmocNCH, CHCHCl, Fmoc CH and 1×Fmoc CH$_2$), 4.50-4.61 (1H, m, 1×Fmoc CH$_2$), 4.88 (1H, brs, CHCHCl), 7.27-7.76 (8H, aromatic CH); δ$_C$ (125 MHz, CDCl$_3$) 47.07/47.16 (Fmoc CH), 51.33/51.50 (FmocNCH$_2$), 55.36/55.77 (CHCl), 60.94/61.26 (FmocNCH), 67.94/68.44 (Fmoc CH$_2$), 71.31 (OCH$_2$C=O), 80.38/81.22 (CHCHCl), 119.98/124.88/ 125.12/125.31/127.09/127.14 and 127.82 (aromatic CH), 141.32/143.42/143.70 and 144.15 (aromatic quaternary), 154.46 (Fmoc C=O), 206.85/206.96 (OCH$_2$C=O).

Solid Phase Chemistry

Fmoc-ketone building blocks (2c-8c, 56, 63, 71, 79) were utilised in a solid phase synthesis of example inhibitors (85-71) of general formulae Ic and Id. The methods used were directly analogous to those described in detail in WO02057270, utilising the 4-{[(Hydrazinocarbonyl)amino] methyl}cyclohexane carboxylic acid trifluoroacetate based linker, solid phase lanterns (ex Mimotopes), standard Fmoc chemistries and acidolytic cleavage followed by semi-preparative HPLC purification (see WO02057270 pg 124-127 for full generic details) through use of the appropriately derivatised 4-(4-alkylpiperazin-1-yl)benzoic acid or 4-(1-alkylpiperidin-4-yl)benzoic acid building block (general synthetic details for preparation are given in WO0158886). Each purified analogue was analysed giving the following characterisation data:

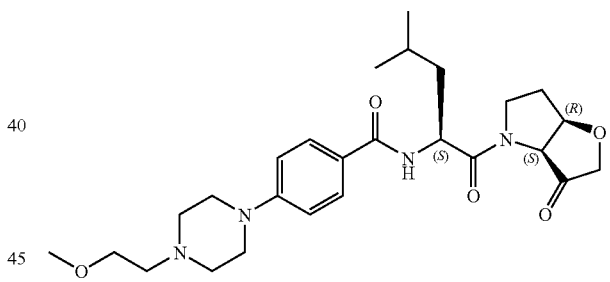

(85)

4-(4-(2-methoxyethyl)piperazin-1-yl)-N-((S)-4-methyl-1-oxo-1-((3aS,6aR)-3-oxo dihydro-2H-furo[3,2-b]pyrrol-4 (5H, 6H, 6aH)-yl)pentan-2-yl)benzamide (85) from (2c); HPLC-MS R$_t$=3.05 min, 487.2 [M+H]$^+$, 505.2 [M+H+18]$^+$, 995.3 [2M+Na]$^+$.

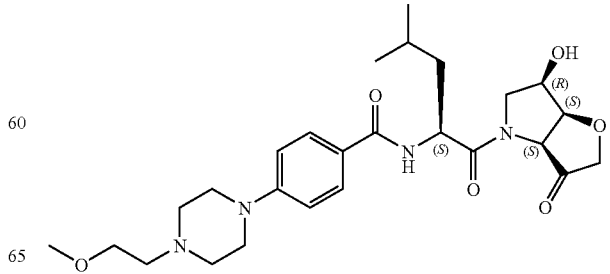

(86)

N-((S)-1-((3aS,6R,6aS)-6-hydroxy-3-oxodihydro-2H-furo[3,2-b]pyrrol-4(5H, 6H, 6aH)-yl)-4-methyl-1-oxopentan-2-yl)-4-(4-(2-methoxyethyl)piperazin-1-yl)benzamide (86) from (3c); HPLC-MS $R_t$=2.59 min, 503.3 [M+H]$^+$, 521.3 [M+H+18]$^+$, 1027.5 [2M+Na]$^+$.

(87)

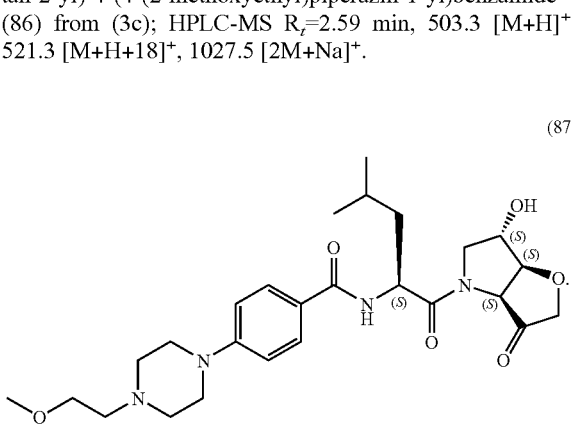

N-((S)-1-((3aS,6S,6aS)-6-hydroxy-3-oxodihydro-2H-furo[3,2-b]pyrrol-4(5H,6H,6aH)-yl)-4-methyl-1-oxopentan-2-yl)-4-(4-(2-methoxyethyl)piperazin-1-yl)benzamide (87) from (4c); HPLC-MS $R_t$=2.83 min, 503.3 [M+H]$^+$, 521.3 [M+H+18]$^+$, 1027.5 [2M+Na]$^+$.

(88)

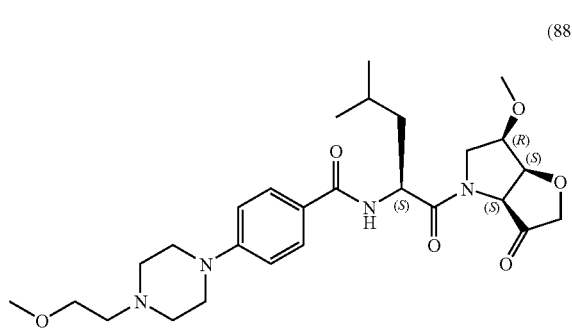

N-((S)-1-((3aS,6R,6aS)-6-methoxy-3-oxodihydro-2H-furo[3,2-b]pyrrol-4(5H, 6H, 6aH)-yl)-4-methyl-1-oxopentan-2-yl)-4-(4-(2-methoxyethyl)piperazin-1-yl)benzamide (88) from (5c); HPLC-MS $R_t$=3.09 min, 517.3 [M+H]$^+$, 535.3 [M+H+18]$^+$, 1055.5 [2M+Na]$^+$.

(89)

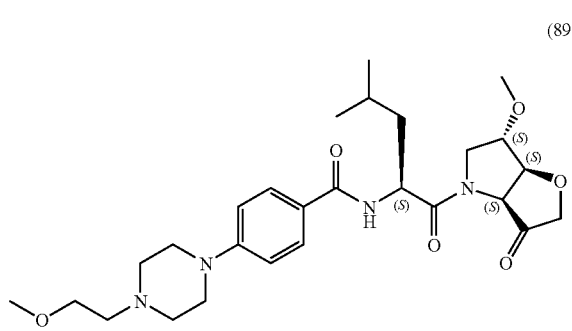

N-((S)-1-((3aS,6S,6aS)-6-methoxy-3-oxodihydro-2H-furo[3,2-b]pyrrol-4(5H, 6H, 6aH)-yl)-4-methyl-1-oxopentan-2-yl)-4-(4-(2-methoxyethyl)piperazin-1-yl)benzamide (89) from (6c); HPLC-MS $R_t$=3.16 min, 517.3 [M+H]$^+$, 535.3 [M+H+18]$^+$, 1055.5 [2M+Na]$^+$.

(90)

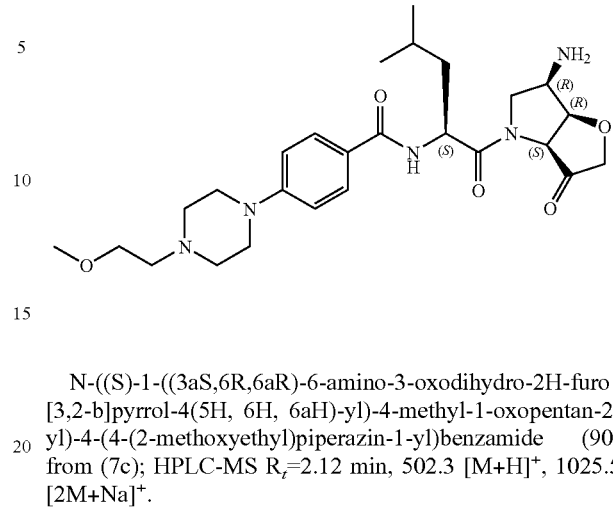

N-((S)-1-((3aS,6R,6aR)-6-amino-3-oxodihydro-2H-furo[3,2-b]pyrrol-4(5H, 6H, 6aH)-yl)-4-methyl-1-oxopentan-2-yl)-4-(4-(2-methoxyethyl)piperazin-1-yl)benzamide (90) from (7c); HPLC-MS $R_t$=2.12 min, 502.3 [M+H]$^+$, 1025.5 [2M+Na]$^+$.

(91)

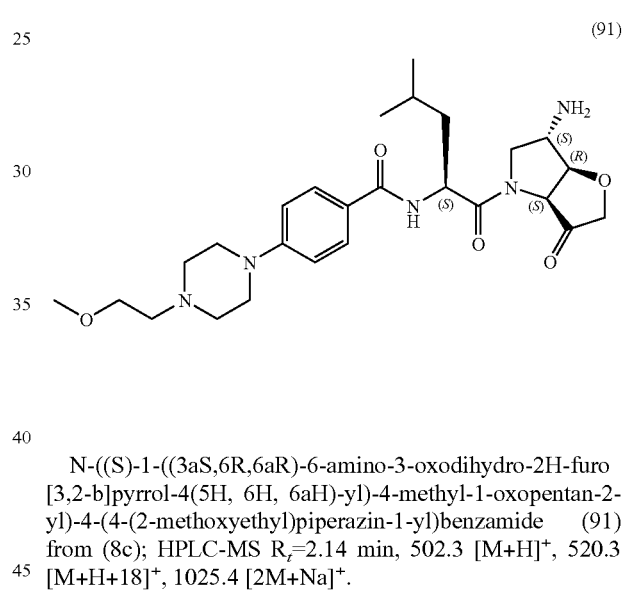

N-((S)-1-((3aS,6R,6aR)-6-amino-3-oxodihydro-2H-furo[3,2-b]pyrrol-4(5H, 6H, 6aH)-yl)-4-methyl-1-oxopentan-2-yl)-4-(4-(2-methoxyethyl)piperazin-1-yl)benzamide (91) from (8c); HPLC-MS $R_t$=2.14 min, 502.3 [M+H]$^+$, 520.3 [M+H+18]$^+$, 1025.4 [2M+Na]$^+$.

(71)

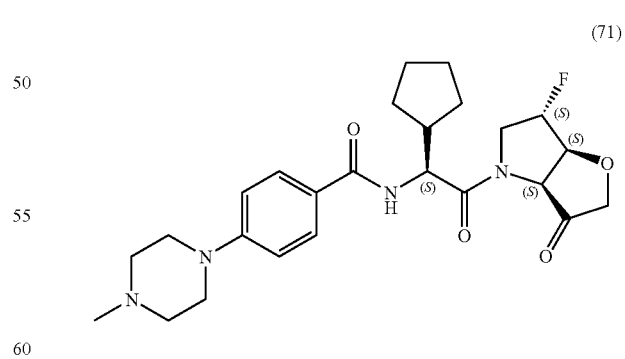

N-((S)-1-cyclopentyl-2-((3aS,6S,6aS)-6-fluoro-3-oxodihydro-2H-furo[3,2-b]pyrrol-4(5H,6H,6aH)-yl)-2-oxoethyl)-4-(4-methylpiperazin-1-yl)benzamide (92) from (63); HPLC-MS $R_t$=3.00 min, 473.1 [M+H]$^+$, 491.3 [M+H+18]$^+$.

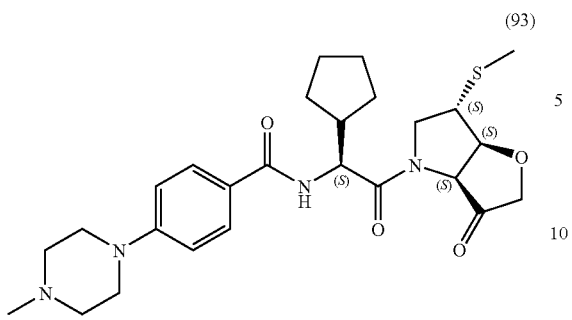

(93)

N-((S)-cyclopentyl-2-((3aS,6S,6aS)-6-methylthio-3-oxodihydro-2H-furo[3,2-b]pyrrol-4(5H,6H,6aH)-yl)-2-oxoethyl)-4-(4-methylpiperazin-1-yl)benzamide (93) from (56); HPLC-MS $R_t$=3.50 min, 501.1 [M+H]$^+$, 519.2 [M+H+18]$^+$.

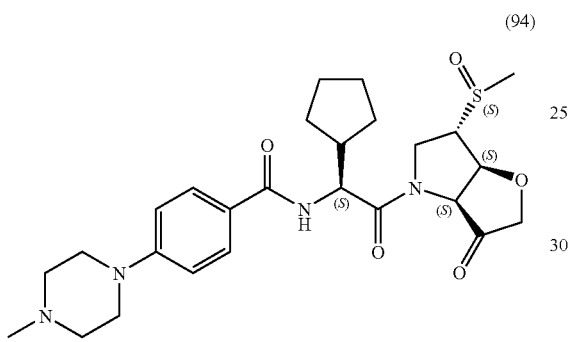

(94)

N-((S)-1-cyclopentyl-2-((3aS,6S,6aS)-6-methylsulfinyl-3-oxodihydro-2H-furo[3,2-b]pyrrol-4(5H,6H,6aH)-yl)-2-oxoethyl)-4-(4-methylpiperazin-1-yl)benzamide (94) from (56) and oxidation whilst on solid phase using Dess Martin periodinane in DCM overnight; HPLC-MS $R_t$=2.23 min, 517.2 [M+H]$^+$, 535.2 [M+H+18]$^+$.

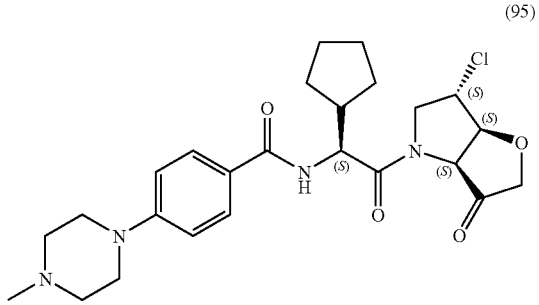

(95)

N-((S)-2-((3aS,6S,6aS)-6-chloro-3-oxodihydro-2H-furo[3,2-b]pyrrol-4(5H,6H,6aH)-yl)-1-cyclopentyl-2-oxoethyl)-4-(4-methylpiperazin-1-yl)benzamide (95) from (71); HPLC-MS $R_t$=3.80 min, 489.2/491.2 [M+H]$^+$, 507.2/509.2 [M+H+18]$^+$.

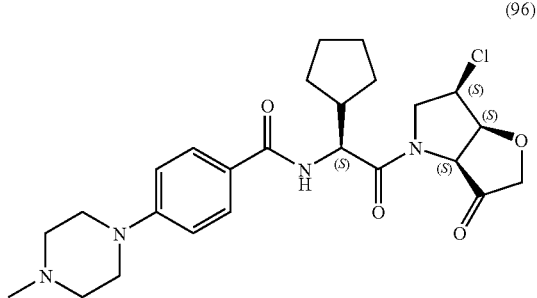

(96)

N-((S)-2-((3aS,6R,6aS)-6-chloro-3-oxodihydro-2H-furo[3,2-b]pyrrol-4(5H,6H,6aH-yl)-1-cyclopentyl-2-oxoethyl)-4-(4-methylpiperazin-1-yl)benzamide (96) from (79); HPLC-MS $R_t$=3.77 min, 489.2/491.2 [M+H]$^+$, 507.2/509.2 [M+H+18]$^+$.

Solution Phase Chemistry

Alternatively, the free base or hydrochloride salt of the bicyclic alcohol building block (e.g. compound 2 g or compound (69)) are utilised in a solution phase synthesis of compounds of general formula I as follows;

4-(4-methylpiperazin-1-yl)-N-(1-((3aS6aR)-3-oxo-hexahydro-2H-furo[3,2-b]pyrrole-4-carbonyl)cyclopentyl)benzamide (97)

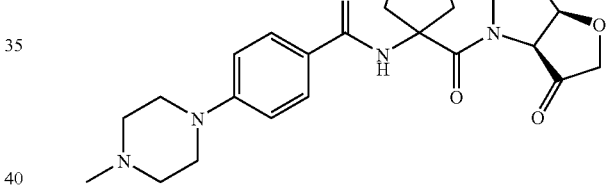

HPLC-MS 314.2, 441.3 [M+H]$^+$, 903.4 [2M+Na]$^+$, 921.4 [2M+Na+18]$^+$.

(i) Preparation of benzyl 1-((3R,3aR,6aR)-3-hydroxyhexahydro-2H-furo[3,2-b]pyrrole-4-carbonyl)cyclopentylcarbamate. Hydrochloride salt (2 g) (100 mg, 0.6 mmol) was dissolved in anhydrous DMF (1 mL) with stirring and NMM (1 eq. 61.7 mg, 67 μL) was added. Benzyl 1-(fluorocarbonyl)cyclopentylcarbamate (1 eq. 45% reagent, 356 mg, prepared following general methods detailed in Babu, V. V. S. et al, Ind. J. Chem., 39B(5), 384-6, 2000) was added in anhydrous DMF (2 mL) and the reaction stirred at ambient temperature for 5 h. The mixture was reduced in vacuo and partitioned between DCM (20 mL) and saturated NaHCO$_3$ (20 mL). The organic phase was washed with pH 3HCl (20 mL), brine (20 mL), dried (Na$_2$SO$_4$), filtered and reduced in vacuo to give a brown oil. Flash chromatography over silica, eluting with ethyl acetate:heptane mixtures 5:95 to 30:70 gave product alcohol (168 mg, 74%) as a tan solid. TLC ($R_f$=0.18, EtOAc:heptane 4:1), analytical HPLC single main peak, $R_t$=10.36 min., HPLC-MS 375.2 [M+H]$^+$, 771.3 [2M+Na]$^+$; [α]$_D^{22}$+2.6° (c=16.3, CHCl$_3$); δ$_C$ (125 MHz, CDCl$_3$, 300K) 23.89/24.10 (CCH$_2$CH$_2$), 32.49 (NCH$_2$CH$_2$), 36.70/36.93 (CCH$_2$CH$_2$), 46.02 (NCH$_2$CH$_2$), 66.74 (CCH$_2$CH$_2$), 66.95 (CH$_2$Ph), 72.53 (C$_\alpha$), 74.03 (CHOHCH$_2$), 77.20 (CHOHCH$_2$), 79.58 (C$_\beta$), 128.10/128.31/128.40/128.48/128.60 (CH aromatic), 136.14 (quarternary CH aromatic), 154.38 (OCONH), 171.98 (CCON).

(ii) Preparation of N-(1-((3R,3aR,6aR)-3-hydroxyhexahydro-2H-furo[3,2-b]pyrrole-4-carbonyl)cyclopentyl)-4-(4-methylpiperazin-1-yl)benzamide. Methanol (5 mL) was added dropwise to a mixture of 10% palladium on charcoal (20 mg) and benzyl 1-((3R,3aR,6aR)-3-hydroxyhexahydro-2H-furo[3,2-b]pyrrole-4-carbonyl)cyclopentyl carbamate (115 mg, 0.31 mmol) under an atmosphere of argon. The argon was replaced by hydrogen then the suspension was stirred for 16 hours before filtering the mixture through celite in vacuo. The filter cake was washed with ethanol (10 mL) then the solvents removed in vacuo from the filtrate. The residue was azeotroped with toluene (2×3 mL) to obtain (1-aminocyclopentyl)((3R,3aR,6aR)-3-hydroxydihydro-2H-furo[3,2-b]pyrrol-4(5H,6H,6aH)-yl)methanone which was used without further purification.

4-(4-methylpiperazin-1-yl)benzoic acid (1.1 eq., 75 mg, 0.34 mmol), HBTU (1.05 eq., 123 mg, 0.32 mmol), HOBT (1.05 eq., 50 mg, 0.32 mmol) and NMM (2.1 eq., 71 µL, 0.65 mmol) were suspended in anhydrous DMF (2 mL) and sonicated for 5 mins. The mixture was then added to (1-aminocyclopentyl)((3R,3aR,6aR)-3-hydroxydihydro-2H-furo[3,2-b]pyrrol-4(5H,6H,6aR)-yl)methanone (89 mg, ~0.31 mmol) and stirred at 60° C. overnight. The mixture was reduced in vacuo and partitioned between DCM (15 mL) and saturated NaHCO$_3$ (20 mL). The organic phase was washed with brine (15 mL), dried (Na$_2$SO$_4$), filtered and reduced in vacuo to give an orange gum. Flash chromatography over silica, eluting with methanol:CHCl$_3$ mixtures 0:100 to 10:90 gave product alcohol (25.0 mg, 18%) as an oily orange solid. TLC (R$_f$=0.30, MeOH:CHCl$_3$ 15:85), analytical HPLC single main peak, R$_t$=5.98 min., HPLC-MS 222.2 [M+2H]$^{2+}$, 314.2, 443.3 [M+H]$^+$, 465.2 [M+Na]$^+$, 907.4 [2M+Na]$^+$.

(iii) Oxidation to Compound 97. N-(1-((3R,3aR,6aR)-3-hydroxyhexahydro-2H-furo[3,2-b]pyrrole-4-carbonyl)cyclopentyl)-4-(4-methylpiperazin-1-yl)benzamide (22.5 mg, 0.051 mmol) was dissolved in anhydrous dichloromethane (2 mL) with stirring under argon. Dess-Martin periodinane (43 mg, 0.1 mmol) was added and the mixture stirred at ambient temperature overnight. The mixture was diluted with DCM (5 mL) and washed with 1N NaOH (5 mL), brine (10 mL each) and dried (Na$_2$SO$_4$). The organic layer was filtered and reduced in vacuo to leave a tan solid (15.2 mg). Analysis by HPLC-MS showed desired ketone; HPLC-MS 314.2, 441.3 [M+H]$^+$, 903.4 [2M+Na]$^+$, 921.4 [2M+Na+18]$^+$.

4-(4-methylpiperazin-1-yl)-N-(1-((3aS,6aR)-3-oxo-hexahydro-2H-furo[3,2-b]pyrrole-4-carbonyl)cyclohexyl)benzamide (98)

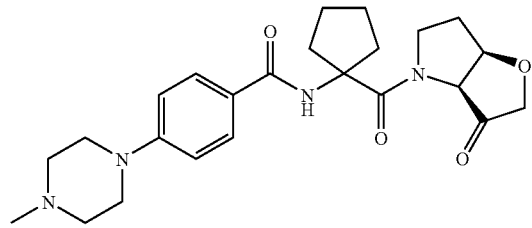

HPLC-MS R$_t$=2.28 min, 328.2, 457.3 [M+H]$^+$, 935.4 [2M+Na]$^+$.

(i) Preparation of benzyl 1-((3R,3aR,6aR)-3-hydroxyhexahydro-2H-furo[3,2-b]pyrrole-4-carbonyl)cyclohexylcarbamate. Hydrochloride salt (2 g) (100 mg, 0.6 mmol) was dissolved in anhydrous DMF (1 mL) with stirring and NMM (1 eq. 61.7 mg, 67 µL) was added. Benzyl 1-(fluorocarbonyl)cyclohexylcarbamate (1 eq. 90% reagent, 187 mg, prepared following general methods detailed in Babu, V. V. S. et al, Ind. J. Chem., 39B(5), 384-6, 2000) was added in anhydrous DMF (2 mL) and the reaction stirred at ambient temperature for 5 h. The mixture was reduced in vacuo and partitioned between DCM (20 mL) and saturated NaHCO$_3$ (20 mL). The organic phase was washed with pH 3 HCl (20mL), brine (20 mL), dried (Na$_2$SO$_4$), filtered and reduced in vacuo to give a brown oil. Flash chromatography over silica, eluting with ethyl acetate:heptane mixtures 5:95 to 20:80 gave product alcohol as 2 fractions (35 mg, 15% and 60 mg, 26%) as white solids. TLC (R$_f$=0.22, EtOAc:heptane 4:1), analytical HPLC single main peak, R$_t$=11.84 min., HPLC-MS 389.2 [M+H]$^+$, 799.4 [2M+Na]$^+$; [α]$_D^{22}$=−7.3° (c=5.5, CHCl$_3$); δ$_C$ (125 MHz, CDCl$_3$, 300K) 21.05/21.14/21.23/21.42/21.52 (CCH$_2$CH$_2$CH$_2$), 24.95/25.25 (CCH$_2$CH$_2$CH$_2$), 31.26 (NCH$_2$CH$_2$ or CCH$_2$CH$_2$CH$_2$), 31.86/32.24/32.54 (NCH$_2$CH$_2$ or CCH$_2$CH$_2$CH$_2$), 44.79/45.82 (NCH$_2$CH$_2$), 58.82/59.06 (CCH$_2$CH$_2$CH$_2$), 66.96 (CH$_2$Ph), 73.07 (C$_α$), 73.75/73.96 (CHOHCH$_2$), 77.25/77.47 (CHOHCH$_2$), 79.21 (C$_β$), 128.13/128.40/128.44/128.56/128.62 (CH aromatic), 136.12 (quarternary CH aromatic), 153.99 (OCONH), 172.88 (CCON).

(ii) Preparation of N-(1-((3R,3aR,6aR)-3-hydroxyhexahydro-2H-furo[3,2-b]pyrrole-4-carbonyl)cyclohexyl)-4-(4-methylpiperazin-1-yl)benzamide. Methanol (3 mL) was added dropwise to a mixture of 10% palladium on charcoal (17 mg) and benzyl 1-((3R,3aR,6aR)-3-hydroxyhexahydro-2H-furo[3,2-b]pyrrole-4-carbonyl)cyclohexyl carbamate (77 mg, 0.2 mmol) under an atmosphere of argon. The argon was replaced by hydrogen then the suspension was stirred for 90 mins before filtering the mixture through celite in vacuo. The filter cake was washed with ethanol (10 mL) then the solvents removed in vacuo from the filtrate. The residue was azeotroped with toluene (2×3 mL) to obtain (1-aminocyclohexyl)((3R,3aR,6aR)-3-hydroxydihydro-2H-furo[3,2-b]pyrrol-4(5H,6H,6aH)-yl)methanone which was used without further purification.

4-(4-methylpiperazin-1-yl)benzoic acid (1.1 eq., 49 mg, 0.22 mmol), HBTU (1.05 eq., 80 mg, 0.21 mmol), HOBT (1.05 eq., 33 mg, 0.21 mmol) and NMM (2.1 eq., 47 µL, 0.42 mmol) were suspended in anhydrous DMF (2 mL) and sonicated for 5 mins. The mixture was then added to (1-aminocyclohexyl)((3R,3aR,6aR)-3-hydroxydihydro-2H-furo[3,2-b]pyrrol-4(5H,6H,6aH)-yl)methanone (51 mg, ~0.2 mmol) and stirred at 60° C. overnight. The mixture was reduced in vacuo and partitioned between DCM (15 mL) and saturated NaHCO$_3$ (20 mL). The organic phase was washed with brine (15 mL), dried (Na$_2$SO$_4$), filtered and reduced in vacuo to give an orange gum. Flash chromatography over silica, eluting with methanol:CHCl$_3$ mixtures 0:100 to 8:92 gave product alcohol (12.0 mg, 13%) as an orange film. TLC (R$_f$=0.23, MeOH:CHCl$_3$ 10:90), analytical HPLC single main peak, R$_t$=7.39 min., HPLC-MS 229.2 [M+2H]$^{2+}$, 328.2, 457.3 [M+H]$^+$, 935.5 [2M+Na]$^+$.

(iii) Oxidation to Compound 98. N-(1-((3R,3aR,6aR)-3-hydroxyhexahydro-2H-furo[3,2-b]pyrrole-4-carbonyl)cyclohexyl)-4-(4-methylpiperazin-1-yl)benzamide (11 mg, 0.024 mmol) was dissolved in anhydrous dichloromethane (2 mL) with stirring under argon. Dess-Martin periodinane (21 mg, 0.048 mmol) was added and the mixture stirred at ambient temperature overnight. The mixture was diluted with DCM (5 mL) and washed with 1N NaOH (5 mL), brine (10 mL each) and dried (Na$_2$SO$_4$). The organic layer was filtered and reduced in vacuo to leave a white solid (8.8 mg). Analysis by HPLC-MS showed desired ketone; HPLC-MS 328.2, 455.2 [M+H]+, 931.4 [2M+Na]+.
Preparation of N-((S)-2-((3aS. 6S,6aS-6-Chloro-3-oxodihydro-2H-furo[3,2-b]pyrrol-4(5H, 6H,6aH)-yl)-1-cyclopent-1-2-oxoethyl)-4-(4-methylpiperazin-1-yl)benzamide (95). Following Scheme 19.

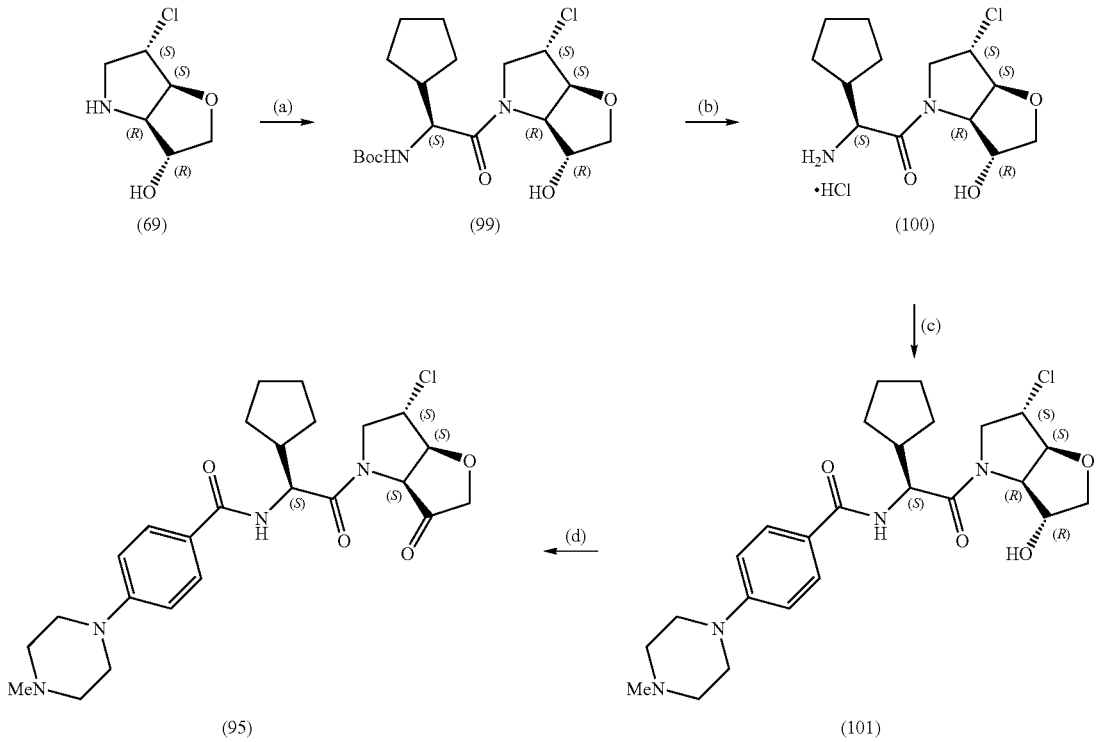

(a) Boc-Cpg-F, DMF; or Boc-Cpg-OH, HBTU, HOBt, NMM, DMF; (b) HCl, 1,4-dioxane; (c) 4-(4-Methylpiperazin-1-yl)benzoic acid, HBTU, HOBt, NMM, DMF; (d) Dess-Martin periodinane, DCM.

(i) tert-Butyl (S)-2-((3R,3aR,6S,6aS)-6-chloro-3-hydroxydihydro-2H-furo[3,2-b]pyrrol-4(5H, 6H, 6aH)-yl)-1-cyclopentyl-2-oxoethylcarbamate (99). A solution of (S)-tert-butyl 1-cyclopentyl-2-fluoro-2-oxoethylcarbamate (4.77 g, 19.47 mmol) in dimethylformamide (15 mL) was added under argon to (3R,3aR,6S,6aS)-6-chlorohexahydro-2H-furo[3,2-b]pyrrol-3-ol (69) (assumed to be 18.54 mmol). The mixture was stirred for 2 hours then the solvents removed in vacuo. Flash chromatography over silica, eluting with ethyl acetate:heptane mixtures 10:90 to 50:50 gave alcohol (99) as a white solid (3.56 g, 49%). TLC (R$_f$=0.45, EtOAc:heptane 2:1), HPLC-MS 333.1/335.1 [M+2H-$^t$Bu]+, 389.2/391.2 [M+H]+, 411.2/413.2 [M+Na]+, 799.3/801.3 [2M+Na]+; [α]$_D^{20.5}$ −46.7° (c=2.03, CHCl$_3$); δ$_H$ (500 MHz, CDCl$_3$) mixture of rotamers major:minor 7:3; 1.10-1.82 (8H, m, CH$_2$CH$_2$CH$_2$CH$_2$), 1.40 (9H, s, OC(CH$_3$)$_3$), 2.14-2.25 (1H, m, BocNHCHCH), 3.56-3.63 (1.4H, m, 1×NCH$_2$CHCl major and 1×OCH$_2$CHOH major), 3.78 (0.3H, dd, J=12.14 and 3.82 Hz, 1×NCH$_2$CHCl minor), 3.83-3.90 (0.6H, m, 2×OCH$_2$CHOH minor), 4.10-4.15 (1.4H, m, 1×OCH$_2$CHOH major and 1×NCH$_2$CHCl major), 4.22 (0.3H, t, J=8.96 Hz, BocNHCH minor), 4.24-4.29 (1.4H, m, OCH$_2$CHOH major and NCH$_2$CHCl major), 4.29-4.34 (0.3H, m, NCH$_2$CHCl minor), 4.33 (0.3H, d, J=4.41 Hz, 1×NCH$_2$CHCl minor), 4.40 (0.7H, t, J=9.88 Hz, BocNHCH major), 4.40-4.42 (0.3H, brs, OCH$_2$CHOH minor), 4.52 (0.7H, dd, J=5.34 and 1.01 Hz, OCH$_2$CHOHCH major), 4.60 (0.3H, d, J=4.40 Hz, OCH$_2$CHOHCH minor), 4.72 (1H, d, J=5.23 Hz, OCH-CHCl), 5.30 (0.3H, brd, J=5.08 Hz, NH minor), 5.34 (0.7H, brd, J=10.06 Hz, NH major); δ$_C$ (125 MHz, CDCl$_3$) 24.74/24.95/25.38/28.41/28.88/29.16 and 29.32 (CH$_2$CH$_2$CH$_2$CH$_2$), 28.24/28.29 (OC(CH$_3$)$_3$), 42.57/43.67 (BocNHCHCH), 52.16/53.92 (NCH$_2$CHCl), 55.44/55.68 (BocNHCH), 57.02/58.30 (CHCl), 68.64/69.82 (OCH$_2$CHOHCH), 73.69/75.20 (OCH$_2$CHOH), 74.97/77.25 (CHOH), 80.81 (OC(CH$_3$)$_3$), 85.88/88.30 (OCH-CHCl), 155.57/156.49 (Boc C=O), 171.98/172.44 (CH$_2$NC=O).

(ii) Preparation of (S)-2-Amino-1-((3R,3aR,6S,6aS)-6-chloro-3-hydroxydihydro-2H-furo[3,2-b]pyrrol-4(5H, 6H, 6aH)-yl)-2-cyclopentylethanone hydrochloride (100). A solution of HCl in 1,4-dioxane (4.0M, 45 mL, 180 mmol) was added to Boc-alcohol (99) (3.54 g, 9.11 mmol). The mixture was stirred for 2 hours 15 minutes then the solvents were removed in vacuo and the residue azeotroped with toluene (3×25 mL) to leave hydrochloride salt (100) as a white solid which was used without further purification (assumed quantitative). TLC (R$_f$=0.0, EtOAc:heptane 3:1), HPLC-MS 289.1/291.1 [M+H]+, 599.2 [2M+Na]+.

(iii) Preparation of N-((S)-2-((3R,3aR,6S,6aS)-6-Chloro-3-hydroxydihydro-2H-furo[3,2-b]pyrrol-4(5H, 6H, 6aH)-yl)-1-cyclopentyl-2-oxoethyl)-4-(4-methyl piperazin-1-yl)benzamide (101). 4-Methylmorpholine (2.09 mL, 19.14 mmol) was added to a suspension of 2-(1H-benzotriazole-1-yl)-1,1,3,3-tetramethyluronium hexafluorophosphate (HBTU, 3.63 g, 9.57 mmol), 1-hydroxybenzotriazole monohydrate (1.46 g, 9.57 mmol) and 4-(4-methylpiperazin-1-yl)benzoic acid (2.21 g, 10.02 mmol, ex Maybridge) in dimethylformamide (15 mL). The suspension was shaken and sonicated for 5 minutes before adding to a solution of hydrochloride salt (100) (prepared as above, assume 9.11 mmol) in dimethylformamide (10 mL). The activated acid reaction flask was rinsed into the bulk reaction mixture with an additional aliquot of dimethylformamide (10 mL). The reaction was stirred for 19 hours then the majority of solvents removed in vacuo. The residue was dissolved in dichloromethane (200 mL) and washed with saturated sodium hydrogen carbonate solution (200 mL). The aqueous phase was extracted with dichloromethane (1×100 mL then 1×50 mL) then the combined organic layers washed with brine (100 mL), then dried ($Na_2SO_4$), filtered and reduced in vacuo. Flash chromatography over silica, eluting with methanol:dichloromethane mixtures 1:99 to 7:93 gave alcohol (101) as an orange solid (3.57 g, 80%). TLC ($R_f$=0.25-0.30 double spot, MeOH:$CH_2Cl_2$ 4:96), analytical HPLC broad main peak, $R_t$=9.60-10.96 min., HPLC-MS 491.2/493.2 [M+H]$^+$, 1003.4 [2M+Na]$^+$; $[\alpha]_D^{26.0}$ −36.9° (c=2.04, CHCl$_3$); $\delta_H$ (500 MHz, CDCl$_3$) mixture of rotamers major:minor 4:1; 1.20-1.85 (8H, m, CH$_2$CH$_2$CH$_2$CH$_2$), 2.29-2.42 (1H, m, NHCHCH), 2.33 (3H, s, NCH$_3$), 2.54 (4H, brt, J=5.66 Hz, CH$_2$CH$_2$NCH$_3$), 3.27-3.33 (4H, m, CH$_2$CH$_2$NCH$_3$), 3.56-3.63 (1.6H, m, 1×OCH$_2$CHOH major and 1×NCH$_2$CHCl major), 3.82-3.91 (0.4H, m, 1×OCH$_2$CHOH minor and 1×NCH$_2$CHCl minor), 4.08-4.13 (1H, m, 1×OCH$_2$CHOH major and 1×OCH$_2$CHOH minor), 4.15 (0.8H, dd, J=13.63 and 1.10 Hz, 1×NCH$_2$CHCl major), 4.27 (0.8H, d, J=3.73 Hz, CHCl major), 4.31-4.35 (1H, m, OCH$_2$CHOH major and CHCl minor), 4.38 (0.2H, d, J=12.1 Hz, 1×NCH$_2$CHCl minor), 4.46-4.48 (0.2H, m, OCH$_2$CHOH minor), 4.59-4.63 (1H, m, OCH$_2$CHOHCH), 4.76 (0.2H, d, J=5.2 Hz, OCHCHCl minor), 4.73 (0.8H, d, J=5.22 Hz, OCHCHCl major), 4.80 (0.2H, t, J=9.8 Hz, NHCH minor), 4.99 (0.8H, t, J=9.79 Hz, NHCH major), 6.76 (0.2H, d, J=9.7 Hz, NH minor), 6.81 (0.8H, d, J=9.71 Hz, NH major), 6.83-6.88 (2H, m, aromatic CH), 7.67-7.71 (2H, m, aromatic CH); $\delta_C$ (125 MHz, CDCl$_3$) 24.71/25.37/29.00 and 29.32 (CH$_2$CH$_2$CH$_2$CH$_2$), 42.96/43.94 (NHCHCH), 46.11 (NCH$_3$), 47.56/47.72 (NCH$_2$CH$_2$NCH$_3$), 52.22 (NCH$_2$CHCl), 54.34/54.76 (NCH$_2$CH$_2$NCH$_3$), 54.46/54.71 (NHCH), 57.02/58.22 (CHCl), 68.67/69.99 (OCH$_2$CHOHCH), 73.79 (OCH$_2$CHOH), 74.83/78.38 (CHOH), 85.87/88.29 (OCHCHCl), 114.01/114.13/128.57 and 128.78 (aromatic CH), 122.29/123.34 (aromatic quaternary), 153.43/153.72 (aromatic quaternary), 166.64/167.36 (NHC=O), 171.72/172.25 (CH$_2$NC=O).

(iv) N-((S)-2-((3aS,6S,6aS)-6-Chloro-3-oxodihydro-2H-furo[3,2-b]pyrrol-4(5H, 6H, 6aH)-yl)-1-cyclopentyl-2-oxoethyl)-4-(4-methylpiperazin-1-yl)benzamide (95). Dess-Martin periodinane (6.00 g, 14.15 mmol) was added to a stirred solution of alcohol (101) (3.47 g, 7.07 mmol) in dichloromethane (80 mL) under an atmosphere of argon. The mixture was stirred for 21.5 hours then diluted with dichloromethane (550 mL). The organic phase was washed with aqueous sodium hydroxide solution (1M, 210 mL) then the aqueous extracted with dichloromethane (210 mL). The organic layer was washed with aqueous sodium hydroxide solution (1M, 210 mL) then brine (210 mL), then dried (Na$_2$SO$_4$), filtered and reduced in vacuo to leave N-((S)-2-((3aS,6S,6aS)-6-chloro-3-oxodihydro-2H-furo[3,2-b]pyrrol-4(5H, 6H, 6aH)-yl)-1-cyclopentyl-2-oxoethyl)-4-(4-methypiperazin-1-yl)benzamide as a pale orange solid (2.62 g, 76%). Analytical HPLC main broad peak, $R_t$=9.50-11.30 min., HPLC-MS 3.80 mins 489.1/491.2 [M+H]$^+$, 507.2/509.2 [M+H$_2$O+H]$^+$, $[\alpha]_D^{24.0}$ −91.0° (c=2.58, CHCl$_3$); $\delta_H$ (500 MHz, CDCl$_3$) mixture of rotamers major:minor 4:1; 1.20-1.90 (8H, m, CH$_2$CH$_2$CH$_2$CH$_2$), 2.27-2.39 (1H, m, NHCHCH), 2.32 (3H, brs, NCH$_3$), 2.53 (4H, brt, J=4.96 Hz, CH$_2$NCH$_3$), 3.26-3.31 (4H, m, CH$_2$CH$_2$NCH$_3$), 3.55-3.78 (0.2H, m, 1×NCH$_2$CHCl minor), 3.96 (0.8H, dd, J=12.37 and 3.82 Hz, 1×NCH$_2$CHCl major), 4.01 (0.8H, d, J=17.07 Hz, 1×OCH$_2$C=O major), 4.04 (0.2H, d, J=17 Hz, 1×OCH$_2$C=O minor), 4.13 (0.8H, d, J=17.14 Hz, 1×OCH$_2$C=O major), 4.20 (0.2H, d, J=17 Hz, 1×OCH$_2$C=O minor), 4.25-4.32 (0.4H, m, CHCl minor and 1×NCH$_2$CHCl minor), 4.39 (0.8H, d, J=2.71 Hz, CHCl major), 4.51 (0.8H, d, J=12.39 Hz, 1×NCH$_2$CHCl major), 4.65-4.72 (0.2H, m, NCHC=O minor), 4.80-4.89 (1.6H, m, OCHCHCl major and NHCH major), 4.93 (0.8H, d, J=4.96 Hz, NCHC=O major), 4.97-5.01 (0.2H, m, OCHCHCl minor), 5.38 (0.2H, m, NHCH minor), 6.69-6.92 (3H, m, NH and 2× aromatic CH), 7.63-7.73 (2H, m, aromatic CH); $\delta_C$ (125 MHz, CDCl$_3$) 24.88/25.28/25.38/28.26/28.99 and 29.36 (CH$_2$CH$_2$CH$_2$CH$_2$), 43.31/43.84 and 43.87 (NHCHCH), 46.10 (NCH$_3$), 47.47/47.69 and 47.81 (NCH$_2$CH$_2$NCH$_3$), 53.64 (NCH$_2$CHCl), 54.26 (NHCH), 54.75 (NCH$_2$CH$_2$NCH$_3$), 58.31 (CHCl), 60.28/60.31 (OCH$_2$C(=O)CH), 68.44 (OCH$_2$C(=O)CH hydrate), 70.94 (OCH$_2$C=O), 77.48 (OCH$_2$C=O hydrate), 85.63/87.18 and 89.64 (OCHCHCl), 102.08 (OCH$_2$C=O hydrate), 113.95/114.13/114.17/128.56/128.60 and 128.87 (aromatic CH), 122.05/123.34 (aromatic quaternary), 153.73/153.43 (aromatic quaternary), 166.68/167.93 (NHC=O), 172.16/172.41 (CH$_2$NC=O), 206.08/206.46 (ketone C=O).

Formation of EXAMPLE Hydrochloride Salts

EXAMPLE ketone (free base) (1 mmol) was dissolved in acetonitrile (16.7 mL) and standardised 0.1N HCl (1.5 eq, 15.0 mL) was added. The mixture was frozen and lyophilised to leave the EXAMPLE hydrochloride salt as a solid.

Example A

Assays for Cysteine Protease Activity

The compounds of this invention may be tested in one of a number of literature based biochemical assays that are designed to elucidate the characteristics of compound inhibition. The data from these types of assays enables compound potency and the rates of reaction to be measured and quantified. This information, either alone or in combination with other information, would allow the amount of compound required to produce a given pharmacological effect to be determined.

In vitro Cathepsin K Inhibition Measurements

Stock solutions of substrate or inhibitor were made up to 10 mM in 100% dimethylsulfoxide (DMSO) (Rathburns, Glasgow, U.K.) and diluted as appropriately required. In all cases the DMSO concentration in the assays was maintained at less than 1% (vol./vol.). The equilibrium inhibition constants ($K_i^{ss}$) for each compound were measured under steady-state conditions monitoring enzyme activity as a function of inhibitor concentration. The values were calculated on the assumption of pure competitive behaviour (Cornish-Bowden, A. *Fundamentals of enzyme kinetics* Portland Press; 1995, 93-128). Human recombinant cathepsin K (0.25 nM final; B. Turk, Josef, Stefan Institute, Ljubljana, Slovenia), was routinely assayed in 100 mM sodium acetate; pH 5.5 containing 1 mM EDTA, 10 mM L-cysteine and 1.8 µM Z-Leu-Arg-AMC ([S]=$K_M$).

Measurement of the Apparent Macroscopic Binding (Michaelis) Constants ($K_M^{app}$) for Substrates The apparent macroscopic binding constant ($K_M^{app}$) for each substrate was calculated, from the dependence of enzyme activity as a function of substrate concentration. The observed rates were plotted on the ordinate against the related substrate concentration on the abscissa and the data fitted by direct regression analysis (Prism v 3.02; GraphPad, San Diego, USA) using Equation 1 (Cornish-Bowden, A. *Fundamentals of enzyme kinetics* Portland Press; 1995, 93-128).

$$v_i = \frac{V_{max}^{app} \cdot [S_o]}{[S_o] + K_M^{app}} \tag{1}$$

In Equation 1 '$v_i$' is the observed initial rate, '$V_{max}^{app}$' is the observed maximum activity at saturating substrate concentration, '$K_M^{app}$' is the apparent macroscopic binding (Michaelis) constant for the substrate, '[$S_o$]' is the initial substrate concentration.

Measurement of the Inhibition Constants

The apparent inhibition constant ($K_i$) for each compound was determined on the basis that inhibition was reversible and occurred by a pure-competitive mechanism. The $K_i$ values were calculated, from the dependence of enzyme activity as a function of inhibitor concentration, by direct regression analysis (Prism v 3.02) using Equation 2 (Cornish-Bowden, A., 1995).

$$v_i = \frac{V_{max}^{app} \cdot [S]}{[S] + \{K_M^{app} \cdot ([I]/K_i)\}} \tag{2}$$

In Equation 2 '$v_i$' is the observed residual activity, '$V_{max}^{app}$' is the observed maximum activity (i.e. in the absence of inhibitor), '$K_M^{app}$' is the apparent macroscopic binding (Michaelis) constant for the substrate, '[S]' is the initial substrate concentration, '$K_i$' is the apparent dissociation constant and '[I]' is the inhibitor concentration.

In situations where the apparent dissociation constant ($K_i^{app}$) approached the enzyme concentrations, the $K_i^{app}$ values were calculated using a quadratic solution in the form described by Equation 3 (Morrison, J. F. *Trends Biochem. Sci.*, 7, 102-105, 1982; Morrison, J. F. *Biochim. Biophys. Acta.*, 185, 269-286, 1969; Stone, S. R. and Hofsteenge, *J. Biochemistry*, 25, 4622-4628, 1986).

$$v_i = \frac{F\left\{ E_o - I_o - K_i^{app} + \sqrt{(E_o - I_o - K_i^{app})^2 + 4 \cdot K_i^{app} \cdot E_o} \right\}}{2} \tag{3}$$

$$K_i^{app} = K_i(1 + [S_o]/K_M^{app}) \tag{4}$$

In Equation 3 '$v_i$' is the observed residual activity, 'F' is the difference between the maximum activity (i.e. in the absence of inhibitor) and minimum enzyme activity, '$E_o$' is the total enzyme concentration, '$K_i^{app}$' is the apparent dissociation constant and '$I_o$' is the inhibitor concentration. Curves were fitted by non-linear regression analysis (Prism) using a fixed value for the enzyme concentration. Equation 4 was used to account for the substrate kinetics, where '$K_i$' is the inhibition constant, '[$S_o$]' is the initial substrate concentration and '$K_M^{app}$' is the apparent macroscopic binding (Michaelis) constant for the substrate (Morrison, 1982).

The Second-order Rate of Reaction of Inhibitor with Enzyme

Where applicable, the concentration dependence of the observed rate of reaction ($k_{obs}$) of each compound with enzyme was analysed by determining the rate of enzyme inactivation under pseudo-first order conditions in the presence of substrate (Morrison, J. F., *TIBS*, 102-105, 1982; Tian, W. X. and Tsou, C. L., *Biochemistry*, 21, 1028-1032, 1982; Morrison, J. F. and Walsh, C. T., from Meister (Ed.), *Advances in Enzymol.*, 61, 201-301, 1988; Tsou, C. L., from Meister (Ed.), *Advances in Enzymol.*, 61, 381-436, 1988). Assays were carried out by addition of various concentrations of inhibitor to assay buffer containing substrate. Assays were initiated by the addition of enzyme to the reaction mixture and the change in fluorescence monitored over time. During the course of the assay less than 10% of the substrate was consumed.

$$F = v_s t + \frac{(v_o - v_s)[1 - e^{(k_{obs} \cdot -t)}]}{k_{obs}} + D \tag{5}$$

The activity fluorescence progress curves were fitted by non-linear regression analysis (Prism) using Eq. 5 (Morrison, 1969; Morrison, 1982); where 'F' is the fluorescence response, 't' is time, '$v_o$' is the initial velocity, '$v_s$' is the equilibrium steady-state velocity, '$k_{obs}$' is the observed pseudo first-order rate constant and 'D' is the intercept at time zero (i.e. the ordinate displacement of the curve). The second order rate constant was obtained from the slope of the line of a plot of $k_{obs}$ versus the inhibitor concentration (i.e. $k_{obs}/[I]$). To correct for substrate kinetics, Eq. 6 was used, where '[$S_o$]' is the initial substrate concentration and '$K_M^{app}$' is the apparent macroscopic binding (Michaelis) constant for the substrate.

$$k_{inact} = \frac{k_{obs}(1 + [S_o]/K_M^{app})}{[I]} \tag{6}$$

Compounds of the invention were tested by the above described assays and observed to exhibit cathepsin K inhibitory activity with an in vitro Ki inhibitory constant of less than or equal to 100 μM.

Various modifications and variations of the described aspects of the invention will be apparent to those skilled in the art without departing from the scope and spirit of the invention. Although the invention has been described in connection with specific preferred embodiments, it should be understood that the invention as claimed should not be unduly limited to such specific embodiments. Indeed, various modifications of the described modes of carrying out the invention which are obvious to those skilled in the relevant fields are intended to be within the scope of the following claims.

The invention claimed is:

1. A process for preparing a compound of formula Ia, Ib, Ic or Id, or a pharmaceutically acceptable salt, complex or prodrug thereof,

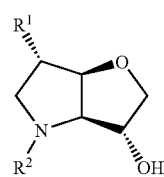

Ia

-continued

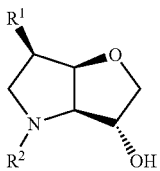
Ib

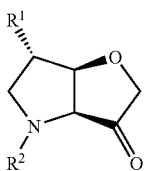
Ic

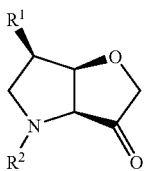
Id wherein:
$R^1$ is selected from H, $N_3$, $NH_2$, $NHR^3$, $NR^4R^5$, OH, $OR^6$, OTs, OMs, Me, Et, $CF_3$, F, Cl, Br, SH, $SR^7$, $SOR^7$, $SO_2R^7$, NH—$PG_2$, O—$PG_3$ and S—$PG_4$, wherein each of $PG_2$, $PG_3$ and $PG_4$ is independently a protecting group and Ts and Ms are tosyl and mesyl group respectively;

$R^2$ is H or a protecting group $PG_1$ or a group of formula U—$(V)_m$—$(W)_n$—$(X)_o$—Y— or a group of formula $(U)_p$—$(X_2)_s$—$(Y_1)_k$—$Y_2$—;

$R^{3-7}$ are each independently alkyl or cycloalkyl or aryl;
$R^{3-7}$ are each independently alkyl or cycloalkyl or aryl;
or $R^4$ and $R^5$ are linked to form a cyclic group together with the nitrogen to which they are attached;

Y is $CR^8R^9$—CO—, where $R^8$, $R^9$ are each independently selected from H, alkyl, cycloalkyl, Ar, Ar-alkyl, cycloalkyl(alkyl), heteroaryl or heteroaryl(alkyl), each of which may be optionally substituted by $R^{49}$, or $R^8$ and $R^9$ are linked to the adjacent backbone carbon atom to form a spiro-$C_5$-$C_6$ cycloalkyl group;

in the group $(X)_o$, X is $CR^{10}R^{11}$, where $R^{10}$ and $R^{11}$ are independently selected from H, alkyl, cycloalkyl, Ar and Ar-alkyl, and o is 0, 1, 2 or 3;

in the group $(W)_n$, W is O, S, C(O), S(O) or $S(O)_2$ or $NR^{12}$, where $R^{12}$ is selected from H, alkyl, cycloalkyl, Ar and Ar-alkyl, and n is 0 or 1;

in the group $(V)_m$, V is C(O), C(S), S(O), $S(O)_2$, $S(O)_2NH$, OC(O), NHC(O), NHS(O), $NHS(O)_2$, OC(O)NH, C(O)NH or $CR^{13}R^{14}$, where $R^{13}$ and $R^{14}$ are independently selected from H, alkyl, cycloalkyl, Ar and Ar-alkyl, and m is 0, 1, 2 or 3; provided that when m is greater than one, $(V)_m$ contains a maximum of one carbonyl or sulphonyl group;

$Y_2$ is OC(O)—, SC(O)— or $NR^{15}C(O)$—;

or where $(U)_p$, $(X_2)_s$, and $(Y_1)_k$ are absent, $Y_2$ is $R^{47}OC(O)$—, $R^{47}SC(O)$— or $R^{15}R^{45}NC(O)$—, where $R^{47}$ is alkyl or aryl, and $R^{15}$ and $R^{45}$ are each independently selected from H and alkyl, or $R^{15}$ and $R^{45}$ are linked to form a cyclic group together with the nitrogen to which they are attached;

in the group $(Y_1)_k$, each $Y_1$ is independently $CR^{16}R^{17}$, and 'k' is 0, 1, 2 or 3;

or when 'k' is 1, $Y_1$ may additionally be selected from

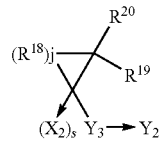

where $Y_3$ is methylene or absent;
$R^{18}$ is selected from $CR^{21}R^{22}$;
'j' is 1, 2, 3 or 4, where when 'j' is 2, 3 or 4, one $R^{18}$ may additionally be selected from O, S, $SO_2$, $NR^{23}$ and —$N(R^{23})C(O)$—;

or when 'k' is 1, 2, or 3 and $(U)_p$ and $(X_2)_s$ are absent, the terminal $Y_1$ group is selected from $CR^{16}R^{17}R^{43}$ and

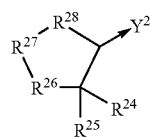

$R^{26}$ is selected from $CR^{29}R^{30}$, O, $NR^{31}$;
$R^{27}$ is selected from $CR^{32}R^{33}$, O, $NR^{34}$;
except when $R^{26}$ is O, then $R^{27}$ is selected from $CR^{32}R^{33}$ and $NR^{34}$;
$R^{28}$ is selected from $CR^{35}R^{36}$, $CH(NHR^{37})$ and C(O);
in the group $(X_2)_s$, each $X_2$ is independently $CR^{38}R^{39}$, O, S, C(O), $S(O)_2$ or $NR^{40}$;
's' is 0, 1 or 2, provided that when $(Y_1)_k$ is absent, $(X_2)_s$ is $CR^{38}R^{39}$ or is absent, and also provided that when 's' is 2, $(X_2)_s$ contains a minimum of one $CR^{38}R^{39}$; and when $(U)_p$ is absent and 's' is 1 or 2, the terminal $X_2$ group is $CR^{38}R^{39}R^{44}$;

each U is independently a 5- to 7-membered monocyclic or a 8- to 11-membered bicyclic ring which is either saturated or unsaturated and which includes up to four heteroatoms as shown below:

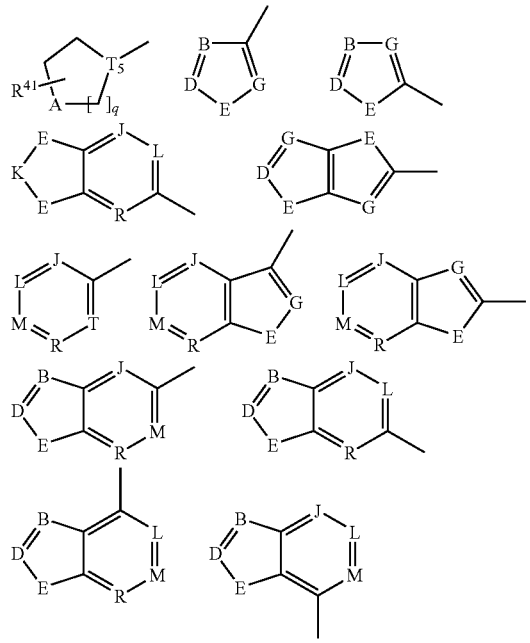

-continued

[chemical structures]

wherein R⁴¹ is:

H, alkyl, cycloalkyl, Ar-alkyl, Ar, OH, O-alkyl, O-cycloalkyl, O-Ar-alkyl, OAr, SH, S-alkyl, S-cycloalkyl, S-Ar-alkyl, SAr, SO-alkyl, SO-cycloalkyl, SO—Ar-alkyl, SO—Ar, SO₂H, SO₂-alkyl, SO₂-cycloalkyl, SO₂-Ar-alkyl, SO₂Ar, NH-alkyl, NH₂, NH-cycloalkyl, NH—Ar-alkyl, NHAr, NHCO-alkyl, NHCO-cycloalkyl, NHCO—Ar-alkyl, NHCOAr, N(alkyl)₂, N(cycloalkyl), or N(Ar-alkyl)₂ or NAr₂ or, when part of a CHR⁴¹ or CR⁴¹ group, R⁴¹ may be halogen;

A is selected from:
CH₂, CHR⁴¹, O, S, SO₂, NR⁴² and N-oxide (N→O), where R⁴¹ is as defined above; and R⁴² is selected from H, alkyl, cycloalkyl, Ar and Ar-alkyl;

B, D and G are each independently selected from:
CR⁴¹, where R⁴¹ is as defined above, N and N-oxide (N→O);

E is selected from:
CH₂, CHR⁴¹, O, S, SO₂, NR⁴² and N-oxide (N→O), where R⁴¹ and R⁴² are defined as above;

K is selected from:
CH₂, CHR⁴², where R⁴² is defined as above;

J, L, M, R, T, T₂, T₃ and T₄ are independently selected from:
CR⁴¹ where R⁴¹ is as defined above, N and N-oxide (N→O);

T₅ is selected from:
CH and N;

T₆ is selected from:
NR⁴², SO₂, OC(O), C(O), and N(R⁴²)C(O);

T₇ is selected from:
O, S, NR⁴⁶

'q' is 1, 2 or 3;

'p' is or 1;

R¹⁶⁻¹⁷, R¹⁹⁻²², R²⁴⁻²⁵, R²⁹⁻³⁰, R³²⁻³³, R³⁵⁻³⁶, R³⁸⁻³⁹ and R⁴³⁻⁴⁴ are each independently selected from H, alkyl, cycloalkyl, Ar-alkyl, Ar and halogen; and R²³, R³¹, R³⁴, R³⁷, R⁴⁰ and R⁴⁶ are each independently selected from H, alkyl, cycloalkyl, Ar-alkyl and Ar;

R⁴⁹ is H, alkyl, cycloalkyl, Ar-alkyl, Ar, OH, O-alkyl, O-cycloalkyl, O—Ar-alkyl, OAr, SH, S-alkyl, S-cycloalkyl, S-Ar-alkyl, SAr, SO-alkyl, SO-cycloalkyl, SO—Ar-alkyl, SO—Ar, SO₂H, SO₂-alkyl, SO₂-cycloalkyl, SO₂—Ar-alkyl, SO₂Ar, NH-alkyl, NH₂, NH-cycloalkyl, NH—Ar-alkyl, NHAr, NHCO-alkyl, NHCO-cycloalkyl, NHCO—Ar-alkyl, NHCOAr, N(alkyl)₂, N(cycloalkyl), or N(Ar-alkyl)₂ or NAr₂ or halogen;

said process comprising the steps of:
(i) treating a compound of formula Iva or Ivb with an oxidizing agent to form a compound of formula Va or Vb, respectively;

[structure of IVa]

IVa

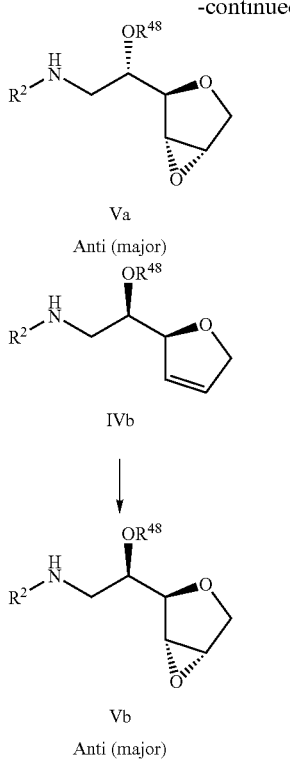

Va
Anti (major)

IVb

Vb
Anti (major)

wherein R[48] is alkyl, tosyl, or mesyl; and
(ii) converting the compound of formula Va or Vb into a compound of formula VIa or VIb, respectively;

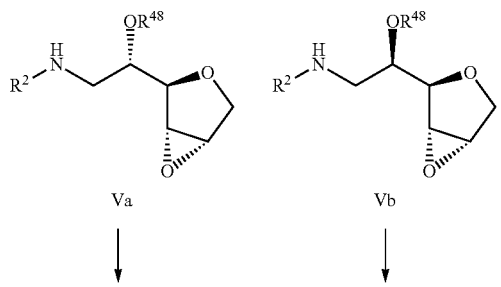

Va    Vb

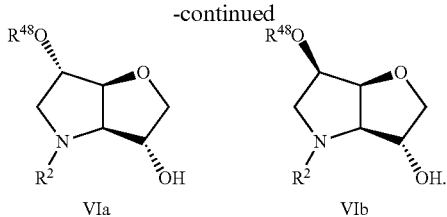

VIa    VIb

2. A process according to claim 1 wherein the oxidising agent is a hydrogen peroxide/alkylnitrile mixture or a dioxirane.

3. A process according to claim 1 wherein R[2] is $PG_1$, wherein $PG_1$ is a urethane protecting group selected from benzyloxycarbonyl, tert-butoxycarbonyl, fluoren-9-yl-methoxycarbonyl, 1-(biphenyl-4-yl)-1-methylethoxycarbonyl, α,α-dimethyl-3,5-dimethoxylbenzyloxy-carbonyl, p-methoxybenzyloxycarbonyl, p-nitrobenzyloxy-carbonyl, allyloxycarbonyl and trichloroethoxycarbonyl;

R[48] is methyl, tert-butyl or tosyl; and

R[1] is H, $N_3$, $NH_2$, NH-Boc, OBu, OMe or OTs.

4. The process according to claim 1, wherein a compound of formula Va or Vb in step (ii) is treated with sodium hydride.

5. The process according to claim 1, wherein step (ii) is carried out in THF.

6. The process according to claim 1, wherein

R[2] is U—(V)$_m$—(W)$_n$—(X)$_o$—Y—;

Y is CHR[9]OC or CR[8]R[9]CO;

X is a simple alkyl group;

o is 0 or 1;

W is O, S, $SO_2$, S(O), C(O) or NR[51], wherein R[51] is H or $C_{1-4}$-alkyl;

n is 0 or 1;

V is C(O), OC(O), NHC(O) or CHR[52], wherein R[52] is H or $C_{1-4}$-alkyl;

m is 0 or 1; and

U is an optionally substituted 5- or 6-membered saturated or unsaturated heterocycle or Ar group, or an optionally substituted saturated or unsaturated 9- or 10-membered heterocycle or Ar group.

* * * * *